(12) United States Patent
Huntington et al.

(10) Patent No.: US 11,492,404 B2
(45) Date of Patent: *Nov. 8, 2022

(54) INHIBITION OF CYTOKINE-INDUCED SH2 PROTEIN IN NK CELLS

(71) Applicant: The Walter and Eliza Hall Institute of Medical Research, Parkville (AU)

(72) Inventors: Nicholas D. Huntington, Parkville (AU); Sandra E. Nicholson, Parkville (AU)

(73) Assignee: The Walter and Eliza Hall Institute of Medical Research

( * ) Notice: Subject to any disclaimer, the term of this patent is extended or adjusted under 35 U.S.C. 154(b) by 0 days.

This patent is subject to a terminal disclaimer.

(21) Appl. No.: 17/719,825

(22) Filed: Apr. 13, 2022

(65) Prior Publication Data

US 2022/0267447 A1  Aug. 25, 2022

Related U.S. Application Data

(60) Continuation of application No. 17/393,466, filed on Aug. 4, 2021, now Pat. No. 11,339,220, which is a continuation of application No. 17/379,128, filed on Jul. 19, 2021, now Pat. No. 11,279,760, which is a continuation of application No. 17/115,896, filed on Dec. 9, 2020, now Pat. No. 11,104,735, which is a division of application No. 16/060,996, filed as application No. PCT/AU2016/051252 on Dec. 16, 2016, now Pat. No. 10,975,149.

(30) Foreign Application Priority Data

Dec. 16, 2015  (AU) .............................. 2015905220

(51) Int. Cl.
| | | |
|---|---|---|
| C07K 16/28 | (2006.01) |
| A61K 38/17 | (2006.01) |
| C07K 16/22 | (2006.01) |
| G01N 33/566 | (2006.01) |
| G01N 33/68 | (2006.01) |
| C07K 16/18 | (2006.01) |
| A61K 31/713 | (2006.01) |
| A61K 39/395 | (2006.01) |
| A61K 35/17 | (2015.01) |
| A61K 38/04 | (2006.01) |
| C12N 5/0783 | (2010.01) |
| A61P 35/02 | (2006.01) |
| A61P 35/00 | (2006.01) |
| A61K 31/506 | (2006.01) |
| A61K 39/00 | (2006.01) |

(52) U.S. Cl.
CPC ........ *C07K 16/2818* (2013.01); *A61K 31/506* (2013.01); *A61K 31/713* (2013.01); *A61K 35/17* (2013.01); *A61K 38/04* (2013.01); *A61K 38/1709* (2013.01); *A61K 39/395* (2013.01); *A61P 35/00* (2018.01); *A61P 35/02* (2018.01); *C07K 16/18* (2013.01); *C07K 16/22* (2013.01); *C07K 16/2803* (2013.01); *C12N 5/0646* (2013.01); *G01N 33/566* (2013.01); *G01N 33/6863* (2013.01); *A61K 2039/505* (2013.01); *A61K 2039/507* (2013.01)

(58) Field of Classification Search
None
See application file for complete search history.

(56) References Cited

U.S. PATENT DOCUMENTS

| | | |
|---|---|---|
| 2002/0147307 A1 | 10/2002 | Hilton et al. |
| 2003/0022311 A1 | 1/2003 | Dunnington et al. |
| 2003/0191058 A1 | 10/2003 | Nicholson et al. |
| 2006/0269519 A1 | 11/2006 | Chen et al. |
| 2007/0179089 A1 | 8/2007 | Norton et al. |
| 2012/0282646 A1 | 11/2012 | Choi et al. |

FOREIGN PATENT DOCUMENTS

| | | |
|---|---|---|
| WO | 2000/020624 A1 | 4/2000 |
| WO | 2000/037636 A1 | 6/2000 |
| WO | 2001/032912 A1 | 5/2001 |
| WO | 2006/112869 A2 | 10/2006 |
| WO | 2012/078540 A1 | 6/2012 |

OTHER PUBLICATIONS

Aman et al., 1999 "CIS Associates with the Interleukin-2 Receptor b Chain and Inhibits Interleukin-2-dependent Signaling", The Journal of Biological Chemistry, vol. 274, pp. 30266-30272.

Ge et al., 2012 "LNCaP Prostate Cancer Cells with Autocrine Interleukin-6 Expression Are Resistant to IL-6-induced Neuroendocrine Differentiation due to Increased Expression of Suppressors of Cytokine Signaling", Prostate, 72(12):1306-1316.

(Continued)

*Primary Examiner* — Daniel C Gamett
(74) *Attorney, Agent, or Firm* — Fox Rothschild LLP

(57) ABSTRACT

The present invention relates to therapeutic and prophylactic methods based on inhibition of CIS in NK cells. In particular, the present invention relates to treating or preventing a NK-responsive condition by administering to a subject a CIS inhibitor, or administering CIS-inhibited NK cells. The invention further relates to methods for identifying a CIS inhibitor, and for determining a likelihood of cancer response to treatment with CIS inhibition.

12 Claims, 47 Drawing Sheets

Figure 1:
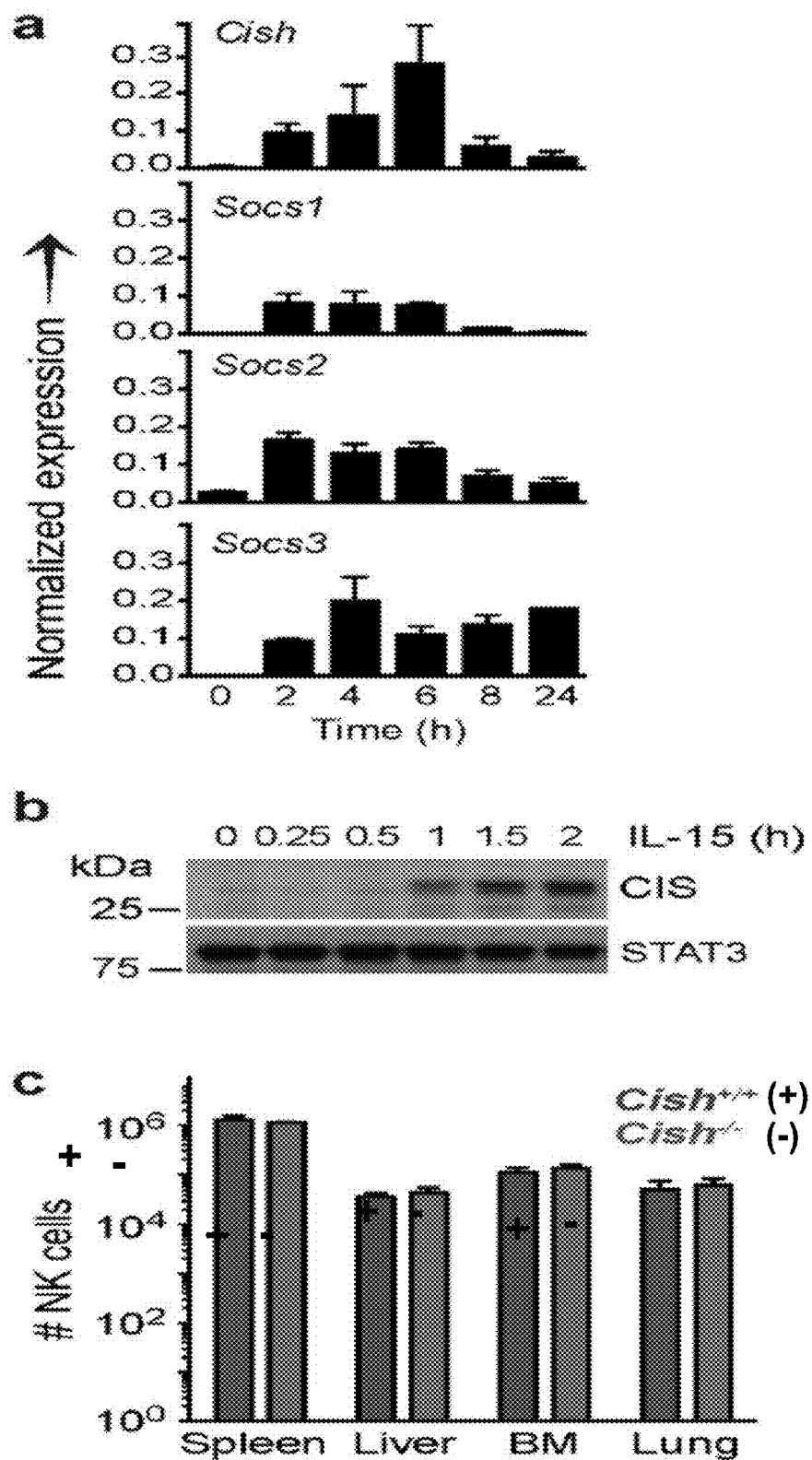
Figure 1:
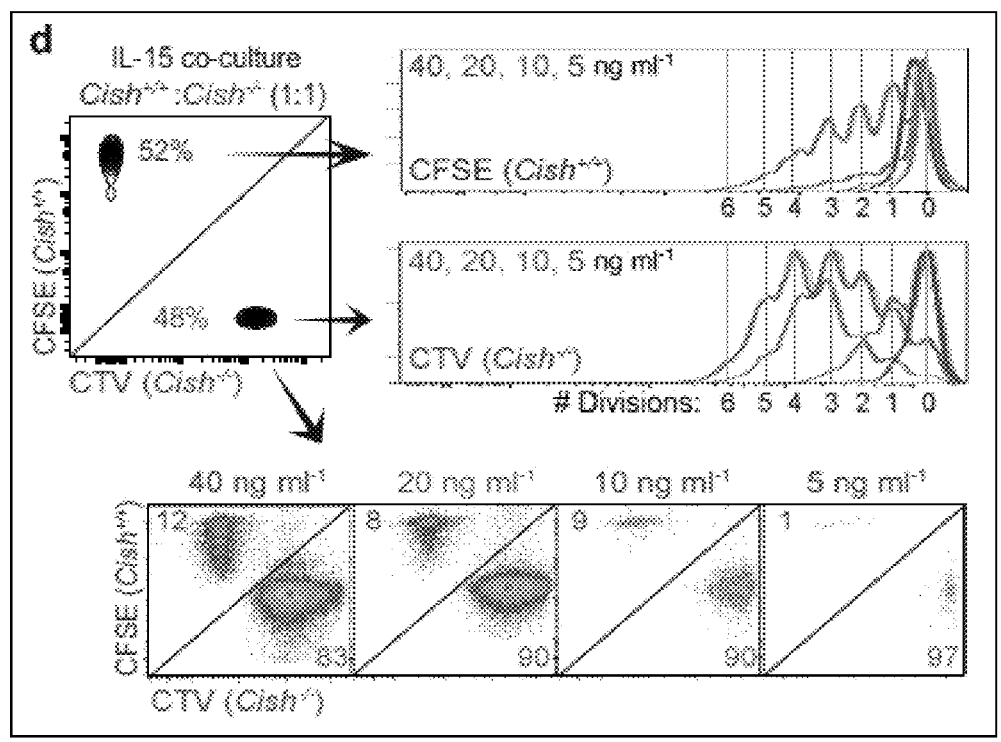
Figure 1:
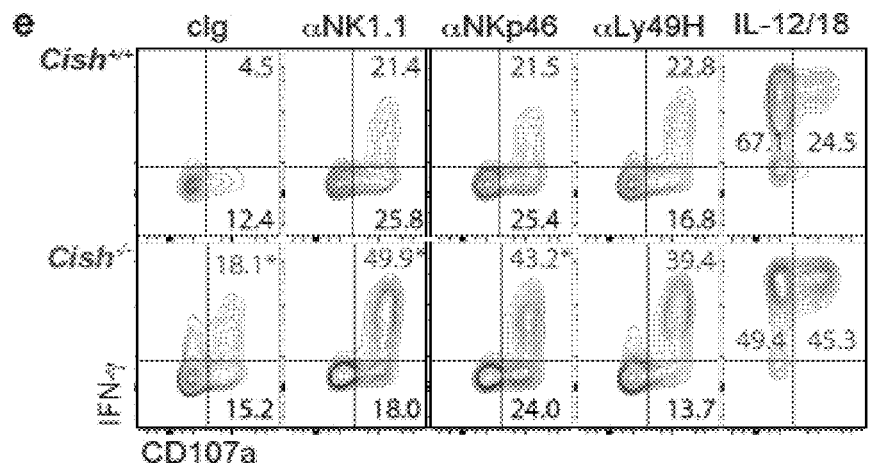
Figure 1:
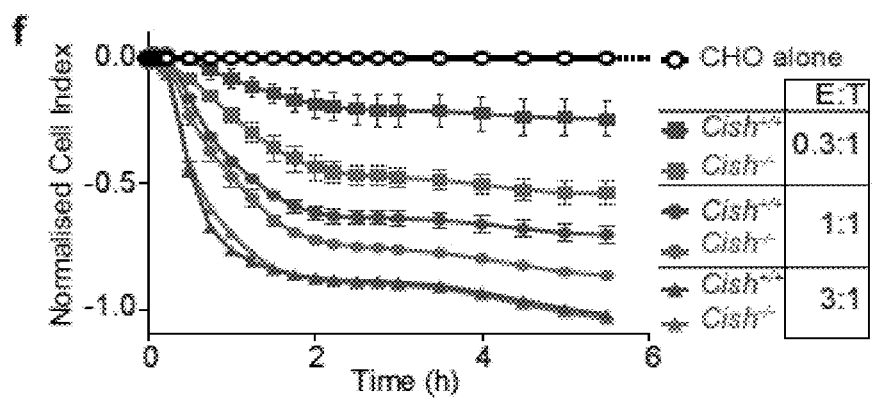
Figure 1:
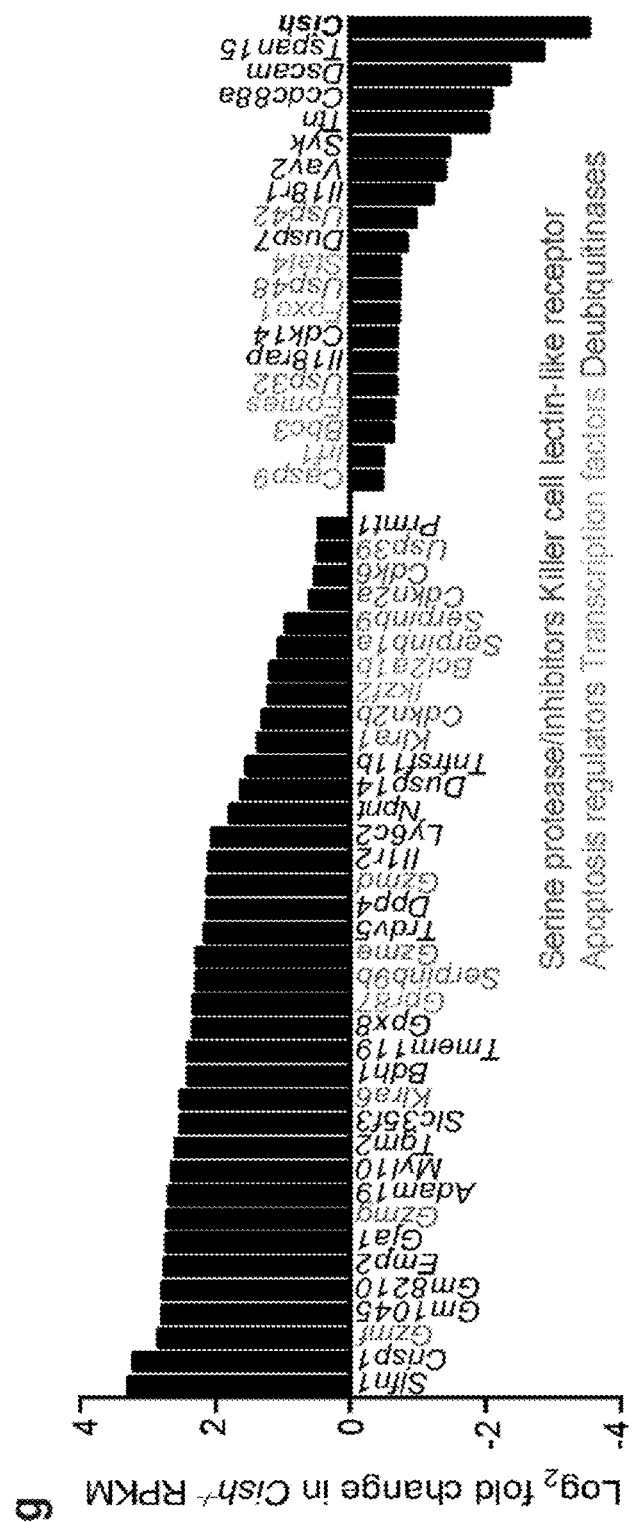

Specification includes a Sequence Listing.

(56) References Cited

OTHER PUBLICATIONS

Hashimoto et al., 2009 "RSV replication is attenuated by counteracting expression of the suppressor of cytokine signaling (SOCS) molecules", Virology, 391:162-170.

Palmer et al., 2015 "Cish actively silences TCR signaling in CD8+ T cells to maintain tumor tolerance", J. Exp. Med., 212(12):2095-2113.

Hu et al., 2009 "MicroRNA-98 and let-7 Confer Cholangiocyte Expression of Cytokine-Inducible Src Homology 2-Containing Protein in Response to Microbial Challenge", J. Immunol., 183:1617-1624.

Piessevaux et al., 2008 "Elongin B/C Recruitment Regulates Substrate Binding by CIS", J. Biol. Chem., 283(31):21334-21346.

International Search Report for PCT/AU2016/051252 (dated Feb. 20, 2017).

International Preliminary Report on Patentability for PCT/AU2016/051252 (dated Jun. 28, 2018).

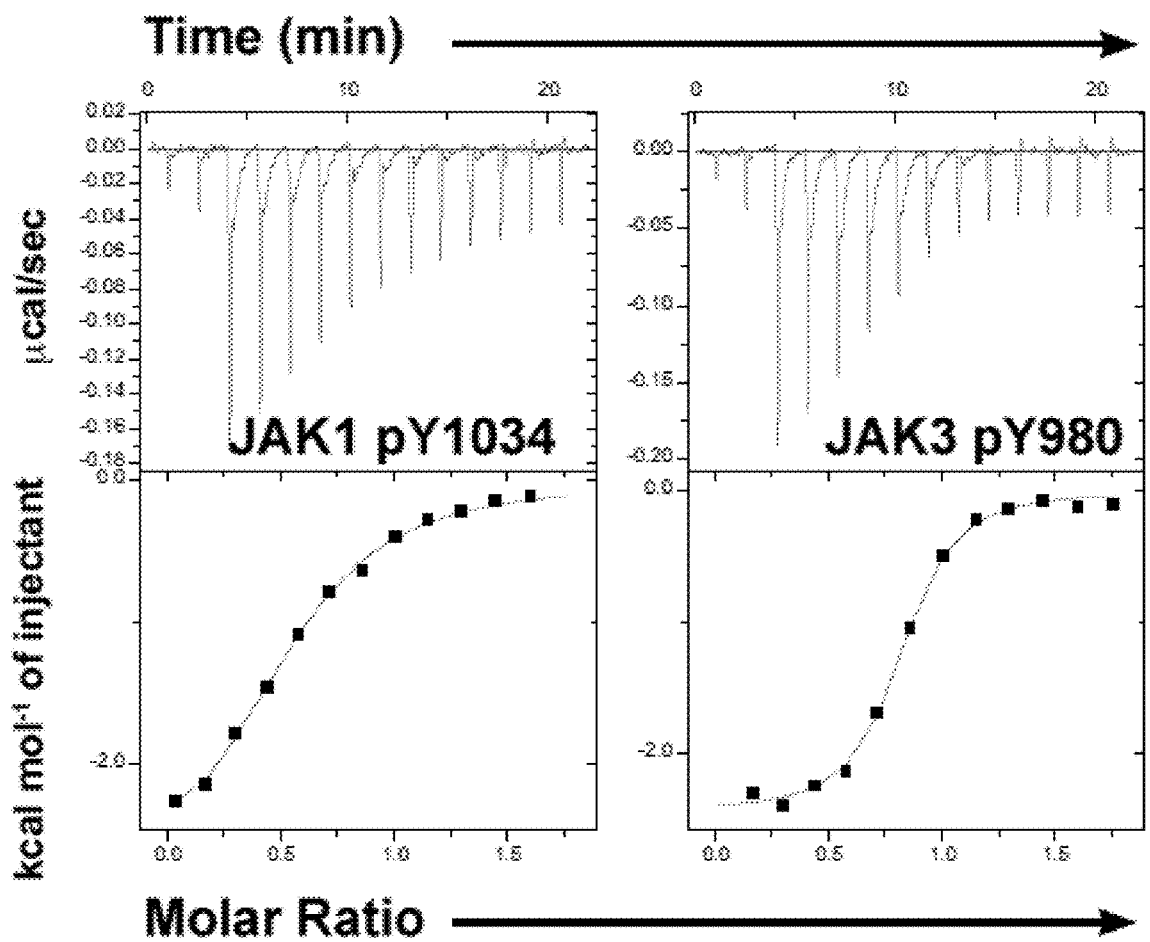

| Ligand | $K_D$ (μM) | ΔH (kcal/mol) | Sequence | |
|---|---|---|---|---|
| IL-2Rβ (pY338) | 7.0 ± 2 | -2.7 ± 0.3 | NGQpYFFFHLPDA | SEQ ID NO:21 |
| IL-2Rβ (pY355) | 0.94 ± 0.3 | -5.4 ± 0.9 | CQVpYFTYDPYSE | SEQ ID NO:3 |
| IL-2Rβ (pY358) | >10 | N.D. | YFTpYDPYSEEDP | SEQ ID NO:22 |
| IL-2Rβ (pY361) | 1.5 ± 0.2 | -6.3 ± 0.4 | YDPpYSEEDPDEG | SEQ ID NO:4 |
| IL-2Rβ (pY392) | 1.8 ± 0.7 | -3.5 ± 0.3 | DDApYCTFPSRDD | SEQ ID NO:5 |
| mIL-2Rβ (pY392) | 1.5 ± 0.3 | -4.0 ± 1.0 | QDDpYCAFPPRDD | SEQ ID NO:23 |
| IL-2Rβ (pY510) | >10 | N.D. | TDApYLSLQELQG | SEQ ID NO:24 |
| IL-2Rγ (pY303) | >10 | N.D. | LVTEpYQGNFSA | SEQ ID NO:25 |
| IL-2Rγ (pY325) | >10 | N.D. | LQPDpYSERFCH | SEQ ID NO:26 |
| IL-2Rγ (pY357) | >10 | N.D. | IHSPpYWPPPCY | SEQ ID NO:27 |
| IL-2Rγ (pY363) | >10 | N.D. | PPPCpYSLKPEA | SEQ ID NO:28 |

FIG. 9 (continued)

(SEQ ID NO:29)

INHIBITION OF CYTOKINE-INDUCED SH2 PROTEIN IN NK CELLS

CROSS-REFERENCE TO RELATED APPLICATIONS

This application is a continuation of U.S. patent application Ser. No. 17/393,466 filed Aug. 4, 2021, which is a continuation of U.S. patent application Ser. No. 17/379,128 filed Jul. 19, 2021 (now U.S. Pat. No. 11,279,760), which is a continuation of U.S. patent application Ser. No. 14/115,896 filed Dec. 9, 2020 (now U.S. Pat. No. 11,104,735), which is a divisional of U.S. patent application Ser. No. 16/060,996 filed Jun. 11, 2018 (now U.S. Pat. No. 10,975,149), which is a National Stage Application under 35 U.S.C. § 371 of International Application No. PCT/AU2016/051252 filed Dec. 16, 2016, which claims the benefit of priority to Australian Patent Application No. 2015905220 filed Dec. 16, 2015, the disclosures all of which are hereby incorporated by reference in their entireties.

FIELD OF THE INVENTION

The specification relates generally to the field of therapeutic agents. More particularly, the specification relates to methods for preventing or treating health conditions amenable to NK cell-mediated therapies.

SEQUENCE LISTING

The instant application contains a Sequence Listing which has been submitted electronically in ASCII format and is hereby incorporated by reference in its entirety. The ASCII copy, created on Dec. 9, 2020, is named Sequence_Listing.txt and is 51.11 bytes in size.

BACKGROUND OF THE INVENTION

The role of the immune system in suppressing tumour growth and infection is well known, and it is now accepted that avoiding immune detection is an important factor in cancer development. For example, cytotoxic lymphocytes such as natural killer (NK) and CD8 effector T cells contribute to anti-tumour immunity through cancer immunoediting. However, tumours and infectious agents (e.g., viruses) exploit a variety of mechanisms to disable these cytotoxic lymphocytes. The pleiotropic cytokine IL-15 is an important regulator of NK cell development, homeostasis and activation, yet its effects on NK cell activation are short-lived, which limits the effectiveness of NK cell-mediated responses in the context of a variety of cancers and infections. To date, there has been a great deal of interest in understanding the inhibitory signals that curb NK cell responses, but it is still unclear how intracellular IL-15 signalling is switched off.

Thus, there is an ongoing need to identify new strategies to unleash NK cell responses for the effective treatment of a variety of potentially NK cell-responsive health conditions, including cancer, while avoiding the devastating side effects of most chemotherapeutic agents.

SUMMARY OF THE INVENTION

The present inventors have found that inhibition of the cytokine-induced SH2 protein (CIS) can be used to treat a number of NK-cell-responsive conditions including certain cancers and infections.

Accordingly, in one aspect the present invention provides is a method for treating a subject suffering from a NK cell-responsive condition or at risk of suffering from a NK cell-responsive condition, comprising administering a CIS inhibitor to the subject.

In another aspect, the present invention provides a method for adoptive cell therapy or prophylaxis comprising administering CIS-inhibited NK cells to a subject suffering from a NK cell-responsive condition or at risk of suffering from a NK cell-responsive condition. In some embodiments the CIS-inhibited NK cells are autologous. In other embodiments the CIS-inhibited NK cells are allogeneic. In some embodiments the CIS-inhibited NK cells are NK cells contacted with a CIS inhibitor.

In some embodiments the CIS-inhibited NK cells are NK cells genetically modified to have reduced expression of CIS such as by gene editing with programmable nucleases or by gene silencing (RNA interference). In some embodiments the genetically modified CIS-inhibited NK cells are $Cish^{-/-}$. In some embodiments the $Cish^{-/-}$ NK cells are human $Cish^{-/-}$ NK cells.

In relation to any of the above aspects, in some embodiments the CIS inhibitor to be administered or used to generate CIS-inhibited NK cells, is a peptide, a peptidomimetic, a small molecule, a polynucleotide, or a polypeptide. In some embodiments the CIS inhibitor competitively inhibits binding of CIS to JAK1 and/or JAK3. In some embodiments the CIS inhibitor competitively inhibits binding of CIS to phosphorylated JAK1 (e.g., JAK1 phosphorylated at Tyr1034) and/or phosphorylated JAK3 (e.g., JAK3 phosphorylated at Tyr980). In further embodiments the CIS inhibitor competitively inhibits binding of CIS to one or more of Elongin B, Elongin C or Cullin-5.

In some embodiments, where the CIS inhibitor is a peptide, the peptide is a phosphopeptide or a phosphomimetic peptide.

In some embodiments, where the CIS inhibitor is a polypeptide, the polypeptide is an anti-CIS antibody or an antigen-binding fragment thereof.

In some embodiments, where the CIS inhibitor is a polynucleotide, the polynucleotide is a dsRNA. In some embodiments the dsRNA CIS inhibitor is an shRNA, siRNA, or miRNA. In some embodiments the polynucleotide is provided as a vector for expression of the polynucleotide CIS inhibitor. In some embodiments the vector is a viral vector. In some embodiments the polynucleotide CIS inhibitor encodes a dominant negative inhibitor of CIS. In some embodiments the encoded dominant negative inhibitor comprises the amino acid sequence of CIS comprising a R107K substitution. In other embodiments the encoded dominant negative inhibitor comprises the amino acid sequence of CIS with an L223A substitution.

In some embodiments, where the CIS inhibitor is a polynucleotide, the polynucleotide is a chemically modified mRNA. In some embodiments the chemically modified mRNA encodes a dominant negative inhibitor of CIS (e.g., CIS-R107K).

In some embodiments, where the CIS inhibitor is a small molecule, the small molecule CIS inhibitor destabilizes CIS. In some embodiments, where the small molecule CIS inhibitor acts by destabilizing CIS, the small molecule CIS inhibitor is a deubiquitinase inhibitor.

In some embodiments any of the above-mentioned methods of treatment or prophylaxis further include administering IL-15 or an IL-15 agonist to the subject.

In other embodiments any of the above-mentioned methods of treatment or prophylaxis further include administering a B-Raf protein kinase inhibitor, or a MEK protein kinase inhibitor.

In some embodiments, any of the above-mentioned methods of treatment or prophylaxis further include administering an immunotherapeutic agent. Examples of such immunotherapeutic agents include, but are not limited to, an antibody against the programmed cell death 1 receptor (PD-1), an antibody against the programmed death-ligand 1 (PD-L1), an antibody against cytotoxic T-lymphocyte-associated protein 4 (CTLA-4), an antibody against transforming growth factor beta (TGF-b), an antibody against Tactile (CD96), or a combination thereof. In some embodiments, any of the above treatments may further include administration of a TGF-beta receptor antagonist.

In some embodiments of the above-mentioned methods of treatment or prophylaxis, the subject is suffering from a cancer or determined to be at risk of suffering from a cancer or an infection.

In some embodiments, where the subject is suffering from a cancer, the cancer is characterized by the presence of a tumour. In some embodiments, where the subject is suffering from or at risk of suffering from a cancer, the cancer is metastatic melanoma, metastatic prostate cancer, metastatic breast cancer, triple negative breast cancer, bladder cancer, brain cancer, esophageal cancer, liver cancer, head and neck cancer, squamous cell lung cancer, non small lung cell cancer, Merkel cell carcinoma, sarcoma, hepatocellular cancer, multiple myeloma, pancreatic cancer, colorectal carcinoma, cervical cancer, gastric carcinoma, kidney cancer, metastatic renal cell carcinoma, leukemia, ovarian cancer, and malignant glioma. In some preferred embodiments the cancer is metastatic melanoma, metastatic prostate cancer, or metastatic breast cancer. In some embodiments, where the subject is suffering from a cancer, the subject has received an allogeneic tissue graft associated with treatment for cancer.

In other embodiments, where the subject is suffering from or at risk of suffering from an infection, the infection is a viral infection. In some embodiments, where the subject is suffering from a viral infection, the viral infection is an infection by a herpes simplex virus, an adenovirus, a vaccinia virus, a human cytomegalovirus, an influenza virus, a poxvirus, or a papillomavirus.

In another aspect, the present invention provides a method for identifying a CIS inhibitor, comprising:
i) contacting CIS or a fragment thereof with at least one CIS binding partner in the presence of a test agent; and
ii) determining whether the test agent competes with the CIS protein binding partner for binding to CIS or the fragment thereof; and
iii) optionally, identifying the test agent as a CIS inhibitor if, in step ii), it is shown to compete with the CIS protein binding partner for binding to CIS or the fragment thereof. In some embodiments the CIS binding partner is selected from among JAK1, JAK3, IL-2Rβ, Elongin B, Elongin C, and Cullin5 or a fragment thereof.

In a related aspect, the present invention provides a method for identifying a CIS inhibitor, comprising:
i) contacting CIS or a fragment thereof with a test agent; and
ii) determining whether the test agent binds to CIS or the fragment thereof. In some embodiments this method further comprises determining if the test agent competes with a CIS PEST domain peptide or CIS N-terminal peptide for binding to CIS or the fragment thereof. In some embodiments, the sequence of the CIS PEST domain peptide is selected from the group consisting of SEQ ID NO:29, SEQ ID NO:30, SEQ ID NO:32, and SEQ ID NO:37. In some embodiments the sequence of the N-terminal peptide is selected from the group consisting of SEQ ID NO:31 and SEQ ID NO:34.

In another related aspect, the present invention provides a method for identifying a CIS inhibitor, comprising:
i) incubating phosphorylated JAK1 protein or a CIS binding fragment thereof, in vitro, in the presence of:
(a) a trimeric complex comprising CIS or a fragment thereof comprising at least the SH2 domain and SOCS box; Elongin B; and Elongin C;
(b) a ubiquitination mixture; and
(c) a test agent; and
ii) determining whether the test agent inhibits CIS-induced ubiquitination of the phosphorylated JAK1 protein or fragment relative to the level of CIS-induced ubiquitination in the absence of the test agent. In some embodiments the ubiquitination mixture comprises: Cullin 5, Rbx2, E1, E2 and free ubiquitin.

In a further related aspect, the present invention provides a method for identifying a CIS inhibitor, comprising:
i) incubating JAK1 protein or fragment thereof comprising the JH1 kinase domain thereof, in vitro, in the presence of:
(a) a trimeric complex comprising CIS or a fragment thereof comprising at least the SH2 domain and SOCS box; Elongin B; and Elongin C;
(b) a JAK1 kinase substrate; and
(c) a test agent; and
ii) determining whether the test agent increases phosphorylation of the JAK1 kinase substrate relative to phosphorylation of the JAK1 kinase substrate in the absence of the test agent. In some embodiments the JAK1 kinase substrate is STAT5 protein or a STAT5 peptide.

In another related aspect, the present invention provides a method for identifying, in silico, a CIS inhibitor, comprising:
i) generating a three dimensional structural model of a CIS or a fragment thereof; and.
ii) designing or screening in silico for a test agent that binds to the modelled structure. In some embodiments the three dimensional structural model is a complex of CIS or a fragment thereof bound to a JAK1 protein or a CIS-binding fragment thereof; or a JAK3 protein or a CIS-binding fragment thereof.

In another related aspect, the present invention provides a method for identifying a CIS inhibitor, comprising:
i) providing a cell that expresses CIS; and
ii) determining whether a test agent reduces CIS activity in the cell when compared to a cell not contacted with the test agent. In some embodiments the CIS activity to be assessed is inhibition of JAK1 kinase activity, inhibition of STAT5 tyrosine phosphorylation, down-regulation of STAT5 promoter activity, or increased degradation of JAK1. In some embodiments the cell to be used in the method is a NK cell. In some embodiments, where the cell to be used is a NK cell, step ii) includes determining the effect of the test agent on an IL 15 inducible response in NK cells. In some embodiments the IL-15 inducible response is NK cell proliferation, interferon-γ (IFN-γ) production, intracellular granzyme expression, JAK1 tyrosine phosphorylation, JAK1 degradation, modulation of gene expression, or cytotoxicity.

In some embodiments the test agent to be used in the cell-based screening method was previously determined to be a candidate CIS inhibitor in any of the other CIS inhibitor identification methods described.

In some embodiments of any of the above-mentioned methods for identifying a CIS inhibitor, a test agent is a peptide, a peptidomimetic, a small molecule, a polynucleotide, or a polypeptide.

In some embodiments of any of the above-mentioned methods for identifying a CIS inhibitor, the amino acid sequence of CIS or the fragment thereof comprises an amino acid sequence at least 80% identical to any one of SEQ ID NOs:6-10.

In another aspect, the present invention provides the use of a CIS inhibitor in the manufacture of a medicament for treating or preventing a NK cell-responsive condition in a subject.

In a further aspect, the present invention provides the use of CIS-inhibited NK cells in the manufacture of a medicament for treating or preventing a NK cell-responsive condition in a subject.

In another aspect, the present invention provides the use of a CIS inhibitor as a medicament for treating or preventing a NK cell-responsive condition in a subject.

In another aspect, the present invention provides the use of CIS-inhibited NK cells as a medicament for treating or preventing a NK cell-responsive condition in a subject.

In a further aspect, the present invention provides a CIS inhibitor for use in the treatment or prevention of a NK cell-responsive condition.

In yet another aspect, the present invention provides a method for determining a likelihood of responsiveness to treatment with CIS inhibition in a patient in a patient suffering from a tumour, the method comprising determining a level of IL-15 in the tumour microenvironment, wherein an elevated level of IL-15 in the tumour microenvironment relative to a threshold level of IL-15 indicates a higher likelihood of responsiveness to the treatment.

In a related aspect, the present invention provides a method assessing induction of elevated Cish expression in tumour-infiltrating NK cells in a subject suffering from a tumour, the method comprising determining a level of IL-15 in the tumour microenvironment, wherein an elevated level of IL-15 in the tumour microenvironment relative to a threshold level of IL-15 indicates induction of elevated Cish expression in the tumour-infiltrating NK cells.

Also provided is a method for increasing responsiveness of NK cells to IL-15, the method comprising inhibiting CIS in the NK cells. In an embodiment, such a method comprises administering a CIS inhibitor to a subject. In another embodiment, a method for increasing responsiveness of NK cells to IL-15 comprises reducing the expression of CIS in the NK cells. In some embodiments, the reduction of CIS expression is carried out in NK cells ex vivo. In other embodiments, the reduction of CIS expression is NK cells in vivo (e.g., in a human subject).

Any embodiment herein shall be taken to apply mutatis mutandis to any other embodiment unless specifically stated otherwise. For instance, as the skilled person would understand examples of inhibitors and health conditions outlined above for the methods of the invention equally apply to the use and pharmaceutical compositions of the invention.

The present invention is not to be limited in scope by the specific embodiments described herein, which are intended for the purpose of exemplification only. Functionally-equivalent products, compositions and methods are clearly within the scope of the invention, as described herein.

Throughout this specification, unless specifically stated otherwise or the context requires otherwise, reference to a single step, composition of matter, group of steps or group of compositions of matter shall be taken to encompass one and a plurality (i.e. one or more) of those steps, compositions of matter, groups of steps or group of compositions of matter.

The invention is hereinafter described by way of the following non-limiting Examples and with reference to the accompanying figures.

BRIEF DESCRIPTION OF THE ACCOMPANYING DRAWINGS

FIG. 1—CIS-deficient NK cells display superior proliferation, survival and killing in response to IL-15. (a) Cultured wild-type NK cells were washed and starved of IL-15 prior to incubation with 50 ng ml$^{-1}$ IL-15 for the indicated times. Cells were harvested and analysed by Q-PCR for expression of SOCS mRNA. (b) NK cells were treated as in (a), lysed and analysed by Western blotting for CIS protein expression. (c) NK cells (NK1.1$^+$NKp46$^+$TCR-$\beta^-$) were profiled by flow cytometry and enumerated in bone marrow, liver, lung and spleens of wild-type (Cish') and Cish-deficient (Cish$^{-/-}$) mice. (d) Cish$^{+/+}$ and Cish$^{-/-}$ NK cells were labelled with CFSE and CTV, respectively, and cultured at a ratio of 1:1 in increasing concentrations of IL-15 (5-40 ng ml$^{-1}$) for 5 days prior to analysis by flow cytometry. Plots are representative of 5 independent experiments. (e) Freshly isolated splenic Cish$^{+/+}$ and Cish$^{-/-}$ NK cells were cultured in IL-15 in tissue culture plates coated with an immunoglobulin control (cIg; negative control), anti-NK1.1, anti-NKp46, anti-Ly49H (confers anti-viral response) antibodies or IL-12/IL-18 (positive control) for 4 h and analysed for IFN-$\gamma$ production and CD107a (LAMP-1) expression by flow cytometry. (f) Cish$^{+/+}$ and Cish$^{-/-}$ NK cells were expanded in IL-15 and co-cultured with CHO target cells at the indicated NK:CHO (E:T; Effector:Target) ratios over time. Normalized CHO Cell Index was determined using the xCELLigence system. (g) Cish$^{+/+}$ and Cish$^{-/-}$ NK cells were cultured in IL-15 for 7 days and RNA sequencing performed. Selected genes differentially expressed in Cish$^{-/-}$ NK cells are shown as reads per kilobase of exon per million reads (RPKM). See also FIG. 8 and Table 1.

Figure 2:
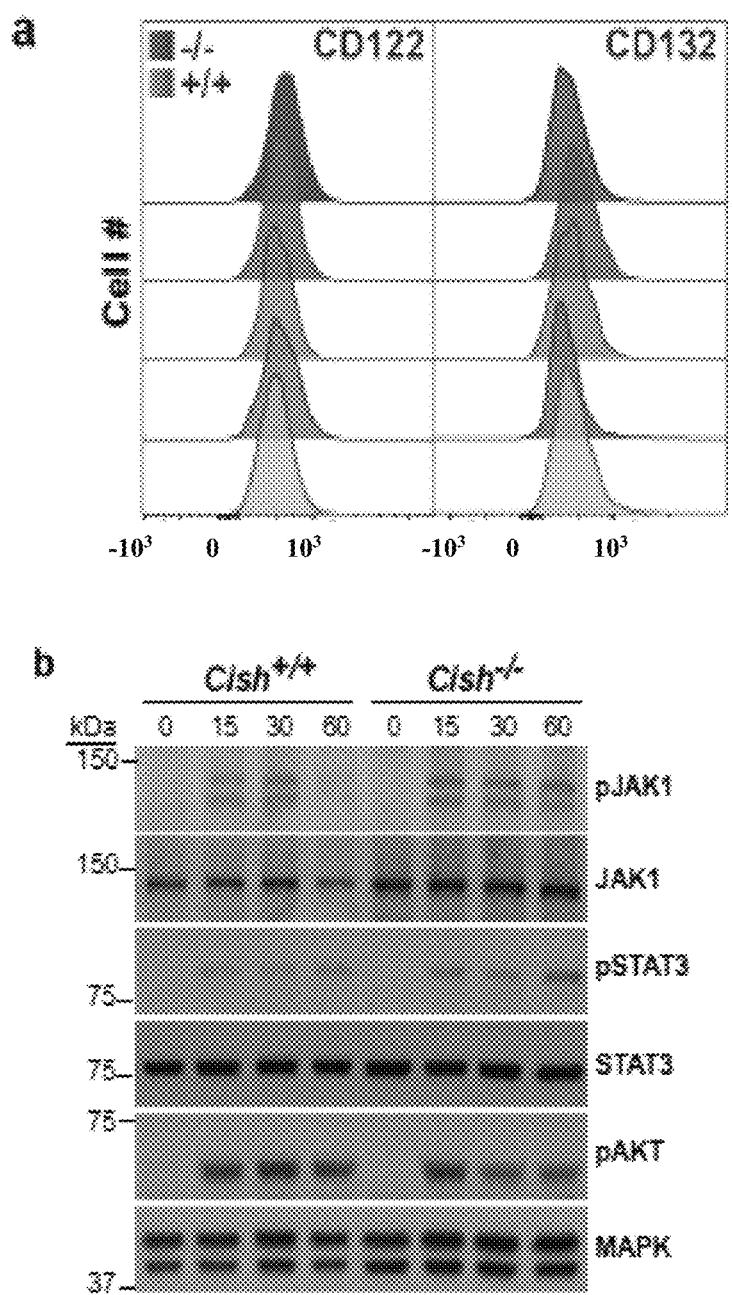
Figure 2:
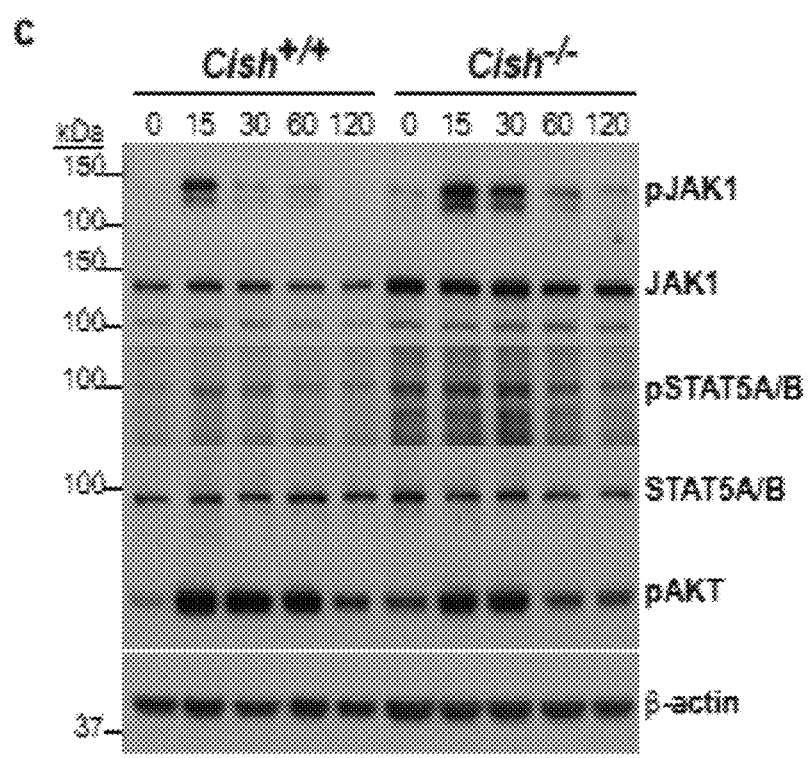
Figure 2:
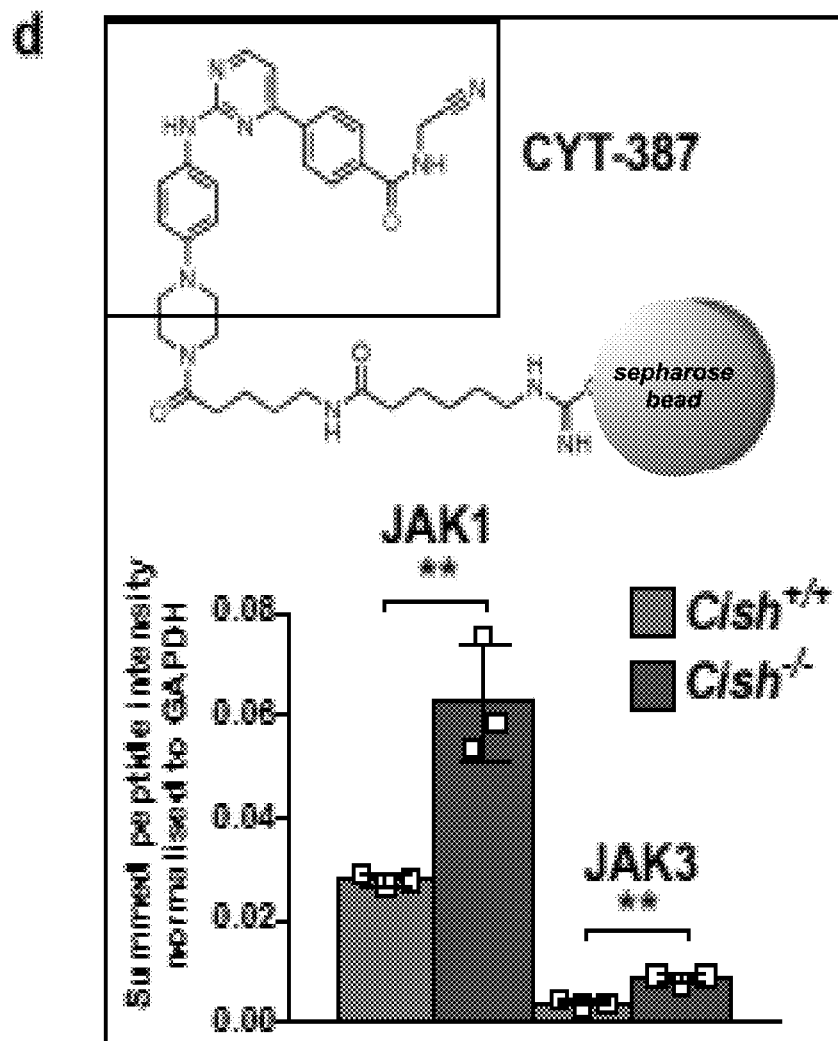
Figure 2:
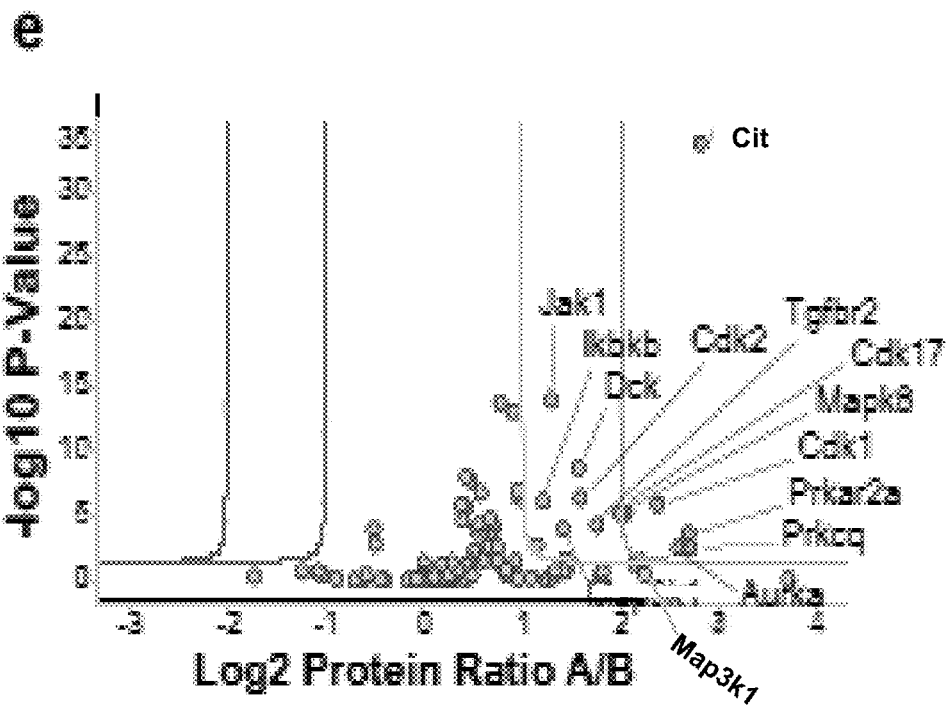
Figure 2:
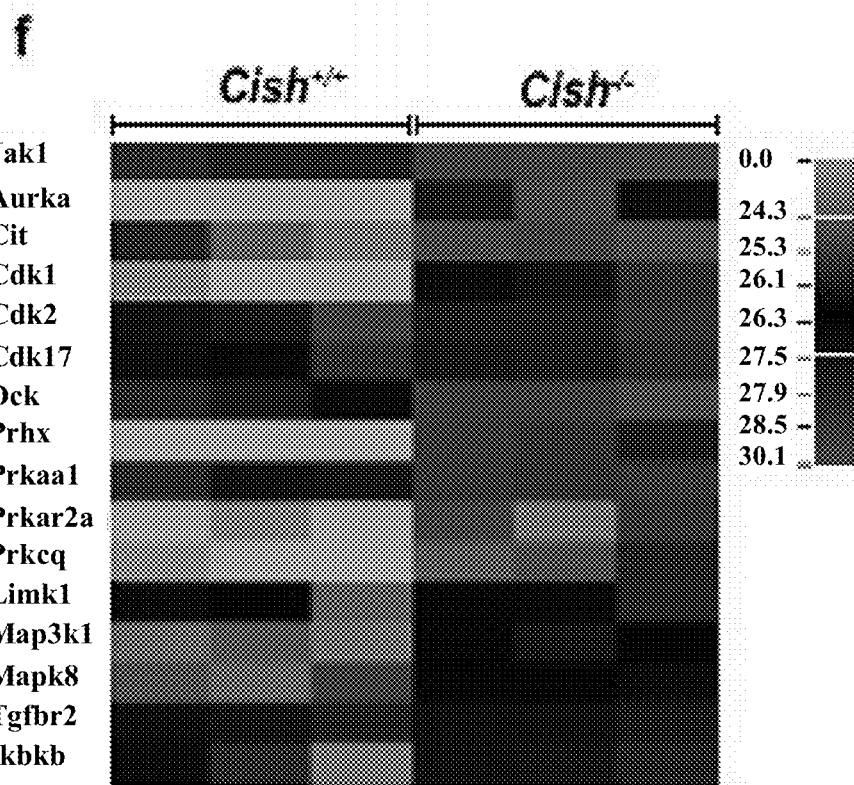

FIG. 2—CIS negatively regulates IL-15 signalling by targeting JAK/STAT signalling. (a) Cish$^{+/+}$ and Cish$^{-/-}$ NK cells were purified and cultured ex vivo for 21 h in 50 ng ml$^{-1}$ IL-15. IL-2R$\beta$ (CD122) and IL-2R$\gamma$ (CD132) surface expression was determined by flow cytometry. Each histogram represents NK cells derived from individual mice. (b) NK cells were purified from Cish$^{+/+}$ and Cish$^{-/-}$ spleens and incubated in vitro with 50 ng ml$^{-1}$ IL-15. (c) Alternatively, NK cells were purified and cultured for 7-10 days, washed and rested without IL-15 for 4 h, prior to IL-15 treatment. Cells were lysed and analysed by Western blotting with antibodies to the indicated phosphorylated (p) and total proteins. (d) A modified N-linker analogue of the JAK inhibitor CYT387 was coupled to NHS-sepharose beads and used as an affinity reagent to enrich JAK kinases from cell lysates generated as in (c). Enriched kinases were eluted, digested with trypsin and analyzed by mass spectrometry. Summed JAK1 and JAK3 peptide intensities are shown from Cish$^{+/+}$ and Cish$^{-/-}$ NK cells. Mean±S.E.M. **p<0.005; n=3 biological replicates (e & f) CYT-387 enrichment identified 69 unique protein kinases, 16 of which exhibited significant differential expression. Volcano plot (e) shows the Log 2 protein ratios following the quantitative pipeline analysis (CishCish$^{+/+}$ vs Cish$^{-/-}$). The red and yellow lines represent a 2-fold change in protein expression (log 2 ratio of 1), while the blue and green lines represent a 4-fold change (log 2 ratio of 2); dots are colored accordingly and represent individual proteins. Proteins with a −log10 p-value of 1.3 or greater were deemed differentially abundant. Heat map (f) displaying Log2-transformed summed peptide intensities (non-imputed) for kinases with significant differential expression. Data from individual replicates are shown (n=3). Green to red indicates increasing expression levels. Gene Ontology analysis revealed an enrichment of kinases involved in cell cycle and DNA replication in Cish$^{-/-}$ NK cells. See also FIG. 8.

Figure 3:
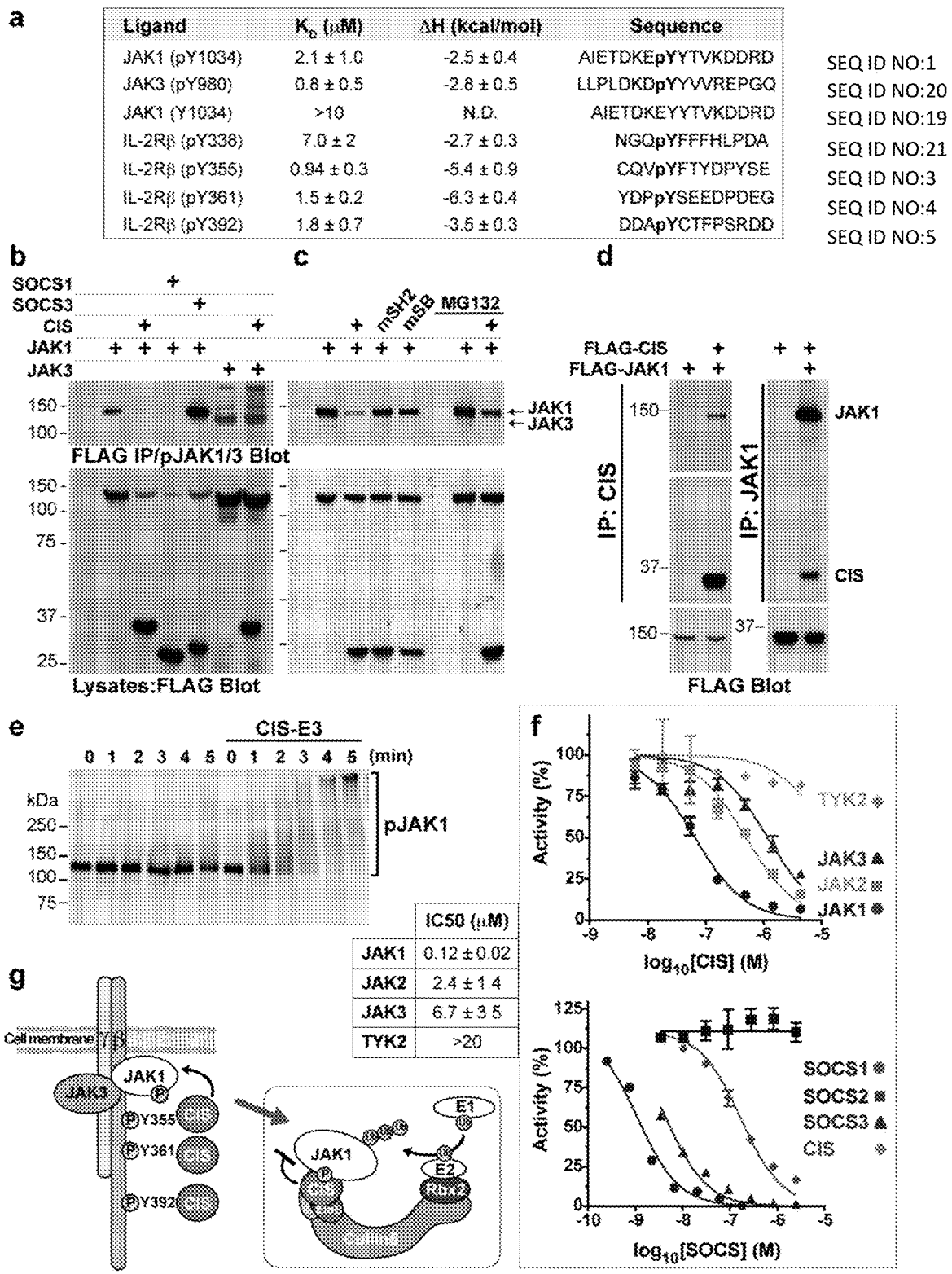

FIG. 3—CIS binds to the JAK activation loop to inhibit JAK1 kinase activity and target it for proteasomal degradation. (a) Isothermal calorimetry (ITC) was used to measure the affinity of hCIS-SH2-BC binding to phosphopeptides corresponding to tyrosines within the JAK1/3 kinase domain activation loops and IL-2Rβ cytoplasmic domains. Tabular view of the results, showing mean±S.D. from two independent experiments. N.D.=Not detectable, p=phosphorylated. (b & c) Flag-tagged JAK1 and JAK3 were expressed in 293T cells together with Flag-tagged-CIS, SOCS1, SOCS3 or CIS mutants in which the SH2 domain (mSH2; R107K) or the Cullin-5 binding site in the SOCS box had been mutated (mSB; P241A/L242A/P243A). In some instances, cells were treated with the proteasome inhibitor, MG132. Cells were lysed and proteins immunoprecipitated using anti-FLAG-beads, prior to Western blotting with antibodies to detect phosphorylated (p) JAK1 and JAK3. Protein expression levels are shown by anti-FLAG blots of whole cell lysates (lower panels). (d) FLAG-tagged JAK1 and CIS were co-expressed in 293T cells and immunoprecipitated (IP) using either anti-CIS (upper left panel) or anti-JAK1 antibodies (upper right panel). Western blotting with anti-FLAG antibodies revealed the presence of specific CIS-JAK complexes in each instance (upper panels). Protein levels are shown in the lower panels by anti-FLAG blot of cell lysates. (e) Using a cell-free system, FLAG-JAK1 was incubated with (+) and without (−) the CIS-E3 ligase complex (CIS-SH2-BC with Cullin5 and Rbx2), together with ubiquitin, E1 and E2 enzymes at 37° C. for the times indicated. JAK1 ubiquitination was visualised by Western blotting with antibodies to phosphorylated JAK1. (f) Kinase inhibition assays were performed with the kinase domain (JH1) of all four JAKs and CIS, SOCS1, SOCS2 or SOCS3. CIS preferentially inhibited JAK1 JH1 activity (upper panel), whilst SOCS1, 3 and CIS inhibited JAK1 JH1 activity to varying degrees (lower panel). Data were normalised to no-CIS controls. Inset table: IC$_{50}$ values; Average±S.E.M.; n=3-5 independent experiments). (g) Diagram illustrating the in vitro E3 ligase ubiquitination components and proposed model for CIS-mediated inhibition of JAK activity, whereby CIS recruitment to the receptor complex promotes binding to active JAK1 and results in kinase inhibition and proteasomal degradation. eloB: elongin B; C: elongin C. See also FIG. 9.

Figure 4:
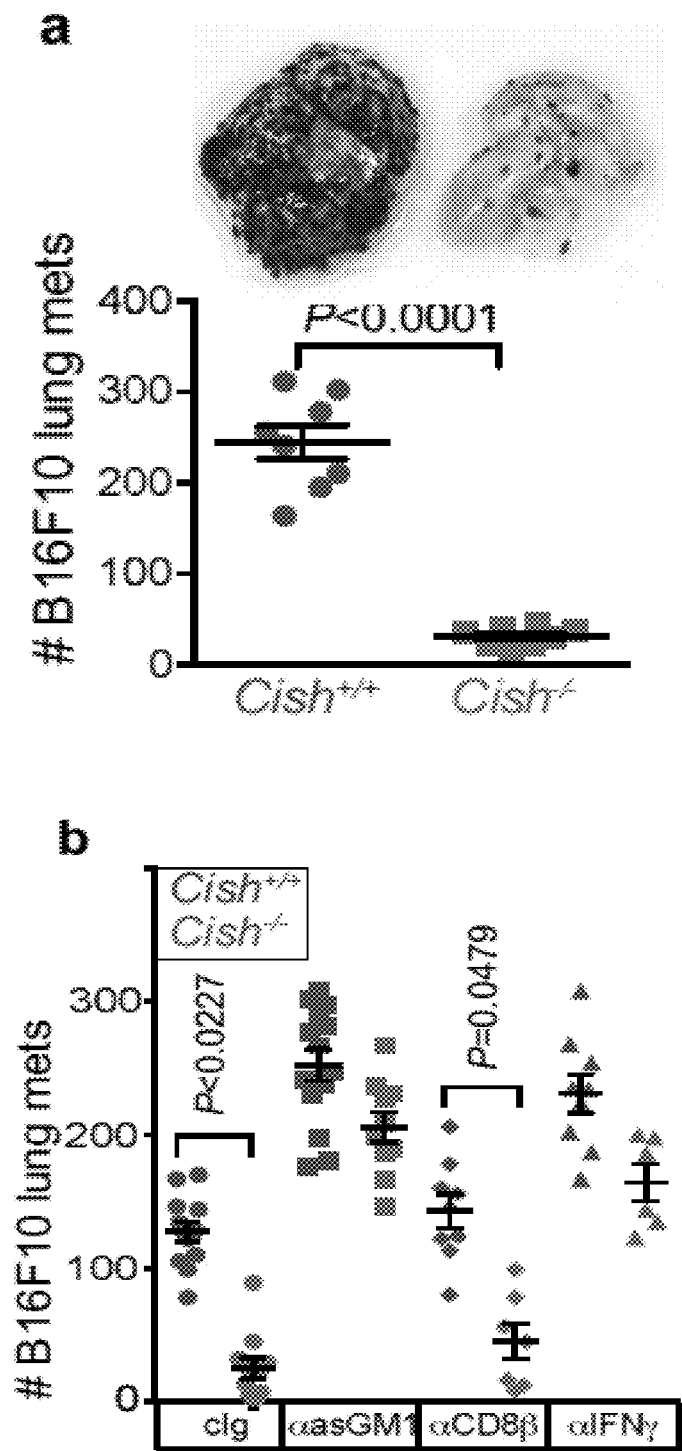
Figure 4:
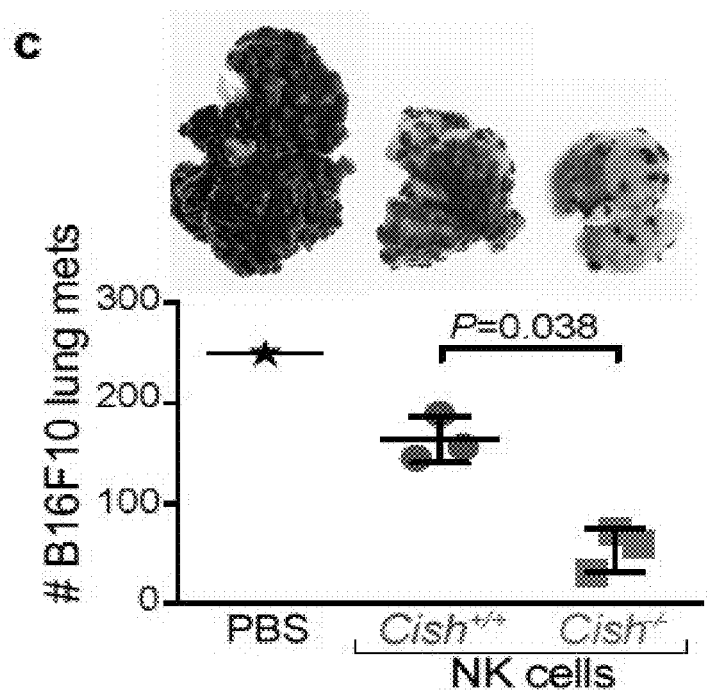
Figure 4:
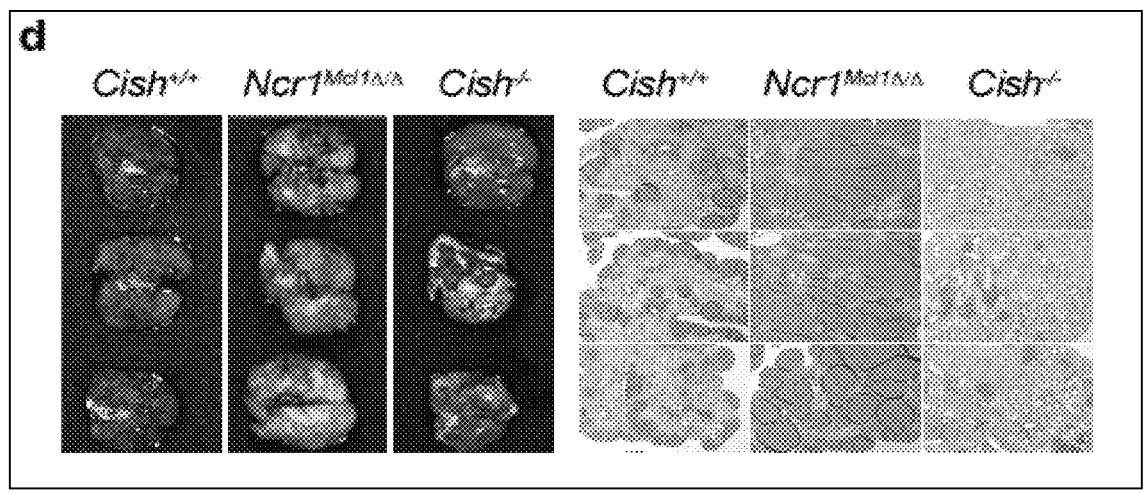
Figure 4:
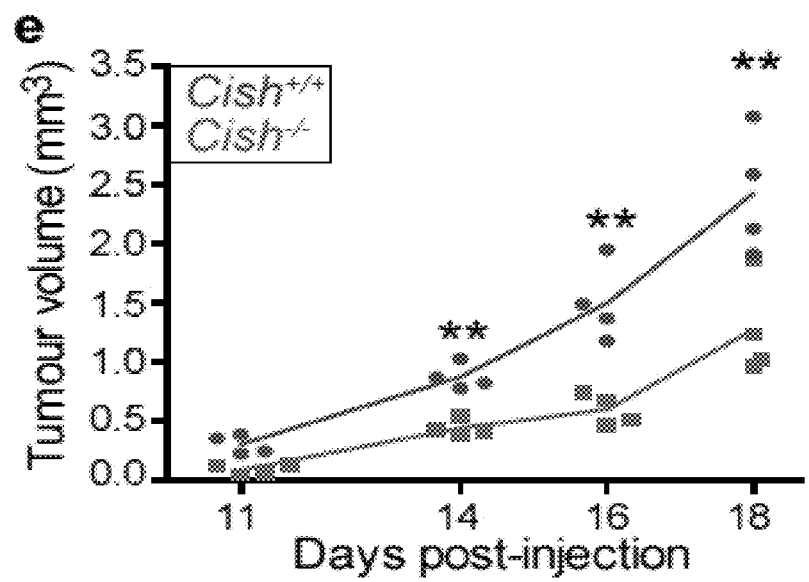
Figure 4:
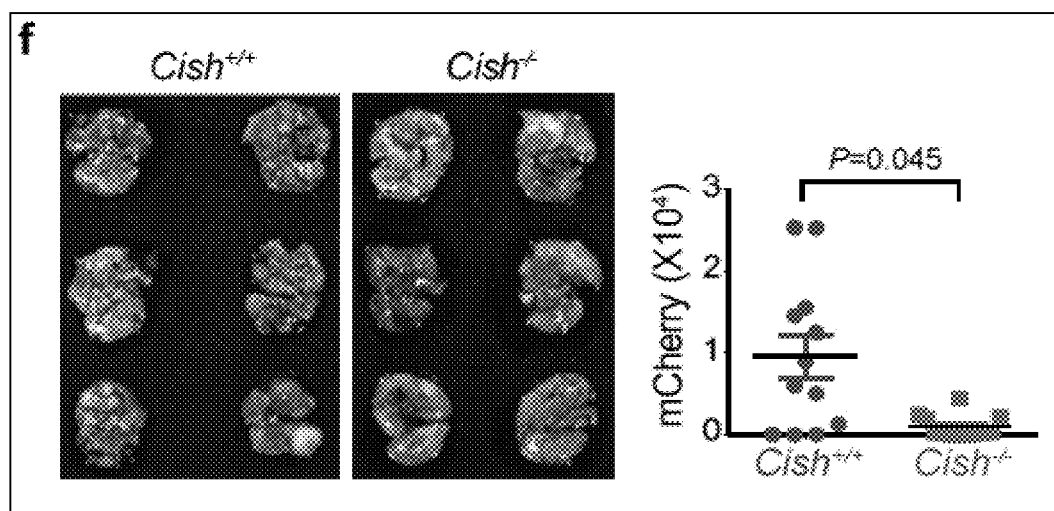
Figure 4:
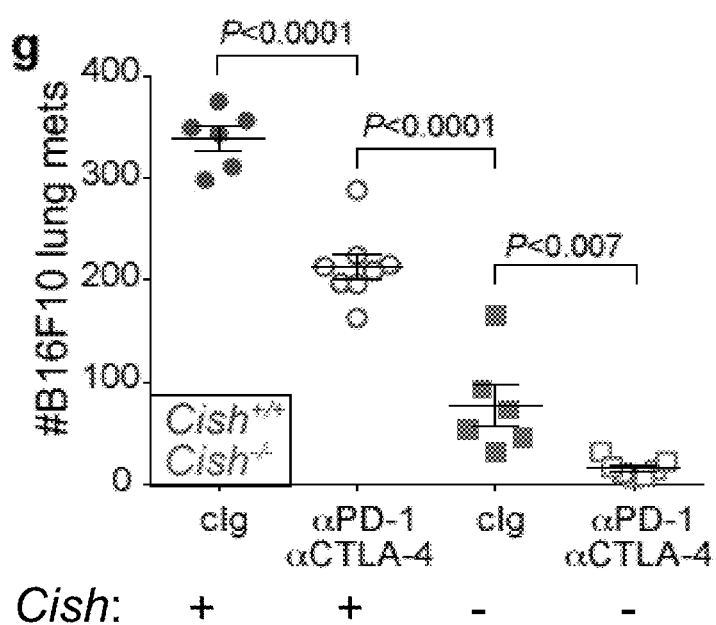

FIG. 4—Loss of Cish controls experimental lung tumour metastases. Cish$^{+/+}$ and Cish$^{-/-}$ mice were injected i.v. with (a) 3×10$^5$ B16F10 melanoma cells or (b) 2×10$^5$ B16F10 melanoma and treated on days −1, 0 and 6 relative to tumour inoculation with either control Ig (cIg), anti-CD8 (αCD8; CD8 T cell depletion), anti-asialoGM1 (αasGM1; NK cell depletion) or anti-IFNγ (αIFNγ; neutralising), antibodies. Mice were sacrificed day 14 post-tumour injection. (c) NK cell-deficient (Ncr1$^{Mcl1\Delta/\Delta}$) mice were injected i.v. with 3×10$^6$ in vitro expanded Cish$^{+/+}$ or Cish$^{-/-}$ NK cells or PBS, 8 h prior to injection with 1×10$^5$ B15F10 melanoma cells. Mice received a second injection of 1.5×10$^6$ in vitro expanded Cish$^{+/+}$ or Cish$^{-/-}$ NK cells or PBS, 24 h post-tumour inoculation and were sacrificed at day 18 post-tumour injection. (a-c) The metastatic burden (mets) was quantified in the lungs by counting colonies on the lung surface. (d) Cish$^{+/+}$, Cish$^{-/-}$ and Ncr1$^{Mcl1\Delta/\Delta}$ (NK-null) mice were injected i.v. with 5×10$^5$E0771 mCherry$^+$ breast cancer cells and lung metastasis analysed by IVIS (fluorescence emission; left panels) or H&E stained histological sections (right panels). (e) 1×10$^5$E0771 cells were implanted into the mammary fat pad of Cish$^{+/+}$ and Cish$^{-/-}$ mice and tumour size measured over time. (f) Orthotopic E0771 tumours generated as in (e) were surgically removed at 400-600 mm$^3$ and spontaneous lung metastases measured in the lungs 14 days later by IVIS and RT-PCR for mCherry mRNA expression. (g) Cish$^{+/+}$ and Cish$^{-/-}$ mice were injected i.v. with B16F10 lung carcinoma (7.5×10$^5$ cells). On days 0, 3 and 6 relative to tumour inoculation, mice received either control Ig or combination anti-PD-1/anti-CTLA-4 antibodies. The metastatic burden was quantified after 13 days by counting colonies on the lung surface. Mean±S.E.M. and all data (n) are shown. Representative whole lungs (a, c, d, f) and (d) histology sections from individual mice are shown. Significant differences between groups were determined by a (a, c, g) Mann-Whitney U test (b) Kruskal Wallis with post Dunn's test or (e) Mantel-Cox test. See also FIG. 10.

Figure 5:
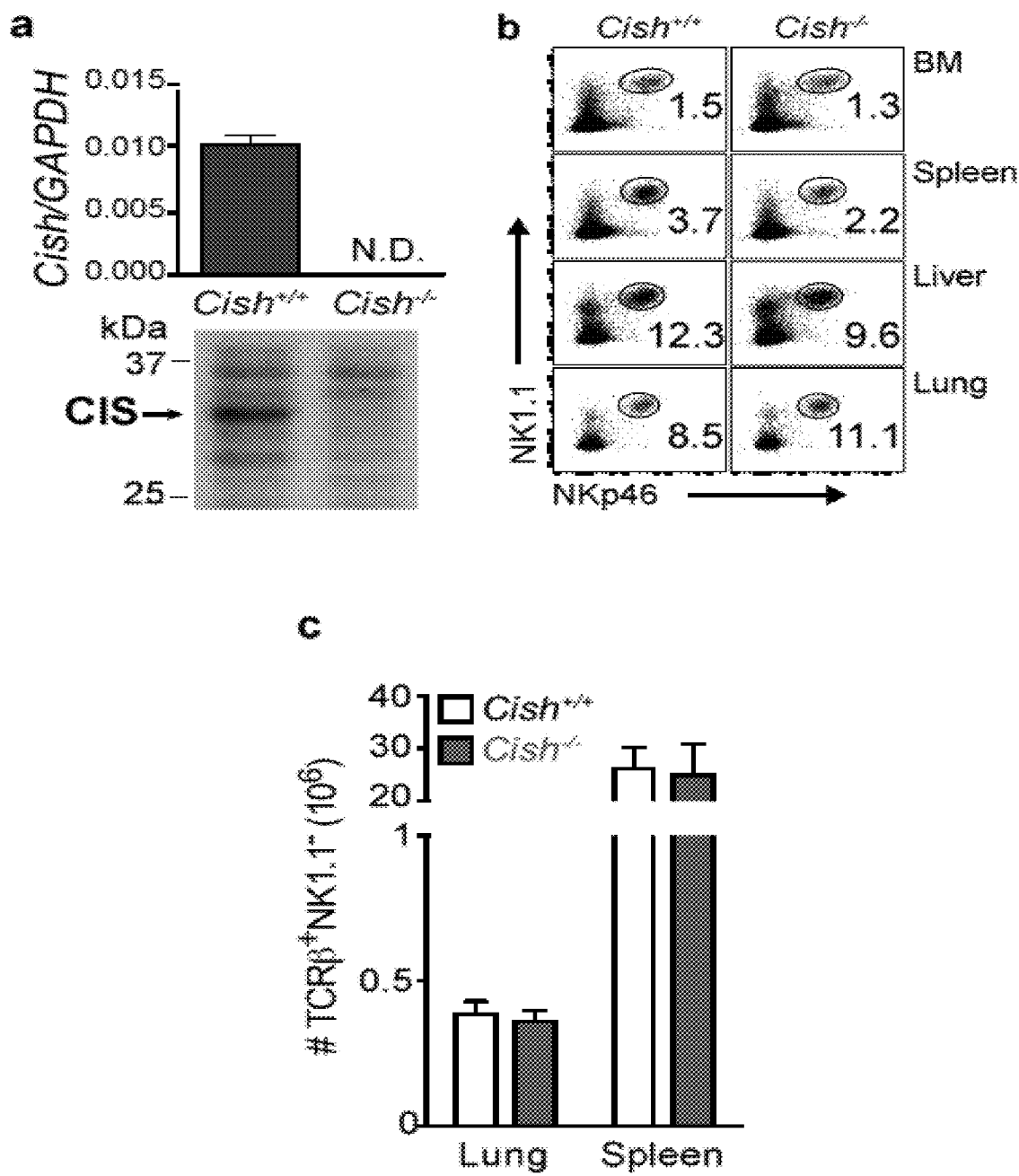
Figure 5:
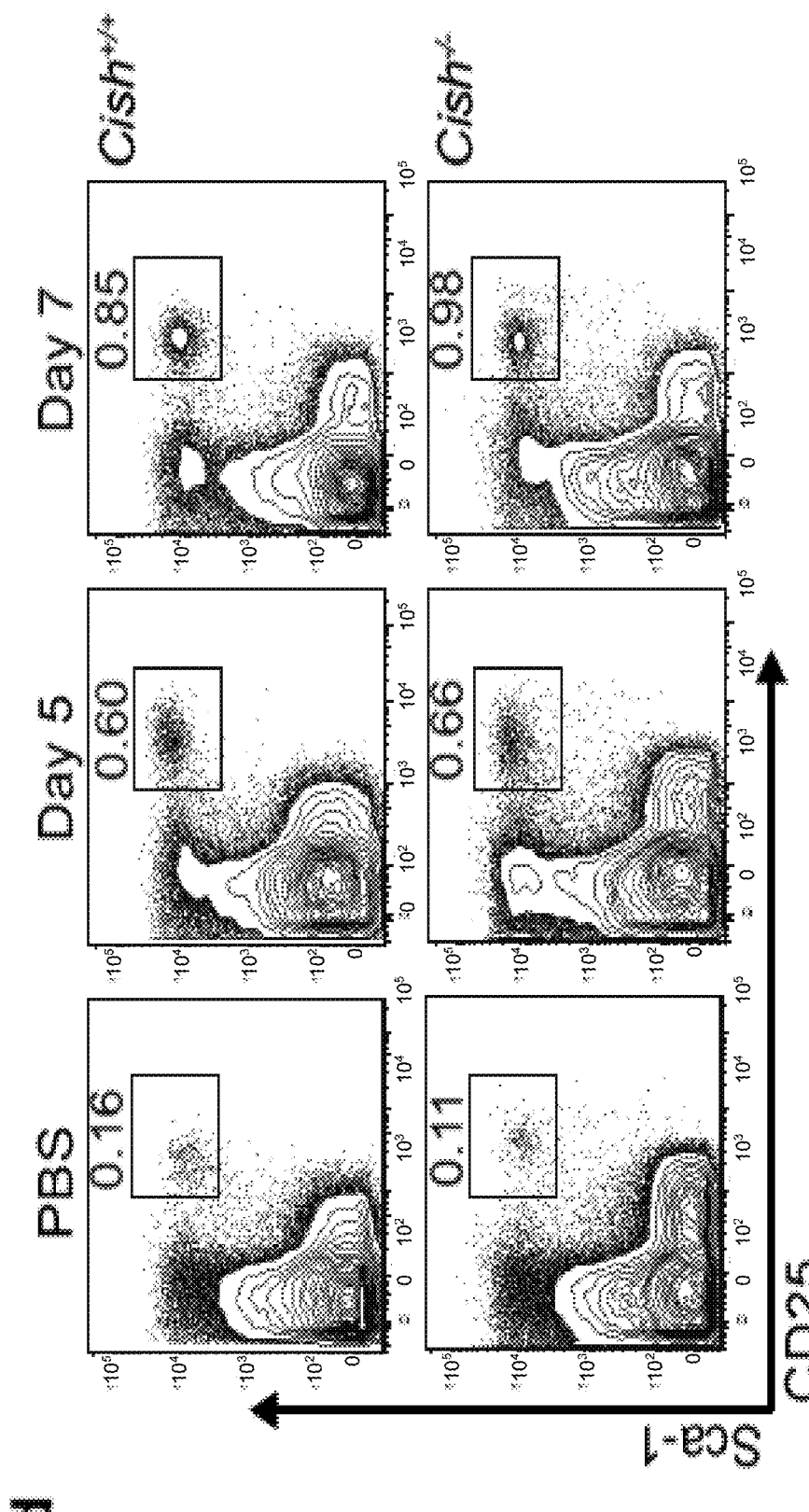
Figure 5:
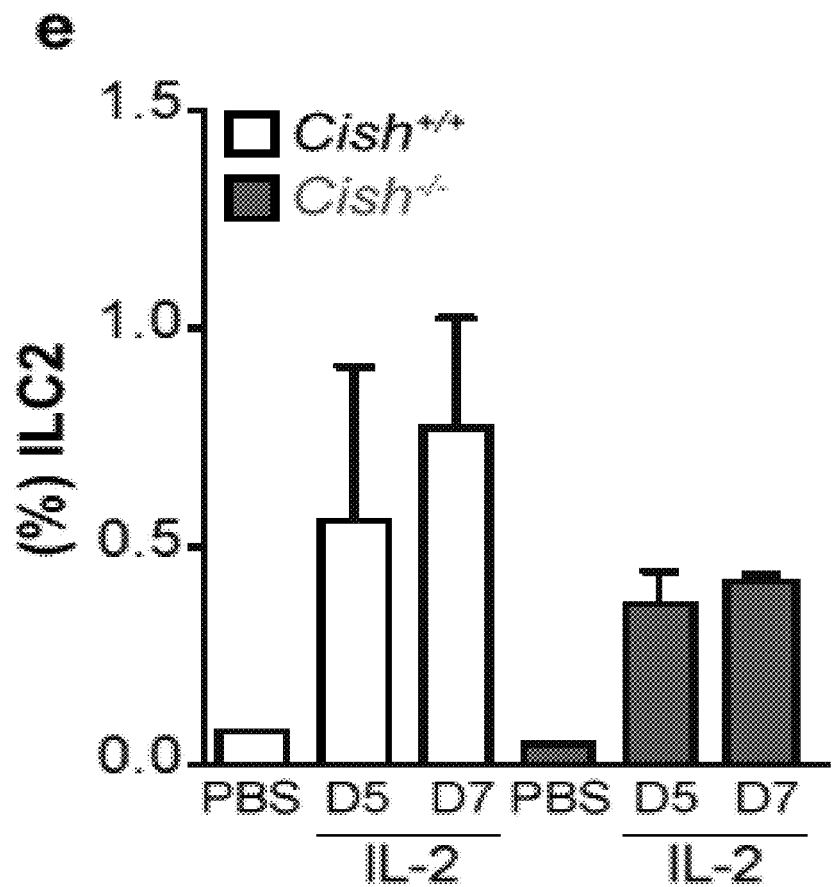
Figure 5:
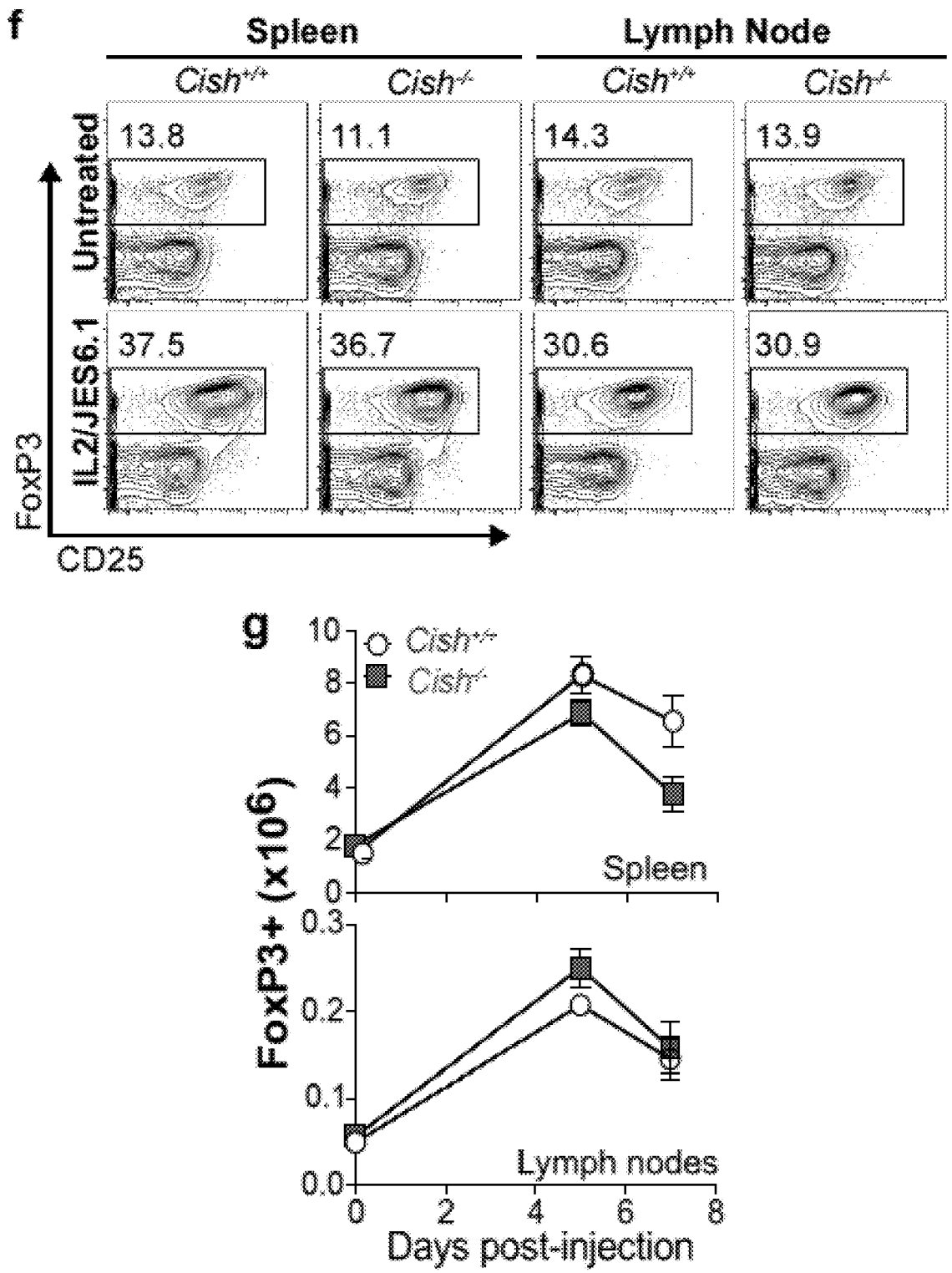

FIG. 5—Analysis of NK, T cells, Tregs, ILC2 and regulatory T cells in Cish-deficient mice. (a) Cish$^{-/+}$ or Cish$^{-/-}$ NK cells were cultured in IL-15, lysed and Cish mRNA analysed by Q-PCR. Data were normalised to expression of GAPDH mRNA (upper panel). N.D.: not detected. Cish$^{+/+}$ or Cish$^{-/-}$ NK cells were cultured in IL-15 and the proteasomal inhibitor MG132 for 4 h prior to cell lysis and CIS protein detected in whole cell lysates by Western blotting (lower panel). (b) NK cells (NK1.1$^+$NKp46$^+$TCR-β$^-$) and (c) T cells (NK 1.1$^-$TCR-β$^+$) were analysed in the indicated organs from Cish$^{+/-}$ and Cish$^{-/-}$ mice by flow cytometry. (d & e) ILC2 Cish$^{+/+}$ and Cish$^{-/-}$ were treated with PBS or IL-2 complexed with anti-IL-2 antibodies (IL-2-JES6.1) every 2 days and were sacrificed after 5 or 7 days (D5, D7). Representative flow cytometry plots of ILC2 in the bone marrow gated on CD3/19/NK1.1/B220/Gr1 negative cells. (e) Frequency of ILC2 in the bone marrow following IL-2-JES6.1 treatment. (a, c, e) Mean±S.E.M. n=3 biological replicates. (f) Regulatory T cells (Tregs) Expression of FoxP3 and CD25 on CD4$^+$ cells from spleen and lymph nodes of Cish$^{-/+}$ and Cish$^{-/-}$ mice before and 5 days after IL-2-JES6.1 treatment. Representative flow cytometry plots are shown. (g) Expansion and contraction of Tregs in the spleen and lymph nodes following IL-2-JES6.1 complex treatment (Mean±S.E.M., n=1-2 mice per group).

Figure 6:
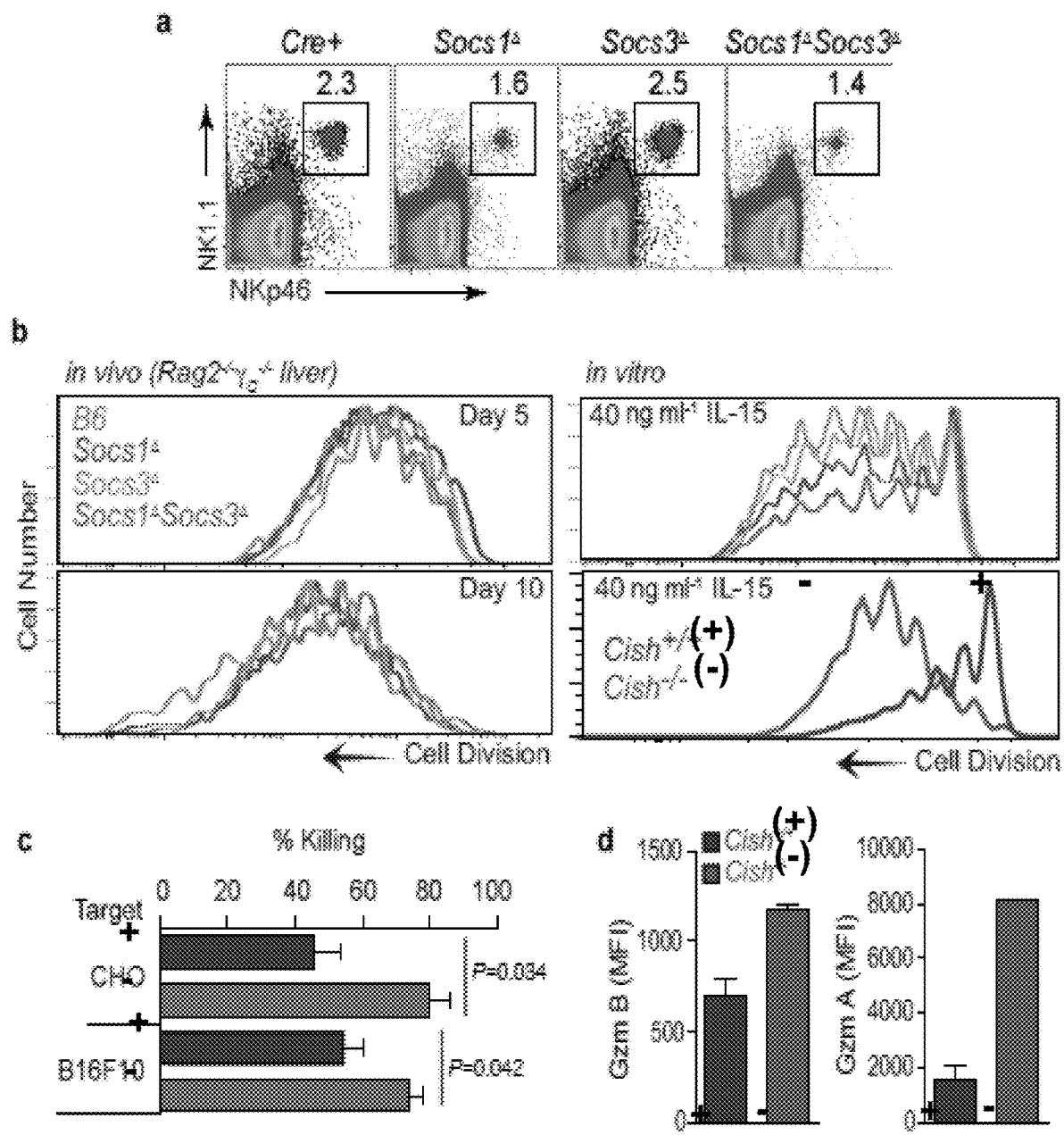

FIG. 6—Loss of Socs1 and/or Socs3 does not alter IL-15 responses in NK cells. (a) Socs3$^{+/-}$ ERT2$^{Cre/+}$ (Cre+), Socs1$^{-/-}$Ifnγ$^{-/-}$ (Socs1Δ), Socs3$^{fl/fl}$ERT2$^{Cre/1}$ (Socs3Δ), and Socs1$^{-/-}$Ifnγ$^{-/-}$ Socs3$^{fl/fl}$ERT2$^{Cre/+}$ (Socs1Δ Socs3Δ) mice were treated with 4-hydroxytamoxifen (4-OHT; to induce Socs3 deletion) by oral gavage and splenic NK cells analysed 14 days later by flow cytometry. (b) Splenic NK cells (TCR-β$^-$N1.1$^+$NKp46$^+$) from mice in (a) were FACS sorted and cultured in IL-15 (50 ng ml$^{-1}$) for 7 days before being CFSE labelled and either i.v. transferred into alymphoid Rag2$^{-/-}$gc$^{-/-}$ recipients or cultured in IL-15 (50 ng ml$^{-1}$) in vitro. Five and ten days post-transfer, recipient livers were analysed for donor NK cells by flow cytometry. In vitro cultures were analysed on day 5. $Cish^{+/+}$ and $Cish^{-/-}$ NK cell cultures serve as a reference for differential proliferation (lower right panel). (c) Enhanced effector function in $Cish^{-/-}$ NK cells. $Cish^{+/+}$ and $Cish^{-/-}$ NK cells were cultured for 7 days prior to co-culture with CHO or B16F10 target cells at a ratio of 1:1. Target cell killing at 5 h was determined by relative changes in electrical impedance using the xCELLigence system. $Cish^{+/+}$ and $Cish^{-/-}$ NK cells achieved maximal killing at 9:1 effector:target ratios (defined as 100% killing). (d) $Cish^{+/+}$ and $Cish^{-/-}$ mice were injected with RMA-m157 cells i.p and peritoneal NK cells analysed 18 h later for intracellular granzyme-A and granzyme-B production by flow cytometry. Mean±SD of two experiments. n=2 mice. MFI: Mean Fluorescence Index.

Figure 7:
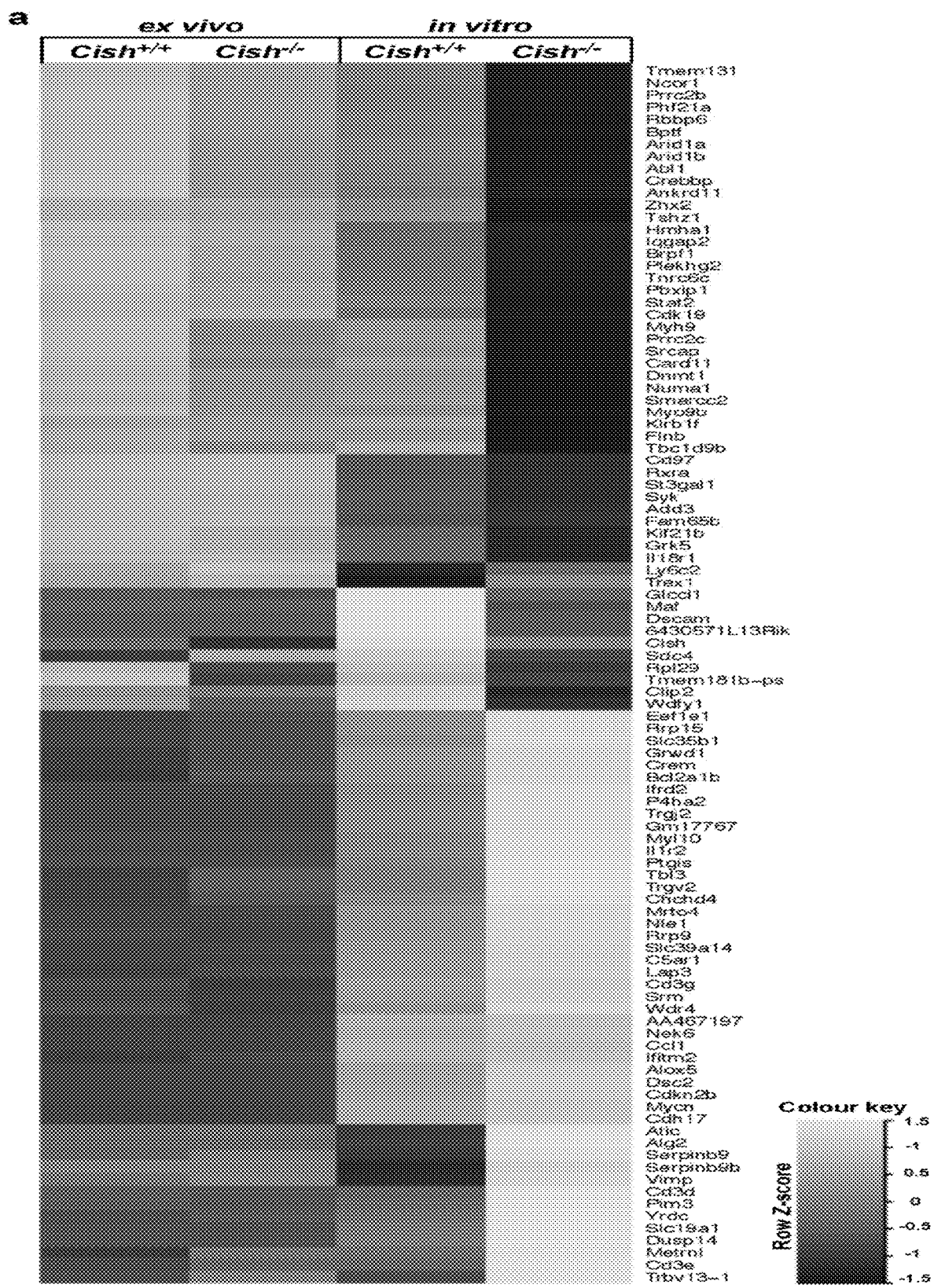
Figure 7:
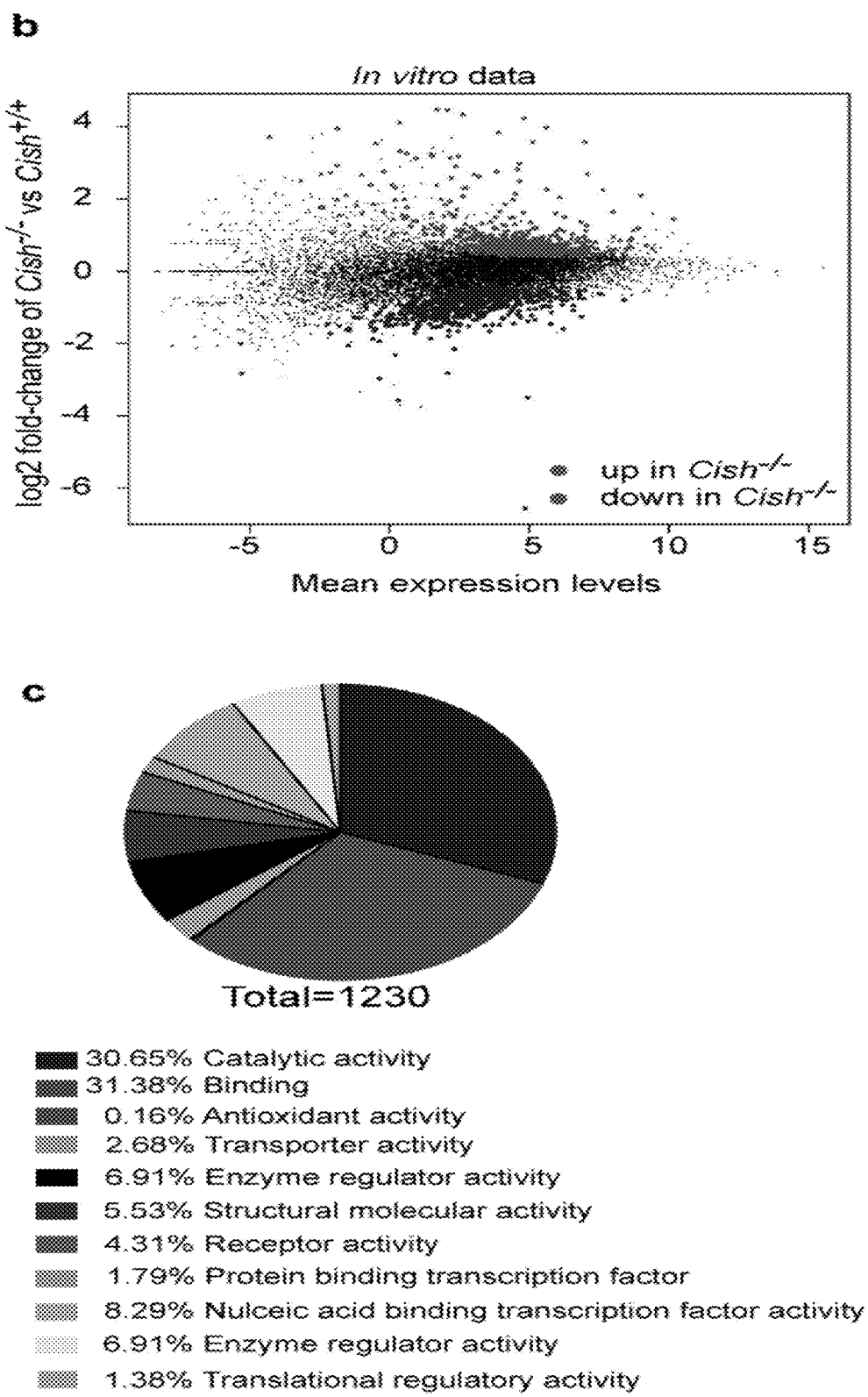

FIG. 7—Transcriptome profiling of in vitro cultured and ex vivo $Cish^{-/-}$ NK cells. 100 bp single-ended RNAseq was performed on freshly sorted ex vivo $Cish^{+/-}$ and $Cish^{-/-}$ NK cells, and on $Cish^{+/+}$ and $Cish^{-/-}$ NK cells that had been cultured for 7 days in IL-15 (50 ng $mL^{-1}$). (a) Relative expression levels (Z-scores) of the top ~100 most differentially expressed genes in $Cish^{-/-}$ cells are shown in the heatmap, colour-coded according to the legend. Rows are scaled to have a mean of 0 and an s.d. of 1. n=2 biological replicates. (b) Mean-difference plot of the cultured NK cell data generated in FIG. 3, showing Log2-fold change versus mean expression. (c) Functional analysis of the 1230 differentially expressed genes observed in IL-15 cultured $Cish^{-/-}$ NK cells. Gene ontology was performed using the PANTHER classification system. Major gene networks are shown as a percentage of total differentially expressed genes in $Cish^{-/-}$ cells.

Figure 8:
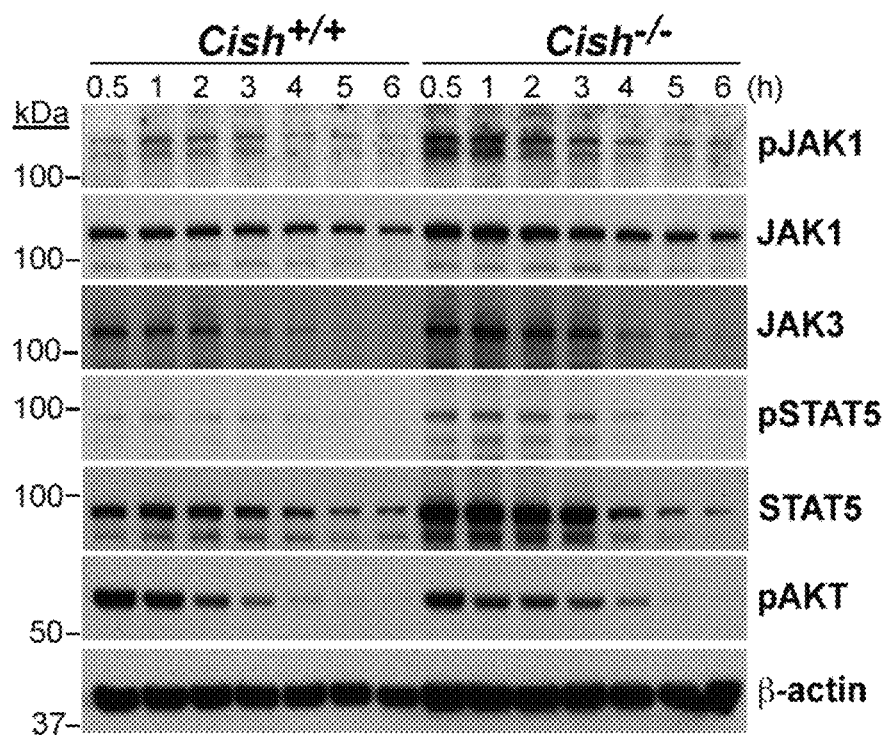
Figure 8:
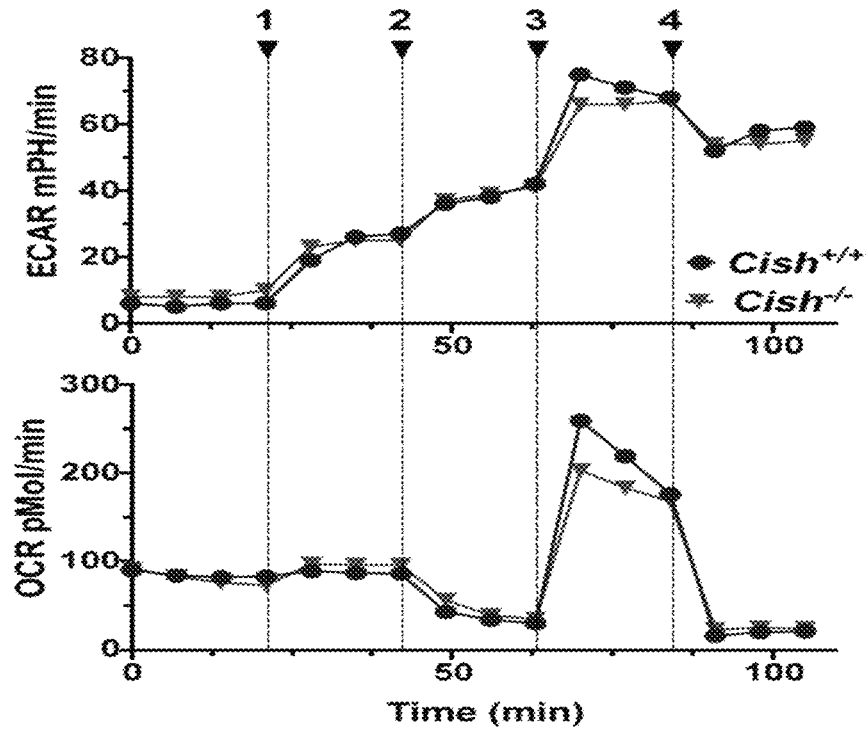
Figure 8:
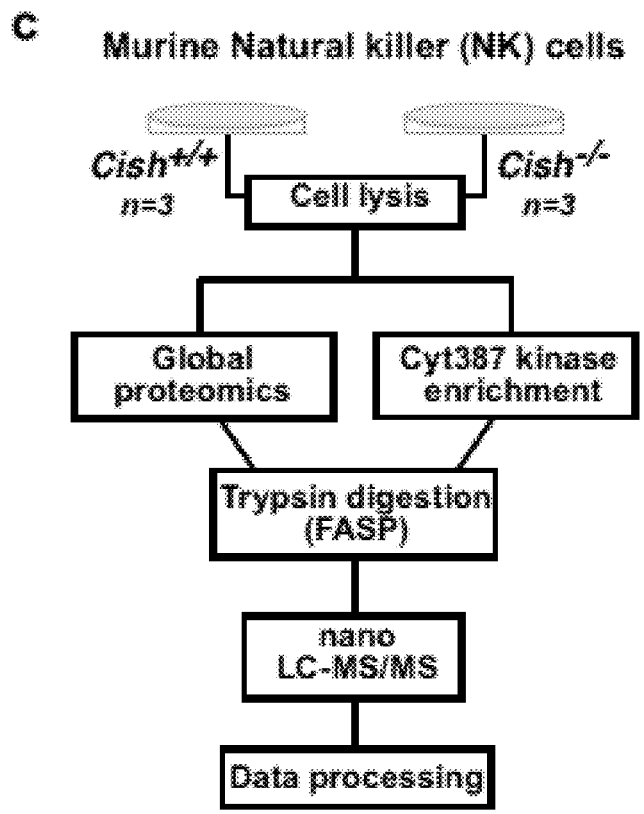
Figure 8:
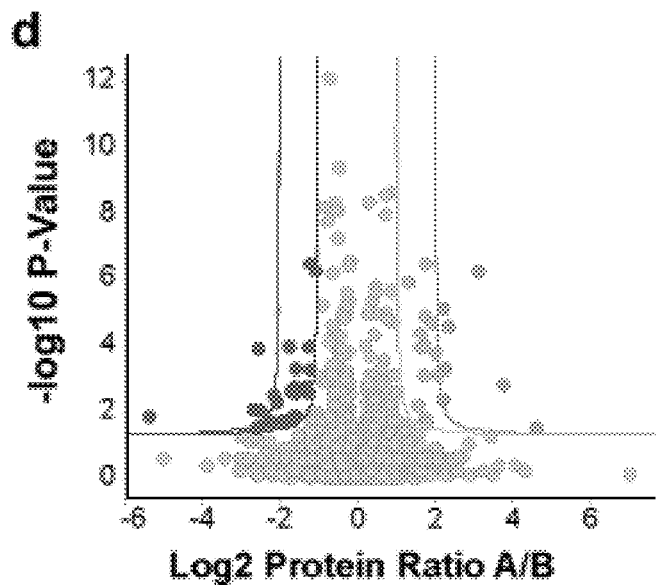
Figure 8:
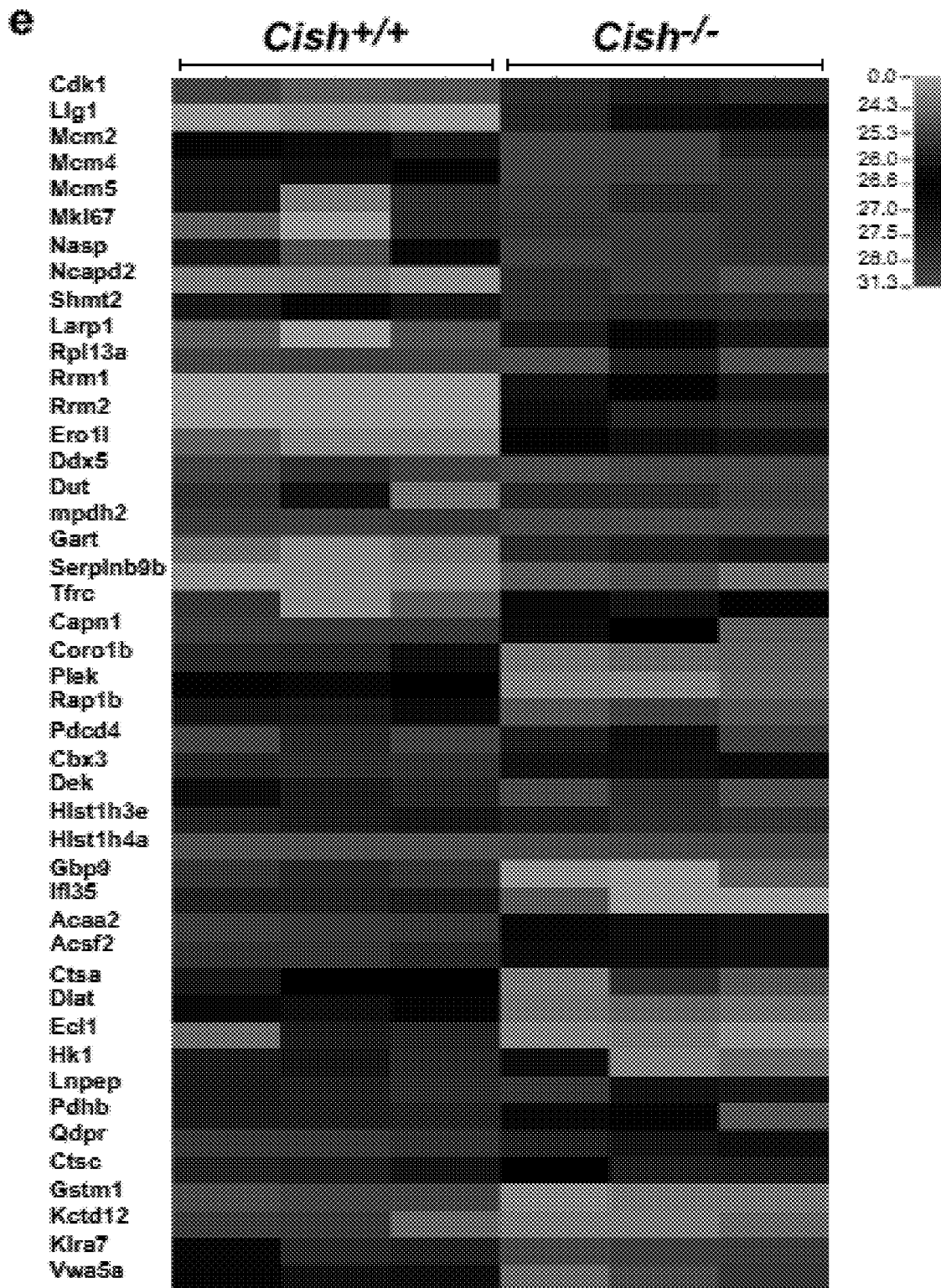

FIG. 8—$Cish^{-/-}$ NK cells display increased JAK/STAT signalling and normal respiration and glycolysis. (a) $Cish^{-/+}$ and $Cish^{-/-}$ NK cells were cultured and washed free of IL-15-containing media. Cells were lysed at various times post-wash as indicated. Levels of phosphorylated (p) and total signaling proteins were analysed by Western blotting with specific antibodies. (b) $Cish^{-/-}$ NK cell respiration and glycolysis is unperturbed. $Cish^{+/+}$ and $Cish^{-/-}$ NK cells were cultured in the presence of IL-15 and the extracellular acidification rater (ACR; glycolysis) and oxygen consumption rate (OCR; mitochondrial respiration) measured using the XF Analyzer system. Glucose (1), Oligomycin (2), FCCP and pyruvate (3) and Antimycin A/Rotenone (4) were added at times indicated by the numbered arrows. (c) Overview of the proteomic workflow used in this study. Equal numbers of cultured NK cells derived from $Cish^{+/+}$ and $Cish^{-/-}$ mice were lysed and subjected to kinase enrichment using NHS-CYT-387 beads. Protein eluates from the CYT-387 resin, in addition to a portion of whole cell lysate (pre-kinase enrichment) were subjected to trypsin digestion and nanoLC-MS/MS. (d) Label-free quantification of global protein expression. Volcano plot showing the Log2 protein ratios following the quantitative pipeline analysis ($Cish^{+/+}$ vs $Cish^{-/-}$) from WCL. The red and yellow lines represent a 2-fold change in protein expression (log 2 ratio of 1), while blue and green lines represent a 4-fold change (log 2 ratio of 2); dots are colored accordingly and represent individual proteins. Proteins with a $-\log_{10}$ p-value of 1.3 or greater (corresponding to a p-value of ≤0.05) were deemed differentially abundant. (e) Heat map displaying Log2-transformed summed peptide intensities (non-imputed) for proteins with significantly differential expression in (d). Data from individual biological replicates are shown (n=3). Green to red indicates increasing expression levels.

Figure 9:
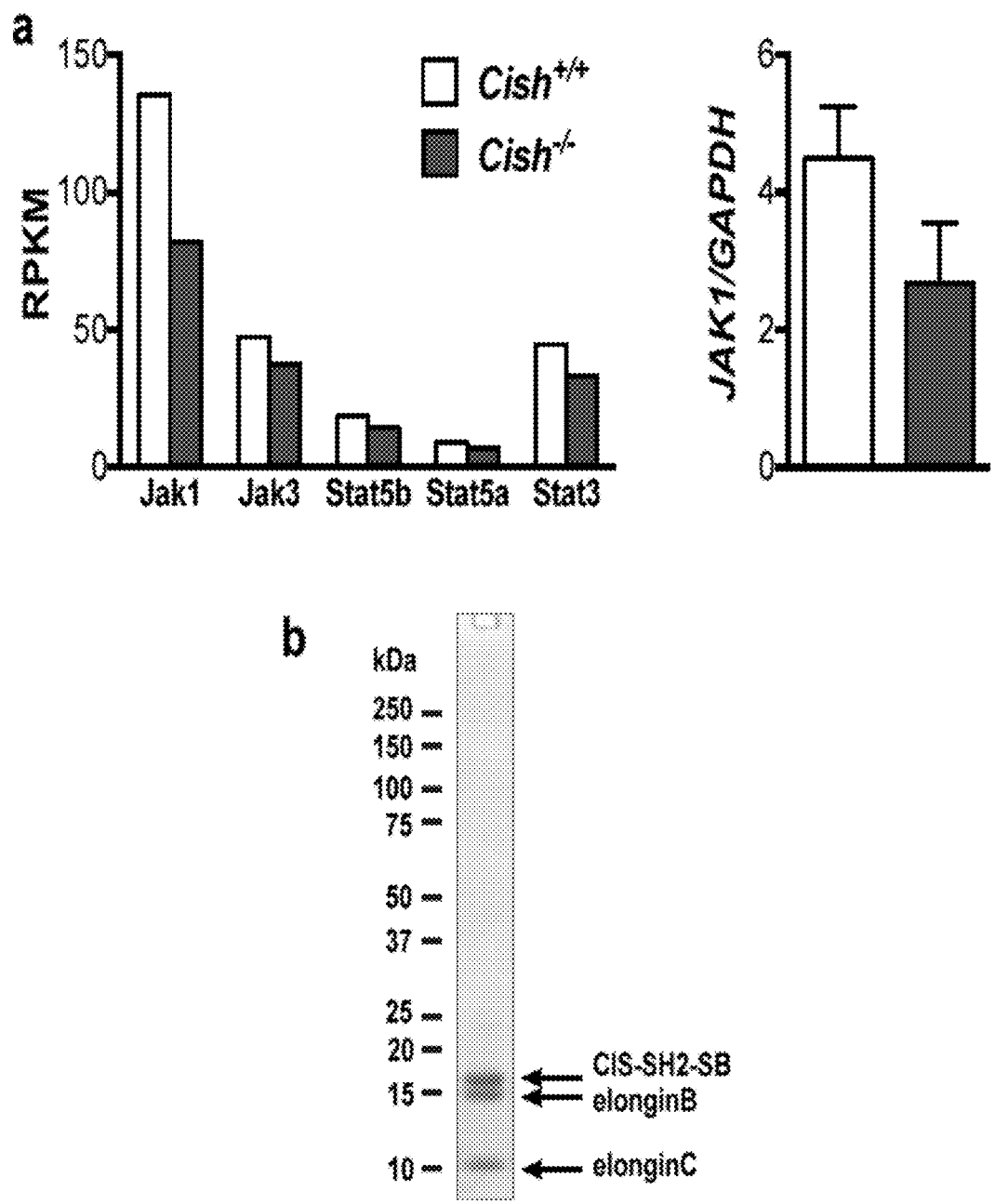
Figure 9:
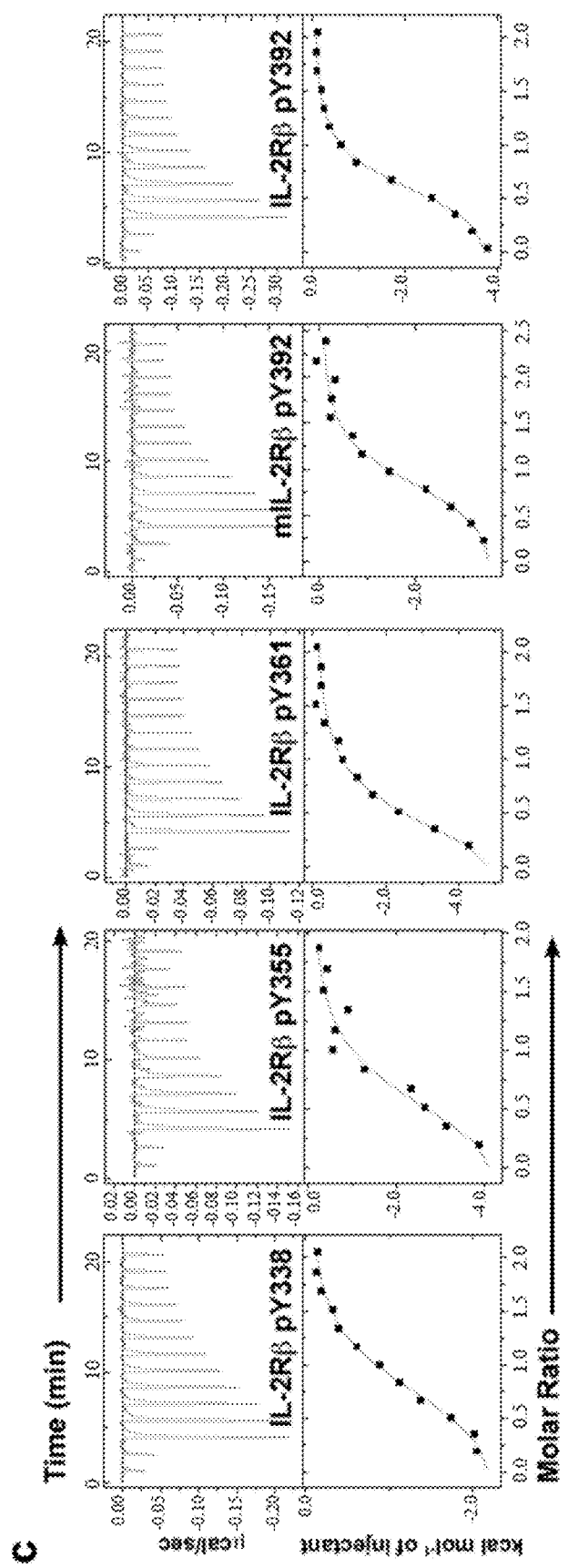
Figure 9:
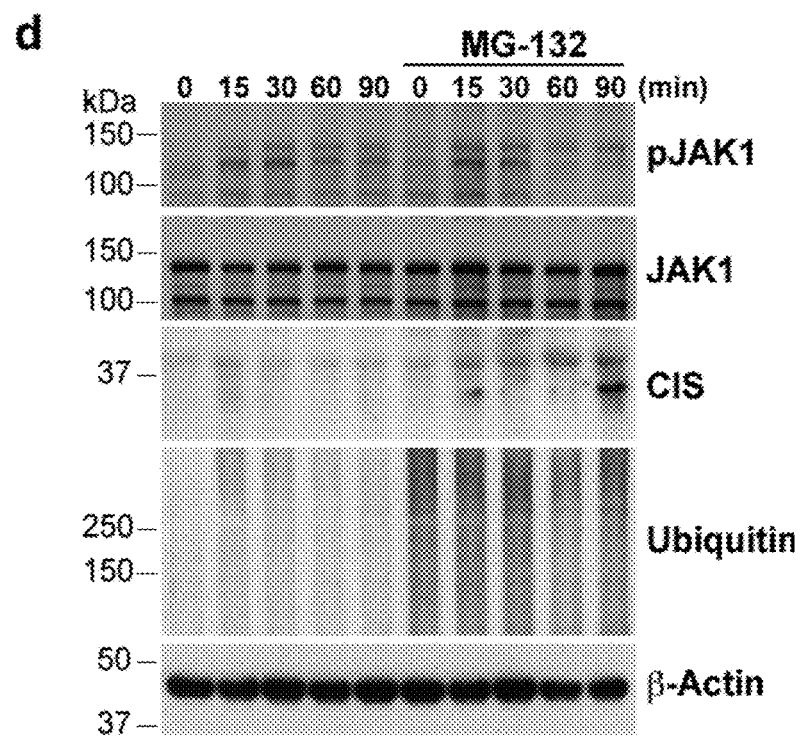
Figure 9:
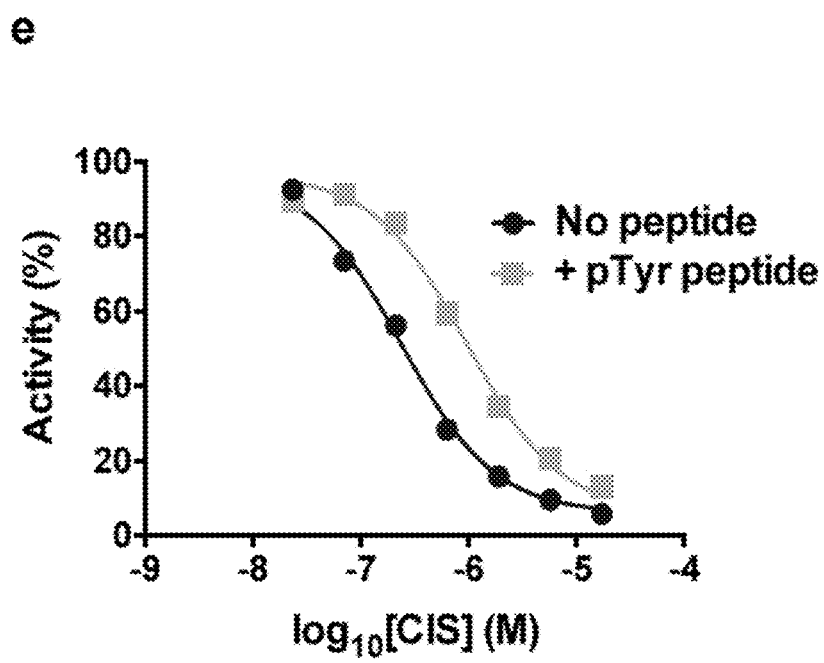

FIG. 9—CIS targets JAK and the IL-2R complex. (a) Cultured NK cells from wild-type and $Cish^{-/-}$ mice were lysed, mRNA purified and analysed by RNAseq. Mean RPKM values for duplicate samples (left panel). JAK1 mRNA levels were analysed by Q-PCR (right panel). Mean±S.D., n=3. (b) 4-12% Coomassie-stained SDS-PAGE gel showing purified hCIS-SH2-BC complex, elongin B and elongin C. (c) Isothermal calorimetry (ITC) was used to measure the affinity of hCIS-SH2-BC binding to phosphopeptides corresponding to tyrosines within the JAK1/3 kinase domain activation loops and IL-2Rβ and γ cytoplasmic domains. 300 µM phosphopeptides were titrated into a 30 µM solution of the GST-CIS-SH2-BC ternary complex. ITC titration curves and tabular view of some results (inset) showing mean±S.D. from two independent experiments. N.D.=Not detectable, p=phosphorylated. The titration curves all fitted well to a single-site model. (d) Cultured wild-type NK cells were washed and starved of IL-15 for 4 h, with and without addition of the proteasomal inhibitor, MG132. Cells were then stimulated with 50 ng $ml^{-1}$ IL-15 for the indicated times, prior to cell lysis and Western blotting with antibodies to the indicated proteins. (e) Kinase inhibition assays were performed with the kinase domain (JH1) of JAK1 in the presence of CIS-SH2-BC with and without excess JAK1-Y1034 phosphopeptide as a competitor. The pY1034 peptide partially reduced CIS-mediated inhibition. Data were normalised to no-CIS controls.

Figure 10:
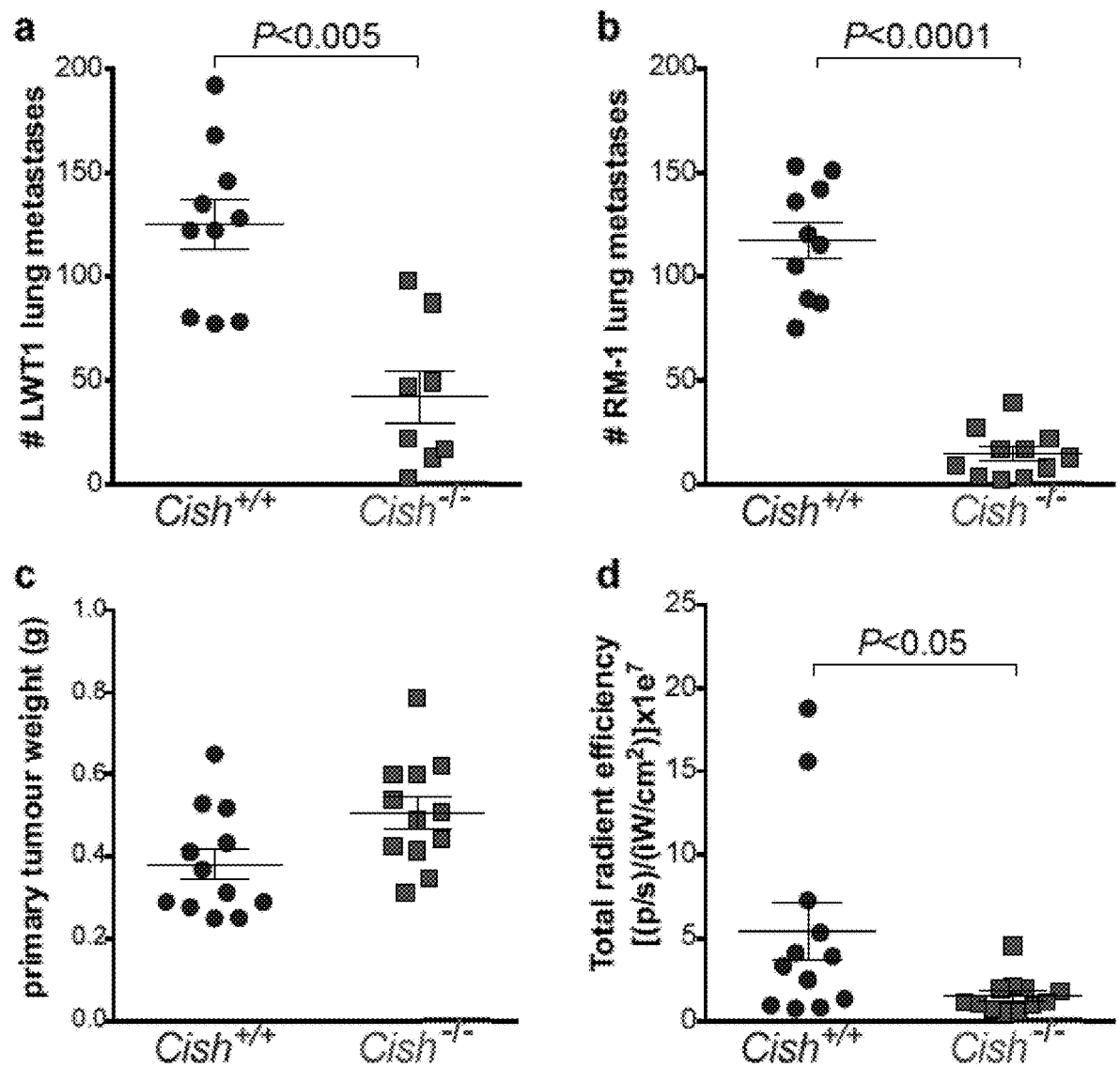

FIG. 10—$Cish^{-/-}$ NK cells protect against experimental lung metastases. $Cish^{+/+}$ and $Cish^{-/-}$ mice were injected i.v. with (a) $2\times10^5$ LWT1 (B-RAF mutant) melanoma or (b) $2\times10^5$ RM-1 prostate carcinoma cells. The metastatic burden was quantified in the lungs after 14 days by counting colonies on the lung surface. (c & d) $1\times10^5$E0771.LMB-mCherry+ cells were implanted into the mammary fat pad of $Cish^{+/+}$ and $Cish^{-/-}$ mice, surgically removed at 400-600 $mm^3$ and (c) weighed post-excision. Spontaneous lung metastases (d) were measured 14 days later by IVIS for mCherry fluorescence. (d; vertical axis: total radiant efficiency $[(p/s)/IW/cm^2)]\times10^7$). Mean±S.E.M of indicated (n) are shown. Statistical differences between groups were determined by a Mann-Witney U test (a, b) or unpaired Student's t test (d).

Figure 11:
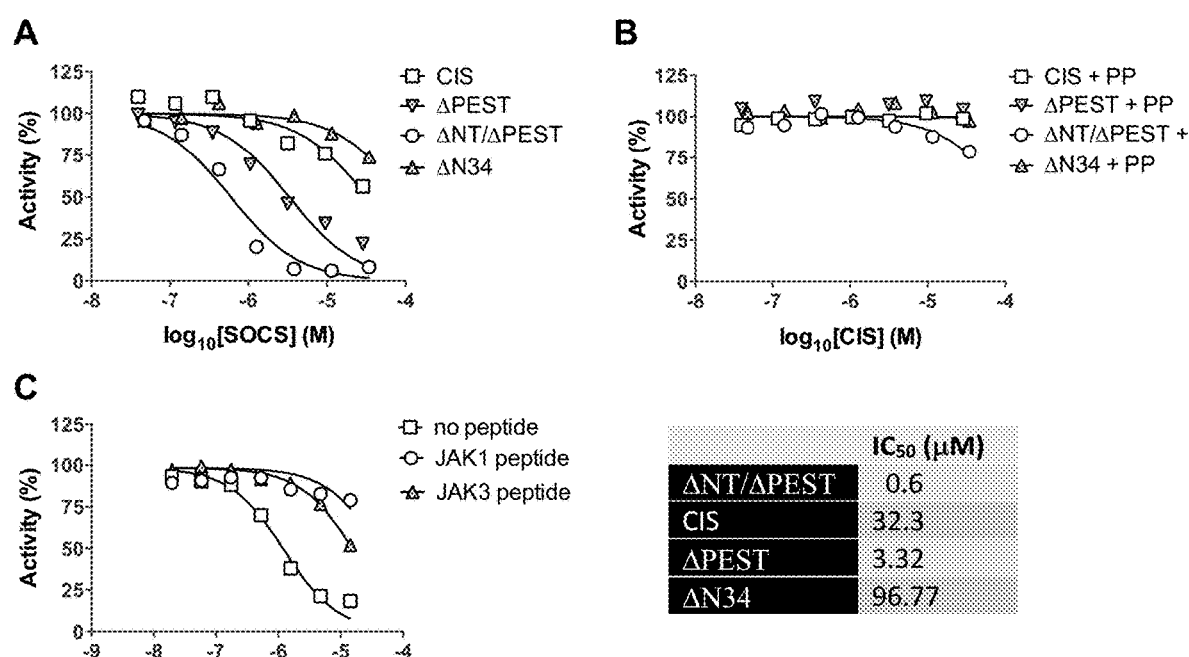

FIG. 11—Deletion of the CIS N-terminal region or PEST enhances the ability of CIS to inhibit JAK1 kinase activity, and CIS-SH2 interaction with phosphopeptide is required for CIS inhibition of JAK1 kinase activity. Kinase inhibition assays were performed with the kinase domain (JH1) of JAK1 in the presence of increasing amounts of human full-length CIS (CIS), CIS lacking the PEST motif (ΔPEST), CIS lacking both the N-terminal region and the PEST motif (ΔNT/ΔPEST), or CIS lacking the N-terminal 34 residues (ΔN34), without (a) or with (b), excess phenyl phosphate (PP) as a competitor. (c) Alternatively, 50 µM JAK1-Y1034 or JAK3-Y980,Y981 phosphopeptides were used as competitor. Data were normalised to no-CIS controls. All CIS constructs contained the SOCS box and were expressed and purified as a trimeric complex consisting of CIS, elongin B and elongin C. Inset: table shows IC50 values for (a).

Figure 12A:
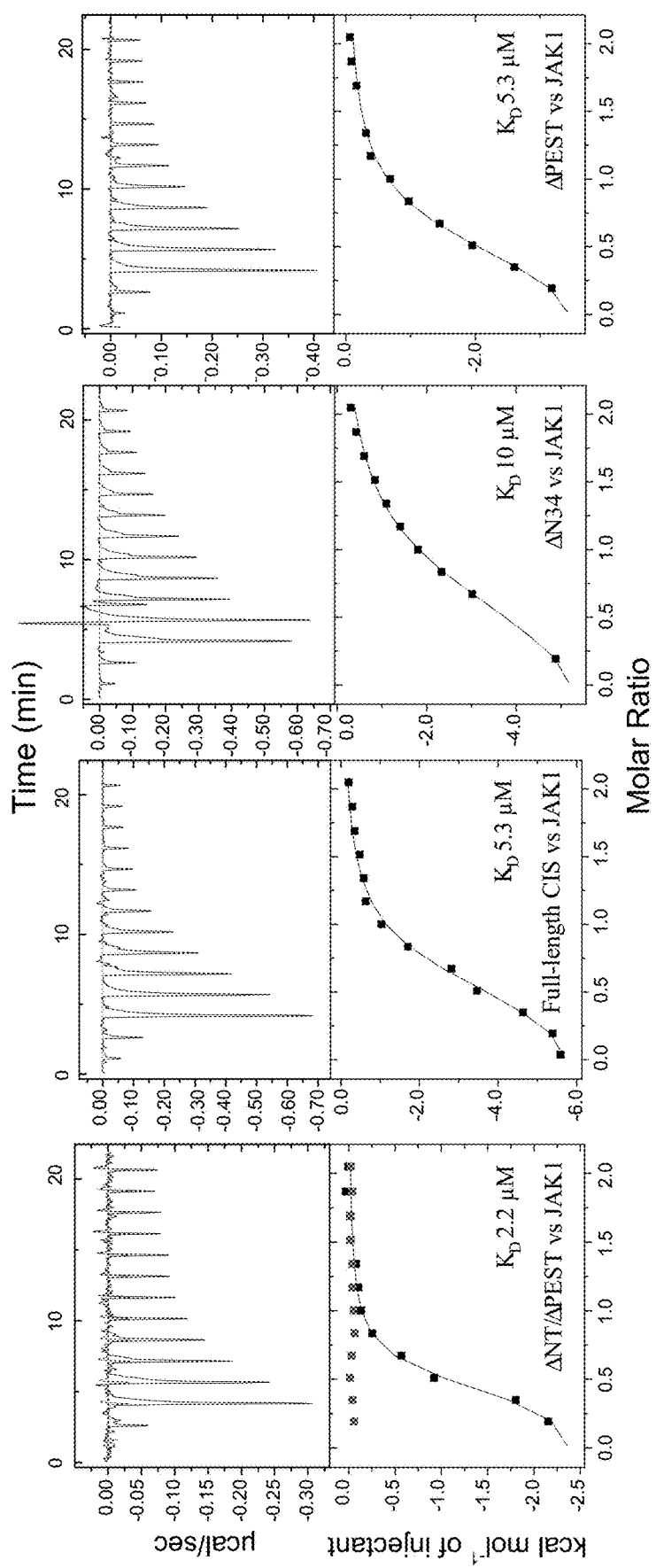
Figure 12B:
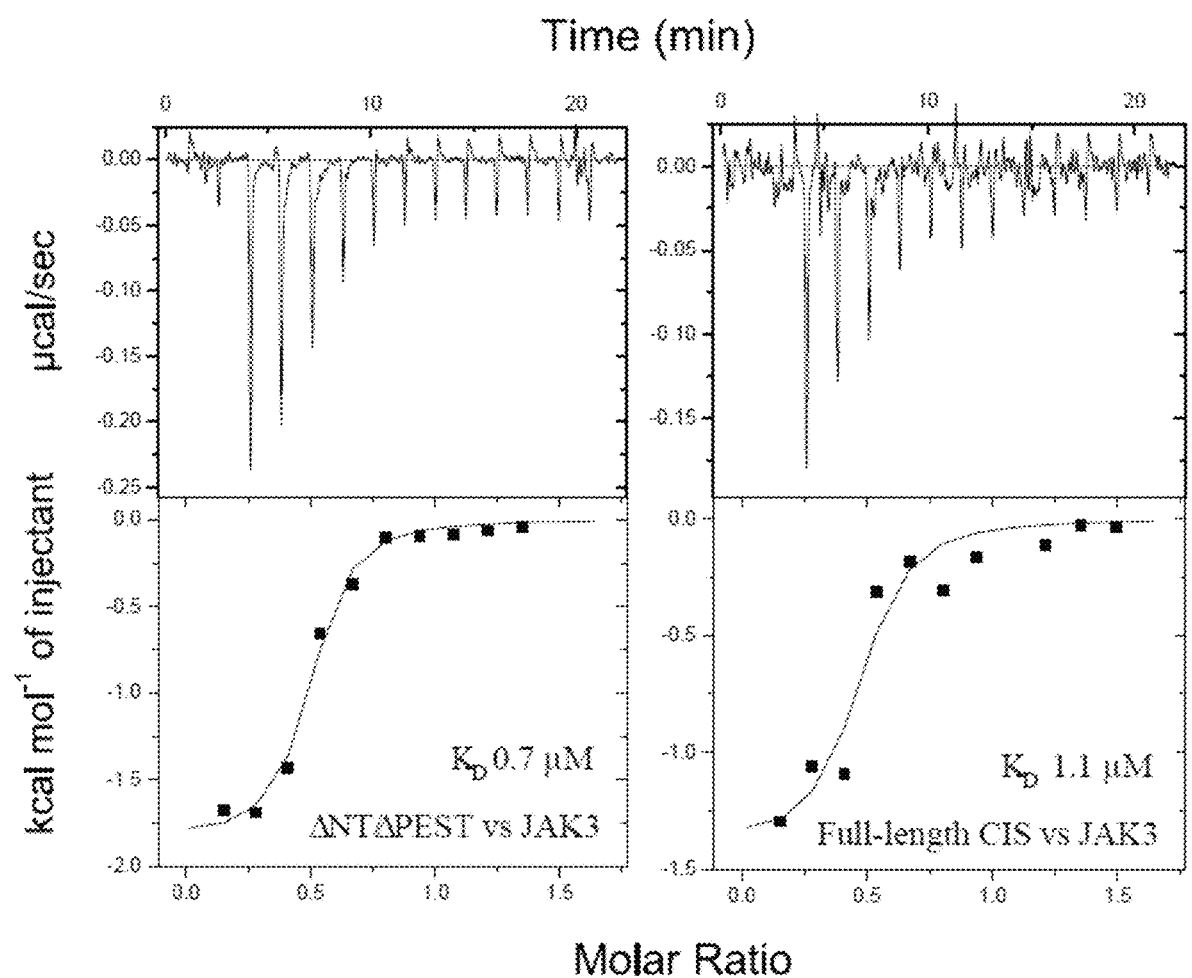

FIGS. 12A-B—Deletion of the CIS N-terminal region or PEST motif does not have a major impact on binding to phosphopeptide. FIG. 12A shows isothermal calorimetry (ITC) was used to measure the affinity of human full-length CIS, CIS lacking the PEST motif (ΔPEST), CIS lacking both the N-terminal region and the PEST motif (ΔNT/ΔPEST), or CIS lacking the N-terminal 34 residues (ΔN34) binding to phosphopeptides corresponding to tyrosines within the JAK1 kinase domain activation loop (JAK1-Y1034). FIG.

12B shows the affinity of human full-length CIS and CISΔNT/ΔPEST binding to phosphopeptides corresponding to tyrosines within the JAK3 kinase domain activation loop (JAK3-Y980,Y981). 300 μM phosphopeptides were titrated into a 30 μM solution of the GST-CIS-SH2-BC ternary complex. ITC titration curves are shown. The titration curves all fitted well to a single-site model.

Figure 13:
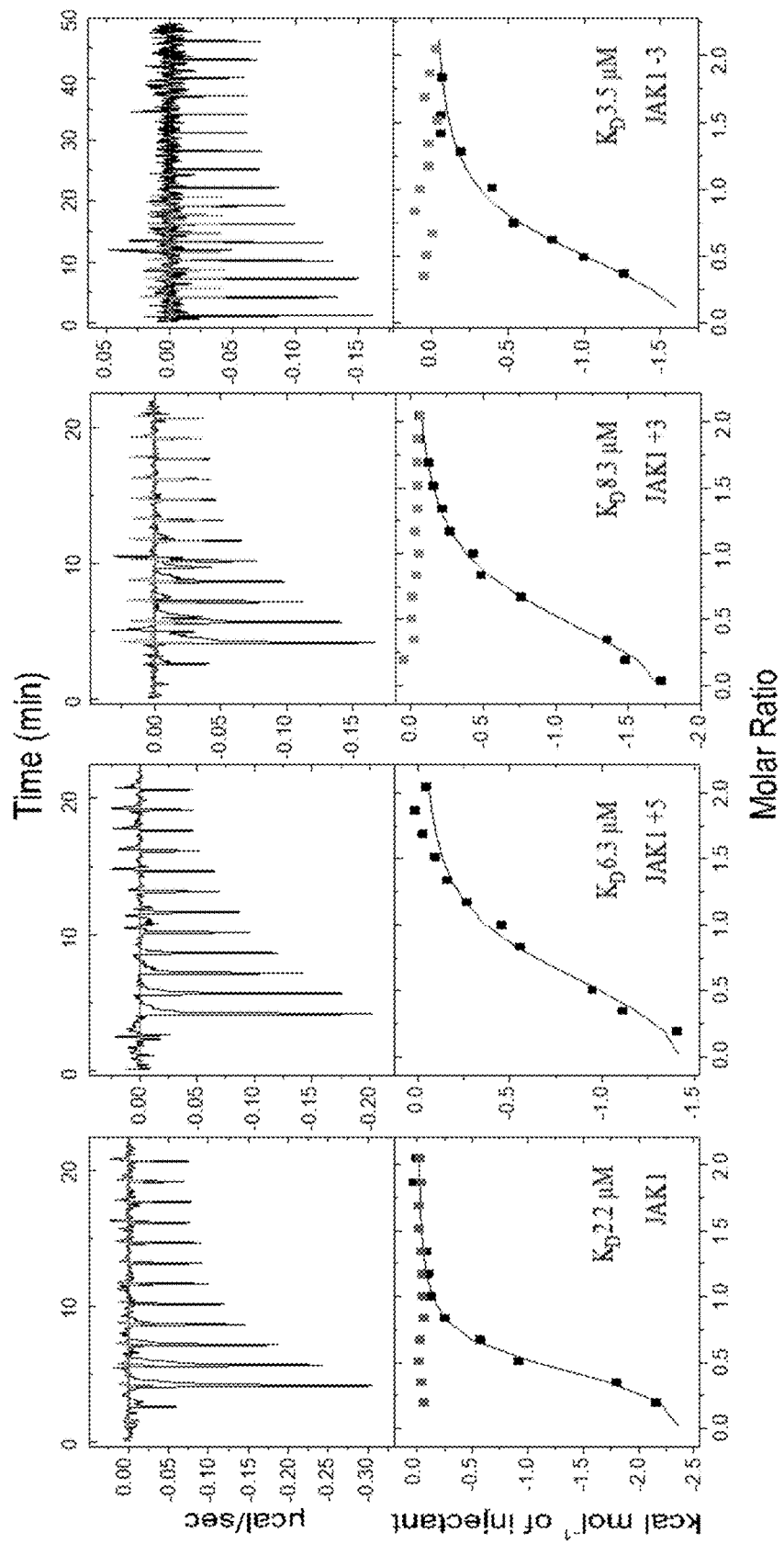

FIG. 13—CIS-SH2 domain binds to an extended peptide interface. Isothermal calorimetry (ITC) was used to measure the affinity of CIS lacking both the N-terminal region and the PEST motif (ΔNT/ΔPEST) binding to phosphopeptides corresponding to tyrosines within the JAK1 kinase domain activation loop (JAK1-Y1034). Peptides were either wild-type or contained an alanine substitution at the +5, +3 or −3 position. 300 μM phosphopeptides were titrated into a 30 μM solution of the GST-CIS-SH2-BC ternary complex. ITC titration curves are shown. The titration curves all fitted well to a single-site model.

Figure 14:
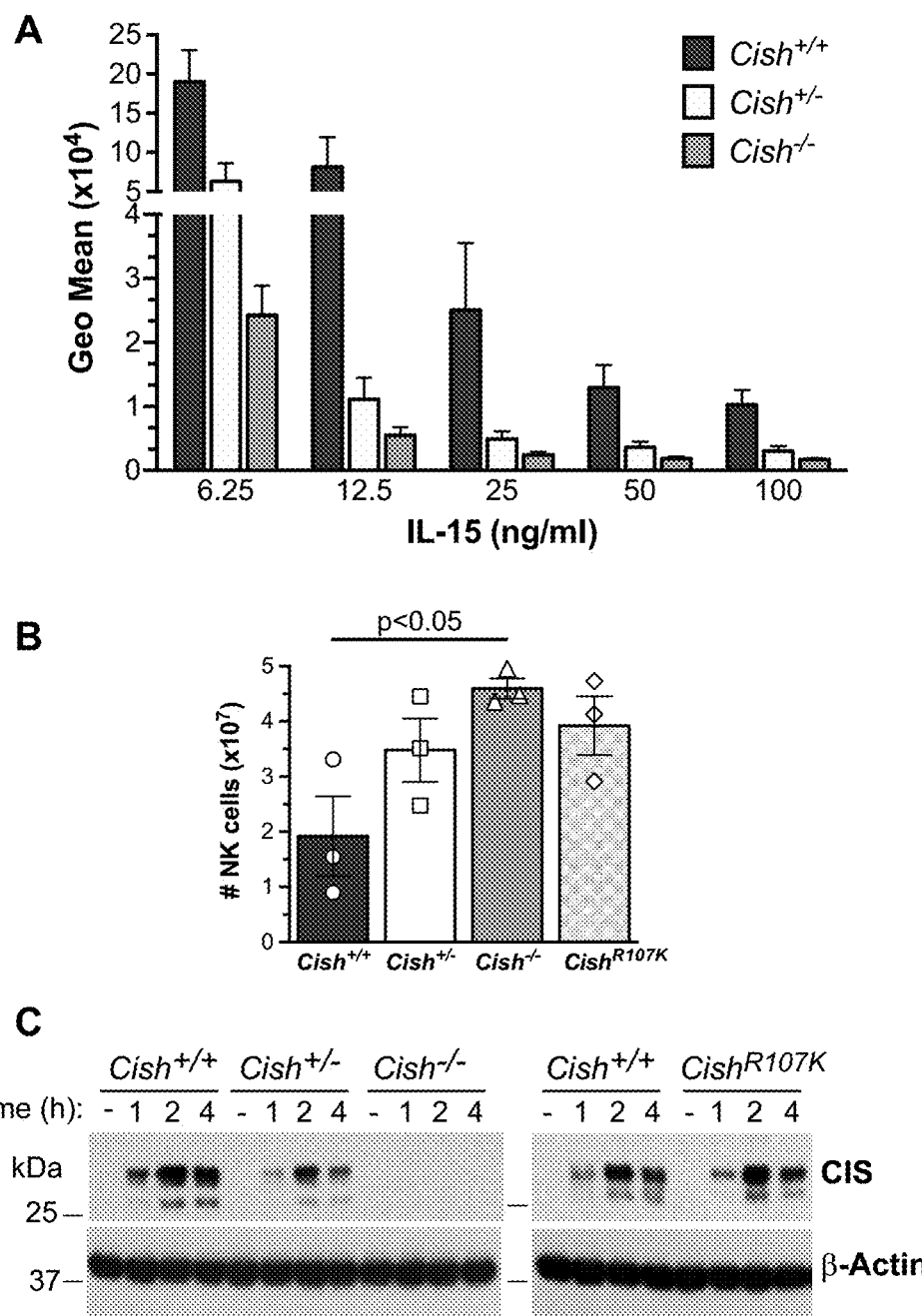

FIG. 14—CIS inhibition is dose dependent and requires a functional SH2 domain. (a) NK cells were purified from the spleens of $Cish^{-/-}$, $Cish^{+/-}$ and $Cish^{+/+}$ mice, labeled with the cell tracking dye CTV and cultured for 6 days in an increasing concentration of IL-15, prior to flow cytometry analysis. A decrease in total fluoresence (Geo Mean) indicates an increase in proliferation. (b) Equal numbers of NK cells from the spleens of $Cish^{-/-}$, $Cish^{+/-}$ and $Cish^{+/+}$ mice were expanded in IL-15 for 10 days. Absolute NK cell numbers post-culture. (c) NK cells were then washed free of cytokine and rested for 4 h prior to treatment with 100 ng/mL IL-15 and 10 μM MG132, as indicated. Cell lysates were analyzed by immunoblotting with the indicated antibodies to CIS and actin as a loading control.

Figure 15:
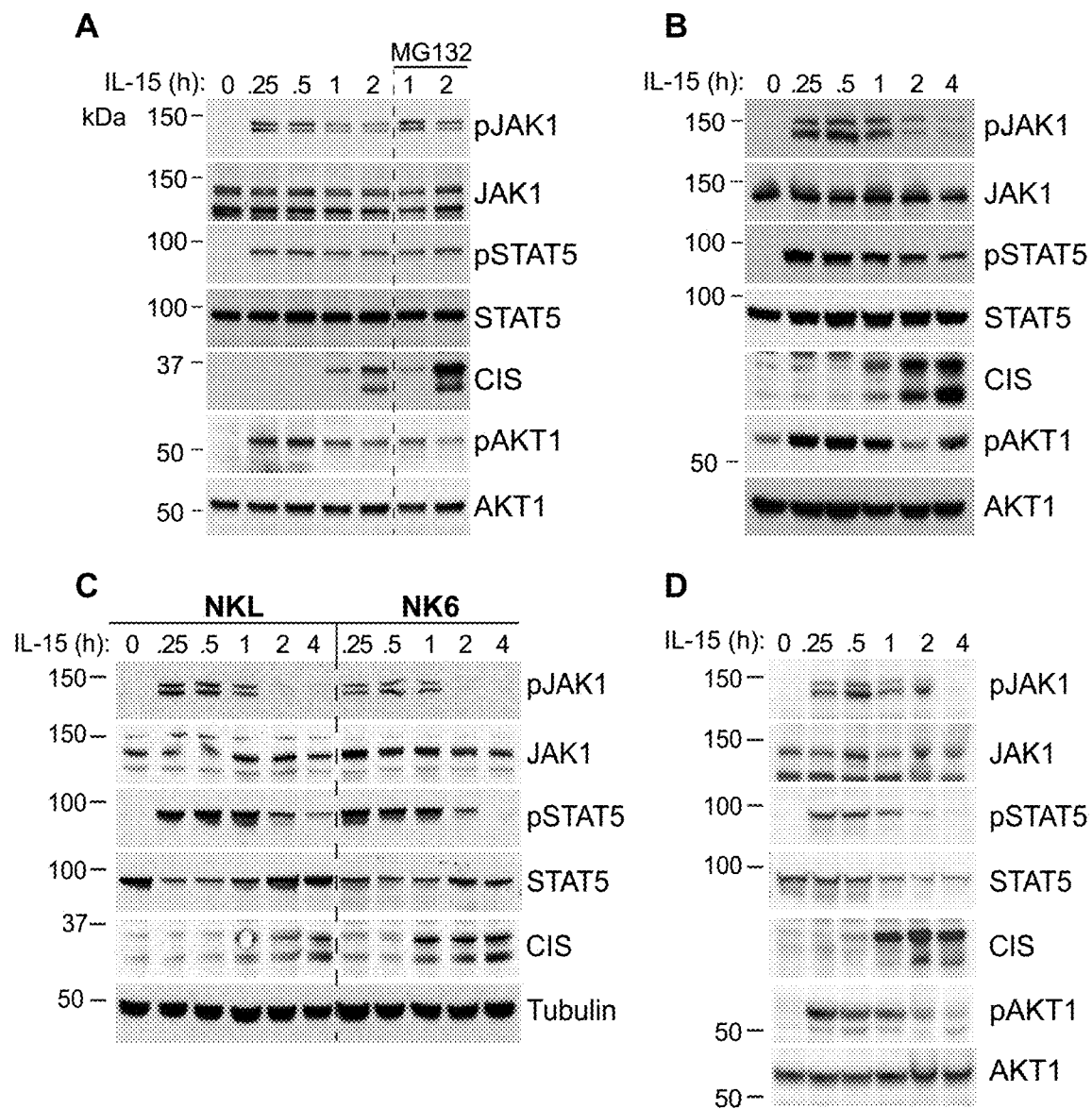

FIG. 15—The kinetics of CIS induction are consistent with inhibition of JAK/STAT signalling in human NK cells. Patient-derived human NK cells (a) or NK lymphoma cell lines (b) SNK-10, (c) NKL and NK6, (d) NK-92 were washed free of cytokine and rested for 4 h (a) or 16 h (b-d) prior to treatment with IL-15 for the indicated times. In some instances, cells were incubated with the proteasomal inhibitor MG132 (10 μM). Cells were lysed and analysed by immunoblotting with antibodies to the indicated phosphorylated (p) and total proteins.

Figure 16:
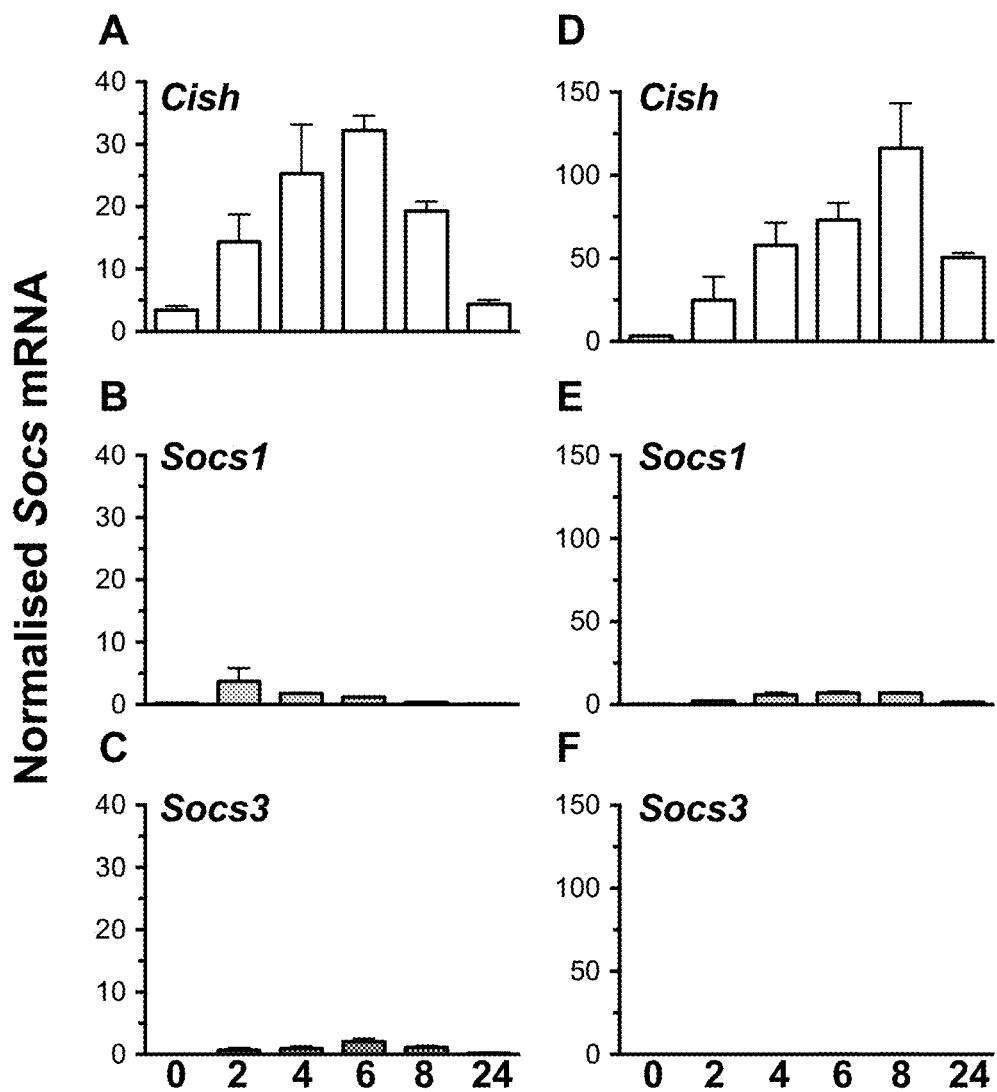

FIG. 16—The kinetics of Cish mRNA induction are consistent with inhibition of JAK/STAT signalling in human NK cells. Human NK lymphoma cell lines KHYG-1 (a-c) and NK-92 (D-F) were washed free of cytokine and rested overnight prior to treatment with IL-15 for the indicated times. Cells were lysed and analyzed by real-time quantitative PCR (Q-PCR) for Cish, Socs1, Socs3 mRNA expression. Relative expression was determined by normalizing the amount of each gene of interest to the housekeeping gene 18s ribosomal RNA. Each condition had three biological replicates and measurements were performed in duplicate.

Figure 17:
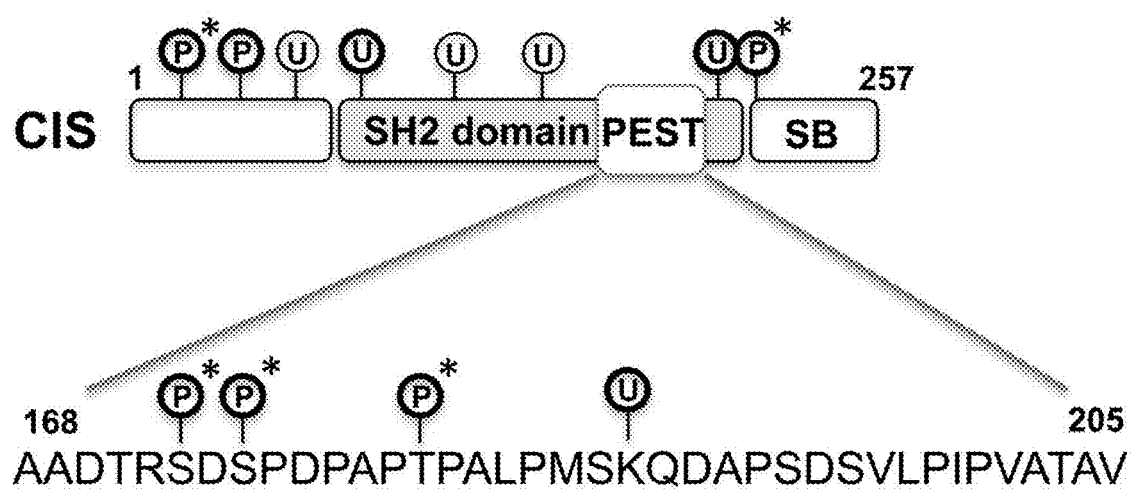

FIG. 17—Schematic summarising the ubiquitination (U) and phosphorylation (P) sites identified by mass spectrometry. P=phosphorylation, U=ubiquitination, *indicates residues are conservation between mouse and human CIS. FLAG-tagged mouse CIS was expressed in 293T cells and purified by affinity enrichment using anti-FLAG antibodies, prior to digestion with trypsin and LC-MS/MS analysis. Bold circles indicate residues identified in this study. Other ubiquitination sites were reported in Jensik et al., 2015.

Figure 18:
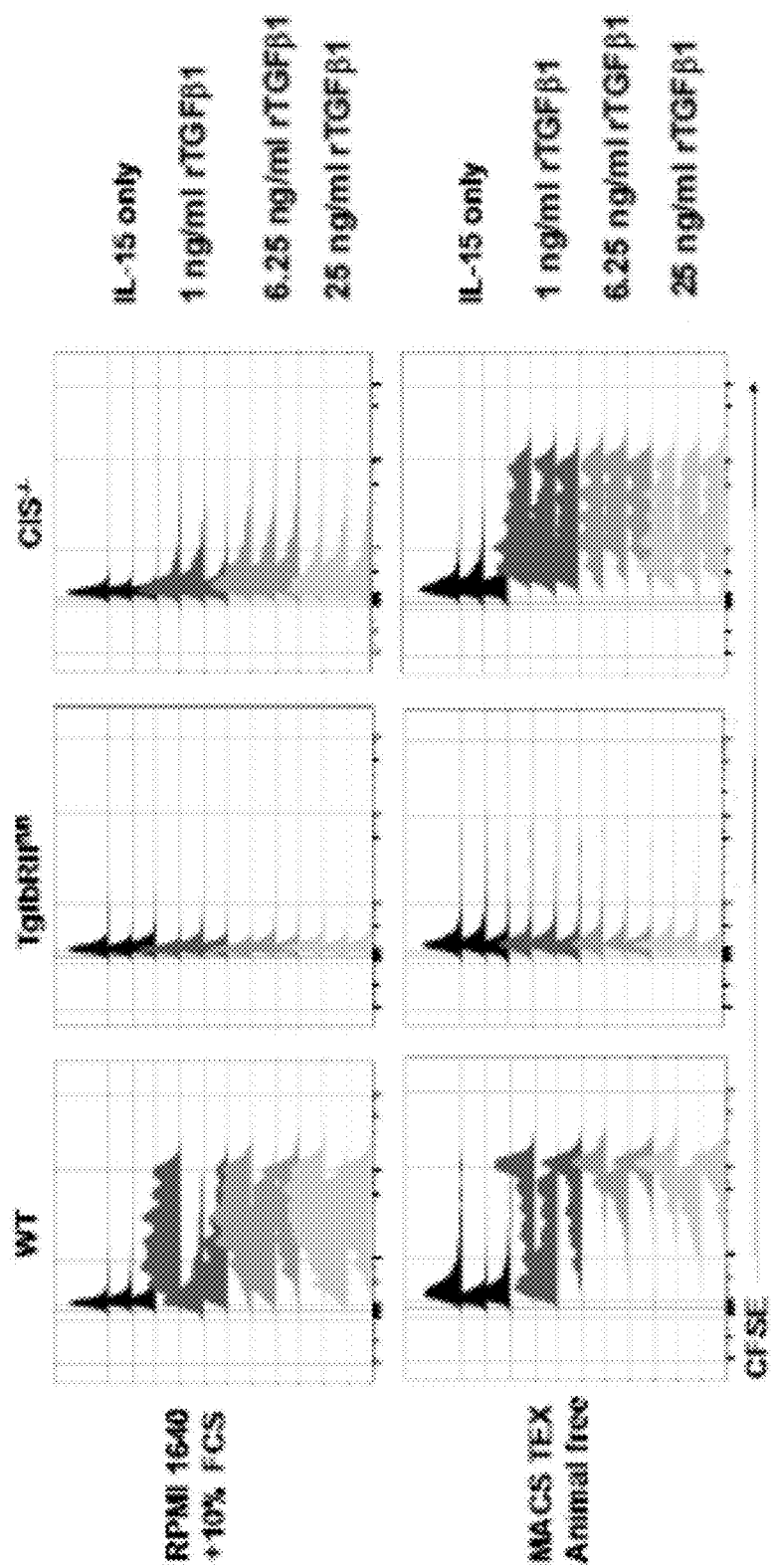

FIG. 18—TGFβ blocks IL-15-driven proliferation in wild-type, but not CIS-deficient NK cells. Splenic NK cells from wild-type (WT), TGFβRII-deficient ($TgfRII^{fl/fl}$) or $Cish^{-/-}$ mice (20,000 cells/well $Lin^{neg}CD49a^{neg}CD49b^{+}$ $NK1.1^{-}NKp46^{+}$) were labeled with CFSE and cultured in RPMI or TGF-β-free media (MaxTex) for 5 days in the following conditions; rIL-15 (50 ng/mL), rIL-15 (50 ng/mL) with rTGFb1 (1 ng/mL), rIL-15 (50 ng/mL) with rTGFb1 (6.25 ng/mL) or rIL-15 (50 ng/mL) with rTGFb1 (25 ng/mL). Loss of CFSE (proliferation) was monitored by FACS.

Figure 19:
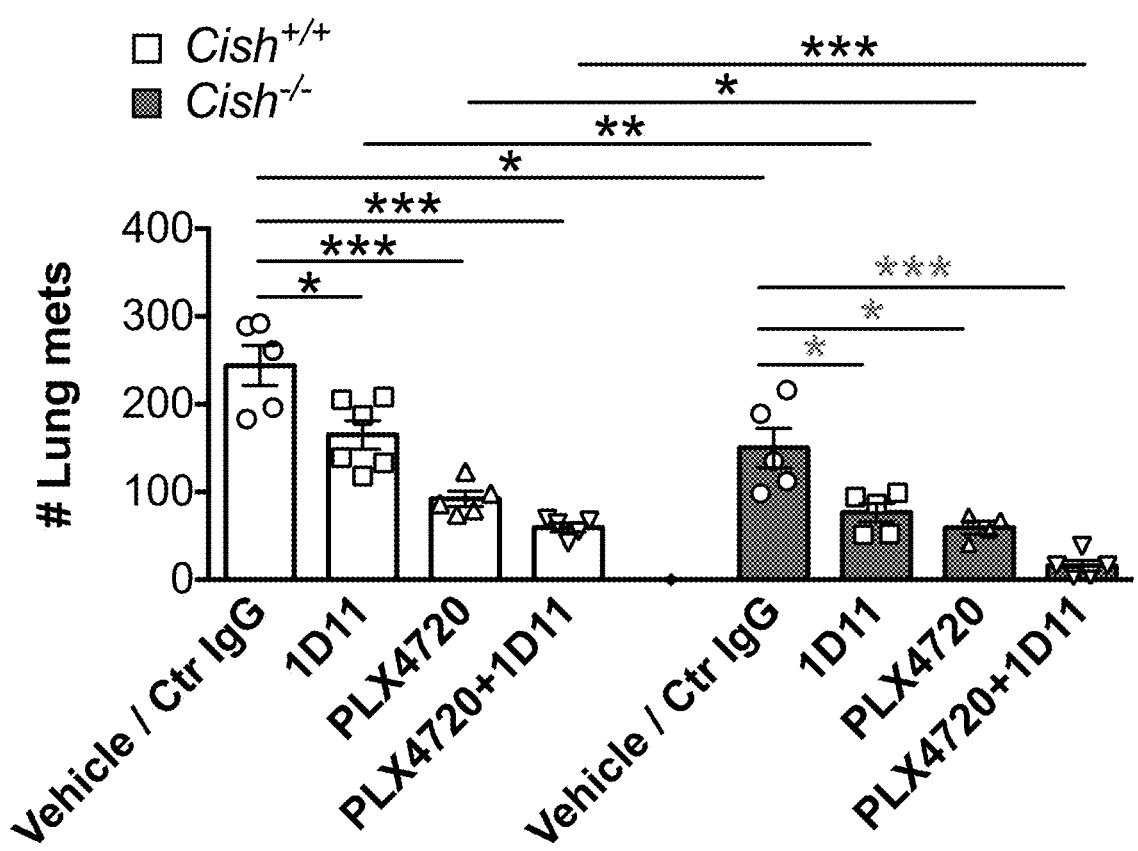

FIG. 19—TGFβ or BRAF (B-Raf protein kinase) inhibition together with Cish-deletion is superior to either treatment alone or in combination. $Cish^{+/+}$ and $Cish^{-/-}$ mice were injected with $1\times10^6$ BRAF mutant melanoma cell lines (SM1LWT1) and either control (ctr) Ig, anti-TGF-β (1D11) antibodies, BRAF inhibitor (PLX4720) or 1D11 and PLX4720. Melanoma burden in the lungs was measured at day 14 post-injection, by macroscopic counting. Mean±S.E.M. *p<0.05, p<0.005, *p<0.0005.

Figure 20:
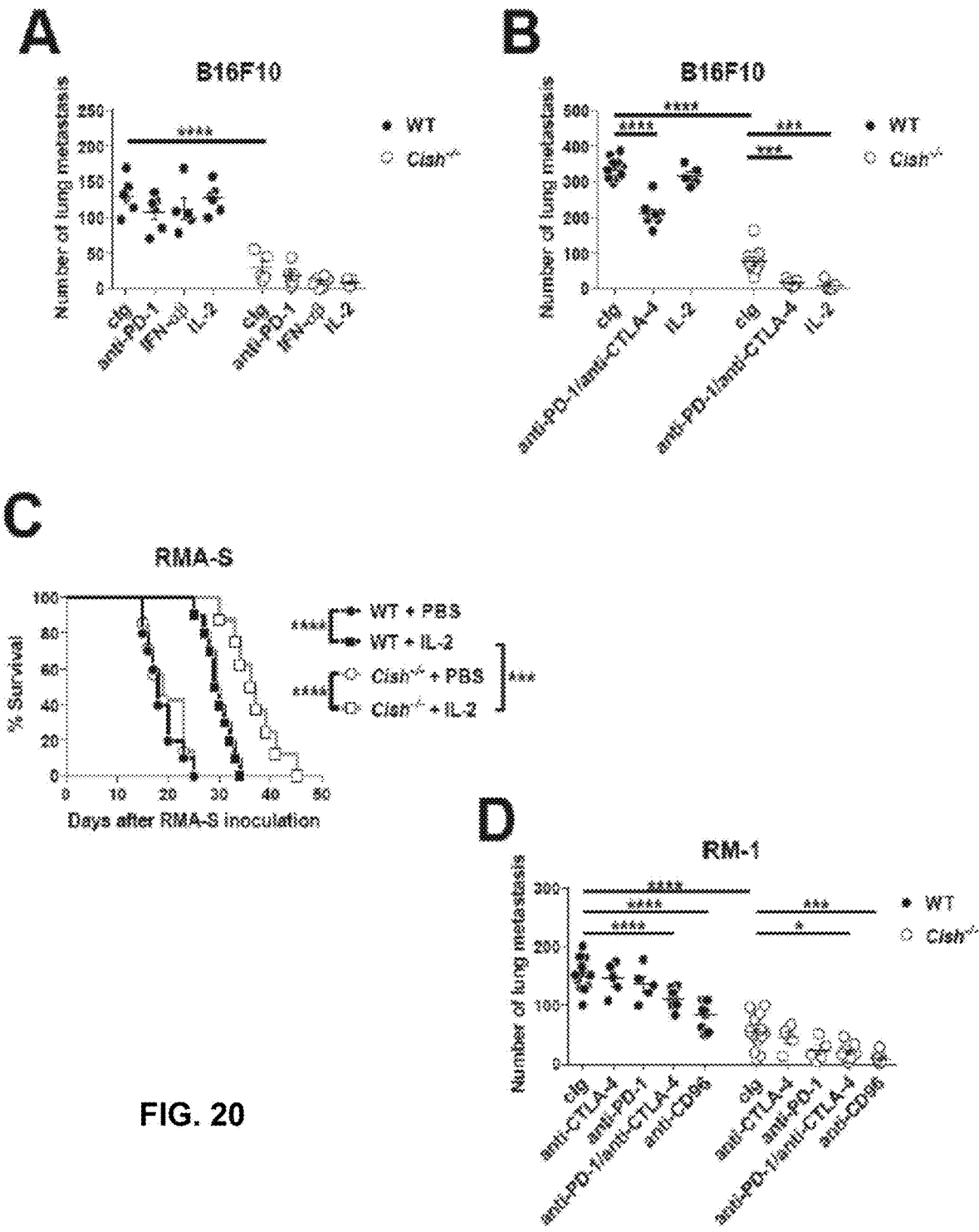
Figure 20:
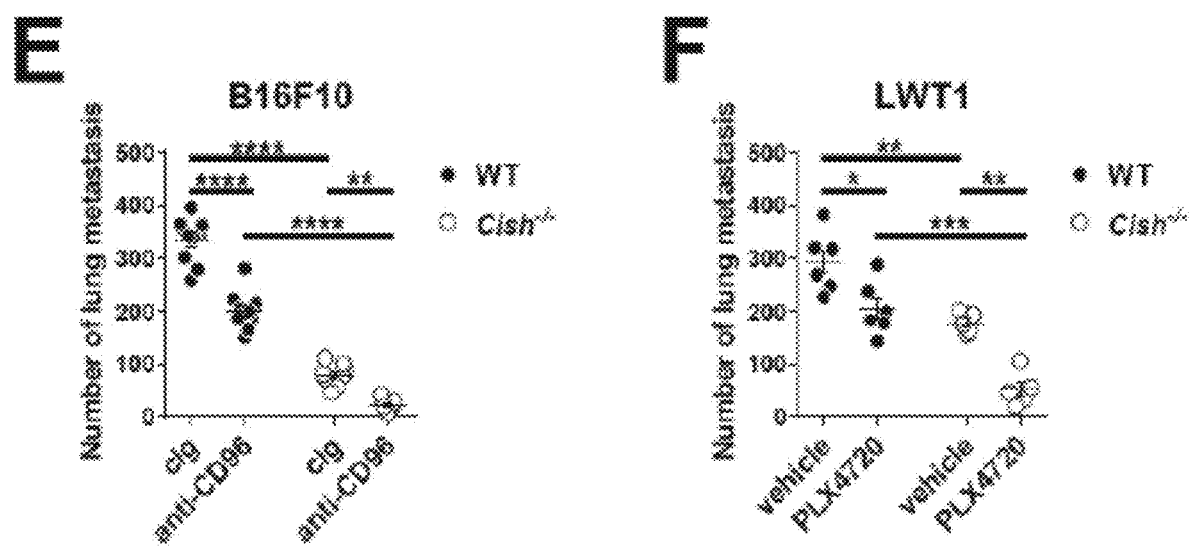

FIG. 20—Combining Cish-deficiency and checkpoint inhibitors or cytokine stimulation shows an improved anti-metastatic effect. (A) Groups of 5-6 B6.WT ($Cish^{-/+}$) or $B6.Cish^{-/-}$ mice were injected i.v. with $2\times10^5$ B16F10 melanoma cells and treated with either control Ig (cIg) (250 μg i.p. on days 0, 3 and 6), anti-PD-1 (250 μg i.p. on days 0, 3 and 6), mouse IFN-αβ (25 μg i.p. on days 0, 1, 2 and 3) or recombinant IL-2 (10,000 IU i.p. on days 0, 1, 2 and 3). (B) Groups of 5-11 B6.WT ($Cish^{+/+}$) or $B6.Cish^{-/-}$ mice were injected i.v. with $7.5\times10^5$ B16F10 melanoma cells and treated with either cIg (250 μg i.p. on days 0, 3 and 6), anti-PD1/anti-CTLA-4 combination (250 μg i.p. each on days 0, 3 and 6), or recombinant IL-2 (10,000 IU i.p. on days 0, 1, 2, 3 and 4). (C) Groups of 7-10 B6.WT ($Cish^{+/+}$) and $B6.Cish^{-/-}$ mice were injected i.p. with $1\times10^5$ parental RMA-S cells and treated with either PBS or recombinant IL-2 (100,000 IU i.p. on days 0, 1, 2, 3 and 4). Mice were monitored for tumor development and were euthanized at the point of abdominal swelling and discomfort. Improved survival between groups was assessed by the Log-rank Mantel-Cox test. (D) Groups of 5-15 B6.WT (Cish') or $B6.Cish^{-/-}$ mice were injected i.v. with $5\times10^5$ RM-1 prostate carcinoma cells and treated with either cIg, anti-CD96, anti-PD-1, anti-CTLA-4 or anti-PD1/anti-CTLA-4 combination (250 i.p. each on days 0 and 3). (E) Groups of 8-10 B6.WT ($Cish^{-/+}$) or $B6.Cish^{-/-}$ mice were injected i.v. with $7.5\times10^5$ B16F10 melanoma cells and treated with either 250 μs cIg or anti-CD96 mAb (i.p. on days 0 and 3). (F) Groups of 5-6 B6.WT ($Cish^{+/+}$) or $B6.Cish^{-/-}$ mice were injected i.v. with $7.5\times10^5$ LWT1 melanoma cells and treated with either vehicle or PLX4720 (10 mg/kg i.p., daily from day 0 to 6). Lungs were harvested on (A, D, F) day 14 or (B, E) day 13 and macrometastases counted. Individual mice are shown by each symbol and the results are plotted as mean±SEM. Statistically significant differences as indicated were determined by one-way ANOVA with Tukey post-test (for multiple comparisons) (*: p<0.5; : p<0.01; *: p<0.001; ****: p<0.0001).

Figure 21:
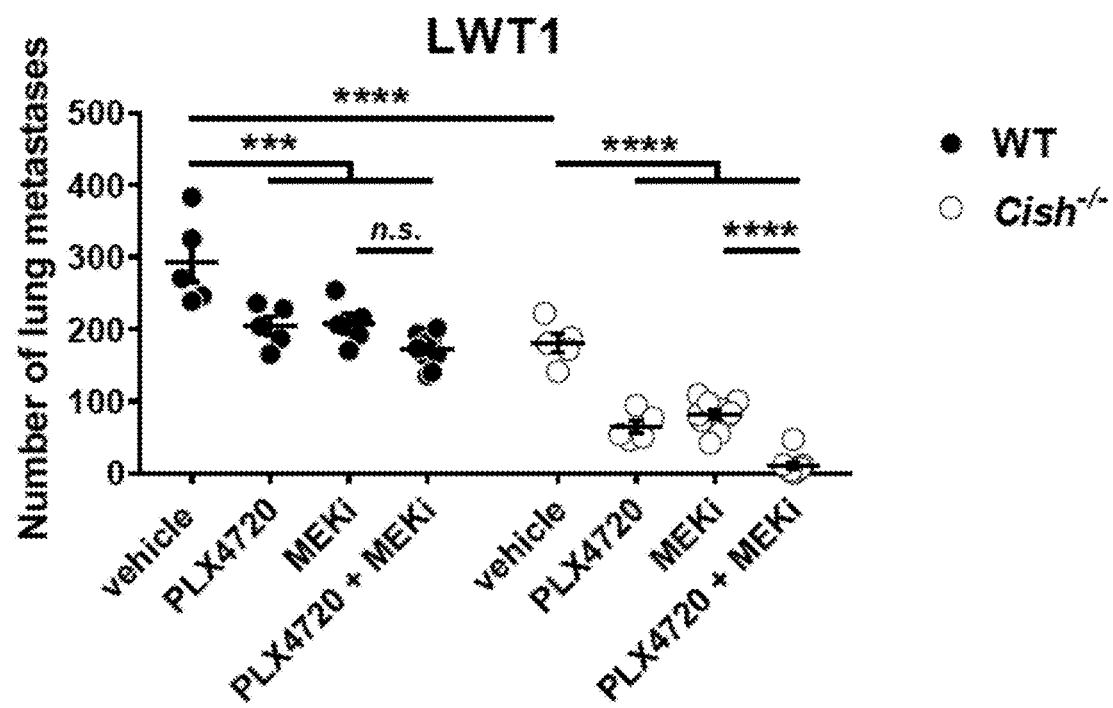

FIG. 21—Combining Cish-deficiency with BRAF or MEK kinase inhibitors demonstrates an improved anti-metastatic effect. Groups of 5-10 B6.WT ($Cish^{+/+}$) and $B6.Cish^{-/-}$ mice were inoculated i.v. with $7.5\times10^5$ LWT1 melanoma cells and treated with either vehicle, BRAF inhibitor (PLX4720; daily for 6 days; 10 mg/kg i.p.) and/or MEK inhibitor (MEKi; trametinib, days 0 and 3, 0.6 mg/kg oral gavage). Lungs were harvested on day 14 and macrometastases counted. Individual mice are shown by each symbol and the results are plotted as mean±S.E.M. Statistically significant differences as indicated were determined by one-way ANOVA with Tukey post-test (for multiple comparisons) (n.s. not significant; *: p<0.001; **: p<0.0001).

Figure 22:
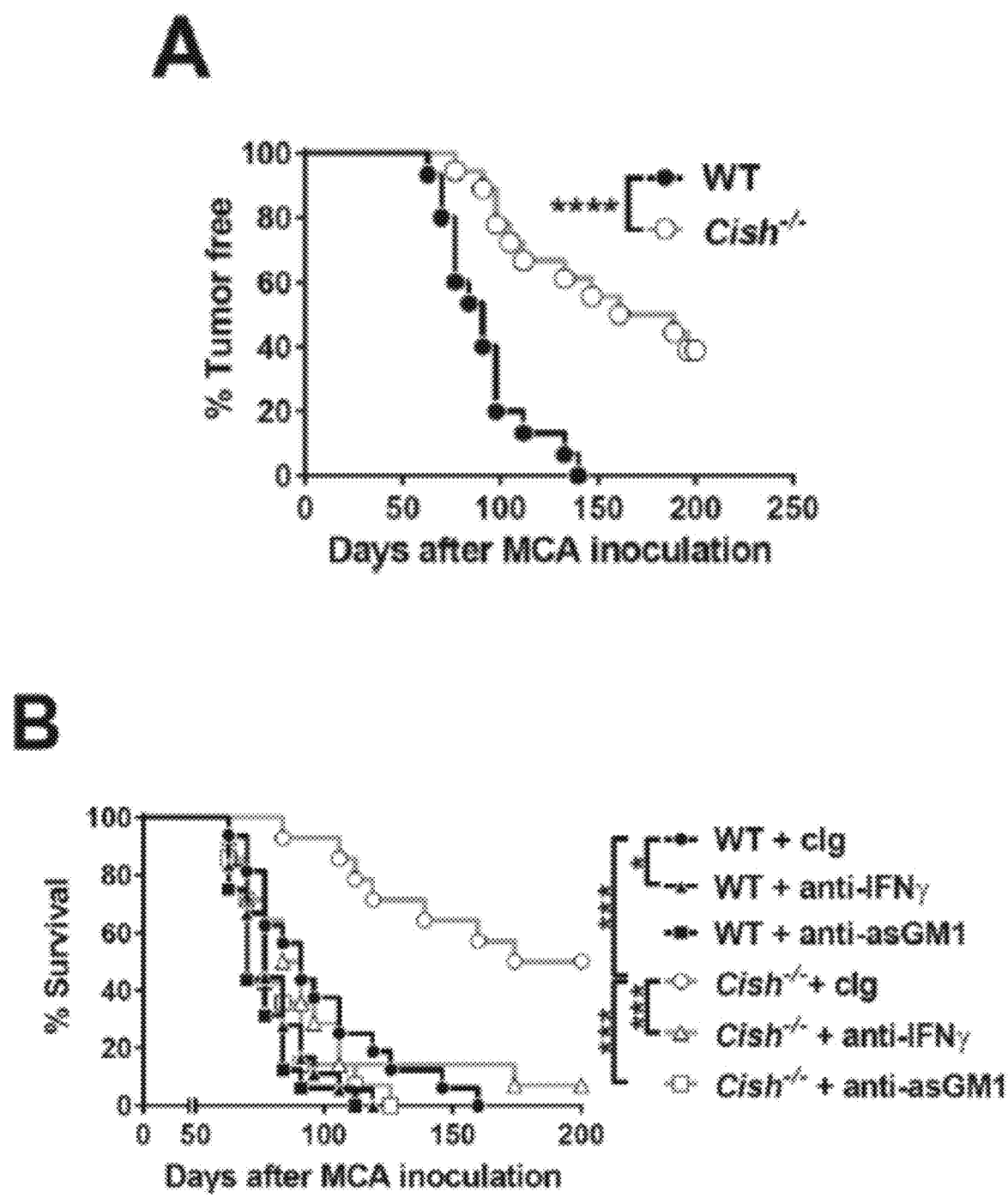

FIG. 22—Cish-deficient mice are protected from MCA-induced tumor development. (A) Groups of 15 B6.WT (Cish$^{+/+}$) and 18 B6.Cis/r male mice were inoculated s.c. in the hind flank with 300 μg of MCA in 0.1 ml of corn oil. Mice were then monitored for fibrosarcoma development over 250 days, and data were recorded as a percentage of tumor free mice (tumors >3 mm in diameter were recorded as positive). (B) Groups of 16-18 B6.WT (Cish$^{+/+}$) and 14 B6.Cish$^{-/-}$ male mice were inoculated s.c. in the hind flank with 300 μg of MCA in 0.1 ml of corn oil. Mice were treated with either 250 μg hamster cIg, 50 μg anti-asialoGM1 (anti-asGM1; NK cell depletion) or 250 μg anti-IFN-γ antibodies injected i.p. on days −1, 0, 7, 12, 24, 28, 35 and 42. Mice were monitored for fibrosarcoma development over 200 days. Tumors were measured every week with a caliper square as the product of two perpendicular diameters (mm$^2$). Mice were euthanized when the tumor reached >150 mm$^2$ in square-diameter. Statistically significant survival differences between the groups were determined by Log-rank Mantel-Cox test (A) followed by Bonferroni-correction for multiple testing (B) (*: p<0.05; ***: p<0.001).

Figure 23:
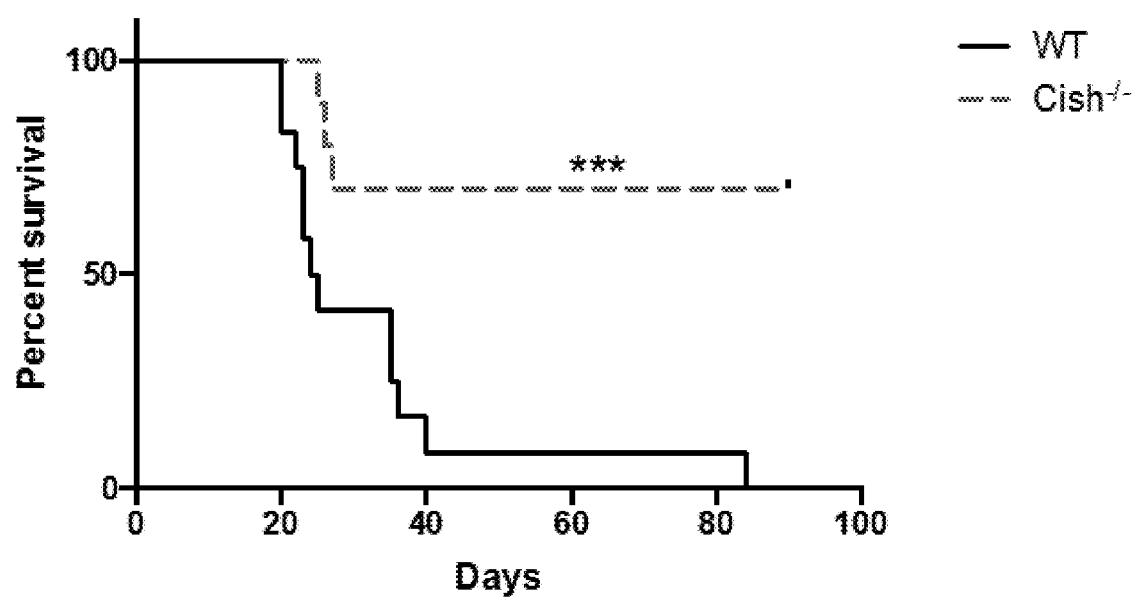

FIG. 23—Cish-deficient mice show enhanced survival in an acute myeloid leukemia model. Cish$^{+/+}$ (WT) and Cish$^{-/-}$ mice were injected i.v. with 5×10$^5$ MLL-AF9 cells. Mice were euthanised when an enlarged spleen and/or hind-leg paralysis was detected, according to ethical guidelines. Survival curve results are from two independent experiments. Each group had n≥5 mice per experiment. ***p<0.05.

Figure 24:
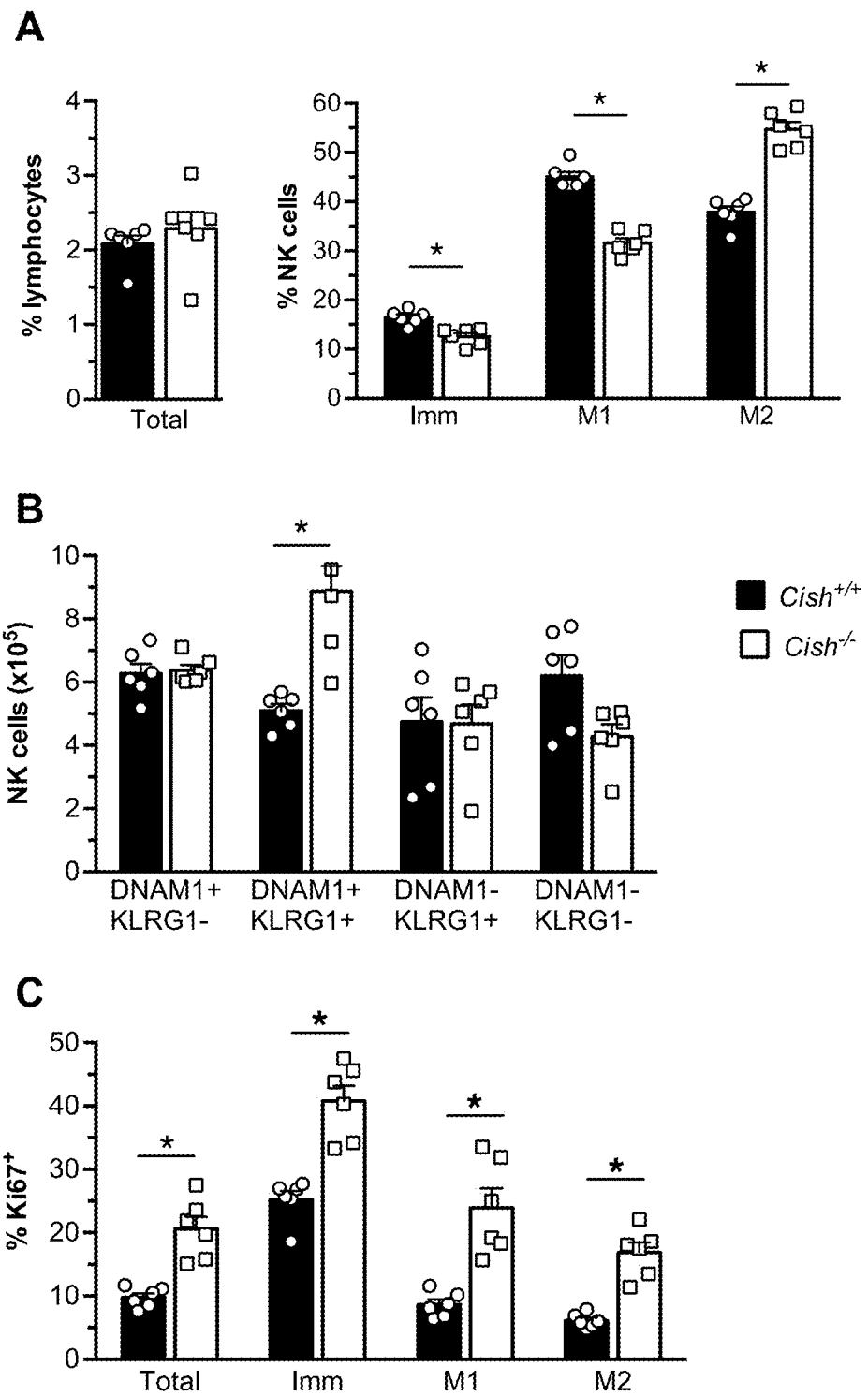

FIG. 24—Loss of CIS function in NK cells results in enhanced turnover and differentiation towards more mature NK cells in vivo. Spleens were harvested from Cish$^{-/-}$ and Cish$^{+/+}$ mice and processed into single cell suspensions. Surface and intracellular staining was performed by flow cytometry to determine: (A) The percentage of Cish$^{+/+}$ and Cish$^{-/-}$ cells in different NK cell subsets. Total NK cells were identified as being NK1.1+ NKp46+ and were further subdivided into immature NK cells (CD27+ CD11b−; Imm), M1 (CD27+ CD11b+) and M2 (CD27− CD11b+) subsets, with M2 denoting the most mature and cytotoxic NK cell population. (B) The number of DNAM1+ KLRG1+ NK cells. In general, DNAM+ cells show greater production of pro-inflammatory cytokines and heightened response to IL-15, whilst KLRG1 is considered to be an alternative maturation marker (C) The percentage of Ki67+ cells in each NK cell subset (Imm, M1, M2). Ki67 is a marker for cellular proliferation. n=6 mice per group. p<0.05. Collectively, these data show that although the total number of NK cells did not differ between Cish$^{-/+}$ and Cish$^{-/-}$ mice, Cish$^{-/-}$ NK cells were more mature and likely to display increased cytokine production and cytotoxicity, with all Cish$^{-/-}$ subsets showing increased cell cycling.

Figure 25:
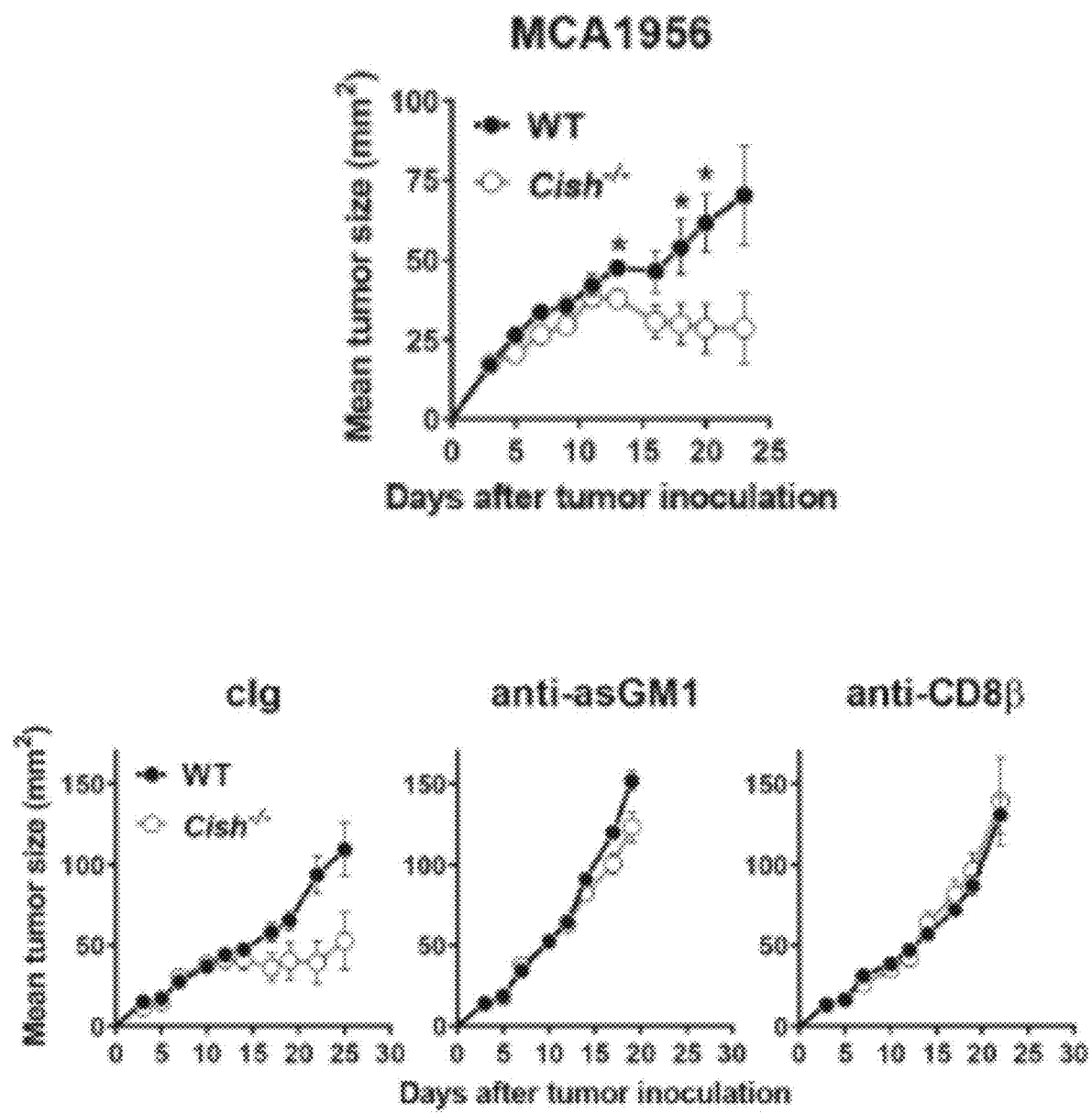

FIG. 25—Enhanced control of MCA1956 sarcoma requires both NK cells and CD8 T cells. Groups of 6-7 B6.WT (WT; Cish$^{+/+}$) and B6. Cish$^{-/-}$ mice were injected s.c. with 1×10$^6$ MCA1956 fibrosarcoma cells and treated on days −1, 0, 7 and 14 relative to tumor inoculation with either control Ig (cIg: 50 μg rabbit IgG plus 100 μg rat IgG1), 50 μg anti-asialoGM1 (anti-asGM1; NK cell depletion) or 100 μg anti-CD8β (CD8$^+$ T cell depletion). Mean±SEM of 6-7 mice per group. Statistically significant differences between WT and Cish$^{-/-}$ groups as indicated were determined by a Mann-Whitney U test (*p<0.05).

Figure 26:
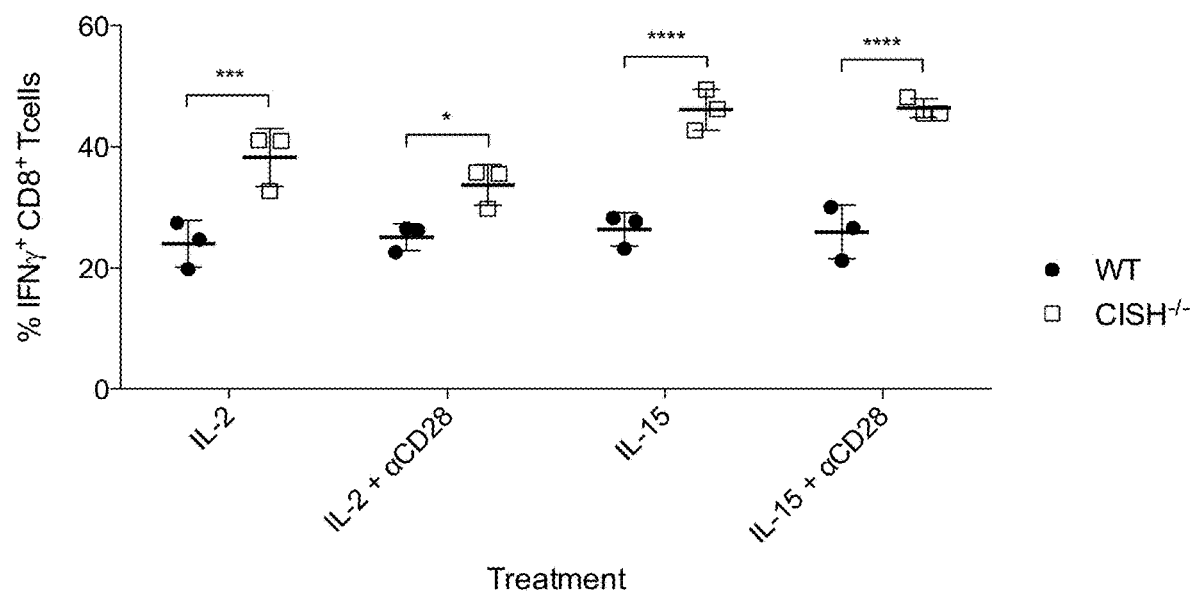

FIG. 26—Cish$^{-/-}$ CD8+ T cells show enhanced IFNγ production. Peripheral lymph node CD8+ T cells from Cish$^{+/+}$ (WT) and Cish$^{-/-}$ mice were cultured for 4 days under the indicated conditions and production of IFNγ in response to 4 h PMA/ionomycin evaluated by flow cytometry. n=3 mice. Mean±S.E.M. *P<0.0005, **P<0.0001. Data were analysed using a 2way ANOVA.

Figure 27:
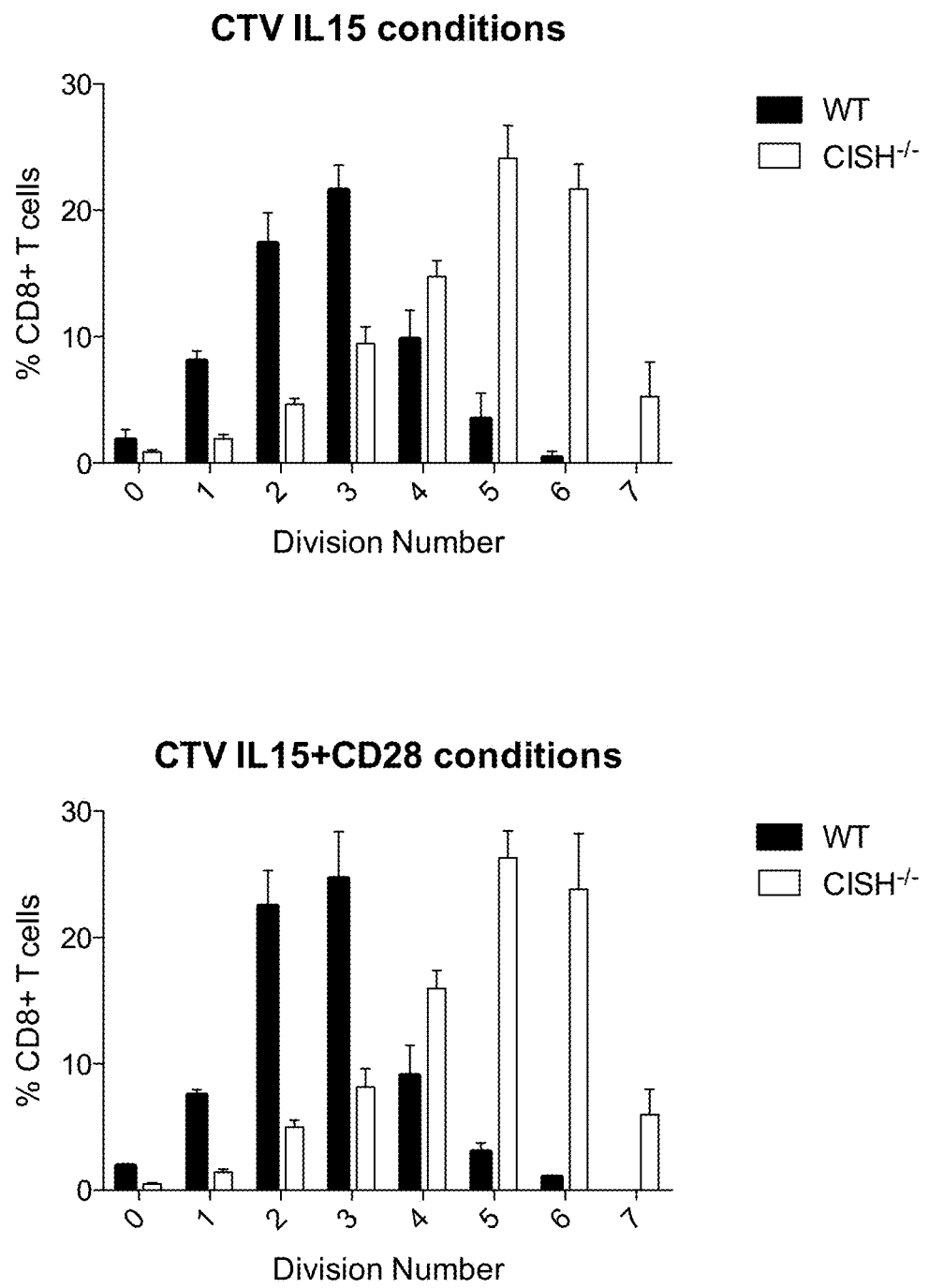

FIG. 27—Cish$^{-/-}$ CD8+ T cells show enhanced proliferation under activating conditions. Peripheral lymph node CD8+ T cells from Cish$^{+/+}$ (WT) and Cish$^{-/-}$ mice were co-cultured for 4 days in IL-15 with (lower) or without (upper) αCD28 stimulation (no αCD3). The percentage of cells occupying each division was evaluated by flow cytometry. This data represents n=3 mice per genotype. Mean±S.E.M. are indicated.

Figure 28:
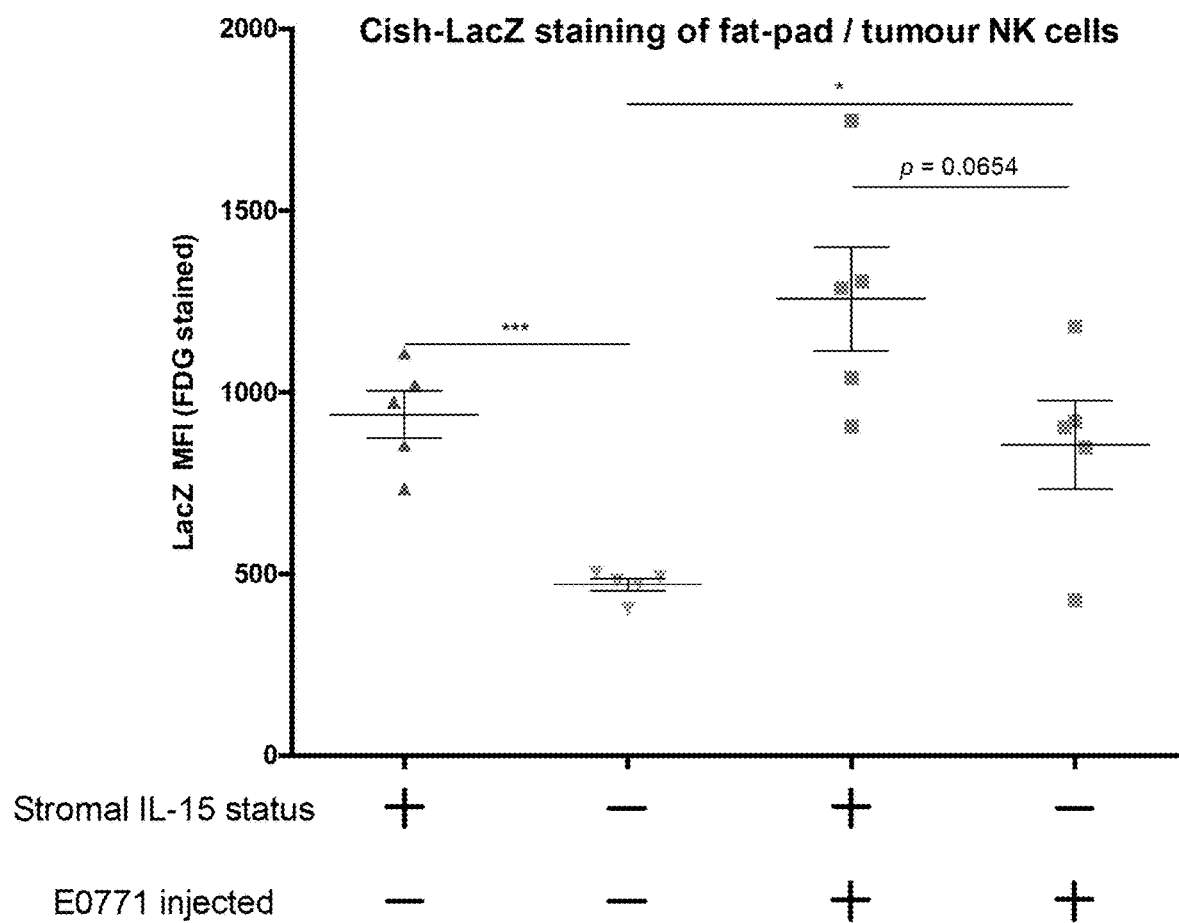

FIG. 28—IL-15 levels in tumors and tumor microenvironment regulate Cish expression levels in resident NK cells. IL-15$^{+/+}$ or IL-15$^{-/-}$ mice (stromal IL-15 status + or − respectively) were lethally irradiated and reconstituted with Cish$^{LacZ/+}$ bone marrow. 10 weeks later these chimeric mice were challenged with 1×10$^5$ E0771 breast cancer cells injected in the mammary fat pad or left unchallenged. One week later mice were sacrificed, mammary tumors were harvested and dissociated and tumour resident NK cells were stained for β-galactosidase (Cish expression) and analyzed by flow cytometry. Mean±SEM are indicated. Statistical significance is indicated and determined by Student's t-test.

KEY TO THE SEQUENCE LISTING

SEQ ID NO:1 JAK1 activation loop phosphopeptide
SEQ ID NO:2 JAK1 phosphomimetic peptide
SEQ ID NO:3 IL-2Rϑ phosphopeptide
SEQ ID NO:4 IL-2Rϑ phosphopeptide
SEQ ID NO:5 IL-2Rϑ phosphopeptide
SEQ ID NO:6 human CIS protein isoform 1
SEQ ID NO:7 human CIS protein isoform 1 fragment
SEQ ID NO:8 human CIS protein isoform 1 SOCS Box
SEQ ID NO:9 Mus musculus CIS protein isoform 1
SEQ ID NO:10 Rattus norvegicus CIS protein
SEQ ID NO:11 Homo sapiens JAK1 protein
SEQ ID NO:12 Homo sapiens JAK3 protein
SEQ NO:13 Homo sapiens IL-2 Receptor Subunit Beta precursor
SEQ ID NO:14 Homo sapiens Elongin B
SEQ ID NO:15 Homo sapiens Elongin C
SEQ ID NO:16 Homo sapiens Cullin-5
SEQ ID NO:17 Homo sapiens JAK1 protein JH1 kinase domain peptide
SEQ ID NO:18 STAT5b peptide
SEQ ID NO:19 JAK1 peptide
SEQ ID NO:20 JAK3 peptide
SEQ ID NO:21 IL-2Rϑ phosphopeptide
SEQ ID NO:22 IL-2Rϑ phosphopeptide
SEQ ID NO:23 mIL-2Rϑ phosphopeptide
SEQ ID NO:24 IL2Rϑ phosphopeptide
SEQ ID NO:25 IL2Rγ phosphopeptide
SEQ ID NO:26 IL2Rγ phosphopeptide
SEQ ID NO:27 IL2Rγ phosphopeptide
SEQ ID NO:28 IL2Rγ phosphopeptide
SEQ ID NO:29 CIS PEST domain peptide
SEQ ID NO:30 CIS PEST domain phosphopeptide
SEQ ID NO:31 CIS N-terminal phosphopeptide
SEQ ID NO:32 CIS PEST domain phosphopeptide
SEQ ID NO:33 CIS SH2/SB domain phosphopeptide
SEQ ID NO:34 CIS N-terminal glycosylated peptide
SEQ ID NO:35 CIS SH2 glycosylated peptide
SEQ ID NO:36 CIS SH2 glycosylated peptide
SEQ ID NO:37 CIS PEST glycosylated peptide
SEQ ID NO:38 CIS SH2/SB domain glycosylated peptide

DETAILED DESCRIPTION OF THE INVENTION

General Techniques and Definitions

Unless specifically defined otherwise, all technical and scientific terms used herein shall be taken to have the same meaning as commonly understood by one of ordinary skill in the art (e.g., in cell culture, cell biology, molecular genetics, cancer biology and treatment thereof, infectious disease especially acute infections, immunology, pharmacology, protein chemistry, and biochemistry).

Unless otherwise indicated, the cell culture and immunological techniques utilized in the present invention are standard procedures, well known to those skilled in the art. Such techniques are described and explained throughout the literature in sources such as, J. Perbal, A Practical Guide to Molecular Cloning, John Wiley and Sons (1984), J. Sambrook et al., Molecular Cloning: A Laboratory Manual, Cold Spring Harbour Laboratory Press (1989), T. A. Brown (editor), Essential Molecular Biology: A Practical Approach, Volumes 1 and 2, IRL Press (1991), D. M. Glover and B. D. Hames (editors), DNA Cloning: A Practical Approach, Volumes 1-4, IRL Press (1995 and 1996), and F. M. Ausubel et al. (editors), Current Protocols in Molecular Biology, Greene Pub. Associates and Wiley-Interscience (1988, including all updates until present), Ed Harlow and David Lane (editors) Antibodies: A Laboratory Manual, Cold Spring Harbour Laboratory, (1988), and J. E. Coligan et al. (editors) Current Protocols in Immunology, John Wiley & Sons (including all updates until present).

As used herein, the term about, unless stated to the contrary, refers to +/−10%, more preferably +/−5%, of the designated value.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

As used in this application, the term "or" is intended to mean an inclusive "or" rather than an exclusive "or". That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. Further, at least one of A and B and/or the like generally means A or B or both A and B. In addition, the articles "a" and "an" as used in this application and the appended claims may generally be construed to mean "one or more" unless specified otherwise or clear from context to be directed to a singular form.

The term "CIS inhibitor" as used herein, refers to any agent that inhibits CIS signalling activity in NK cells. Such agents can act to specifically reduce CIS signalling activity in NK cells by any of a number of different modes of action including, but not limited to, reducing total levels of CIS protein such as by reducing CIS mRNA levels, inhibiting its binding to target proteins such (e.g., JAK1) or its interaction with signalling complex binding partners such as Elongin B and Elongin C. Specifically excluded from "CIS inhibitors" as used herein, are agents that broadly or globally affect proteins in addition to CIS (e.g., alkylating agents or cross-linking agents) or inhibit basic cellular processes, e.g., translation (e.g., translational inhibitors) or non-selectively alter protein degradation. Examples of CIS inhibitors include, for example, polynucleotides (e.g., siRNAs and mRNAs), small molecules, peptides, polypeptides, or combinations thereof. In some embodiments one or more of such CIS inhibitors are used in combination with a delivery and/or targeting agent, e.g., including nanoparticle-mediated delivery.

The term "competitive inhibitor" or "competitively inhibits" as used herein, refers to a mode of inhibition of a target protein in which an inhibitor binds to a functionally critical site on a target protein itself (e.g., a ligand binding site) or on a ligand (e.g., a binding partner protein) for the target protein thereby sterically hindering interaction of the protein target with the ligand. The competitive inhibitor may, but does not necessarily, have higher affinity for a biologically active site for which it competes.

The term "CIS-inhibited NK cells" as used herein, refer to NK cells in which CIS activity is suppressed by any of a number strategies alone or in combination. For example, CIS-inhibited NK cells include, but are not limited to, Cish "knock out" NK cells in which the Cish gene has been genetically deleted or modified such as by gene editing; CIS protein "knock down" NK cells in which expression of CIS protein has been reduced by use of a gene silencing strategy (e.g., with siRNA or RNAi) or expression of a dominant-negative CIS sequence variant, or dominant-negative CIS fragment; or, alternatively, CIS-inhibited NK cells are NK cells that have been exposed to a CIS inhibitor (e.g., a small molecule compound, a peptide, or peptidomimetic agent) that inhibits the activity of CIS, e.g., by inhibiting its binding to target proteins (e.g., JAK1) or its interaction with signalling complex binding partners such as Elongin B and Elongin C, or Cullin-5. Alternatively, the CIS inhibitor may be a peptide or fragment derived from CIS that acts in trans to inhibit CIS activity. In some embodiments the CIS-inhibited NK cells are irreversibly CIS-inhibited, e.g., by genetic modification. In other embodiments the CIS-inhibited NK cells are reversibly CIS-inhibited so that over time CIS inhibition in the cells decreases.

The term "fragment" as used herein, refers to a biologically active portion of a protein (e.g., a CIS fragment) that retains at least one functional or structural domain. For example, a CIS fragment may include an SH2 domain and a SOCS box, and a JAK1 fragment may include a JH1 kinase domain. In some cases the activity of a fragment refers to its ability to specifically bind to a binding partner (e.g., a protein or fragment thereof). As used herein, "fragment" does not encompass a full-length protein.

The term "NK cell-responsive condition" as used herein, refers to a condition that is amenable to effective treatment by one or more NK cell activities (e.g., NK cell cytotoxicity-induced tumour cell death or death of infected cells, and production of interferon-γ (IFN-γ)). Examples of NK cell-responsive conditions include, but are not limited to cancers (e.g., melanoma, prostate cancer, breast cancer, and liver cancer) and infections, such as viral infections (e.g., infections by HSV, hepatitis viruses, human cytomegaloviruses, influenza viruses, flaviviruses, and HIV-1), bacterial infections (e.g., infections by Mycobacteria, *Listeria*, and *Staphylococcus*), and protozoan infections (e.g., infections by *Plasmodium*), and fungal infections (e.g., infections by *Aspergillus*).

The term "peptide" as used herein, refers to a polymer of amino acids ranging from two to about fifty amino acids (e.g., 4, 6, 8, 10, 12, 15, 20, 25, 30, 35, 40, or 45 amino acids in length). The term peptide encompasses both unmodified peptides, phosphorylated peptides (e.g., phosphopeptides), and otherwise chemically derivatized peptides, but not peptidomimetics.

The term "polypeptide" or "protein" as used herein, refer to a polymer of amino acids generally greater than about 50 amino acids in length and typically having table characteristic secondary and tertiary structures.

As the skilled person would understand, CIS inhibitors and CIS-inhibited NK cells will be administered in a therapeutically effective amount. The terms "effective amount" or "therapeutically effective amount" as used herein, refer to a sufficient amount of a CIS inhibitor being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the CIS inhibitor required to provide a clinically significant decrease in disease symptoms without undue adverse side effects. An appropriate "effective amount" in any individual case may be determined using techniques, such as a dose escalation study. The term "therapeutically effective amount" includes, for example, a prophylactically effective amount. An "effective amount" of a CIS inhibitor is an amount effective to achieve a desired pharmacologic effect or therapeutic improvement without undue adverse side effects. It is understood that "an effect amount" or "a therapeutically effective amount" can vary from subject to subject, due to variation in metabolism of the compound of any of age, weight, general condition of the subject, the condition being treated, the severity of the condition being treated, and the judgment of the prescribing physician. By way of example only, therapeutically effective amounts may be determined by routine experimentation, including but not limited to a dose escalation clinical trial. Where more than one therapeutic agent is used in combination, a "therapeutically effective amount" of each therapeutic agent can refer to an amount of the therapeutic agent that would be therapeutically effective when used on its own, or may refer to a reduced amount that is therapeutically effective by virtue of its combination with one or more additional therapeutic agents.

The term "small molecule" as used herein, refers to a molecule having a molecular weight below 2000 daltons.

The term "chemically modified mRNA" or "chemically modified siRNAs" as used herein refers to synthetic RNAs generated in vitro, where a proportion (e.g., 10%, 30%, 50%, or 100%) of at least one type of nucleotide, e.g., cytosine, is chemically modified to increase its stability within cells or otherwise in vivo. For example, in some cases modified cystosines are 5-methylcytosines. Such polynucleotides are particularly useful for delivery/transfection to cells in vivo, especially when combined with a transfection/delivery agent. In some cases, a chemically modified mRNA is a chemically modified mRNA in which a majority of (e.g., all) cystosines are 5-methylcytosines, and where a majority (e.g., all) of uracils are pseudouracils. The synthesis and use of such modified RNAs are described in, e.g., WO 2011/130624.

The terms "treating" or "treatment" as used herein, refer to both direct treatment of a subject by a medical professional (e.g., by administering a therapeutic agent to the subject), or indirect treatment, effected, by at least one party, (e.g., a medical doctor, a nurse, a pharmacist, or a pharmaceutical sales representative) by providing instructions, in any form, that (i) instruct a subject to self-treat according to a claimed method (e.g., self-administer a drug) or (ii) instruct a third party to treat a subject according to a claimed method. Also encompassed within the meaning of the term "treating" or "treatment" are prevention or reduction of the disease to be treated, e.g., by administering a therapeutic at a sufficiently early phase of disease to prevent or slow its progression.

The term "at risk" as used herein, refers to a probability of developing a health condition that is higher than in the general population. Accordingly, treatment of an individual considered to be "at risk" of a particular condition is designed to prevent a subject from the developing the condition or at least to reduce the risk of developing the condition to a level no higher than that found in general population as a whole.

The terms "co-administration" or the like, as used herein, are meant to encompass administration of the selected therapeutic agents to a single patient, and are intended to include treatment regimens in which the agents are administered by the same or different route of administration or at the same or different time.

Methods of Treatment

The methods described herein include treating a subject suffering from a NK cell-responsive condition, or at risk of suffering from a NK-responsive condition, by administering a therapeutically or prophylactically effective amount of a CIS inhibitor. As described herein, CIS (UniprotKB Q9NSE2) acts as a potent checkpoint suppressor of IL-15 induced responses in NK cells. Without being bound by theory, it is believed that inhibiting the function of CIS in NK cells, greatly sensitizes these cells to IL-15 and sustains their activation to achieve a therapeutic effect.

In other embodiments, the method for adoptive cell therapy includes administering CIS-inhibited NK cells to a subject suffering from a NK cell-responsive condition.

In some embodiments the subject suffering from an NK cell-responsive, or at risk of suffering from a NK cell-responsive, condition is suffering from a proliferative disorder such as a cancer. In some embodiments the subject suffering from a cancer is suffering from a cancer that is characterized by the presence of one or more tumours in the subject. Examples of cancers suitable for treatment by the methods of the invention include, but are not limited to, cancer is metastatic melanoma, metastatic prostate cancer, metastatic breast cancer, triple negative breast cancer, bladder cancer, brain cancer, esophageal cancer, liver cancer, head and neck cancer, squamous cell lung cancer, non small lung cell cancer, Merkel cell carcinoma, sarcoma, hepatocellular cancer, multiple myeloma, pancreatic cancer, colorectal carcinoma, cervical cancer, gastric carcinoma, kidney cancer, metastatic renal cell carcinoma, leukemia, ovarian cancer, and malignant glioma. In some preferred embodiments the cancer is metastatic melanoma, metastatic prostate cancer, or metastatic breast cancer. In some embodiments subject has received an allogeneic tissue graft associated with treatment for cancer, e.g., after hematopoietic stem cell transplantation used for treatment of a leukemia.

Also described herein is a method for increasing responsiveness of NK cells to IL-15 by inhibiting CIS in the NK cells. In some embodiments the responsiveness of NK cells to IL-15 is increased by inhibiting CIS in NK cells ex vivo (e.g., in cultured NK cells). In other embodiments the responsiveness of NK cells to IL-15 is increased by inhibiting CIS in NK cells in vivo, e.g., by administration of a CIS inhibitor to a subject. In some embodiments such a method comprises reducing the expression of CIS in NK cells ex vivo. Optionally, the NK cells in which CIS expression is reduced ex vivo may be autologous NK cells derived from a subject and to be subsequently transplanted into the donor patient following reduction of CIS expression ex vivo. In other embodiments, the NK cells may be allogeneic NK cells, i.e., obtained from a donor source different from a recipient subject. In some embodiments, the subject is a cancer patient. In other embodiments, the subject is an NK cell donor. Optionally, such methods may include contacting NK cells ex vivo or in vivo with exogenous IL-15.

Diagnostic Methods

As disclosed herein, IL-15 induces Cish expression as part of a negative feedback loop that curtails NK-cell immune response to tumours. As disclosed herein, where the level of IL-15 is elevated in the microenvironment a particular tumour/tumour type, Cish expression in tumour-infiltrating NK cells is also increased. While not wishing to be bound by theory, it is believed that increased Cish expression in tumour-infiltrating NK cells indicates an increased likelihood that Cish inhibition will be effective in enhancing NK-mediated immune response to a tumour. Accordingly, in some embodiments, a likelihood of responsiveness to treatment with Cish inhibition in a patient in a patient suffering from a tumour is assessed by determining a level of IL-15 in the tumour microenvironment (e.g., by a tumour biopsy), wherein an elevated level of IL-15 in the tumour microenvironment relative to a threshold level of IL-15 indicates a higher likelihood of responsiveness to the treatment.

Similarly, in some embodiments induction of elevated Cish expression in tumour-infiltrating NK cells in a subject suffering from a tumour is assayed by determing a level of IL-15 in the tumour microenvironment, wherein an elevated level of IL-15 in the tumour microenvironment relative to a threshold level of IL-15 indicates induction of elevated Cish expression in the tumour-infiltrating NK cells.

A "threshold" level of IL-15 can be determined based on, e.g., comparison of a control tissue level of IL-15. Suitable threshold levels can readily be determined by the skilled person using routine experimentation.

In other embodiments the subject to be treated suffers from an infection. In some embodiments the infection to be treated is a viral infection, including without limitation, infections by herpes simplex virus, an adenovirus, a vaccinia virus, a human cytomegalovirus, an influenza virus, a poxvirus, or a papillomavirus. In other embodiments where the subject suffering from an NK cell-responsive condition is suffering from a bacterial infection, e.g., an infection by Mycobacteria, *Listeria*, or *Staphylococcus*. In other embodiments the subject to be treated is suffering from a protozoan infection (e.g., *Plasmodium* infection). In further embodiments the subject to be treated is suffering from a fungal infection (e.g., an *Aspergillus* infection).

As used herein, the term "subject" can be any animal. In one example, the animal is a vertebrate. For example, the animal can be a mammal, avian, chordate, amphibian or reptile. Exemplary subjects include but are not limited to human, primate, livestock (e.g. sheep, cow, chicken, horse, donkey, pig), companion animals (e.g. dogs, cats), laboratory test animals (e.g. mice, rabbits, rats, guinea pigs, hamsters), captive wild animal (e.g. fox, deer). In one example, the mammal is a human.

Symptoms, diagnostic tests, and prognostic tests for each of the above-mentioned conditions are known in the art. See, e.g., *Harrison's Principles of Internal Medicine©*." 19th ed., Vols 1 & 2, 2015, The McGraw-Hill Companies, Inc.

A number of animal models are useful for establishing a range of therapeutically effective doses of CIS inhibitors for treating any of the foregoing NK-responsive conditions. For example, a number of mouse models of cancer have been established, e.g., for melanoma (Walker et al., 2011), for prostate cancer (Grabowska et al., 2014) and for breast cancer (Borowsky, 2011).

CIS Inhibitors

CIS inhibition, as used herein, refers to reducing one or more of net Cish gene expression, net CIS protein levels, or a CIS activity (e.g., its inhibition of JAK1 kinase activity or its targeting of JAK1 for proteolysis). Inhibition of CIS may include at least about a 10% to a 100% reduction in CIS activity level in the presence of, or resulting from, a given dose of the CIS inhibitor relative to CIS activity level in its absence, e.g., a 10%, 20%, 30%, 40%, 50%, 60%, 70%, 80%, 85%, 90%, 95%, or another percent reduction in CIS activity from about 10% to about 100%. In some embodiments a CIS inhibitor is administered to a subject to be treated. In other embodiments a CIS inhibitor is applied ex vivo to NK cells to obtain CIS-inhibited NK cells, which are subsequently administered to the subject as the therapeutic agent. In some embodiments a CIS inhibitor is a reversible CIS inhibitor. In other embodiments the CIS inhibitor is an irreversible CIS inhibitor.

Examples of types of CIS inhibitors useful for the invention include, but are not limited to, a peptide, a peptidomimetic, a small molecule, a polynucleotide, or a polypeptide.

Peptides

In some embodiments the CIS inhibitor to be used in the methods of treatment is a peptide. Suitable peptides can inhibit the ability of CIS to increase ubiquitination of JAK1 and/or inhibit the ability of CIS to reduce JAK1 kinase enzymatic activity, e.g., phosphorylation of its target proteins. In some embodiments the peptide is a phosphopeptide which binds to CIS and thereby competitively inhibits the ability of CIS to interact with the endogenously phosphorylated target proteins. In some embodiments the phosphopeptide is derived from the amino acid sequence of the JAK1 activation loop and corresponds to amino acids 1027-1042 (the activation loop sequence shown below) of JAK1, where Tyr1034 is phosphorylated:

$$A^{1027}\text{IETDKEpYYTVKDDRD} \quad \text{(SEQ ID NO: 1)}$$

Alternatively, the peptide can be a JAK1 activation loop phosphomimetic peptide such as (SEQ ID NO:2) $K^{1032}$E-[$F_2$PMP]$_2$-TV, where [$F_2$PMP]$_2$ is a phosphotyrosyl mimetic 4-(phosphonodifluoromethyl)phenylalanine moiety, as described in Yao et al. (2005).

In other embodiments the peptide is a phosphopeptide or phosphomimetic peptide the sequence of which is derived from the cytoplasmic domain of IL-2Rϴ (GenBank Accession No. NP_000869.1). For example:

$$C^{352}\text{QVpYFTYDPYSE} \quad \text{(SEQ ID NO: 3)}$$

$$Y^{358}\text{DPpYSEEDPDEG} \quad \text{(SEQ ID NO: 4)}$$

$$D^{389}\text{DApYCTFPSRDD} \quad \text{(SEQ ID NO: 5)}$$

In some embodiments the peptide CIS inhibitor is a phosphopeptide or phosphomimetic peptide comprising the amino acid sequence of one of SEQ ID NOs:1-5. In other embodiments the amino acid sequence of the peptide CIS inhibitor consists of one of SEQ ED NOs:1-5.

Peptides used in the methods of the invention may be prepared by various synthetic methods of peptide synthesis via condensation of one or more amino acid residues, in accordance with conventional peptide synthesis methods. Preferably, peptides are synthesized according to standard solid-phase methodologies, such as may be performed on an Applied Biosystems Model 430A peptide synthesizer (Applied Biosystems, Foster City, Calif.), according to manufacturer's instructions. Other methods of synthesizing peptides, either by solid phase methodologies or in liquid phase, are well known to those skilled in the art. When solid-phase synthesis is utilized, the C-terminal amino acid is linked to an insoluble resin support that can produce a detachable bond by reacting with a carboxyl group in a C-terminal amino acid. For example, in some cases an insoluble resin support used is p-hydroxymethylphenoxymethyl polystyrene (HMP) resin. Other useful resins include, but are not limited to: phenylacetamidomethyl (PAM) resins for synthesis of some N-methyl-containing peptides (this resin is used with the Boc method of solid phase synthesis; and MBHA (p-methylbenzhydrylamine) resins for producing peptides having C-terminal amide groups. During the course of peptide synthesis, branched chain amino and carboxyl groups may be protected/deprotected as needed, using commonly-known protecting groups. In some embodiments, N-I-amino groups are protected with the base-labile 9-fluorenylmethyloxycarbonyl (Fmoc) group or t-butyloxycarbonyl (Boc groups). Side-chain functional groups consistent with Fmoc synthesis may be protected with the indicated protecting groups as follows: arginine (2,2,5,7,8-pentamethylchroman-6-sulfonyl); asparagine (O-t-butyl ester); cysteine glutamine and histidine (trityl); lysine (t-butyloxycarbonyl); serine and tyrosine (t-butyl). Modification utilizing alternative protecting groups for peptides and peptide derivatives will be apparent to those of skill in the art.

Peptidomimetics

In some embodiments a CIS inhibitor is a peptidomimetic. All peptides are susceptible to enzymatic degradation in vivo. Therefore, peptidomimetics which retain or even enhance the biological activity of the basic peptide but have a greater circulating half life are particularly advantageous for use in the treatment methods of the invention. Peptidomimetics, for example peptidomimetics based on peptides having the amino acid sequence of any of SEQ ID NOs:1-5 the required phosphomimetic modifications may be readily synthesised in large amounts by non-fermentation methods.

While a peptidic backbone is characterised by one or more internal peptide bonds, a peptide will have peptide bonds linking each amino acid residue. Thus, a compound wherein one or more amide bond has been replaced by an alternative linker but wherein at least one amide bond remains is considered a peptidomimetic.

Peptidomimetic backbones will generally be linear or linear strings of fused cyclic groups which mimic the peptide backbone.

A peptidomimetic is typically characterised by retaining the polarity, three dimensional size and functionality (bioactivity) of its peptide equivalent but wherein the peptide bonds have been replaced, often by more stable linkages. By 'stable' is meant more resistant to enzymatic degradation by hydrolytic enzymes. Generally, the bond which replaces the amide bond (amide bond surrogate) conserves many of the properties of the amide bond, e.g. conformation, steric bulk, electrostatic character, possibility for hydrogen bonding etc. Chapter 14 of "Drug Design and Development", Krogsgaard, Larsen, Liljefors and Madsen (Eds) 1996, Horwood Acad. Pub provides a general discussion of prior art techniques for the design and synthesis of peptidomimetics. Suitable amide bond surrogates include the following groups: N-alkylation, retro-inverse amide, thioamide, thioester, phosphonate, ketomethylene, hydroxymethylene, fluorovinyl, vinyl, methyleneamino, methylenethio, alkane and sulfonamido.

Peptides and peptidomimetics will generally have a backbone of 4 to 20, preferably 7 to 16 atoms in length. Molecules having backbones at the upper end of these ranges will generally comprise beta and/or gamma amino acids or their equivalents.

In some embodiments, peptidomimetics will be derived based on CIS autoinhibitory peptide sequences. In some embodiments, the CIS autoinhibitory peptide sequence is a PEST peptide sequence, e.g., a peptide sequence selected from among SEQ ID NOs:29, 30, 32, and 37. In other embodiments, the CIS autoinhibitory peptide sequence is a CIS N-terminal peptide sequence, e.g., selected from among SEQ ID NOs: 31 and 34.

Small Molecules

In some embodiments, a CIS inhibitor is a small molecule. In some embodiments, the small molecule binds specifically to CIS and reduces its activity, e.g., the interaction of CIS with binding partners or target proteins. Suitable small molecule CIS inhibitors for use in the invention can be identified using screening methods defined herein. For example, the compound may bind to the Src homology 2 (SH2) domain of CIS (amino acids 66-216 of human CIS; UniprotKB Q9NSE2; and SEQ ID NO:6), the SOCS box 6), or the N-terminal region of CIS (amino acids 1-65).

In some embodiments, the compound that is administered may be a precursor compound, commonly referred to as a "prodrug" which is inactive or comparatively poorly active, but which, following administration, is converted (i.e., metabolised) to a an active CIS inhibitor. In those embodiments, the compound that is administered may be referred to as a prodrug. Alternatively or in addition, the compounds that are administered may be metabolized to produce active metabolites which have activity in reducing the expression of CIS activity in the population of cells when compared to isogenic cells lacking the compound. The use of such active metabolites is also within the scope of the present disclosure.

Depending on the substituents present in the compound, the compound may optionally be present in the form of a salt. Salts of compounds which are suitable for use in the described methods are those in which a counter-ion is pharmaceutically acceptable. Suitable salts include those formed with organic or inorganic acids or bases. In particular, suitable salts formed with acids include those formed with mineral acids, strong organic carboxylic acids, such as alkane carboxylic acids of 1 to 4 carbon atoms which are unsubstituted or substituted, for example, by halogen, such as saturated or unsaturated dicarboxylic acids, such as hydroxycarboxylic acids, such as amino acids, or with organic sulfonic acids, such as ($C_{1-4}$)-alkyl- or aryl-sulfonic acids which are substituted or unsubstituted, for example by halogen. Pharmaceutically acceptable acid addition salts include those formed from hydrochloric, hydrobromic, sulphuric, nitric, citric, tartaric, acetic, phosphoric, lactic, pyruvic, acetic, trifluoroacetic, succinic, perchloric, fumaric, maleic, glycolic, lactic, salicylic, oxaloacetic, methanesulfonic, ethanesulfonic, p-toluenesulfonic, formic, benzoic, malonic, naphthalene-2-sulfonic, benzenesulfonic, isethionic, ascorbic, malic, phthalic, aspartic, and glutamic acids, lysine and arginine. Pharmaceutically acceptable base salts include ammonium salts, alkali metal salts, for example those of potassium and sodium, alkaline earth metal salts, for example those of calcium and magnesium, and salts with organic bases, for example di cyclohexylamine, N-methyl-D-glucomine, morpholine, thiomorpholine, piperidien, pyrrolidine, a mono-, di- or tri-lower alkylamine, for example ethyl-, tbutyl-, diethyl-, diisopropyl-, triethyl-, tributyl- or dimethyl-propylamine, or a mono-, di- or trihydroxy lower alkylamine, for example mono-, di- or triethanolamine. Corresponding internal salts may also be formed.

Those skilled in the art of organic and/or medicinal chemistry will appreciate that many organic compounds can form complexes with solvents in which they are reacted or from which they are precipitated or crystallised. These complexes are known as "solvates". For example, a complex with water is known as a "hydrate". Solvates, such as hydrates, exist when the drug substance incorporates solvent, such as water, in the crystal lattice in either stoichiometric or non-stoichiometric amounts. Drug substances are routinely screened for the existence of solvates such as hydrates since these may be encountered at any stage. Accordingly it will be understood that the compounds useful for the present invention may be present in the form of solvates, such as hydrates. Solvated forms of the compounds which are suitable for use in the invention are those wherein the associated solvent is pharmaceutically acceptable. For example, a hydrate is an example of a pharmaceutically acceptable solvate.

The compounds useful for the present invention may be present in amorphous form or crystalline form. Many compounds exist in multiple polymorphic forms, and the use of the compounds in all such forms is encompassed by the present disclosure. Small molecules useful for the present disclosure can be identified using standard procedures such as screening a library of candidate compounds for binding to CIS, and then determining if any of the compounds which bind reduce CIS activity. In some embodiments, screening for a compound of the invention comprises assessing whether the compound inhibits CIS activity in cells. Small molecules useful for the present invention can also be identified using procedures for in silico screening as described herein, which can include screening of known library compounds, to identify candidates which reduce CIS activity. In some embodiments a small molecule CIS inhibitor is an irreversible CIS inhibitor. In other embodiments a small molecule CIS inhibitor is a reversible CIS inhibitor.
Polynucleotides In some embodiments a CIS inhibitor is a polynucleotide, which may inhibit CIS activity by at least one of a number of different mechanisms as described.
RNA Interference In some embodiments the polynucleotide CIS inhibitor acts by reducing expression of CIS protein by targeting its mRNA. For example, the polynucleotide can be an RNAi.

The terms "RNA interference", "RNAi" or "gene silencing" refer generally to a process in which a double-stranded RNA molecule reduces the expression of a nucleic acid sequence with which the double-stranded RNA molecule shares substantial or total homology. However, it has been shown that RNA interference can also be achieved using non-RNA double stranded molecules (see, for example, US 20070004667).

In some embodiments, a CIS inhibitor comprises nucleic acid molecules comprising and/or encoding double-stranded regions for RNA interference against the Cish mRNA (human Cish mRNA: GenBank Accession No. NM_013324.5) encoding CIS. The nucleic acid molecules are typically RNA but may comprise chemically-modified nucleotides and non-nucleotides.

The double-stranded regions should be at least 19 contiguous nucleotides, for example about 19 to 23 nucleotides, or may be longer, for example 30 or 50 nucleotides, or 100 nucleotides or more. The full-length sequence corresponding to the entire gene transcript may be used. Preferably, they are about 19 to about 23 nucleotides in length.

The degree of identity of a double-stranded region of a nucleic acid molecule to the targeted transcript should be at least 90% and more preferably 95-100%. The nucleic acid molecule may of course comprise unrelated sequences which may function to stabilize the molecule.

The term "short interfering RNA" or "siRNA" as used herein refers to a nucleic acid molecule which comprises ribonucleotides capable of inhibiting or down regulating gene expression, for example by mediating RNAi in a sequence-specific manner, wherein the double stranded portion is less than 50 nucleotides in length, preferably about 19 to about 23 nucleotides in length. For example the siRNA can be a nucleic acid molecule comprising self-complementary sense and antisense regions, wherein the antisense region comprises nucleotide sequence that is complementary to nucleotide sequence in a target nucleic acid molecule or a portion thereof and the sense region having nucleotide sequence corresponding to the target nucleic acid sequence or a portion thereof. The siRNA can be assembled from two separate oligonucleotides, where one strand is the sense strand and the other is the antisense strand, wherein the antisense and sense strands are self-complementary.

As used herein, the term siRNA is meant to be equivalent to other terms used to describe nucleic acid molecules that are capable of mediating sequence specific RNAi, for example micro-RNA (miRNA), short hairpin RNA (shRNA), short interfering oligonucleotide, short interfering nucleic acid (siNA), short interfering modified oligonucleotide, chemically-modified siRNA, post-transcriptional gene silencing RNA (ptgsRNA), and others. In addition, as used herein, the term RNAi is meant to be equivalent to other terms used to describe sequence specific RNA interference, such as post transcriptional gene silencing, translational inhibition, or epigenetics. For example, siRNA molecules can be used to epigenetically silence genes at both the post-transcriptional level or the pre-transcriptional level. In a non-limiting example, epigenetic regulation of gene expression by siRNA molecules can result from siRNA mediated modification of chromatin structure to alter gene expression.

By "shRNA" or "short-hairpin RNA" is meant an RNA molecule where less than about 50 nucleotides, preferably about 19 to about 23 nucleotides, is base paired with a complementary sequence located on the same RNA molecule, and where said sequence and complementary sequence are separated by an unpaired region of at least about 4 to about 15 nucleotides which forms a single-stranded loop above the stem structure created by the two regions of base complementarity.

Included shRNAs are dual or bi-finger and multi-finger hairpin dsRNAs, in which the RNA molecule comprises two or more of such stem-loop structures separated by single-stranded spacer regions.

Once designed, the nucleic acid molecules comprising a double-stranded region can be generated by any method known in the art, for example, by in vitro transcription, recombinantly, or by synthetic means.

Modifications or analogs of nucleotides can be introduced to improve the properties of the nucleic acid molecules. Improved properties include increased nuclease resistance and/or increased ability to permeate cell membranes. Accordingly, the terms "nucleic acid molecule" and "double-stranded RNA molecule" includes synthetically modified bases such as, but not limited to, inosine, xanthine, hypoxanthine, 2-aminoadenine, 6-methyl-, 2-propyl- and other alkyl-adenines, 5-halo uracil, 5-halo cytosine, 6-aza cytosine and 6-aza thymine, pseudo uracil, 4-thiuracil, 8-halo adenine, 8-aminoadenine, 8-thiol adenine, 8-thiol alkyl adenines, 8-hydroxyl adenine and other 8-substituted adenines, 8-halo guanines, 8-amino guanine, 8-thiol guanine, 8-thioalkyl guanines, 8-hydroxyl guanine and other substituted guanines, other aza and deaza adenines, other aza and deaza guanines, 5-trifluoromethyl uracil and 5-trifluoro cytosine.

Chemically modified siRNAs particularly suited for in vivo delivery are described in the art in, e.g., WO2014201306, WO2007051303. Exemplary siRNAs that can be used to target Cish mRNA are commercially available, e.g., from ThermoFisher (Cat Nos: 146713 and 146714); Origene (Cat. No. SR300830), and MyBioSource (Cat. No. MBS8232244).

Polynucleotides Encoding Peptides or Polypeptides

In some embodiments a polynucleotide-based CIS inhibitor encodes a polypeptide or polypeptide, so that delivery of the polynucleotide to NK cells results in expression of an encoded peptide or polypeptide CIS protein inhibitor. In some embodiments the encoded peptide or polypeptide once expressed in NK cells inhibits interaction of endogenous CIS protein with one or more of its interaction partners (e.g., Elongin B, Elongin C, or Cullin-5) or a target protein (e.g., Tyr1034-phosphorylated JAK1 or IL-2Rβ phosphorylated at any of Tyr355, Tyr361, or Tyr392).

In some embodiments the polynucleotide encodes a dominant negative suppressor of CIS activity. In one embodiment the encoded dominant negative suppressor is CIS comprising an amino acid sequence with an $^{107}$Arg→$^{107}$Lys (R107K) mutation in which the SH2 domain is inactivated. In other embodiments the encoded dominant negative suppressor is CIS comprising an amino acid sequence with mutations in the Cullin-5 binding site in the SOCS box (e.g., P241A/L242A/P243). In other embodiments the encoded dominant negative suppressor is CIS comprising an amino acid sequence with an L223A substitution.

In some embodiments, the polynucleotide CIS inhibitor encodes a programmable nuclease which inhibits CIS activity by inactivating or reducing expression of the Cish gene. As used herein, the term "programmable nuclease" relates to nucleases that are "targeted" ("programmed") to recognize and edit a pre-determined genomic location. In some embodiments the encoded polypeptide is a programmable nuclease "targeted" or "programmed" to introduce a genetic modification into the Cish gene or regulatory region thereof. In some embodiments, the genetic modification is a deletion or substitution in the Cish gene or in a regulatory region thereof. Such programmable nucleases are particularly useful for generating CIS-inhibited Cish$^{-/-}$ NK cells ex vivo, e.g., for generating Cish$^{-/-}$ autologous NK cells for use in adoptive cell therapy.

In some embodiments, the programmable nuclease may be programmed to recognize a genomic location by a combination of DNA-binding zinc-finger protein (ZFP) domains. ZFPs recognize a specific 3-bp in a DNA sequence, a combination of ZFPs can be used to recognize a specific a specific genomic location. In some embodiments, the programmable nuclease may be programmed to recognize a genomic location by transcription activator-like effectors (TALEs) DNA binding domains. In an alternate embodiment, the programmable nuclease may be programmed to recognize a genomic location by one or more RNA sequences. In an alternate embodiment, the programmable nuclease may be programmed by one or more DNA sequences. In an alternate embodiment, the programmable nuclease may be programmed by one or more hybrid DNA/RNA sequences. In an alternate embodiment, the programmable nuclease may be programmed by one or more of an RNA sequence, a DNA sequences and a hybrid DNA/RNA sequence.

Programmable nucleases that can be used in accordance with the present disclosure include, but are not limited to, RNA-guided engineered nuclease (RGEN) derived from the bacterial clustered regularly interspaced short palindromic repeat (CRISPR)-cas (CRISPR-associated) system, zinc-finger nuclease (ZFN), transcription activator-like nuclease (TALEN), and argonautes.

In some embodiments, the nuclease is a RNA-guided engineered nuclease (RGEN). In some embodiments the RGEN is from an archaeal genome or is a recombinant version thereof. In some embodiments the RGEN is from a bacterial genome or is a recombinant version thereof. In some embodiments the RGEN is from a Type I (CRISPR)-cas (CRISPR-associated) system. In some embodiments the RGEN is from a Type II (CRISPR)-cas (CRISPR-associated) system. In some embodiments the RGEN is from a Type III (CRISPR)-cas (CRISPR-associated) system. In some embodiments the nuclease is a class I RGEN. In some embodiments the nuclease is a class II RGEN. In some embodiments the RGEN is a multi-component enzyme. In some embodiments the RGEN is a single component enzyme. In some embodiments the RGEN is CAS3. In some embodiments the RGEN is CASIO. In some embodiments the RGEN is CAS9. In some embodiments the RGEN is Cpf1 (Zetsche et al., 2015). In some embodiments the RGEN is targeted by a single RNA or DNA. In some embodiments the RGEN is targeted by more than one RNA and/or DNA. In some embodiments the programmable nuclease may be a DNA programmed argonaute (WO 14/189628).

In some embodiments the polynucleotide CIS inhibitor is provided in an expression vector to be delivered in vivo or in vitro to NK cells using any of a number of transfection methods known in the art, e.g., recombinant virus transduction, liposome-based transfection, electroporation, or nanoparticle based transfection.

As used herein, an "expression vector" is a DNA or RNA vector that is capable of effecting expression of one or more polynucleotides in a host cell (e.g., a NK cell). The vector is typically a plasmid or recombinant virus. Any suitable expression vector can be used, examples of which include, but are not limited to, a plasmid or viral vector. In some embodiments, the viral vector is a retrovirus, a lentivirus, an adenovirus, a herpes virus, or an adeno-associated viral vector.

Such vectors will include one or more promoters for expressing the polynucleotide such as a dsRNA for gene silencing. Suitable promoters include, but are not limited to, the retroviral LTR; the SV40 promoter; and the human cytomegalovirus (CMV) promoter. Cellular promoters such as eukaryotic cellular promoters including, but not limited to, the histone, RNA polymerase III (in the case of shRNA or miRNA expression), and β-actin promoters, can also be used. In some embodiments the promoter is an NK cell-selective promoter such as the human NKp46 promoter (see, e.g., Walzer et al., 2007). The selection of a suitable promoter will be apparent to those skilled in the art from the teachings contained herein.

In other embodiments the polynucleotide CIS inhibitor is a synthetic, chemically modified mRNA that encodes a dominant negative CIS. Chemically modified mRNAs and their synthesis is described in detail in, e.g., WO 2011/130624. Typically, chemically modified mRNAs comprise (i) a 5' synthetic cap for enhanced translation; (ii) modified nucleotides that confer RNAse resistance and an attenuated cellular interferon response, which would otherwise greatly reduce translational efficiency; and (iii) a 3' poly-A tail. Typically, chemically modified mRNAs are synthesized in vitro from a DNA template comprising an SP6 or T7 RNA polymerase promoter-operably linked to an open reading frame encoding the dominant-negative CIS. The chemically modified mRNA synthesis reaction is carried in the presence of a mixture of modified and unmodified nucleotides. In some embodiments modified nucleotides included in the in vitro synthesis of chemically modified mRNAs are pseudouridine and 5-methyl-cytosine. A key step in cellular mRNA processing is the addition of a 5' cap structure, which is a 5'-5' triphosphate linkage between the 5' end of the RNA and a guanosine nucleotide. The cap is methylated enzymatically at the N-7 position of the guanosine to form mature mCAP. When preparing dominant-negative CIS chemically modified mRNAs, a 5' cap is typically added prior to transfection of NK cells in order to stabilize the modified mRNA and significantly enhance translation. In some embodiments a 4:1 mixture of a cap analog to GTP is used in transcription reactions to obtained 5'-capped chemically modified mRNAs. In preferred embodiments, the Anti Reverse Cap Analog (ARCA), 3'-O-Me-m7G(5')ppp(5')G is used to generate a chemically modified mRNA that can be efficiently translated in NK cells. Systems for in vitro synthesis are commercially available, as exemplified by the mRNAExpress™. mRNA Synthesis Kit (System Biosciences, Mountain View, Calif.). The synthesis and use of such modified RNAs for in vitro and in vivo transfection are described in, e.g., WO 2011/130624, and WO/2012/138453.

Polypeptides

In some embodiments a CIS inhibitor is a polypeptide, which may inhibit CIS activity by at least one of a number of different mechanisms, e.g., specifically binding to CIS or a CIS binding partner thereby reducing interaction of CIS and the binding partner, or, alternatively, competing with CIS for interaction with a binding partner.

Antibodies

In some embodiments a CIS inhibitor is an antibody or CIS-binding fragment thereof that binds to CIS and inhibits its interaction with binding partners or target proteins. Preferably, the antibody is an antibody modified to penetrate or be taken up (passively or actively) in mammalian cells, and particularly NK cells.

The term "antibody" as used herein includes polyclonal antibodies, monoclonal antibodies, bispecific antibodies, fusion diabodies, triabodies, heteroconjugate antibodies, and chimeric antibodies. Also contemplated are antibody fragments that retain at least substantial (about 10%) antigen binding relative to the corresponding full length antibody. Such antibody fragments are referred to herein as "antigen-binding fragments". Antibodies include modifications in a variety of forms including, for example, but not limited to, domain antibodies including either the VH or VL domain, a dimer of the heavy chain variable region (VHH, as described for a camelid), a dimer of the light chain variable region (VLL), Fv fragments containing only the light (VL) and heavy chain (VH) variable regions which may be joined directly or through a linker, or Fd fragments containing the heavy chain variable region and the CH1 domain.

A scFv consisting of the variable regions of the heavy and light chains linked together to form a single-chain antibody and oligomers of says such as diabodies and triabodies are also encompassed by the term "antibody". Also encompassed are fragments of antibodies such as Fab, (Fab')2 and FabFc2 fragments which contain the variable regions and parts of the constant regions. Complementarity determining region (CDR)-grafted antibody fragments and oligomers of antibody fragments are also encompassed. The heavy and light chain components of an Fv may be derived from the same antibody or different antibodies thereby producing a chimeric Fv region. The antibody may be of animal (for example mouse, rabbit or rat) or human origin or may be chimeric or humanize.

As used herein the term "antibody" includes these various forms. Using the guidelines provided herein and those methods well known to those skilled in the art which are described in the references cited above and in such publications as Harlow & Lane, Antibodies: a Laboratory Manual, Cold Spring Harbor Laboratory, (1988) the antibodies for use in the methods of the present invention can be readily made.

The antibodies may be Fv regions comprising a variable light (VL) and a variable heavy (VH) chain in which the light and heavy chains may be joined directly or through a linker. As used herein a linker refers to a molecule that is covalently linked to the light and heavy chain and provides enough spacing and flexibility between the two chains such that they are able to achieve a conformation in which they are capable of specifically binding the epitope to which they are directed. Protein linkers are particularly preferred as they may be expressed as an intrinsic component of the Ig portion of the fusion polypeptide.

In another embodiment, recombinantly produced single chain scFv antibody, preferably a humanized scFv, is used in the methods of the invention.

In one embodiment, the antibodies have the capacity for intracellular transmission. Antibodies which have the capacity for intracellular transmission include antibodies such as camelids and llama antibodies, shark antibodies (IgNARs), scFv antibodies, intrabodies or nanobodies, for example, scFv intrabodies and VHH intrabodies. Yeast SPLINT antibody libraries are available for testing for intrabodies which are able to disrupt protein-protein interactions. Such agents may comprise a cell-penetrating peptide sequence or nuclear-localizing peptide sequence such as those disclosed in Constantini et al. (2008). Also useful for in vivo delivery are Vectocell or Diato peptide vectors such as those disclosed in De Coupade et al. (2005).

In addition, the antibodies may be fused to a cell penetrating agent, for example a cell-penetrating peptide. Cell penetrating peptides include Tat peptides, Penetratin, short amphipathic peptides such as those from the Pep- and MPG-families, oligoarginine and oligolysine. In one example, the cell penetrating peptide is also conjugated to a lipid (C6-C18 fatty acid) domain to improve intracellular delivery (Koppelhus et al., 2008). Examples of cell penetrating peptides can be found in Howl et al. (2007) and Deshayes et al. (2008). Thus, the invention also provides the therapeutic use of antibodies fused via a covalent bond (e.g. a peptide bond), at optionally the N-terminus or the C-terminus, to a cell-penetrating peptide sequence.

Antibodies which target CIS are available from various sources such as Santa Cruz Biotechnology (e.g., Cat. No. sc-74581).

CIS-Inhibited NK Cells

Any CIS inhibitor suitable for inhibition of CIS in NK cells, ex vivo, e.g., in cultured NK cells to obtain CIS-inhibited NK cells, can be used for adoptive cell therapy for an NK-responsive condition. In some embodiments, the CIS-inhibited NK cells to be administered are autologous, i.e., derived from a subject to be treated. In other embodiments the CIS-inhibited NK cells to be administered are allogeneic NK cells.

In some embodiments, CIS-inhibited NK cells are NK cells genetically modified to have reduced expression of CIS. For example, in some embodiments CIS-inhibited NK cells are obtained by transient or stable transfection or viral transduction of a CIS shRNA or a CIS antisense expression vector, which, when expressed, reduces the expression level of CIS in the genetically modified cells. In other embodiments CIS-inhibited NK cells are genetically modified NK cells in which one or both Cish alleles have been inactivated by a targeted genomic modification, e.g., by deletion of one or more exons, introduction of a stop codon, or inactivation of the promoter. Methods for modification of genomic loci in both cell lines and primary cells are well established in the art. For example, programmable nucleases, e.g., the Cas9-CRISPR system is very efficient and routinely used for targeted disruption of genes.

In other embodiments NK cells are contacted ex vivo with a CIS inhibitor, e.g., a peptide, a peptidomimetic, a polynucleotide, or a polypeptide.

NK cells can be obtained by any of a number of different methods including isolation and expansion of NK cells from a primary source, differentiation and expansion from hematopoietic stem cells (HSCs), differentiation and expansion from human induced pluripotent stem cells (hiPSCs), or differentiation from another pluripotent stem cell type.

In some embodiments NK cells are isolated from a human subject, e.g., a patient to be treated in the case of autologous adoptive cell therapy.

NK cells can be isolated or enriched by staining cells from a tissue source, e.g., peripheral blood, with antibodies to CD56 and CD3, and selecting for CD56$^+$CD3$^-$ cells. TSNK cells can be isolated using a commercially available kit, for example, the NK Cell Isolation Kit (Miltenyi Biotec). NK cells can also be isolated or enriched by removal of cells other than NK cells in a population of cells that comprise the NK cells. For example, NK cells may be isolated or enriched by depletion of cells displaying non-NK cell markers using, e.g., antibodies to one or more of CD3, CD4, CD14, CD19, CD20, CD36, CD66b, CD123, HLA DR and/or CD235a (glycophorin A). Negative isolation can be carried out using a commercially available kit, e.g., the NK Cell Negative Isolation Kit (Dynal). Cells isolated by these methods may be additionally sorted, e.g., to separate CD56$^+$/CD16$^-$ and CD56$^-$/CD16$^+$ cells.

Cell separation can be accomplished by, e.g., flow cytometry, fluorescence-activated cell sorting (FACS), or, preferably, magnetic cell sorting using microbeads conjugated with specific antibodies. The cells may be isolated, e.g., using a magnetic activated cell sorting (MACS) technique, a method for separating particles based on their ability to bind magnetic beads (e.g., about 0.5-100 μm diameter) that comprise one or more specific antibodies, e.g., anti-CD56 antibodies. Magnetic cell separation can be performed and automated using, e.g., an AUTOMACS™. Separator (Miltenyi). A variety of useful modifications can be performed on the magnetic microspheres, including covalent addition of antibody that specifically recognizes a particular cell surface molecule or hapten. The beads are then mixed with the cells to allow binding. Cells are then passed through a magnetic field to separate out cells having the specific cell surface marker. In one embodiment, these cells can then isolated and re-mixed with magnetic beads coupled to an antibody against additional cell surface markers. The cells are again passed through a magnetic field, isolating cells that bound both the antibodies. Such cells can then be diluted into separate dishes, such as microtiter dishes for clonal isolation.

Differentiation of human NK cells from HSCs is described in, e.g., U.S. Pat. No. 8,926,964, and from hiPSCs in U.S. 20130287751.

Methods for culturing and expanding NK cells, particularly human NK cells to obtain clinical grade NK cells for adoptive cell therapy are described in the art, as reviewed in, e.g., Childs et al. (2013).

Administration of CIS Inhibitors

In some embodiments, a method for treating a subject suffering from a NK-responsive condition or preventing such a condition, includes administration of a pharmaceutical composition containing at least one CIS inhibitor, or a pharmaceutically acceptable salt, pharmaceutically acceptable N-oxide, pharmaceutically active metabolite, pharmaceutically acceptable prodrug, or pharmaceutically acceptable solvate thereof, in therapeutically effective amounts to said subject.

A CIS inhibitor, is administered to prevent, cure or at least partially arrest the symptoms of a patient already suffering from and/or diagnosed as having a NK-responsive condition, e.g., a cancer or an infection. Amounts effective for this use will depend on the severity and course of the infection, previous therapy, the patient's health status, weight, response to the treatment, and the infectious agent's resistance to treatment. It is considered well within the skill of the art for one to determine such therapeutically effective amounts by routine experimentation (including, but not limited to, a dose escalation clinical trial).

In prophylactic applications, compositions containing a CIS inhibitor are administered to a patient susceptible to or otherwise at risk of developing an NK-responsive condition, e.g., a cancer or an infection, for example, in the case of an individual who is immunocompromised (for prevention of infection) or highly susceptible, based on a genotype, to a particular type of cancer. Such an amount is defined to be a "prophylactically effective amount or dose" i.e., a dose sufficient to prevent or reduce the onset of infection. In this use, the precise amounts also depend on the particular condition, the patient's state of health, weight, timing, etc. It is considered well within the skill of the art for one to determine such prophylactically effective amounts by routine experimentation (e.g., a dose escalation clinical trial).

In a case where a subject's status does improve, upon reliable medical advice, the administration of a CIS inhibitor may be given continuously; alternatively, the dose of drug being administered may be temporarily reduced or temporarily suspended for a certain length of time (i.e., a "drug holiday"). The length of the drug holiday can vary between 2 days and 1 year, including by way of example only, 2 days, 3 days, 4 days, 5 days, 6 days, 7 days, 10 days, 12 days, 15 days, 20 days, 28 days, 35 days, 50 days, or 60 days. The dose reduction during a drug holiday may be from 10%-100%, including, by way of example only, 10%, 15%, 20%, 25%, 30%, 35%, 40%, 45%, 50%, 55%, 60%, 65%, 70%, 75%, 80%, 85%, 90%, 95%, or 100%.

The amount of a given CIS inhibitor that will be suitable as a therapeutically effective dose will vary depending upon factors such as the type and potency of the CIS inhibitor to be administered, the severity/stage of the subject's health condition, the characteristics (e.g., weight) of the subject or host in need of treatment, and prior or concurrent treatments, but can nevertheless be routinely determined in a manner known in the art according to the particular circumstances surrounding the case, including, e.g., the specific agent being administered, the route of administration, the condition being treated, and the subject or host being treated. In general, however, doses employed for adult human treatment will typically be in the range of 0.02-5000 mg per day, or from about 1-1500 mg per day. The desired dose may conveniently be presented in a single dose or as divided doses administered simultaneously (or over a short period of time) or at appropriate intervals, for example as two, three, four or more sub-doses per day.

The foregoing ranges are merely suggestive, as the number of variables in regard to an individual treatment regime is large, and considerable excursions from these recommended values are not uncommon. Such dosages may be altered depending on a number of variables, not limited to the activity of the CIS inhibitor to be used, the type and severity of NK cell-responsive condition to be treated, the mode of administration, and the judgment of the practitioner.

Toxicity and therapeutic efficacy of such therapeutic regimens can be determined by standard pharmaceutical procedures in cell cultures or experimental animals, including, but not limited to, the determination of the $LD_{50}$ (the dose lethal to 50% of the population) and the $ED_{50}$ (the dose therapeutically effective in 50% of the population). The dose ratio between the toxic and therapeutic effects is the therapeutic index and it can be expressed as the ratio between $LD_{50}$ and $ED_{50}$. CIS inhibitors exhibiting high therapeutic indices are preferred. The data obtained from cell culture assays and animal studies can be used in formulating a range of dosage for use in human and non-human subjects. The dosage of such compounds lies preferably within a range of circulating concentrations that include the $ED_{50}$ with minimal toxicity. The dosage may vary within this range depending upon the dosage form employed and the route of administration utilized.

Administration of CIS-Inhibited NK Cells

NK-inhibited cells can be administered by any suitable route as known in the art. In some embodiments the cells are administered systemically as an intra-arterial or intravenous infusion. One skilled in the art will appreciate that the selected route of administration of CIS-inhibited NK cells will depend in part on the particular NK-responsive condition to be treated. For example, where the subject suffers from the presence of one or more tumours, in some embodiments, the route administration will include intratumoral administration and/or peritumoral administration. Other exemplary routes of administration include intraperitoneal, intrathecal and intralymphatic.

CIS-inhibited NK cells can be administered to an individual, in any amount or number that results in a detectable therapeutic or prophylactic benefit to the individual, e.g., an effective amount, wherein the individual has a cancer or a viral infection. In some embodiments the dose of CIS-inhibited cells to be administered is simply an absolute numbers of cells, e.g., said individual can be administered about $1\times10^5$ cells, $5\times10^5$ cells, $1\times10^6$ cells, $7\times10^6$ cells, $1\times10^7$ cells, $6\times10^7$ cells, $2\times10^8$ cells, $5\times10^8$ cells, $1\times10^9$ cells, $6\times10^9$ cells, $2\times10^{10}$ cells, $5\times10^{10}$ cells, or $1\times10^{11}$ cells.

In other embodiments, CIS-inhibited NK cells are administered to a subject by a numbers of cells relative to the weight of the subject to be treated, e.g., at about, $1\times10^5$ cells, $5\times10^5$ cells, $1\times10^6$ cells, $7\times10^6$ cells, $1\times10^7$ cells, $6\times10^7$ cells, $2\times10^8$ cells, $5\times10^8$ cells, $1\times10^9$ cells, or $6\times10^9$ cells per kilogram of the subject to be treated.

In other embodiments, where the subject to be treated suffers from one or more tumours, CIS-inhibited NK cells are administered based on an approximate desired ratio of CIS-inhibited NK cells to an approximated number of tumor cells in the subject to be treated. For example, CIS-inhibited NK cells can be administered in a ratio (NK cells to tumour cells) of about 1:1, 1:1, 3:1, 4:1, 5:1, 9:1, 10:1, 15:125:1, 30:1, 40:1, 50:1, 55:1, 60:1, 65:1, 75:1, 80:1, 90:1, 95:1 or 100:1. Tumour cell numbers can be estimated by, e.g., determining the number of tumour cells in a tissue sample, e.g., a blood sample, biopsy, or the like. In some embodiments, e.g., for solid tumors, tumor cell number estimation can be done by a combination of cell counting in biopsies and tumour imaging to estimate tumor volume and resident cell number.

Combination Treatments

CIS inhibitors and CIS-inhibited NK cell compositions can also be used in combination with other agents of therapeutic value in the treatment of NK-responsive health conditions, e.g., cancer and viral infections. In general, other agents do not necessarily have to be administered in the same pharmaceutical composition, and may, because of different physical and chemical characteristics, preferably be administered by different routes. The determination of the mode of administration and the advisability of administration, where possible, in the same pharmaceutical composition, is well within the knowledge of the skilled clinician. The initial administration can be made according to established protocols known in the art, and then, based upon the observed effects, the dosage, modes of administration and times of administration can be modified by the skilled clinician.

A CIS inhibitor and an additional therapeutic agent may be administered concurrently (e.g., simultaneously, essentially simultaneously or within the same treatment protocol) or sequentially, depending upon the nature and phase of the infection, the condition of the patient, and the actual choice of therapeutic agents used. The determination of the order of administration, and the number of repetitions of administration of each therapeutic agent during a treatment protocol, is well within the knowledge of the skilled physician after evaluation of the disease being treated and the condition of the patient.

It is known to those of skill in the art that therapeutically-effective dosages can vary when the drugs are used in treatment combinations. Methods for experimentally determining therapeutically-effective dosages of drugs and other agents for use in combination treatment regimens are described in the literature. For example, the use of metronomic dosing, i.e., providing more frequent, lower doses in order to minimize toxic side effects, has been described extensively in the literature. Combination treatment further includes periodic treatments that start and stop at various times to assist with the clinical management of the patient.

For combination therapies, dosages of co-administered therapeutic agents will of course vary depending on the type of co-agents employed, on the specific CIS inhibitor, and NK cell-responsive condition to be treated.

It is understood that the dosage regimen to treat, prevent, or ameliorate the condition(s) for which relief is sought, can be modified in accordance with a variety of factors. These factors include the condition from which the subject suffers, as well as the age, weight, sex, diet, and general medical condition of the subject. Thus, the dosage regimen actually employed can vary widely and therefore can deviate from the dosage regimens set forth herein.

The CIS inhibitor and additional therapeutic agent which make up a combination therapy disclosed herein may be a combined dosage form or in separate dosage forms intended for substantially simultaneous administration. The pharmaceutical agents that make up the combination therapy may also be administered sequentially, with either therapeutic compound being administered by a regimen calling for two-step administration. The two-step administration regimen may call for sequential administration of the active agents or spaced-apart administration of the separate active agents. The time period between the multiple administration steps may range from, a few minutes to several hours, depending upon the properties of each pharmaceutical agent, such as potency, solubility, bioavailability, plasma half-life and kinetic profile of the pharmaceutical agent. Circadian variation of various physiological parameters may also be evaluated to determine the optimal dose interval.

In addition, administration or co-administration of a CIS inhibitor for treatment of an infection may be used in combination with procedures that may provide additional or synergistic benefit to the patient. By way of example only, patients may undergo genetic testing to identify genetic variation in their own genome or a pathogen's genome so as to optimize treatment parameters, e.g., the type of CIS inhibitor to be administered, dosing regimen, and co-administration with additional therapeutic agents.

Initial administration can be via any route practical, such as, for example, an intravenous injection, a bolus injection, infusion over 5 minutes to about 5 hours, a pill, a capsule, inhaler, injection, transdermal patch, buccal delivery, and the like, or combination thereof. A compound should be administered as soon as is practicable after the onset of a disease or condition is detected or suspected, and for a length of time necessary for the treatment or prevention of the NK cell-responsive condition.

Optionally, the subject may also be administered IL-15 or an IL-15 agonist at a dose that is therapeutically effective when combined with treatment using a CIS inhibitor. IL-15 agonists include functional homologs of IL-15 such as those described in, e.g., Wu (2013). In other embodiments any of the treatments of the invention may further include administration of one or more immunotherapeutic agents. Immunotherapeutic agents suitable for use in combination with CIS inhibition or CIS inhibition in combination with IL-15 or an IL-15 agonist can include, but are not limited to, an antibody against the programmed cell death 1 receptor (PD-1), an antibody against the programmed death-ligand 1 (PD-L1), an antibody against cytotoxic T-lymphocyte-associated protein 4 (CTLA-4), an antibody against transforming growth factor beta (TGF-b), an antibody against Tactile (CD96), or a combination thereof.

In further embodiments In other embodiments any of the treatments of the invention may further include administration of a B-Raf protein kinase inhibitor or a MEK protein kinase inhibitor. Examples of B-Raf protein kinase inhibitors include, but are not limited to, PLX4032 (Vemurafenib), PLX-4720, Dabrafenib (GSK2118436), AZ628, RAF265 (CHIR-265), Encorafenib (LGX818), SB590885, and combinations thereof. Examples of MEK protein kinase inhibitors include, but are not limited to, Trametinib (GSK1120212), Cobimetinib, Binimetinib (MEK162), Selumetinib (PD-325901), combinations thereof. In some embodiments, any of the above treatments may further include administration of a TGF-beta receptor antagonist. Examples of suitable TGF-beta receptor antagonists include, but are not limited to, Galunisertib (LY2157299), GW 788388, LY 364947, 8268712, SB 525334, and SD208.

Dosage Forms

Compositions useful for the invention can be formulated for administration to a subject via any conventional means including, but not limited to, oral, parenteral (e.g., intravenous, subcutaneous, or intramuscular), buccal, inhalation, intranasal, rectal or transdermal administration routes.

The pharmaceutical compositions which include a CIS inhibitor (e.g., a peptidomimetic) alone or in combination with one or more other therapeutic agents, can be formulated into any suitable dosage form, including but not limited to, aqueous oral dispersions, liquids, mists, gels, syrups, elixirs, slurries, suspensions and the like, for oral ingestion by a patient to be treated, solid oral dosage forms, aerosols, controlled release formulations, fast melt formulations, effervescent formulations, lyophilized formulations, tablets, powders, pills, dragees, capsules, delayed release formulations, extended release formulations, pulsatile release formulations, multiparticulate formulations, and mixed immediate release and controlled release formulations.

Pharmaceutical preparations for oral use can be obtained by mixing one or more solid excipient with one or more of the compounds, optionally grinding the resulting mixture, and processing the mixture of granules, after adding suitable auxiliaries, if desired, to obtain tablets or dragee cores. Suitable excipients include, for example, fillers such as sugars, including lactose, sucrose, mannitol, or sorbitol; cellulose preparations such as, for example, maize starch, wheat starch, rice starch, potato starch, gelatin, gum tragacanth, methylcellulose, microcrystalline cellulose, hydroxypropylmethylcellulose, sodium carboxymethylcellulose; or others such as: polyvinylpyrrolidone (PVP or povidone) or calcium phosphate. If desired, disintegrating agents may be added, such as the cross-linked croscarmellose sodium, polyvinylpyrrolidone, agar, or alginic acid or a salt thereof such as sodium alginate.

In another aspect, dosage forms may include microencapsulated formulations. In some embodiments, one or more other compatible materials are present in the microencapsulation material. Exemplary materials include, but are not limited to, pH modifiers, erosion facilitators, anti-foaming agents, antioxidants, flavoring agents, and carrier materials such as binders, suspending agents, disintegration agents, filling agents, surfactants, solubilizers, stabilizers, lubricants, wetting agents, and diluents.

Microencapsulated formulations of a CIS inhibitor may be formulated by methods known by one of ordinary skill in the art. Such known methods include, e.g., spray drying processes, spinning disk-solvent processes, hot melt processes, spray chilling methods, fluidized bed, electrostatic deposition, centrifugal extrusion, rotational suspension separation, polymerization at liquid-gas or solid-gas interface, pressure extrusion, or spraying solvent extraction bath. In addition to these, several chemical techniques, e.g., complex coacervation, solvent evaporation, polymer-polymer incompatibility, interfacial polymerization in liquid media, in situ polymerization, in-liquid drying, and desolvation in liquid media could also be used. Furthermore, other methods such as roller compaction, extrusion/spheronization, coacervation, or nanoparticle coating may also be used.

The pharmaceutical solid oral dosage forms including formulations can be further formulated to provide a controlled release of the CIS inhibitor. Controlled release refers to the release of one or more active agents from a dosage form in which they are incorporated according to a desired profile over an extended period of time. Controlled release profiles include, for example, sustained release, prolonged release, pulsatile release, and delayed release profiles. In contrast to immediate release compositions, controlled release compositions allow delivery of an agent to a subject over an extended period of time according to a predetermined profile. Such release rates can provide therapeutically effective levels of agent for an extended period of time and thereby provide a longer period of pharmacologic response while minimizing side effects as compared to conventional rapid release dosage forms. Such longer periods of response provide for many inherent benefits that are not achieved with the corresponding short acting, immediate release preparations.

In some embodiments, the solid dosage forms can be formulated as enteric coated delayed release oral dosage forms, i.e., as an oral dosage form of a pharmaceutical composition which utilizes an enteric coating to affect release in the small intestine of the gastrointestinal tract. The enteric coated dosage form may be a compressed or molded or extruded tablet/mold (coated or uncoated) containing granules, powder, pellets, beads or particles of the active ingredient and/or other composition components, which are themselves coated or uncoated. The enteric coated oral dosage form may also be a capsule (coated or uncoated) containing pellets, beads or granules of the solid carrier or the composition, which are themselves coated or uncoated.

The term "delayed release" as used herein refers to the delivery so that the release can be accomplished at some generally predictable location in the intestinal tract more distal to that which would have been accomplished if there had been no delayed release alterations. In some embodiments the method for delay of release is coating. Any coatings should be applied to a sufficient thickness such that the entire coating does not dissolve in the gastrointestinal fluids at pH below about 5, but does dissolve at pH about 5 and above. It is expected that any anionic polymer exhibiting a pH-dependent solubility profile can be used as an enteric coating in the methods and compositions to achieve delivery to the lower gastrointestinal tract. In some embodiments the polymers are anionic carboxylic polymers.

In some embodiments, the coating can, and usually does, contain a plasticizer and possibly other coating excipients such as colorants, talc, and/or magnesium stearate, which are well known in the art. Suitable plasticizers include triethyl citrate (Citroflex 2), triacetin (glyceryl triacetate), acetyl triethyl citrate (Citroflec A2), Carbowax 400 (polyethylene glycol 400), diethyl phthalate, tributyl citrate, acetylated monoglycerides, glycerol, fatty acid esters, propylene glycol, and dibutyl phthalate. In particular, anionic carboxylic acrylic polymers usually will contain 10-25% by weight of a plasticizer, especially dibutyl phthalate, polyethylene glycol, triethyl citrate and triacetin. Conventional coating techniques such as spray or pan coating are employed to apply coatings. The coating thickness must be sufficient to ensure that the oral dosage form remains intact until the desired site of topical delivery in the intestinal tract is reached.

Colorants, detackifiers, surfactants, antifoaming agents, lubricants (e.g., carnuba wax or PEG) may be added to the coatings besides plasticizers to solubilize or disperse the coating material, and to improve coating performance and the coated product.

In other embodiments, the CIS inhibitor formulations are delivered using a pulsatile dosage form. A pulsatile dosage form is capable of providing one or more immediate release pulses at predetermined time points after a controlled lag time or at specific sites. Pulsatile dosage forms may be administered using a variety of pulsatile formulations known in the art. For example, such formulations include, but are not limited to, those described in U.S. Pat. Nos. 5,011,692, 5,017,381, 5,229,135, and 5,840,329. Other pulsatile release dosage forms suitable for use with the present formulations include, but are not limited to, for example, U.S. Pat. Nos. 4,871,549, 5,260,068, 5,260,069, 5,508,040, 5,567,441 and 5,837,284. In one embodiment, the controlled release dosage form is pulsatile release solid oral dosage form including at least two groups of particles, (i.e. multiparticulate) each containing a formulation. The first group of particles provides a substantially immediate dose of the CIS inhibitor upon ingestion. The first group of particles can be either uncoated or include a coating and/or sealant. The second group of particles includes coated particles, which includes from about 2% to about 75%, from about 2.5% to about 70%, or from about 40% to about 70%, by weight of the total dose of the active agents in the formulation, in admixture with one or more binders. The coating includes a pharmaceutically acceptable ingredient in an amount sufficient to provide a delay of from about 2 hours to about 7 hours following ingestion before release of the second dose. Suitable coatings include one or more differentially degradable coatings such as, by way of example only, pH sensitive coatings (enteric coatings) such as acrylic resins either alone or blended with cellulose derivatives, e.g., ethylcellulose, or non-enteric coatings having variable thickness to provide differential release of the formulation.

Many other types of controlled release systems known to those of ordinary skill in the art and are suitable for use with the formulations. Examples of such delivery systems include, e.g., polymer-based systems, such as polylactic and polyglycolic acid, plyanhydrides and polycaprolactone; porous matrices, nonpolymer-based systems that are lipids, including sterols, such as cholesterol, cholesterol esters and fatty acids, or neutral fats, such as mono-, di- and triglycerides; hydrogel release systems; silastic systems; peptide-based systems; wax coatings, bioerodible dosage forms, compressed tablets using conventional binders and the like. See, e.g., U.S. Pat. Nos. 4,327,725, 4,624,848, 4,968,509, 5,461,140, 5,456,923, 5,516,527, 5,622,721, 5,686,105, 5,700,410, 5,977,175, 6,465,014 and 6,932,983.

Liquid formulation dosage forms for oral administration can be aqueous suspensions selected from the group including, but not limited to, pharmaceutically acceptable aqueous oral dispersions, emulsions, solutions, elixirs, gels, and syrups.

The aqueous suspensions and dispersions can remain in a homogenous state, as defined in The USP Pharmacists' Pharmacopeia (2005 edition, chapter 905), for at least 4 hours. The homogeneity should be determined by a sampling method consistent with regard to determining homogeneity of the entire composition. In one embodiment, an aqueous suspension can be re-suspended into a homogenous suspension by physical agitation lasting less than 1 minute. In another embodiment, an aqueous suspension can be re-suspended into a homogenous suspension by physical agitation lasting less than 45 seconds. In yet another embodiment, an aqueous suspension can be re-suspended into a homogenous suspension by physical agitation lasting less than 30 seconds. In still another embodiment, no agitation is necessary to maintain a homogeneous aqueous dispersion.

In addition to the additives listed above, the liquid formulations can also include inert diluents commonly used in the art, such as water or other solvents, solubilizing agents, and emulsifiers. Exemplary emulsifiers are ethyl alcohol, isopropyl alcohol, ethyl carbonate, ethyl acetate, benzyl alcohol, benzyl benzoate, propyleneglycol, 1,3-butylenegly-col, dimethylformamide, sodium lauryl sulfate, sodium docusate, cholesterol, cholesterol esters, taurocholic acid, phosphotidylcholine, oils, such as cottonseed oil, groundnut oil, corn germ oil, olive oil, castor oil, and sesame oil, glycerol, tetrahydrofurfuryl alcohol, polyethylene glycols, fatty acid esters of sorbitan, or mixtures of these substances, and the like.

Injectable Formulations

Formulations suitable for intramuscular, subcutaneous, or intravenous injection may include physiologically acceptable sterile aqueous or non-aqueous solutions, dispersions, suspensions or emulsions, and sterile powders for reconstitution into sterile injectable solutions or dispersions. Examples of suitable aqueous and non-aqueous carriers, diluents, solvents, or vehicles including water, ethanol, polyols (propyleneglycol, polyethylene-glycol, glycerol, cremophor and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions, and by the use of surfactants. Formulations suitable for subcutaneous injection may also contain additives such as preserving, wetting, emulsifying, and dispensing agents. Prevention of the growth of microorganisms can be ensured by various antibacterial and antifungal agents, such as parabens, chlorobutanol, phenol, sorbic acid, and the like. It may also be desirable to include isotonic agents, such as sugars, sodium chloride, and the like. Prolonged absorption of the injectable pharmaceutical form can be brought about by the use of agents delaying absorption, such as aluminum monostearate and gelatin.

For intravenous injections, compounds may be formulated in aqueous solutions, preferably in physiologically compatible buffers such as Hank's solution, Ringer's solution, or physiological saline buffer. For transmucosal administration, penetrants appropriate to the barrier to be permeated are used in the formulation. Such penetrants are generally known in the art. For other parenteral injections, appropriate formulations may include aqueous or nonaqueous solutions, preferably with physiologically compatible buffers or excipients. Such excipients are generally known in the art.

Parenteral injections may involve bolus injection or continuous infusion. Formulations for injection may be presented in unit dosage form, e.g., in ampoules or in multi-dose containers, with an added preservative. The pharmaceutical composition may be in a form suitable for parenteral injection as a sterile suspensions, solutions or emulsions in oily or aqueous vehicles, and may contain formulatory agents such as suspending, stabilizing and/or dispersing agents. Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions. Alternatively, the active ingredient may be in powder form for constitution with a suitable vehicle, e.g., sterile pyrogen-free water, before use.

The pharmaceutical compositions may be in unit dosage forms suitable for single administration of precise dosages. In unit dosage form, the formulation is divided into unit doses containing appropriate quantities of one or more compound. The unit dosage may be in the form of a package containing discrete quantities of the formulation. Non-limiting examples are packaged tablets or capsules, and powders in vials or ampoules. Aqueous suspension compositions can be packaged in single-dose non-reclosable containers. Alternatively, multiple-dose reclosable containers can be used, in which case it is typical to include a preservative in the composition. By way of example only, formulations for parenteral injection may be presented in unit dosage form, which include, but are not limited to ampoules, or in multi-dose containers, with an added preservative.

Methods for Identifying a CIS Inhibitor

Also provided are methods for identifying a CIS inhibitor, i.e., "screening" methods." In some embodiments, a screening method includes, at least, the following steps: (i) contacting CIS or a fragment thereof with at least one CIS binding partner in the presence of a test agent; and (ii) determining whether the test agent competes with the CIS protein binding partner for binding to CIS or the fragment thereof. In some embodiments the CIS binding partner used in the assay is selected from among JAK1, Elongin B, Elongin C and Cullin5 or a fragment thereof.

In some embodiments, the method is carried out in vitro using substantially purified protein components. In other embodiments such methods can be carried out on protein components expressed either natively or heterologously in cells. In some embodiments, one or more of the protein components can also include a tag to facilitate detection of the tagged protein in the assay, e.g., a small epitope tag, a fused fluorescent protein, a fluorophore, or any other label that facilitates direct or indirect detection (e.g., by use of an antibody) of the tagged protein. In other embodiments none of the proteins to be assayed are tagged.

Methods for identifying CIS inhibitors that inhibit its interaction with binding partners and target proteins include, but are not limited to, ELISA-type assays, fluorescent resonance energy transfer (FRET) and time-resolved (TR) FRET assays, and AlphaScreen™ bead-based interactions, chemical cross-linking followed by High-Mass MALDI mass spectrometry (see, e.g. Arkin et al. (2012), *Inhibition of Protein-Protein Interactions: Non-Cellular Assay Formats*; Sittampalam et al eds.; Assay Guidance Manual [Internet]. Bethesda (Md.): Eli Lilly & Company and the National Center for Advancing Translational Sciences). Particularly useful are high throughput assay formats for screening large test agent libraries of suitable test agents.

Alternatively screening for inhibitors of protein-protein interactions can be carried out in cells, e.g., in protein complementation assays, and "two hybrid" "three hybrid") assays using yeast, bacterial, or mammalian assay systems. Such assays and their application to the discovery of protein-protein interaction inhibitors is described in the art, e.g., in Male et al. (2013).

In other embodiments a screening methods includes the steps of: (i) contacting CIS or a fragment thereof with a test agent; and (ii) determining whether the test agent binds to CIS or the fragment thereof. In some embodiments this method further comprises determining if the test agent competes with a CIS PEST domain peptide or CIS N-terminal peptide for binding to CIS or the fragment thereof. While not wishing to be bound by theory, it is believed that such peptides correspond to autoinhibitory domains in CIS. Thus, test agents that can compete with such autoinhibitory peptides for binding to CIS may be expected to also inhibit CIS activity, e.g., resulting in increased JAK kinase activity as described herein. In some embodiments the sequence of a CIS PEST domain peptide to be used in the above assay is selected from the group consisting of SEQ ID NO:29, SEQ ID NO:30, SEQ ID NO:32, and SEQ ID NO:37. In other embodiments the sequence of the N-terminal domain peptide to be used in this assay is selected from among SEQ ID NOs:31 and 34. A number of assays for detecting binding of an analyte to a target protein are known in the art, which include, but are not limited to, optical biosensor assays (e.g., based on surface plasmon resonance, optical gradients, or interferometry), mass spectrometry, isothermal calorimetry, differential scanning calorimeter, and differential scanning fluorimetry, NMR, X-ray crystallography. High throughput affinity-based assays for identification of protein-binding compounds are reviewed in, e.g., Zhu et al. (2009). Also contemplated is the use of small molecule microarrays as described in, e.g., Casalena et al. (2012). Optical or fluorescent detection, such as, for example, fluorescence-activated cell sorting (FACS), using mass spectrometry, MALDI-TOF, biosensor technology, evanescent fiber optics, or fluorescence resonance energy transfer, is clearly encompassed by the present invention.

Screening methods based on monitoring the effect of a test agent on CIS activity to be assessed in vitro are also contemplated. In some embodiments the screening is an in vitro biochemical assay that assesses the effect of a test agent on the ability of CIS to increase ubiquitination of a target protein (e.g., JAK1), where the assay includes the steps of:
  (i) incubating phosphorylated JAK1 protein (e.g., Tyr1034-phosphorylated JAK1) or a CIS-binding fragment thereof, in vitro, in the presence of:
    (a) a trimeric complex comprising CIS or a fragment thereof comprising at least the SH2 domain and SOCS box; Elongin B, and Elongin C;
    (b) a ubiquitination mixture; and
    (c) a test agent; and
  (ii) determining whether the test agent inhibits CIS-induced ubiquitination of the phosphorylated JAK1 protein or CIS-binding fragment thereof relative to the level of CIS-induced ubiquitination in the absence of the test agent. A test agent that decreases CIS-dependent ubiquitination of JAK1 or the fragment is considered a candidate CIS inhibitor.

In an exemplary embodiment the CIS E3 ligase complex (trimeric CIS-Elongin B-Elongin-C together with Cullin5 and Rbx2; 2.5 µM) is incubated with ubiquitin (50 µM), human E1 (100 nM), purified recombinant E2 (UbcH5c, 2.5 µM) and flag-tagged full-length JAK1 in the presence of 2.5 mM Mg/ATP at 37° C. for varying times. FLAG-tagged phospho-JAK1 is generated by expression in 293T cells and recovered using anti-FLAG immunoprecipitation and elution with free FLAG peptide. JAK1 ubiquitination is visualised by Western blotting with anti-phosphorylated JAK1 following separation on 4-20% Tris/Glycine gels. High throughput format screens for modulators of E3 ligase activity have been described in the art, e.g., in Rossi et al. (2014), and such screening platforms are also commercially available, e.g., the UbiPro™ Drug Discovery platform from ProGenra, Inc. (Malvern, Pa., USA).

In other embodiments the screening method for identifying a CIS inhibitor is an in vitro biochemical assay that assesses the effect of a test agent on the ability of CIS to inhibit JAK1 kinase activity, where the assay includes the steps of:
  i) incubating JAK1 protein or a or a fragment thereof comprising the JH1 kinase domain, in vitro, in the presence of:
    (a) a trimeric complex comprising CIS or a fragment thereof comprising at least the SH2 domain and SOCS box; Elongin B, and Elongin C;
    (b) a JAK1 kinase substrate; and
    (c) a test agent; and
  ii) determining whether the test agent increases phosphorylation of the JAK1 kinase substrate relative to phosphorylation of the JAK1 kinase substrate in the absence of the test agent. A test agent that decreases CIS-dependent inhibition of JAK1 kinase activity, i.e, increases JAK1 kinase activity relative to JAK1 kinase activity in the absence of the test agent is considered a candidate CIS inhibitor.

In some embodiments the JAK1 kinase substrate to be tested is STAT5 or a STAT5 peptide. In some embodiments the amino acid sequence of a STAT5 peptide substrate to be used is: SEQ ID NO:18 RRAKAADGYVKPQIKQVV.

Protein kinase assays, including high throughput kinase assays are known in the art as described in, e.g., in Babon et al. (2013) and Von Ahsen et al. (2005). In one exemplary embodiment 130 µM STAT5b peptide (SEQ ID NO:18 RRAKAADGYVKPQIKQVV) is incubated with 5 nM human JAK1 (see SEQ ID NO:11 for corresponding amino acid sequence) at 25° C. for 30-60 min in 20 mM Tris pH 8.0, 100 mM NaCl, 5 mM 2-mercaptoethanol, 0.2 mg ml$^{-1}$ bovine serum albumin, 2 mM MgCl$_2$, 100 µM ATP and 1 µCi γ-[$^{32}$P]ATP. Recombinant trimeric complex CIS-SH2-Elongin B-Elongin C (see SEQ ID NOs:7, 14, and 15 for the corresponding amino acid sequences) is present at concentrations ranging from 0-30 µM. After incubation, the reaction is spotted onto P81 phosphocellulose paper and quenched in 5% H$_3$PO$_4$. The paper is then washed (4×200 ml, 15 min) with 5% H$_3$PO$_4$ and exposed to a phosphorimager plate. Quantitation is performed using phosphorimager software and IC$_{50}$ curves are then calculated based on integrated pixel counts.

In other embodiments, identification of a CIS inhibitor is carried out in silico in a method comprising the steps of: (i) generating a three dimensional structural model of a CIS or a fragment thereof; and (ii) designing or screening in silico for a test agent that binds to the modelled structure. In some embodiments the three dimensional structural model is a complex of JAK1 polypeptide or fragment thereof bound to CIS or a fragment thereof, or a complex of IL-2Rϑ cytoplasmic domain polypeptide or a CIS-binding fragment thereof bound to CIS or a fragment thereof.

A CIS inhibitor can be identified by in silico screening for binding to CIS by any method known to the person skilled in the art. Methods for in silico screening of ligand binding to proteins include, but are not limited to those provided in, e.g., Good, (2001), Zhang et al. (2015), Cerqueira et al. (2015), Kuenemann et al. (2015) and Westermaier et al. (2015).

For a molecule to bind a CIS protein, it will typically require a suitable level of stereochemical complementarity. In general, the design of a molecule possessing stereochemical complementarity can be accomplished by means of techniques that optimize, chemically and/or geometrically, the "fit" between a molecule and a target receptor. There are at least two approaches to designing a molecule, according to the present invention, that complements the stereochemistry of a CIS protein or fragment thereof.

The first approach is to directly dock molecules ("virtual test agents") in silico from a three dimensional structural database, to the receptor site, using mostly, but not exclusively, geometric criteria to assess the goodness of fit of a particular molecule to the site. In this approach, the number of internal degrees of freedom (and the corresponding local minima in the molecular conformation space) is reduced by considering only the geometric (hard sphere) interactions of two rigid bodies, where one body (the active site) contains "pockets" or "grooves" that form binding sites for the second body (the complementing molecule, as ligand).

This approach is illustrated by Ewing et al. (2001) whose algorithm for ligand design is implemented in a commercial software package, DOCK version 4.0, distributed by the Regents of the University of California and further described in a document, provided by the distributor, which is entitled "Overview of the DOCK program suite.". More recently, Autodock 4 has been described. Pursuant to the Kuntz algorithm, the shape of a region of interest is defined as a series of overlapping spheres of different radii. One or more extant databases of crystallographic data, such as the Cambridge Structural Database System maintained by Cambridge University (University Chemical Laboratory, Lensfield Road, Cambridge CB2 1EW, U.K.), the Protein Data Bank maintained by the Research Collaboratory for Structural Bioinformatics (Rutgers University, N.J., U.S.A.), LeadQuest (Tripos Associates, Inc., St. Louis, Mo.), Available Chemicals Directory (Molecular Design Ltd., San Leandro, Calif.), and the NCI database (National Cancer Institute, U.S.A) is then searched for molecules which approximate the shape thus defined.

Molecules identified in this way, on the basis of geometric parameters, can then be modified to satisfy criteria associated with chemical complementarity, such as hydrogen bonding, ionic interactions and Van der Waals interactions. Different scoring functions can be employed to rank and select the best molecule from a database (see, for example, Bohm et al., 1999). The software package FlexX, marketed by Tripos Associates, Inc. (St. Louis, Mo.) is another program that can be used in this direct docking approach.

The second preferred approach entails an assessment of the interaction of respective chemical groups ("probes") with the active site at sample positions within and around the site, resulting in an array of energy values from which three dimensional contour surfaces at selected energy levels can be generated. The chemical probe approach to ligand design is implemented in several commercial software packages, such as GRID (product of Molecular Discovery Ltd., West Way House, Elms Parade, Oxford OX2 9LL, U.K.). Pursuant to this approach, the chemical prerequisites for a site complementing molecule are identified at the outset, by probing the active site with different chemical probes, e.g., water, a methyl group, an amine nitrogen, a carboxyl oxygen, and a hydroxyl. Favoured sites for interaction between the active site and each probe are thus determined, and from the resulting three dimensional pattern of such sites a putative complementary molecule can be generated. This may be done either by programs that can search three dimensional databases to identify molecules incorporating desired pharmacophore patterns or by programs which using the favoured sites and probes as input perform de novo design.

Programs suitable for searching three dimensional databases to identify molecules bearing a desired pharmacophore include: MACCS 3D and ISIS/3D (Molecular Design Ltd., San Leandro, Calif.), ChemDBS 3D (Chemical Design Ltd., Oxford, U.K.), and Sybyl/3DB Unity (Tripos Associates, Inc., St. Louis, Mo.).

Databases of chemical structures are available from a number of sources including Cambridge Crystallographic Data Centre (Cambridge, U.K.), Molecular Design, Ltd., (San Leandro, Calif.), Tripos Associates, Inc. (St. Louis, Mo.), and Chemical Abstracts Service (Columbus, Ohio).

De novo design programs include Ludi (Biosym Technologies Inc., San Diego, Calif.), Leapfrog (Tripos Associates, Inc.), Aladdin (Daylight Chemical Information Systems, Irvine, Calif.), and LigBuilder (Peking University, China).

Mimetics, such as peptido- and organomimetics can be designed to fit, e.g., a peptide binding site with current computer modeling software (using computer assisted drug design or CADD) (Walters, 1993, in "Computer-Assisted Modeling of Drugs", in Klegerman & Groves (eds.), *Pharmaceutical Biotechnology*, 1993, Interpharm Press: Buffalo Grove, Ill., pp. 165-174; and Munson, 1995, *Principles of Pharmacology*, Chapman & Hall, Chapter 12). Also included within the scope of the disclosure are mimetics prepared using such techniques. In one example, a mimetic mimics a phosphopeptide of the JAK1 activation loop known to interact with the CIS SH2 domain.

Mimetics can be generated using software that can derive a virtual peptide model from several peptide structures. This can be done using the software derived from SLATE algorithm (Perkin et al., 1995; Mills et al., 2001; De Esch et al., 2001).

Other approaches to designing peptide analogs, derivatives and mimetics are also well known in the art, see for example Floris et al. (2011).

A molecule found to bind to CIS can be synthesized or obtained in larger quantity from a suitable source such as a commercial supplier. The obtained test agent can then be used in any of the above-described assays to validate its ability to bind to CIS and/or inhibit binding of a CIS binding partner or target protein to CIS or a CIS fragment.

For all of the drug screening assays further refinements to the structure of the drug will generally be necessary and can be made by the successive iterations of any and/or all of the steps provided by the particular drug screening assay.

In other embodiments a method for identifying a CIS inhibitor is a phenotypic assay that includes the steps of: (i) providing a cell that expresses CIS; and (ii) determining whether a test agent reduces CIS activity in the cell when compared to a cell not contacted with the test agent. In some embodiments the cell type to be used in the screening method is a NK cell. In some embodiments, where NK cells are used, determining whether the test agent reduces CIS activity in the cell includes determining the effect of the test agent on an IL-15 inducible response in the NK cells. Suitable IL-15 inducible responses include, but are not limited to, one or more of NK cell proliferation, interferon-γ (IFN-γ) production, intracellular granzyme expression, JAK1 tyrosine phosphorylation, JAK1 degradation, modulation of gene expression, or cytotoxicity. Any of such endpoints can be assessed by any of a number of standard methods known in the art. For example, cell proliferation assays are described in Riss et al. (2013), Assay Guidance Manual [Internet]. Bethesda (Md.): Eli Lilly & Company and the National Center for Advancing Translational Sciences; cytokine quantification assays are described in Whiteside (2002); assays for JAK1 kinase activity are described in, e.g., Babon et al. (2013); assays for ubiquitin-mediated degradation of JAK1 is described in, e.g., Lee et al. (2008);

gene expression assays, e.g., RNAseq is described in, e.g., Hoek et al. (2015); and NK cell-mediated cytotoxicity assays are described in, e.g., Giamann et al. (2006) and Jang et al. (2012). In some embodiments the test agent to be used in a cell based assay is identified initially as a candidate CIS inhibitor in one of the interaction or binding-screening methods. In some embodiments the CIS activity determined in cells is inhibition of JAK1 kinase activity, (e.g., decreased phosphorylation of a STAT5 substrate), inhibition of STAT5 tyrosine phosphorylation, down-regulation of STAT5 promoter activity, or increased degradation of JAK1 in NK cells.

Suitable test agents for the screening methods include peptides, peptidomimetics, small molecules, polynucleotides, or polypeptides, though one of skill in the art will appreciate that where a test agent is directed towards reducing CIS activity by targeting the Cish gene or Cish mRNA, such agents will be assessed in cellular assays.

In some embodiments a suitable CIS or CIS fragment for use in any of the methods for identifying CIS inhibitors comprises an amino acid sequence at least 70% identical to at least one of SEQ ID NOs:6-10, e.g., at least 75%, 80%, 85%, 88%, 90%, 92%, 95%, 99%, or 100% identical to at least one of SEQ ID NOs:6-10.

(SEQ ID NO: 6; human CIS protein isoform 1; UniprotKB Q9NSE2)
MVLCVQGPRPLLAVERTGQRPLWAPSLELPKPVMQPLPAGAFLEEVAEGTPAQTESEPKVLDPE

EDLLCIAKTFSYLRESGWYWGSITASEARQHLQKMPEGTFLVRDSTHPSYLFTLSVKTTRGPTN

VRIEYADSSFRLDSNCLSRPRILAFPDVVSLVQHYVASCTADTRSDSPDPAPTPALPMPKEDAP

SDPALPAPPPATAVHLKLVQPFVRRSSARSLQHLCRLVINRLVADVDCLPLPRRMADYLRQYPF

QL (SEQ ID NO: 7; human CIS protein isoform 1 fragment: residues 66-258 with
a deletion of residues 174-202 i.e., lacking the internal PEST sequence);
used to generate a trimeric complex with Elongins B and C)
DLLCIAKTFSYLRESGWYWGSITASEARQHLQKMPEGTFLVRDSTHPSYLFTLSVKTTRGPTNV

RIEYADSSFRLDSNCLSRPRILAFPDVVSLVQHYVASCTADTRSATAVHLKLVQPFVRRSSARS

LQHLCRLVINRLVADVDCLPLPRRMADYLRQYPFQL (SEQ ID NO: 8; human CIS protein isoform 1 SOCS Box (from GenBank Accession No:
NP_034025.1)
SSARSLQHLCRLVINRLVADVDCLPLPRRMADYLRQYPFQL (SEQ ID NO: 9; *Mus musculus* CIS protein isoform 1; GenBank Accession No: NP_034025.1)
MVLCVQGSCPLLAVEQIGRRPLWAQSLELPGPAMQPLPTGAFPEEVTEETPVQAENEPKVLDPE

GDLLCIAKTFSYLRESGWYWGSITASEARQHLQKMPEGTFLVRDSTHPSYLFTLSVKTTRGPTN

VRIEYADSSFRLDSNCLSRPRILAFPDVVSLVQHYVASCAADTRSDSPDPAPTPALPMSKQDAP

SDSVLPIPVATAVHLKLVQPFVRRSSARSLQHLCRLVINRLVADVDCLPLPRRMADYLRQYPFQ

L (SEQ ID NO: 10; *Rattus norvegicus* CIS protein; GenBank Accession No: AAI61930.1)
MVLCVQGSCPLLVVEQIGQRPLWAQSLELPGPAMQPLPTGAFPEEVTEETPVQSENEPKVLDPEGDLLCI

AKTFSYLRESGWYWGSITASEARQHLQKMPEGTFLVRDSTHPSYLFTLSVKTTRGPTNVRIEYA

DSSFRLDSNCLSRPRILAFPDVVSLVQHYVASCTADTRSDSPDPAPTPALPVPKPDAPGDPVLP

IPVATAVHLKLVQPFVRRSSARSLQHLCRLVINRLVTDVDCLPLPRRMADYLRQYPFQL

In some embodiments the amino acid sequence of CIS or the fragment thereof comprises the amino acid sequence of one of SEQ ID NOs:6-10. In other embodiments the amino acid sequence of CIS or the fragment thereof consists of one of the amino acid sequence of one of SEQ ID NOs:6-10.

In some embodiments, where the CIS binding partner or target protein is selected from among JAK1, JAK3, Elongin B, Elongin C, and Cullin5 or a fragment thereof.

JAK1 or a CIS-binding fragment thereof can comprise an amino acid sequence at least 70% identical to at least one of SEQ ID NOs:11-16, e.g., at least 75%, 80%, 85%, 88%, 90%, 92%, 95%, 99%, or 100% identical to at least one of SEQ ID NOs:11-16.

(SEQ ID NO: 11; Homo sapiens JAK1 protein; UniProtKB-P23458; activation loop denoted in bold; Tyr1034 underlined)
MQYLNIKEDCNAMAFCAKMRSSKKTEVNLEAPEPGVEVIFYLSDREPLRLGSGEYTAEELCIR

AQACRISPLCHNLFALYDENTKLWYAPNRTITVDDKMSLRLHYRMRFYFTNWHGTNDNEQSVWR

HSPKKQKNGYEKKKIPDATPLLDASSLEYLFAQGQYDLVKCLAPIRDPKTEQDGHDIENECLGM

AVLAISHYAMMKKMQLPELPKDISYKRYIPETLNKSIRQRNLLTRMRINNVFKDFLKEFNNKTI

CDSSVSTHDLKVKYLATLETLTKHYGAEIFETSMLLISSENEMNWFHSNDGGNVLYYEVMVTGN

LGIQWRHKPNVVSVEKEKNKLKRKKLENKHKKDEEKNKIREEWNNFSYFPEITHIVIKESVVSI

NKQDNKKMELKLSSHEEALSFVSLVDGYFRLTADAHHYLCTDVAPPLIVHNIQNGCHGPICTEY

AINKLRQEGSEEGMYVLRWSCTDFDNILMTVTCFEKSEQVQGAQKQFKNFQIEVQKGRYSLHGS

DRSFPSLGDLMSHLKKQILRTDNISFMLKRCCQPKPREISNLLVATKKAQEWQPVYPMSQLSFD

RILKKDLVQGEHLGRGTRTHIYSGTLMDYKDDEGTSEEKKIKVILKVLDPSHRDISLAFFEAAS

MMRQVSHKHIVYLYGVCVRDVENIMVEEFVEGGPLDLFMHRKSDVLTTPWKFKVAKQLASALSY

LEDKDLVHGNVCTKNLLLAREGIDSECGPFIKLSDPGIPITVLSRQECIERIPWIAPECVEDSK

NLSVAADKWSFGTTLWEICYNGEIPLKDKTLIEKERFYESRCRPVTPSCKELADLMTRCMNYDP

NQRPFFRAIMRDINKLEEQNPDIVSEKKPATEVDPTHFEKRFLKRIRDLGEGHFGKVELCRYDP

EGDNTGEQVAVKSLKPESGGNHIADLKKEIEILRNLYHENIVKYKGICTEDGGNGIKLIMEFLP

SGSLKEYLPKNKNKINLKQQLKYAVQICKGMDYLGSRQYVHRDLAARNVLVESEHQVKIGDFGL

TKAIETDKE<u>Y</u>YTVKDDRDSPVFWYAPECLMQSKFYIASDVWSFGVTLHELLTYCDSDSSPMALF

LKMIGPTHGQMTVTRLVNTLKEGKRLPCPPNCPDEVYQLMRKCWEFQPSNRTSFQNLIEGFEAL

LK (SEQ ID NO: 12; Homo sapiens JAK3 protein; UniProtKB-P52333; Tyr980 bold and underlined)
MAPPSEETPLIPQRSCSLLSTEAGALHVLLPARGPGPPQRLSFSFGDHLAEDLCVQAAKASGIL

PVYHSLFALATEDLSCWFPPSHIFSVEDASTQVLLYRIRFYFPNWFGLEKCHRFGLRKDLASAI

LDLPVLEHLFAQHRSDLVSGRLPVGLSLKEQGECLSLAVLDLARMAREQAQRPGELLKTVSYKA

CLPPSLRDLIQGLSFVTRRRIRRTVRRALRRVAACQADRHSLMAKYIMDLERLDPAGAAETFHV

GLPGALGGHDGLGLLRVAGDGGIAWTQGEQEVLQPFCDFPEIVDISIKQAPRVGPAGEHRLVTV

TRTDNQILEAEFPGLPEALSFVALVDGYFRLTTDSQHFFCKEVAPPRLLEEVAEQCHGPITLDF

AINKLKTGGSRPGSYVLRRSPQDFDSFLLTVCVQNPLGPDYKGCLIRRSPTGTFLLVGLSRPHS

SLRELLATCWDGGLHVDGVAVTLTSCCIPRPKEKSNLIVVQRGHSPPTSSLVQPQSQYQLSQMT

FHKIPADSLEWHENLGHGSFTKIYRGCRHEVVDGEARKTEVLLKVMDAKHKNCMESFLEAASLM

SQVSYRHLVLLHGVCMAGDSTMVQEFVHLGAIDMYLRKRGHLVPASWKLQVVKQLAYALNYLED

KGLPHGNVSARKVLLAREGADGSPPFIKLSDPGVSPAVLSLEMLTDRIPWVAPECLREAQTLSL

EADKWGFGATVWEVFSGVTMPISALDPAKKLQFYEDRQQLPAPKWTELALLIQQCMAYEPVQRP

SFRAVIRDLNSLISSDYELLSDPTPGALAPRDGLWNGAQLYACQDPTIFEERHLKYISQLGKGN

FGSVELCRYDPLGDNTGALVAVKQLQHSGPDQQRDFQREIQILKALHSDFIVKYRGVSYGPGRQ

SLRLVMEYLPSGCLRDFLQRHRARLDASRLLLYSSQICKGMEYLGSRRCVHRDLAARNILVESE

AHVKIADFGLAKLLPLDKDYYVVREPGQSPIFWYAPESLSDNIFSRQSDVWSFGVVLYELFTYC

DKSCSPSAEFLRMMGCERDVPALCRLLELLEEGQRLPAPPACPAEVHELMKLCWAPSPQDRPSF

SALGPQLDMLWSGSRGCETHAFTAHPEGKHHSLSFS (SEQ ID NO: 13; *Homo sapiens* IL-2 Receptor Subunit Beta precursor; UniProtKB-P14784; Signal peptide amino acids 1-26 underlined; Tyr355, Tyr361; and Tyr392-mature sequence numbering for each- are in bold and underlined)
<u>MAAPALSWRLPLLILLLPLATSWASA</u>AVNGTSQFTCFYNSRANISCVWSQDGALQDTSCQVHAW

PDRRRWNQTCELLPVSQASWACNLILGAPDSQKLTTVDIVTLRVLCREGVRWRVMAIQDFKPFE

NLRLMAPISLQVVHVETHRCNISWEISQASHYFERHLEFEARTLSPGHTWEEAPLLTLKQKQEW

ICLETLTPDTQYEFQVRVKPLQGEFTTWSPWSQPLAFRTKPAALGKDTIPWLGHLLVGLSGAFG

FIILVYLLINCRNTGPWLKKVLKCNTPDPSKFFSQLSSEHGGDVQKWLSSPFPSSSFSPGGLAP

EISPLEVLERDKVTQLLLQQDKVPEPASLSSNHSLTSCFTNQGYFFFHLPDALEIEACQVYFTY

DPYSEEDPDEGVAGAPTGSSPQPLQPLSGEDDAYCTFPSRDDLLLFSPSLLGGPSPPSTAPGGS

GAGEERMPPSLQERVPRDWDPQPLGPPTPGVPDLVDFQPPPELVLREAGEEVPDAGPREGVSFP

WSRPPGQGEFRALNARLPLNTDAYLSLQELQGQDPTHLV (SEQ ID NO: 14; *Homo sapiens* Elongin B; UniProtKB-Q15370)
MDVFLMIRRHKTTIFTDAKESSTVFELKRIVEGILKRPPDEQRLYKDDQLLDDGKTLGECGFTS

QTARPQAPATVGLAFRADDTFEALCIEPFSSPPELPDVMKPQDSGSSANEQAVQ (SEQ ID NO: 15; *Homo sapiens* Elongin C; UniProtKB-Q15369)
MDGEEKTYGGCEGPDAMYVKLISSDGHEFIVKREHALTSGTIKAMLSGPGQFAENETNEVNFRE

IPSHVLSKVCMYFTYKVRYTNSSTEIPEFPIAPEIALELLMAANFLDC

SEQ ID NO: 16; *Homo sapiens* Cullin-5; UniProtKB-Q93034)
MATSNLLKNKGSLQFEDKWDFMRPIVLKLLRQESVTKQQWFDLFSDVHAVCLWDDKGPAKIHQA

LKEDILEFIKQAQARVLSHQDDTALLKAYIVEWRKFFTQCDILPKPFCQLEITLMGKQGSNKKS

NVEDSIVRKLMLDTWNESIFSNIKNRLQDSAMKLVHAERLGEAFDSQLVIGVRESYVNLCSNPE

DKLQIYRDNFEKAYLDSTERFYRTQAPSYLQQNGVQNYMKYADAKLKEEEKRALRYLETRRECN

SVEALMECCVNALVTSFKETILAECQGMIKRNETEKLHLMFSLMDKVPNGIEPMLKDLEEHIIS

AGLADMVAAAETITTDSEKYVEQLLTLFNRFSKLVKEAFQDDPRFLTARDKAYKAVVNDATIFK

LELPLKQKGVGLKTQPESKCPELLANYCDMLLRKTPLSKKLTSEEIEAKLKEVLLVLKYVQNKD

VFMRYHKAHLTRRLILDISADSEIEENMVEWLREVGMPADYVNKLARMFQDIKVSEDLNQAFKE

MHKNNKLALPADSVNIKILNAGAWSRSSEKVFVSLPTELEDLIPEVEEFYKKNHSGRKLHWHHL

MSNGIITFKNEVGQYDLEVTTFQLAVLFAWNQRPREKISFENLKLATELPDAELRRTLWSLVAF

PKLKRQVLLYEPQVNSPKDFTEGTLFSVNQEFSLIKNAKVQKRGKINLIGRLQLTTERMREEEN

EGIVQLRILRTQEAIIQIMKMRKKISNAQLQTELVEILKNMFLPQKKMIKEQIEWLIEHKYIRR

DESDINTFIYMA (SEQ ID NO: 17; *Homo sapiens* JAK1 protein JH1 kinase domain; residues 854-1154)
DIVSEKKPATEVDPTHFEKRFLKRIRDLGEGHFGKVELCRYDPEGDNTGEQVAV)KSLKPESGG

NHIADLKKEIEILRNLYHENIVKYKGICTEDGGNGIKLIMEFLPSGSLKEYLPKNKNKINLKQQ

LKYAVQICKGMDYLGSRQYVHRDLAARNVLVESEHQVKIGDFGLTKAIETDKEYYTVKDDRDSP

VFWYAPECLMQSKFYIASDVWSFGVTLHELLTYCDSDSSPMALFLKMIGPTHGQMTVTRLVNTL

KEGKRLPCPPNCPDEVYQLMRKCWEFQPSNRTSFQNLIEGFEALLK

A polypeptide or class of polypeptides may be defined by the extent of identity (% identity) of its amino acid sequence to a reference amino acid sequence, or by having a greater % identity to one reference amino acid sequence than to another. The % identity of a polypeptide to a reference amino acid sequence is typically determined by GAP analysis (Needleman and Wunsch (1970); GCG program) with parameters of a gap creation penalty=5, and a gap extension penalty=0.3. The query sequence is at least 15 amino acids in length, and the GAP analysis aligns the two sequences over a region of at least 15 amino acids. More preferably, the query sequence is at least 50 amino acids in length, and the GAP analysis aligns the two sequences over a region of at least 50 amino acids. More preferably, the query sequence is at least 100 amino acids in length and the GAP analysis aligns the two sequences over a region of at least 100 amino acids. Even more preferably, the query sequence is at least 250 amino acids in length and the GAP analysis aligns the two sequences over a region of at least 250 amino acids. Even more preferably, the GAP analysis aligns two sequences over their entire length.

A number of considerations are useful to the skilled artisan in determining if a particular amino acid sequence variant of protein or peptide is suitable for use in the invention. These considerations include, but are not limited to: (1) known structure-function relationships for the interactions between a protein or peptide and a known protein binding partner or binding partner motif; (2) the presence of amino acid sequence conservation among naturally occurring homologs (e.g., in paralogs and orthologs) of the protein of interest, as revealed by sequence alignment algorithms. Notably, a number of bioinformatic algorithms are known in the art that successfully predict the functional effect, i.e., "tolerance" of particular amino substitutions in the amino acid sequence of a protein on its function. Such algorithms include, e.g., the "Functional Analysis Through Hidden Markov Models" (FATHMM) algorithm described in Shihab et al. (2013); and the "Sorting Intolerant from Tolerant" algorithm described in Ng et al. (2003); and more recently in Sim et al. (2012).

The SIFT calculator is available online on the website: sift.bii.a-star.edu.sg/. The FATHMM calculator is available online at the website: fathmm.biocompute.org.uk. For any amino acid sequence of interest (e.g., sequences corresponding to any of the SEQ ID NOs provided herein), an "amino acid substitution matrix" can be generated that provides the predicted neutrality or deleteriousness of any given amino acid substitution on the corresponding protein' function, e.g., the ability to bind with an interaction partner.

Non-naturally occurring sequence variants of proteins can be generated by a number of known methods. Such methods include, but are not limited to, "Gene Shuffling" as described in U.S. Pat. No. 6,521,453; "RNA mutagenesis" as described in Kopsidas et al. (2007); and "error-prone PCR methods." Error prone PCR methods can be divided into (a) methods that reduce the fidelity of the polymerase by unbalancing nucleotides concentrations and/or adding of chemical compounds such as manganese chloride, (b) methods that employ nucleotide analogs (see, e.g., U.S. Pat. No. 6,153,745), and (c) methods that utilize 'mutagenic' polymerases.

Confirmation of the retention, loss, or gain of function of the amino acid sequence variants of the proteins used in the assays can be determined in various types of assays according to the protein function being assessed, e.g., binding assays, kinase assays, or ubiquitination assays.

EXAMPLES

Example 1—Materials and Methods

Mice

Cish$^{-/-}$ were generously provided by Prof. James Ihle and Dr Evan Parganas at St. Jude Children's Research Hospital, Memphis USA and were maintained on a C57BL/6 background. Cish+/+ refers to C57BL/6 wild-type control mice. Rosa26-CreERT2 (TaconicArtemis), Socs3-loxP (Croker et al., 2003), Ifng−/−Socs1−/− (Alexander et al., 1999) and Ncr1-iCre (Narni-Mancinelli et al., 2011) mice have been described previously. Male and female mice were used between the ages of 6-14 weeks. All mice were bred and maintained at the Walter and Eliza Hall Institute. Animal experiments followed the National Health and Medical Research Council (NHMRC) Code of Practice for the Care and Use of Animals for Scientific Purposes guidelines and were approved by the Walter and Eliza Hall Institute Animal Ethics Committee or the QIMR Berghofer Medical Research Institute Animal Ethics Committee.

Purification and Culture of NK Cells

Murine natural killer cells were harvested from various organs (spleen, bone marrow, blood) and single-cell suspensions prepared by forcing of organs through 70 μm sieves. Lymphocytes were isolated from liver by suspension in isotonic percoll (Amersham Pharmacia Biotech) and centrifugation at 1800×g. NK cells were purified using anti-CD49b (DX5) Microbeads (Miltenyi Biotec) according to manufacturer's specifications. NK cells were expanded for 5-10 days by culture in Iscove's modified Dulbecco's medium (IMDM) supplemented with 10% (v/v) foetal calf serum (FCS), L-glutamine (1 mM; Gibco), streptomycin (100 μg/mL; Sigma), penicillin (100 IU/mL; Sigma), gentamycin (50 ng ml$^{-1}$; Sigma) and recombinant hIL-15 (50 ng ml$^{-1}$; Peprotech).

RNA Sequencing and Bioinformatic Analysis 100 base pair single-end RNA sequencing was performed for two biological replicates of 1×10$^6$ Cish$^{+/-}$ and Cish$^{-/-}$ NK1.1$^+$NKp46$^+$TCRβ$^-$ NK cells grown in 50 ng ml$^{-1}$ IL-15 for 7 days and two biological replicates of 1×10$^6$ freshly isolated Cish$^{+/+}$ and Cish$^{-/-}$ NK1.1$^+$NKp46$^+$TCRβ$^-$ NK cells using the Illumina HiSeq2000 at the Australia Genomic Research Facility, Melbourne. Reads were aligned to the GRCm38/mm10 build of the *Mus musculus* genome using the Subread aligner. Genewise counts were obtained using FeatureCounts. Reads overlapping exons in annotation build 38.1 of NCBI RefSeq database were included. Genes were filtered from downstream analysis if they failed to achieve a CPM (counts per million mapped reads) value of at least 0.5 in at least two libraries. Counts were converted to log 2 counts per million, quantile normalised and precision weighted with the voom function of the limma package. Linear models and empirical bayes methods were used to assess differential expression in RNAseq experiments. Genes were called differentially expressed if they achieved a false discovery rate of 0.1 or less and also had at least 8 FPKMs (fragments per kilobases per million mapped reads) in one or both of the two cell types being compared. Heat maps were generated using the gplots package, with negative log 2 FPKM values reset to zero. All analyses were carried out using Bioconductor R packages.

In Vitro NK Cell Proliferation Assays

Target cells (CHO, B16F10) were seeded into the wells of 96X E-Plates in 100 μl of media. Cell growth was dynamically monitored with the impedance-based RT-CES® system until they reached log growth phase and formed a monolayer (approximately 24 h). Cultured Cish$^{+/+}$ and Cish$^{-/-}$ NK cells at different concentrations were then added directly to individual wells containing the target cells. For background controls, NK cells were added to wells that contained no target cells, and target cells were added to wells without the addition of NK cells. After addition of NK cells, the system continued to take measurements every 15 min for up to 48 h.

Flow Cytometry and Cell Sorting

Single-cell suspensions were stained with the appropriate monoclonal antibody in phosphate buffered saline (PBS) containing 2% (v/v) FCS. When necessary, intracellular staining was performed by use of the FoxP3/Transcription Factor Staining Buffer Set (eBioscience) according to the manufacturer's instructions. FACS Verse, Fortessa and Arial (BD Biosciences) were used for cell sorting and analysis, with dead cells excluded by propidium iodide or Fluoro-Gold staining. All single cell suspensions were diluted in PBS prior to analysis and enumerated using the Advia hematology analyser (Siemens). Antibodies specific for NK1.1 (PK136; 1:100), CD19 (1D3; 1:500), CD3 (17A2; Biolegend; 1:400) CD122 (TM-b1; 1:200), CD132 (4G3; 1:200), NKp46 (29A1.4; 1:100), TCR-β (H57-5921; 1:500), KLRG1 (2F1; 1:100), CD27 (LG.7F9; 1:200), FoxP3 (FJK-16s; eBioscience; 1:400), CD25 (PC61; BioLegend; 1:100), Sca-1 (D7; 1:100), B220 (RA3-6B2; eBioscience; 1:100), Gr-1 (1A8; 1:200), Granzyme A (GzA-3G8.5; eBioscience; 1:200), Granzyme B (NGZB; eBioscience; 1:200), CD107a (104B; 1:100) and IFN-γ (XMG1.2; 1:100) were from BD Pharmingen unless stated otherwise.

Real Time Quantitative PCR (Q-PCR)

Total RNA was isolated using the RNeasy plus kit (QIAGEN) and cDNA synthesis performed with Superscript III (Invitrogen) according to the manufacturer's instructions. PCR reactions were performed in 10 μL; 5 μL of FastStart SYBR Green Master Mix (Roche), 0.5 μmol of forward and reverse primers and 4 μL of cDNA. Primer sequences and PCR conditions have been described (Kolesnik and Nicholson, 2013). Real-time Q-PCR was performed on an ABI Prism 7900HT sequence detection system (Applied Biosystems). mRNA levels were quantified against standard curves generated using sequential dilutions of an oligonucleotide corresponding to each amplified PCR fragment and using SDS2.2 software (Applied Biosystems). Relative expression was determined by normalising the amount of each gene of interest to the housekeeping gene Glyceraldehyde-3-Phosphate Dehydrogenase (GAPDH). Each condition had three biological replicates and measurements were performed in duplicate. Statistical analysis was performed using an unpaired t-test with a 95% confidence level.

Western Blotting and Transient Transfections

Approximately $1.5 \times 10^8$ NK cells were collected per sample and lysed in 2.5 mL KALB lysis buffer (Nicholson et al., 1995) supplemented with protease inhibitors (Complete Cocktail tablets, Roche), 1 mM PMSF, 1 mM Na$_3$VO$_4$ and 1 mM NaF and incubated for 1 h on ice. Lysates were clarified by centrifugation at 16,060×g for 15 min at 4° C. Protein concentrations were determined by the BCA method (Pierce, Rockford). 293T cells were maintained in DMEM supplemented with 100 U/mL penicillin, 0.1 ng ml$^{-1}$ streptomycin and 10% FCS and were transiently transfected with vector alone or cDNA expressing Flag-tagged mouse Jak1, Jak3, Cish or Cish mutants or Myc-tagged mouse Cish, using FuGene6 (Promega) according to the manufacturer's instructions. In some instances, cells were pre-treated with 10 μM MG132 for 4 h to block proteasomal degradation. 48 h post-transfection cells were lysed in KALB buffer (Nicholson et al., 1995). FLAG proteins were immunoprecipitated using M2-beads (Sigma) and proteins eluted in SDS sample buffer. Immunoprecipitation, gel electrophoresis and Western blotting were performed essentially as described (Linossi et al., 2013). The following primary antibodies were used: antibodies to CIS (Clone D4D9), phospho-STAT3 (Y705); phospho-AKT1 (Ser473), AKT and MAPK were obtained from Cell Signalling Technology. Antibodies to phospho-STAT5A/B (Y694/699) were from Millipore, phospho-JAK1 (Y1022/1023) and STAT5A from Invitrogen, and JAK1, STAT3 and 13-Actin were obtained from Santa Cruz Biotechnology Inc. Rat anti-Flag antibody was a kind gift from Prof. D. Huang & Dr. L. O'Reilly (Walter and Eliza Hall Institute).

Synthesis of CYT-387 Kinase Affinity Reagent and Covalent Coupling to NHS Sepharose An amino-functionalized CYT-387 derivative was prepared using a procedure similar to that described for the synthesis of CYT-387 (See FIG. 6). The modified CYT-387 compound was immobilised onto NHS-activated sepharose 4 Fast Flow beads (GE Healthcare) as previously described (Schirle et al., 2012). Briefly, 1 mL slurry of NHS-sepharose beads was washed twice with 5 mL DMSO, centrifuging at 80× g for 3 min to pellet the matrix in between washes. One packed matrix volume (500 μL) was resuspended with DMSO to make a 50% slurry. CYT-387 (2 μM final) was added to the 1 mL slurry of NHS-beads followed by 20 μL of triethylamine and mixed by inversion. The reaction slurry was incubated overnight at room temperature on an end-over-end rotator protected from light. The following day, 25 μL ethanolamine was added to the reaction and again left to incubate overnight at room temperature on an end-over-end rotator protected from light. The CYT-387-coupled NHS-sepharose beads were washed twice with 5 mL DMSO and the matrix was resuspended in ethanol and stored at 4° C. protected from light.

Kinase Enrichment from Cell Lysates

CYT-387-bound resin was washed twice with KALB lysis buffer prior to kinase enrichment. Six individual kinase enrichments were performed (three per Cish$^{-/-}$ or Cish$^{+/+}$) with 160 μL, of 50% Cyt387-bound resin incubated with 2 mL (~10 mg) of protein lysate. Incubations were performed for 3 h on a rotating wheel protected from light at 4° C. Following incubation, protein-bound Cyt387 resins were washed 3 times with KALB buffer and eluted with 3 consecutive rounds of incubation with 0.5% SDS/5 mM DTT (200 μL, 100 μL, 100 μL) for 3 min at 60° C.

Trypsin Digestion

Eluates of resin-captured proteins along with equal amounts of whole cell lysate (~400 μg) derived from each biological replicate were prepared for mass spectrometry analysis using the FASP protein digestion kit (Protein Discovery, Knoxville, Tenn.) as previously described (Wisniewski et al., 2009), with the following modifications. Proteins were reduced with Tris-(2-carboxyethyl)phosphine (TCEP) (5 mM final concentration), digested with 4 μg of sequence-grade modified Trypsin Gold (Promega) in 50 mM NH$_4$HCO$_3$ and incubated overnight at 37° C. Peptides were then eluted with 50 mM NH$_4$HCO$_3$ in two 40 μL sequential washes and acidified in 1% formic acid (final concentration).

Mass Spectrometry and Data Analysis

Acidified peptide mixtures were analysed by nanoflow reversed-phase liquid chromatography tandem mass spectrometry (LC-MS/MS) on a nanoAcquity system (Waters, Milford, Mass., USA), coupled to a Q-Exactive mass spectrometer equipped with a nanoelectrospray ion source for automated MS/MS (Thermo Fisher Scientific, Bremen, Germany). Peptide mixtures were loaded on a 20 mm trap column with 180 μm inner diameter (nanoAcquity UPLC 2G-V/MTrap 5 mm Symmetry C18) in buffer A (0.1% formic acid, 3% acetonitrile, Milli-Q water), and separated by reverse-phase chromatography using a 150 mm column with 75 μm inner diameter (nanoAcquity UPLC 1.7 μm BEH130 C18) on a 60 min linear gradient set at a constant flow rate of 400 nL/min from 3-55% buffer B (0.1% formic acid, 80% acetonitrile, Milli-Q water). The Q-Exactive was operated in a data-dependent mode, switching automatically between one full-scan and subsequent MS/MS scans of the ten most abundant peaks. The instrument was controlled using Exactive series version 2.1 build 1502 and Xcalibur 3.0. Full-scans (m/z 350-1,850) were acquired with a resolution of 70,000 at 200 m/z. The 10 most intense ions were sequentially isolated with a target value of 10000 ions and an isolation width of 2 m/z and fragmented using HCD with normalised collision energy of 19.5 and stepped collision energy of 15%. Maximum ion accumulation times 27 were set to 50 ms for full MS scan and 200 ms for MS/MS. Underfill ratio was set to 5% and dynamic exclusion was enabled and set to 90 sec. Raw files consisting of high-resolution MS/MS spectra were processed with MaxQuant (version 1.5.0.25) for feature detection and protein identification using the Andromeda search engine36. Extracted peak lists were searched against the UniProtKB/Swiss-Prot Mus musculus database (LudwigNR) and a separate reverse decoy database to empirically assess the false discovery rate (FDR) using a strict trypsin specificity allowing up to 3 missed cleavages. The minimum required peptide length was set to 7 amino acids. Modifications: Carbamidomethylation of Cys was set as a fixed modification, while N-acetylation of proteins, oxidation of Met, the addition of pyroglutamate (at N-termini Glu and Gln), phosphorylation (Ser, Thr and Tyr), deamidation (Asn, Gln and Arg), were set as variable modifications. The mass tolerance for precursor ions and fragment ions were 20 ppm and 0.5 Da, respectively. The "match between runs" option in MaxQuant was used to transfer identifications made between runs on the basis of matching precursors with high mass accuracy (Cox et al., 2014). PSM and protein identifications were filtered using a target-decoy approach at a false discovery rate (FDR) of 1%. Protein identification was based on a minimum of two unique peptides.

Quantitative Proteomics Pipeline

Further analysis was performed using a custom pipeline developed in Pipeline Pilot (Biovia) and R, which utilises the MaxQuant output files allPeptides.txt, peptides.txt and evidence.txt. A feature was defined as the combination of peptide sequence, charge and modification. Features not found in at least half the number of replicates in each group were removed. Proteins identified from hits to the reverse database and proteins with only one unique peptide were also removed. To correct for injection volume variability, feature intensities were normalized by converting to base 2 logarithms and then multiplying each value by the ratio of maximum median intensity of all replicates over median replicate intensity. Features assigned to the same protein differ in the range of intensity due to their chemico-physical properties and charge state. To further correct for these differences, each intensity value was multiplied by the ratio of the maximum of the median intensities of all features for a protein over the median intensity of the feature. Missing values where imputed using a random normal distribution of values with the mean set at mean of the real distribution of values minus 1.8 standard deviations, and a standard deviation of 0.5 times the standard deviation of the distribution of the measured intensities (Cox et al., 2014). The probability of differential expression between groups was calculated using the Wilcoxon Rank Sum test excluding any non-unique sequences and any features with modifications other than oxidation and carbamidomethylation. Probability values were corrected for multiple testing using Benjamini-Hochberg method. Cut-off lines with the function $y=-\log_{10}(0.05)+c/(x-x_0)$ (Keilhauer et al., 2015) were introduced to identify significantly enriched proteins. c was set to 0.2 while $x_0$ was set to 1 representing proteins with a with a 2-fold (log 2 protein ratios of 1 or more) or 4-fold (log 2 protein ratio of 2) change in protein expression, respectively. The log 2-transformed summed peptide intensities (non-imputed) were visualised in a heat map generated in one-matrix CIMminer, a program developed by the Genomics and Bioinformatics Group (Laboratory of Molecular Pharmacology, Center for Cancer Research, National Cancer Institute).

Preparation of GST-CIS Protein for Peptide Screening

A portion of human Cish (encoding residues 66-258) was cloned into the vector pGTVL2. Human Elongin C (residues 17-112) and full length Elongin B were cloned into the vector pACYCDUET as previously described (Bullock et al., 2006). Both plasmids were transformed into BL21(DE3) for co-expression of the CIS/Elongin C/Elongin B ternary complex (CIS-SH2-BC). Cultures in Luria broth media were induced with 0.4 mM isopropyl β-D-1-thiogalactopyranoside (IPTG) overnight at 18° C. and the cells harvested by centrifugation. Pellets were resuspended in 50 mM HEPES pH 7.5, 500 mM NaCl, 5 mM imidazole, 5% glycerol and the cells lysed by sonication. DNA was precipitated by addition of 0.15% polyethyleneimine pH 8 and the insoluble material excluded by centrifugation at 21,000 rpm. The GST-tagged CIS protein complex was purified on a glutathione sepharose column and eluted with 20 mM reduced glutathione in a buffer comprising 50 mM HEPES, 300 mM NaCl, 0.5 mM TCEP. The purified protein was concentrated to 0.75 mg ml$^1$ and stored at −80° C.

Peptide Array Synthesis' and Screening

The peptide arrays were synthesized on functionalized nitrocellulose membranes using an Invatis spot array synthesizer as described (Li and Wu, 2009). For array probing, the membrane-bound peptides were blocked at room temperature for 5 h in 5% skim milk of Tris-buffered saline/ 0.05% Tween-20 (TBS-T), pH 7.2. After washing with TBS-T, 0.8 ng ml$^{-1}$ of GST-CIS-SH2-BC complex was added in blocking buffer and incubated at 4° C. overnight. At the same time, 4 ng ml$^{-1}$ of GST protein was added to a separate peptide array as a negative control under the same experimental conditions. The peptide array membranes were washed with TBS-T 3x, and a peroxidase-labelled anti-GST antibody (Bio-Rad) added at room temperature for 1 h, prior to detection with a chemiluminescence substrate (Bio-Rad Clarity Western ECL Substrate), which was visualised using a Molecular Imager (ChemiDoc XRS; Biorad).

Isothermal Titration Calorimetry (ITC)

Isothermal calorimetric titrations were performed with a Microcal ITC200 (GE Healthcare). Phosphopeptides were obtained from Genscript. An optimised GST-CIS protein construct was prepared in which the internal PEST region (A174-202) was deleted. The resulting ternary GST-CIS-SH2-SB complexes were dialysed against buffer (20 mM Tris pH 8.0, 100 mM NaCl, 2 mM 2-mercaptoethanol). Experiments were performed at 298 K unless stated otherwise. Typically, 12×3.15 µl injections of 300 µM phosphopeptides were titrated into a 30 µM solution of the GST-CIS-SH2-SB ternary complex. The heat of dilution of GST-CIS-SH2-BC was subtracted from the raw data of the binding experiment. Data were analysed using the evaluation software, Microcal Origin version 5.0. The binding curve fitted a single-site binding mode and all Ku values were determined from duplicate experiments.

E3 Ligase Assay

CIS-mediated ubiquitination of JAK1 was performed essentially as described previously (Babon et al., 2013). The CIS E3 ligase complex (CIS-SH2-BC together with Cullin5 and Rbx2; 2.5 µM) was incubated with ubiquitin (50 µM), human E1 (100 nM), purified recombinant E2 (UbcH5c, 2.5 µM) and full-length JAK1 in the presence of 2.5 mM Mg/ATP at 37° C. for varying times. FLAG-tagged JAK1 was generated by expression in 293T cells and recovered using anti-FLAG immunoprecipitation and elution with free FLAG peptide. JAK1 ubiquitination was visualised by Western blotting with anti-phosphorylated JAK1 following separation on 4-20% Tris/Glycine gels.

Kinase Assay

Kinase inhibition assays were performed essentially as described (Babon et al., 2012). Briefly, 130 µM STAT5b peptide (SEQ ID NO:18 RRAKAADGYVKPQIKQVV) was incubated with 5 nM JAK1 at 25° C. for 30-60 min in 20 mM Tris pH 8.0, 100 mM NaCl, 5 mM 2-mercaptoethanol, 0.2 mg ml$^{-1}$ bovine serum albumin, 2 mM MgCl$_2$, 100 µM ATP and 1 mCi γ-[32P]ATP. Recombinant CIS-SH2-BC was present at concentrations ranging from 0-30 µM. After incubation, the reaction was spotted onto P81 phosphocellulose paper and quenched in 5% H$_3$PO$_4$. The paper was washed (4×200 ml, 15 min) with 5% H$_3$PO$_4$ and exposed to a phosphorimager plate (Fuji). Quantitation was performed using Fuji software and IC$_{50}$ curves calculated using Graphpad Prism.

Tumour Cell Lines

The C57BL/6 murine lymphoma cell line RMA is a T cell lymphoma derived from the Rauscher murine leukaemia virus-induced RBL-5 cell line. The cell lines RMA-mCherry and m157+RMA-GFP were generated by transduction with a retroviral vector (murine stem cell vector) encoding mCherry or GFP, respectively. B16F10 melanoma, E0771 and E0771.LMB mCherry+ breast, LWT1 melanoma, and RM-1 prostate carcinoma cell lines, were maintained as previously described (Ferrari de Andrade et al., 2014; Gilfillan et al., 2008; Stagg et al., 2011a and b; Swann et al., 2007; Rautela et al., 2005; Johnstone et al., 2015).

Experimental Tumour Metastasis

Groups of 6-14 mice per experiment were used for experimental tumour metastases. These group sizes were used to ensure adequate power to detect biological differences. No mice were excluded based on pre-established criteria in this study and no active randomization was applied to experimental groups. The investigators were not blinded to the group allocation during the experiment and/or when assessing the outcome. All tumour experiments were performed once unless specifically indicated. Single-cell suspensions of B16F10 melanoma, RM-1 prostate carcinoma, or LWT1 melanoma cells were injected i.v. into the tail vein of the indicated strains of mice (2.5-7.5×10$^5$ cells/mouse). Some mice additionally received either 100 µg anti-CD8β (53.5.8) as indicated to deplete CD8$^+$ T cells, 50 µg anti-asialoGM1 to deplete NK cells, or 250 µg anti-IFN-γ (H22) to neutralize IFN-γ as previously described (Chan et al., 2014; Allard et al., 2013). Some groups of mice received on days 0, 3 and 6 relative to tumour inoculation (day 0) either: control Ig (500 µg i.p., cIg, 1-1) or combination anti-PD-1 (RMP1-14)/anti-CTLA-4 (UC10-4F10) (250 µg i.p. each). Lungs were harvested on day 14 and either fixed in Bouin's solution and B16F10 metastases counted[44] or analysed for NK cell expansion by flow cytometry. For adoptive transfer models, McII$^{f/f}$ Ncr1-iCre mice (Sathe et al., 2014) were injected i.v. with 3×10$^6$ in vitro expanded Cish$^{-/+}$ or Cish$^{-/-}$ NK cells or PBS. Mice were then injected 8 h later with 1×10$^5$ B16F10 melanoma cells. Mice were subsequently treated on day 1 with 1.5×10$^6$ in vitro expanded Cish$^{+/+}$ or Cish$^{-/-}$ NK cells or PBS delivered i.v. Mice were sacrificed on day 18 following tumour injection, and lung perfusion performed. Lungs were then harvested and metastases counted.

Orthotopic E0771.L.MB and Spontaneous E0771 Metastasis

To generate primary tumours, 1×10$^5$ E0771.LMB mCherry+ tumour cells were implanted into the fourth inguinal mammary gland [in 20 µl of PBS] of 8- to 10-week-old female Cish$^{-/-}$ or Cish$^{+/+}$ mice. Primary tumour volume was measured three times per week using electronic callipers. The greatest longitudinal diameter (length) and the greatest transverse diameter (width) were measured. Tumour volumes were estimated by the modified ellipsoidal formula: volume=1/2(length×width$^2$). For spontaneous metastasis experiments, primary tumours were surgically resected at a size of 400-600 mm$^3$. Lungs were harvested 14 days later and metastatic burden quantified by imaging ex vivo using an IVIS Lumina XR-III (Caliper Life Sciences) or by duplex Q-PCR for expression of mCherry relative to vimentin, as described previously (Rautela et al., 2005).

CYT-387 Synthesis

Liquid chromatography mass spectroscopy (LCMS) was carried out using a Finnigan LCQ Advantage Max using reverse phase high performance liquid chromatorgraphy (HPLC) analysis (column: Gemini 3µ C18 20×4.0 mm 110A) Solvent A: Water 0.1% Formic Acid, Solvent B: Acetonitrile 0.1% Formic Acid, Gradient: 10-100% B over 10 min Detection: 100-600 nm and electrospray ionisation (ESI). All compounds submitted for biochemical assay were assessed to have purity ≥95% as measured by HPLC analysis at 254 nm UV absorbance. Chromatography was performed using the CombiFlash® Rf purification system (Teledyne, ISCO, Lincon, Nebr., USA) with pre-packed silica gel columns (particle size 0.040-0.063 mm). All commercial reagents were used as received. Cbz=carboxybenzyl. Benzyl 4-(4-aminophenyl)piperazine-1-carboxylate (S1) and Ethyl 4-(4-chloropyrimidin-2-yl)benzoate (S2) can be prepared as previously described (WO 2014/26242 and WO 2008/109943).

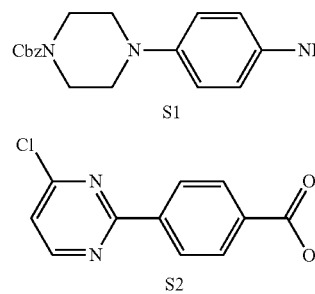
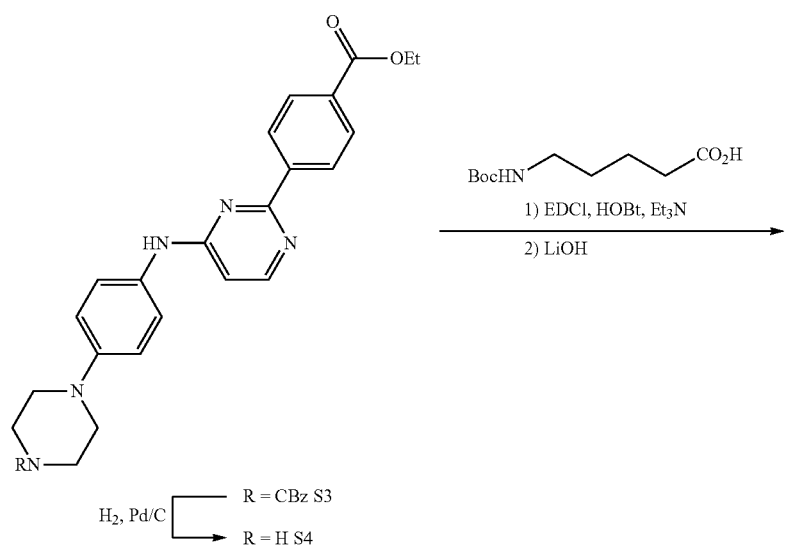
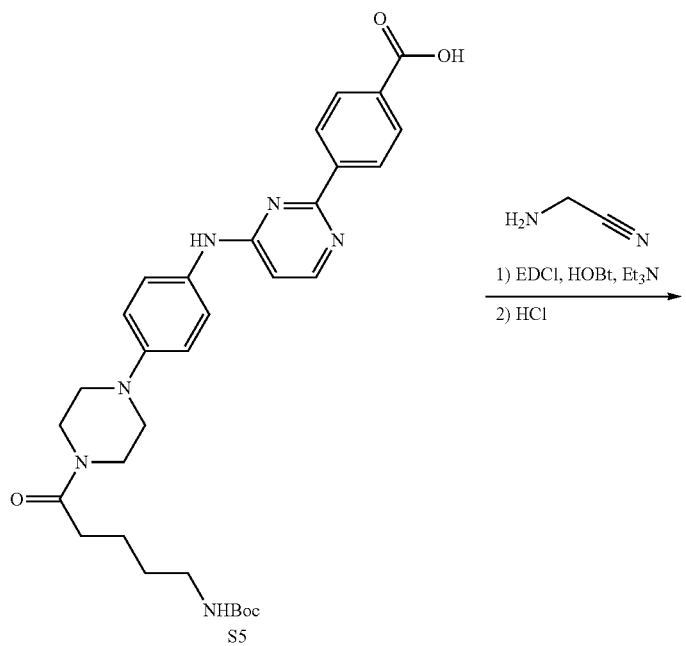

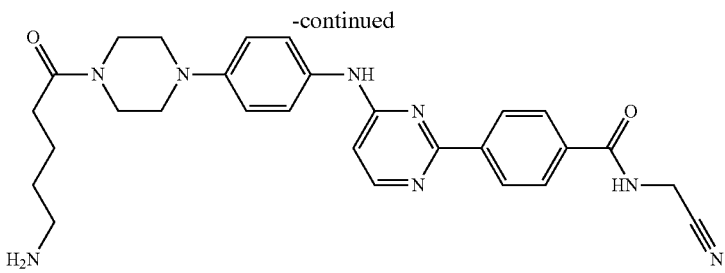

S6

Benzyl 4-(44(2-(4-(ethoxycarbonyl)phenyl)pyrimidin-4-yl)amino)phenyl)piperazine-1-carboxylate (S3)

p-TsOH (0.978 g, 5.13 mmol) was added to a magnetically stirred suspension of pyrimidine S2 (1.50 g, 5.71 mmol) and aniline S1 (2.31 g, 7.42 mmol) in dioxane (20 mL). The mixture was heated to reflux for 24 h. The mixture was cooled, diluted in DCM (250 mL) and washed with NaHCO$_3$ (100 mL) and the aqueous layer was separated and extracted with EtOAc (3×50 mL). The combined organics were dried (Na$_2$SO$_4$), filtered and concentrated onto silica and the material was subjected to flash chromatography (1:9 to 1:0, v/v, EtOAc:cyclohexane). The fractions thus obtained were concentrated and the yellow precipitate was filtered and washed with methanol affording the title compound (S3) (1.61 g, 52%) as a yellow solid. $^1$H NMR (600 MHz, DMSO-d6): δ 9.51 (s, 1H), 8.52 (d, J=5.1 Hz, 1H), 8.25 (d, J=8.3 Hz, 2H), 8.08 (d, J=8.4 Hz, 2H), 7.65 (d, J=9.0 Hz, 2H), 7.37-7.35 (m, 5H), 7.31 (q, J=4.4 Hz, 1H), 6.93 (d, J=9.0 Hz, 2H), 5.09 (s, 2H), 4.33 (q, J=7.1 Hz, 2H), 3.58-3.48 (m, 4H), 3.04-3.03 (m, 4H), 1.33 (t, J=7.1 Hz, 3H). LCMS: $t_R$=6.14 min, m/z=538.0 [M+H]$^+$.

Ethyl 4-(4-((4-(piperazin-1-yl)phenyl)amino)pyrimidin-2-yl)benzoate (S4)

Compound S3 (500 mg, 0.93 mmol) was dissolved in MeOH (75 mL) and THF (50 mL) and the solution was passed through the 'H-cube' at 1 mL/min in full H$_2$ mode using a Pd/C (10%) cartridge at 45° C. The product was collected and concentrated under reduced pressure to afford the title compound (S4) (352 mg, 94%) as a dark solid. $^1$H NMR (600 MHz, CDCl$_3$): δ 8.46 (dd, J=8.0, 5.2 Hz, 1H), 8.16-8.14 (m, 2H), 8.11 (d, J=8.3 Hz, 2H), 7.59 (dd, J=8.9, 1.9 Hz, 1H), 7.55 (d, J=8.9 Hz, 1H), 7.16-7.13 (m, 1H), 6.96 (dt, J=9.1, 4.6 Hz, 2H), 4.41 (q, J=7.1 Hz, 2H), 3.36-3.28 (m, 4H), 3.25-3.18 (m, 4H), 1.42 (t, J=7.1 Hz, 3H). LCMS: $t_R$=5.78 min, m/z=404.0 [M+H]$^+$.

4-(4-((4-(4-(5-((tert-Butoxycarbonyl)amino)pentanoyl)piperazin-1-yl)phenyl)amino)pyrimidin-2-yl)benzoic acid (S5)

To a magnetically stirred solution of N-Boc-aminovaleric acid (194 mg, 0.96 mmol), EDCI (201 mg, 1.05 mmol), HOBt (146 mg, 1.05 mmol), Et$_3$N (232 μL, 1.75 mmol) in DMF (2 mL) was added compound S4 (350 mg, 0.87 mmol) under N$_2$ and the mixture was stirred for 12 h. The reaction mixture was washed with water (2 mL) and the aqueous washings were extracted with EtOAc (2×2 mL). The organic fractions were combined, dried (Na$_2$SO$_4$), filtered and concentrated. The crude material was purified by Flash chromatography to afford a pale yellow solid (373 mg). This material was dissolved in THF/MeOH (2 mL of a 1:3 mixture) and lithium hydroxide (123 mg, 3.09 mmol) was added and the mixture stirred at reflux for 2 h. The mixture was concentrated to yellow solid and suspended in water and acidified to pH=2 with HCl (5% aqueous solution). The precipitate was collected by filtration, washed with MeOH (1 mL) then Et$_2$O (2×1 mL) and dried under reduced pressure affording the title compound (S5) (224 mg, 60%) as red solid. $^1$H-NMR (600 MHz, DMSO-d6): δ 9.49 (s, 1H), 8.52-8.51 (m, 1H), 8.22 (t, J=6.8 Hz, 2H), 8.06 (d, J=8.1 Hz, 2H), 7.65-7.64 (m, 2H), 7.36 (dd, J=4.7, 0.3 Hz, 1H), 6.94-6.91 (m, 2H), 6.77-6.75 (m, 1H), 3.57-3.55 (m, 4H), 3.36 (td, J=1.1, 0.5 Hz, 2H), 3.05-2.99 (m, 4H), 2.91-2.87 (m, 2H), 2.33-2.31 (m, 2H), 1.46-1.45 (m, 2H), 1.34 (s, 9H). LCMS: $t_R$=6.34 min, m/z=575.0 [M+H]$^-$.

4-(4-(0-(4-(5-Aminopentanoyl)piperazin-1-yl)phenyl)amino)pyrimidin-2-yl)-N-(cyanomethyl)benzamide (S6)

To a magnetically stirred solution of compound S5 (190 mg, 0.33 mmol) in DMF (6 mL, anhydrous) at room temperature under N$_2$ was added triethylamine (264 μL, 1.99 mmol) and the mixture was sonicated for 5 min. Then EDCI (76 mg, 0.40 mmol) and HOBt (54 mg, 0.40 mmol) were added and the mixture was stirred for 5 min under N$_2$. Then aminoacetonitrile hydrochloride (61 mg, 0.66 mmol) was added and the reaction was stirred at room temperature under N$_2$ for 12 h. The reaction mixture was concentrated and the crude material was purified by Flash chromatography to afford the coupled product (155 mg, 76%) as a yellow solid. This material was immediately dissolved in dioxane (0.5 mL) then HCl was added (1 mL of a 4 M solution in dioxane) and the reaction mixture stirred for 2 h at room temperature. Then the precipitate was collected by filtration and washed with dioxane before being dissolved in MeOH, and quenched with NH$_3$ (4 M solution in MeOH) then concentrated. The crude material was purified by Flash chromatography to afford the title amine (S6) as a yellow solid (51 mg, 40%). $^1$H-NMR (600 MHz, CD$_3$OD): δ 8.37 (d, J=5.2 Hz, 1H), 8.16 (d, J=8.3 Hz, 2H), 7.91 (d, J=8.3 Hz, 2H), 7.57 (d, 0.1=8.8 Hz, 2H), 7.20 (d, =5.2 Hz, 1H), 6.93 (d, 0.1=8.9 Hz, 2H), 4.34 (s, 2H), 3.69 (t, =5.1 Hz, 2H), 3.63 (t, J=5.0 Hz, 2H), 3.30-3.29 (m, 2H), 3.07 (t, J=5.0 Hz, 2H), 3.03 (t, J=5.1 Hz, 2H), 2.67 (t, J=7.2 Hz, 2H), 2.41 (t, J=7.4 Hz, 2H), 1.62 (dt, J=15.3, 7.6 Hz, 2H), 1.51 (td, J=11.3, 6.1 Hz, 2H). LCMS: $t_R$=4.18 min, m/z=513.0 [M+H]$^+$.

Example 2—IL-15 Induces Expression of SOCS Genes, Including CIS, in NK Cells To date, there has been a great deal of interest in understanding the inhibitory signals that curb NK cell responses, but yet still do not understand how intracellular IL-15 signalling is switched off. Members of the suppressor of cytokine signalling (SOCS) gene family are STAT5 response genes and are often induced to limit the extent of cytokine receptor signalling as part of a classic negative feedback system. In order to investigate which SOCS proteins might regulate IL-15 signalling and hence, NK cell development and function, the inventors first profiled IL-15-induced SOCS expression in cultured NK cells. Cish, Socs1, Socs2 and Socs3 mRNA were induced in NK cells within 2 h of IL-15 treatment, with the early and transient induction of Cish typifying Socs induction by its target cytokine (FIG. 1a). Consistent with the rapid induction of mRNA in saturating concentrations of IL-15, CIS protein was detected in NK cell lysates within 60 minutes of stimulation (FIG. 1b).

Example 3—Cish-Null NK Cells are Hyper-Sensitive to IL-15

To investigate the physiological role of CIS in IL-15 signalling, the inventors utilized a germline Cish-deleted mouse ($Cish^{-/-}$) (Palmer et al., 2015), first confirming that Cish mRNA and protein were absent from NK cells FIG. 5a). Cish-null mice were healthy, fertile and did not present with any phenotypic abnormality when aged to 10 months. The frequency and function of haematopoietic cells appeared normal, including that of conventional $CD4^+$ and $CD8^+$ T cells[9], regulatory T cells and type 2 innate lymphoid cells (ILC2) (FIG. 5b-g). NK cells also developed normally in $Cish^{-/-}$ mice (FIG. 1c, FIG. 5b), as was the case in Socs1 and Socs3 single or doubly-deficient mice FIG. 6a). However, in contrast to Socs1, or Socs3-deficient NK cells, $Cish^{-/-}$ NK cells displayed a profound hyper-proliferation in response to IL-15 in vitro (FIG. 1d, FIG. 6b). When $Cish^{-/-}$ and control C57BL/6 NK cells ($Cish^{+/+}$) were co-cultured 1:1 in a titration of IL-15, $Cish^{-/-}$ NK cells demonstrated enhanced proliferation at concentrations greater than 5 ng $ml^{-1}$ (FIG. 1d). Furthermore, $Cish^{-/-}$ NK cells represented ~95% of cells recovered from co-culture in non-mitogenic IL-15 concentrations, thus demonstrating superior IL-15-mediated NK cell survival in the absence of CIS (FIG. 1d). The hyper-sensitivity of $Cish^{-/-}$ NK cells also manifested in an enhanced IL-15-driven IFN-γ production, that was further heightened with co-stimulation via the activating receptors NKp46 and NK1.1, suggesting an important role for IL-15 in synergising with these receptors (FIG. 1e). When co-cultured with chinese hamster ovarian (CHO) target cells, $Cish^{-/-}$ NK cells displayed greater cytotoxicity at low ratios of NK:target cells when compared to $Cish^{+/+}$ NK cells (FIG. 1f and FIG. 6c). $Cish^{-/-}$ NK cells also killed B16F10 melanoma cells more efficiently than $Cish^{+/+}$ NK cells and displayed greater levels of intracellular granzymes when challenged with RMA-m157 cells, evidence that NK cells are broadly hyper-cytotoxic in the absence of Cish (FIG. 6c, d).

To examine the extent of aberrant IL-15 signalling in Cish-null NK cells, the inventors performed 100 bp single-ended RNA sequencing on $Cish^{+/+}$ and $Cish^{-/-}$ NK cells, either purified directly from the spleen (ex vivo) or following cultivation in IL-15 (in vitro). Very few differentially expressed genes were observed in ex vivo $Cish^{-/-}$ NK cells FIG. 7a) and this, coupled with the normal frequency of $Cish^{-/-}$ NK cells in vivo and low expression of Cish in mature NK cells, suggests that CIS is not a major regulator of NK cell biology in the steady-state. In contrast, more than 1000 differentially expressed genes were detected in $Cish^{-/-}$ NK cells exposed to high concentrations of IL-15 in vitro (FIG. 1g and FIG. 7a, b, c). The highest up-regulated genes included members of the killer cell lectin-like receptor Klra1 and Klra6 and those associated with NK cell effector functions such as the serine proteases Gzme, Gzatf, Gzmd, Gzmg and their inhibitors Serpinb9b, Serpinb9 and Serpin1a (FIG. 1g, FIG. 7a). These findings, together with the superior proliferation and cytotoxicity of $Cish^{-/-}$ NK cells, identify a unique and non-redundant role for CIS as a key negative regulator of IL-15-mediated NK cell effector function. Further, they suggest that CIS acts as an immune checkpoint controlling NK cell responses.

Example 4—JAK1 Levels and Enzymatic Activity are Elevated in the Absence of CIS Protein The SOCS proteins are adapters for an E3 ubiquitin ligase complex, which ubiquitinates SOCS-interacting proteins, targeting them for proteasomal degradation (Zhang et al., 1999). CIS was the first SOCS family protein to be discovered (Matsumoto et al., 1997) and although it was reported to associate with the IL-2 receptor complex (Aman et al., 1999), exactly how this interaction was mediated remained unclear. The hyper-proliferation and enhanced effector capacity of the $Cish^{-/-}$ NK cells could manifest from changes in receptor levels and/or intracellular signalling components. However, $Cish^{+/+}$ and $Cish^{-/-}$ splenic NK cells expressed comparable receptor levels when cultured in the presence of IL-15 (FIG. 2a). The inventors therefore examined receptor proximal signalling events. In both freshly isolated and cultured $Cish^{-/-}$ NK cells, the magnitude of IL-15-stimulated JAK1 tyrosine phosphorylation was increased in comparison to control cells, and was coupled with extended phosphorylation kinetics (FIG. 2b, c and FIG. 8a). Interestingly, levels of total JAK1 protein were elevated in $Cish^{-/-}$ NK cells and this was evident in resting cells prior to stimulation (FIG. 2b, c). Increased JAK phosphorylation correlated with increased phosphorylation of its substrate, STAT5. In contrast, the absence of Cish had no effect on IL-15-dependent AKT phosphorylation (FIG. 2b, c and FIG. 8a), suggesting a unique disconnect between IL-15-driven JAK/STAT and PI3K/mTOR/AKT pathways. This was further confirmed by normal mitochondrial respiration and glycolysis, responses that are known to be regulated by AKT activity (FIG. 8b).

To confirm the elevated JAK1 enzymatic activity and examine how selective the CIS-deficient effects were, the present inventors utilised a mass spectrometry-based approach to quantitate changes in active JAK levels. A pan-JAK inhibitor (derived from CYT-387; JAK1/2/3) was synthesized, coupled to Sepharose beads and used as an affinity-capture reagent, prior to tryptic digest and mass spectrometric analysis. As the inhibitor binds to the ATP binding site in the kinase domain, kinases in the active conformation are preferentially enriched. JAK1 and JAK3 peptides were detected in NK cell lysates with increased number and intensity in $Cish^{-/-}$ cells (FIG. 2d). CYT-387 has known have off-target binding to other kinases, notably TBK1 and CDK2, enabling us to perform a restricted kinome analysis. Sixty-nine kinases were enriched relative to their abundance in cell lysates, with 16 kinases differentially regulated in Gish' cells. Apart from the JAK kinases, the increased activity was largely attributed to kinases involved in regulating cellular proliferation (for example CDK1/2, Prkr, Aurora kinases) (FIG. 2e, f and Table 1). These data are consistent with the hyper-proliferative phenotype and further suggests that many of these may be secondary to the increase in IL-15 signalling. A label-free global proteomic analysis also highlighted changes reflecting the enhanced proliferative capacity (cell cycle, DNA replication, cytoskeletal reorganisation) (FIG. 8c-e and Table 2).

TABLE 1

Quantitative proteomic analysis following CYT-387 affinity enrichment, showing differentially expressed kinases in cultured Cish$^{-/-}$ NK cells, related to FIG. 2.

| Accession Number | Gene Name | Protein Name | Log2 Ratio KO/WT | P-Value KO/WT | Significance KO/WT |
|---|---|---|---|---|---|
| E9QL53 | Cit | Citron Rho-interacting kinase | 2.82 | 9.50E−35 | ++ |
| Q02111 | Prkcq | Protein kinase C theta type | 2.72 | 3.03E−03 | ++ |
| Q8K1M3 | Prkar2a | cAMP-dependent protein kinase type II-alpha regulatory subunit | 2.70 | 2.52E−04 | ++ |
| Q8BP87 | Aurka | Aurora kinase A | 2.59 | 2.69E−03 | ++ |
| Q99JW7 | Cdk1 | Cyclin-dependent kinase 1 | 2.39 | 1.30E−06 | ++ |
| B1AVU1 | Prkx | cAMP-dependent protein kinase catalytic subunit PRKX | 2.22 | 3.49E−02 | + |
| A6P3E4 | Mapk8 | Mitogen-activated protein kinase 8 | 2.06 | 5.71E−06 | ++ |
| Q8K0D0 | Cdk17 | Cyclin-dependent kinase 17 | 2.01 | 6.07E−06 | + |
| Q91ZR8 | Tgfbr2 | TGF-beta receptor type-2 | 1.77 | 5.48E−05 | + |
| Q3U6X7 | Cdk2 | Cyclin-dependent kinase 2 | 1.60 | 4.19E−07 | + |
| Q545E8 | Dck | Deoxycytidine kinase | 1.57 | 1.76E−09 | + |
| Q3TA53 | Limk1 | LIM domain kinase 1 | 1.44 | 2.25E−02 | + |
| P53349 | Map3k1 | Mitogen-activated protein kinase kinase kinase 1 | 1.42 | 1.04E−04 | + |
| Q3URU8 | Jak1 | Tyrosine-protein kinase JAK1 | 1.30 | 1.03E−14 | + |
| Q5D0E0 | Ikbkb | Inhibitor of nuclear factor kappa-B kinase subunit beta | 1.21 | 8.27E−07 | + |
| Q3TUQ7 | Prkaa1 | 5-AMP-activated protein kinase catalytic subunit alpha-1 | 1.15 | 1.91E−03 | + |

TABLE 2

Quantitative proteomic analysis showing differentially expressed proteins in cultured Cish$^{-/-}$ NK cells (see FIG. 10).

| Accession Number | Gene Name | Protein Name | Log2 Ratio KO/WT | P-Value KO/WT | Significance KO/WT |
|---|---|---|---|---|---|
| Q5M9M0 | Rpl13a | 60S ribosomal protein L13a | 4.62 | 3.05E−02 | ++ |
| Q3THV8 | Rrm2 | Ribonucleoside-diphosphate reductase subunit M2 | 3.77 | 1.46E−03 | ++ |
| P49718 | Mcm5 | DNA replication licensing factor MCM5 | 3.13 | 5.62E−07 | ++ |
| Q64737 | Gart | Trifunctional purine biosynthetic protein adenosine-3 | 2.38 | 2.52E−05 | ++ |
| Q61656 | Ddx5 | Probable ATP-dependent RNA helicase DDX5 | 2.27 | 4.77E−04 | ++ |
| Q9DAV6 | Serpinb9b | Serine (Or cysteine) peptidase inhibitor, clade B, member 9b | 2.23 | 4.45E−03 | ++ |
| Q61769 | Mki67 | Protein Mki67 | 2.22 | 7.22E−06 | ++ |
| Q62351 | Tfrc | Transferrin receptor protein 1 | 2.09 | 7.83E−04 | ++ |
| Q99JW7 | Cdk1 | Cyclin-dependent kinase 1 | 2.04 | 1.62E−04 | + |
| Q8R055 | Lig1 | DNA ligase; DNA ligase 1 | 1.94 | 2.01E−05 | + |
| Q6ZQ58 | Larp1 | La-related protein 1 | 1.81 | 2.22E−02 | + |
| Q3UPJ2 | Impdh2 | Inosine-5-monophosphate dehydrogenase | 1.78 | 3.43E−07 | + |
| P97310 | Mcm2 | DNA replication licensing factor MCM2 | 1.74 | 1.26E−05 | + |
| Q05DU8 | Rrm1 | Ribonucleoside-diphosphate reductase | 1.74 | 1.51E−02 | + |
| Q9JJ44 | Dut | Deoxyuridine triphosphatase | 1.73 | 7.83E−04 | + |
| B1AU76 | Nasp | Nuclear autoantigenic sperm protein | 1.71 | 9.46E−05 | + |
| Q8K2Z4 | Ncapd2 | Condensin complex subunit 1 | 1.64 | 4.28E−05 | + |
| Q3TFD0 | Shmt2 | Serine hydroxymethyltransferase | 1.63 | 1.13E−04 | + |

TABLE 2-continued

Quantitative proteomic analysis showing differentially expressed proteins in cultured Cish$^{-/-}$ NK cells (see FIG. 10).

| Accession Number | Gene Name | Protein Name | Log2 Ratio KO/WT | P-Value KO/WT | Significance KO/WT |
|---|---|---|---|---|---|
| Q8R180 | Ero1l | ERO1-like protein alpha | 1.59 | 6.43E-03 | + |
| Q921D5 | Mcm4 | DNA replication licensing factor MCM4 | 1.33 | 1.23E-06 | + |
| Q9WUM3 | Coro1b | Coronin-1B; Coronin | -5.37 | 1.38E-02 | -- |
| Q9JHK5 | Plek | Pleckstrin | -2.67 | 8.31E-03 | -- |
| Q99JI6 | Rap1b | Ras-related protein Rap-1b | -2.60 | 3.14E-02 | -- |
| Q9D051 | Pdhb | Pyruvate dehydrogenase E1 component subunit beta, mitochondrial | -2.53 | 1.24E-04 | -- |
| Q9D8C4 | Ifi35 | Interferon-induced 35 kDa protein homolog | -2.50 | 9.33E-03 | -- |
| Q9CVL7 | Dek | Protein DEK | -2.49 | 2.71E-02 | -- |
| Q3U9B7 | Ctsc | Dipeptidyl peptidase 1 | -2.21 | 1.93E-02 | - |
| Q3UE51 | Hk1 | Hexokinase-1 | -2.15 | 3.09E-03 | -- |
| Q8BMF4 | Dlat | Dihydrolipoyllysine-residue acetyltransferase component of pyruvate dehydrogenase complex, mitochondrial | -2.06 | 4.95E-03 | - |
| Q8BTS3 | Gbp9 | Guanylate-binding protein 9 | -1.94 | 1.83E-02 | - |
| Q9D2D1 | Ctsa | Lysosomal protective protein | -1.77 | 1.09E-04 | - |
| P10649 | Gstm1 | Glutathione S-transferase Mu 1 | -1.74 | 1.83E-02 | - |
| P62806 | Hist1h4a | Histone H4 | -1.70 | 2.41E-03 | - |
| A1L0U3 | Hist1h3e | Histone H3 | -1.66 | 1.83E-02 | - |
| Q6WVG3 | Kctd12 | BTB/POZ domain-containing protein KCTD12 | -1.63 | 1.38E-02 | - |
| D3YWR7 | Qdpr | Dihydropteridine reductase | -1.62 | 1.67E-03 | - |
| Q9DBN7 | Eci1 | Enoyl-CoA delta isomerase 1, mitochondrial | -1.59 | 4.77E-04 | - |
| Q8BWT1 | Acaa2 | 3-ketoacyl-CoA thiolase, mitochondrial | -1.58 | 2.72E-03 | - |
| Q9DCC5 | Cbx3 | Chromobox protein homolog 3 | -1.56 | 1.38E-02 | - |
| Q60654 | Klra7 | Killer cell lectin-like receptor 7 | -1.32 | 1.67E-03 | - |
| Q8C129 | Lnpep | Leucyl-cystinyl aminopeptidase | -1.24 | 2.61E-03 | - |
| Q8C2J1 | Capn1 | Calpain-1 catalytic subunit | -1.23 | 1.03E-04 | - |
| Q61823 | Pdcd4 | Programmed cell death protein 4 | -1.23 | 3.32E-07 | - |
| Q99KC8 | Vwa5a | von Willebrand factor A domain-containing protein 5A | -1.22 | 5.07E-04 | - |
| Q8VCW8 | Acsf2 | Acyl-CoA synthetase family member 2, mitochondrial | -1.08 | 5.17E-07 | - |

Example 5—Identification of Interaction Targets of a CIS-Elongin B-Elongin C Trimeric Complex Like other SOCS proteins, CIS contains an SH2 domain which binds to phosphorylated tyrosine motifs in target proteins and a SOCS box, which together with Elongins B and C, the scaffold protein Cullin 5 and the RING protein Rbx2, constitutes an E3 ubiquitin ligase. Given that the increased levels of total JAK1/3 protein observed in Cish$^{-/-}$ NK cells were not due to increased RNA levels FIG. 9a), the inventors investigated the possibility that CIS might directly reduce JAK protein levels through ubiquitination and proteasomal degradation. Previously, CIS had been shown to interact with the IL-2Rβ and was proposed to regulate signalling by blocking recruitment of STAT proteins to the receptor complex (Matsumoto et al., 1997; Aman et al., 1999); however, there is limited evidence to support the latter proposition. As a preliminary step towards identifying the protein targets that were being regulated by CIS, the inventors performed a screen using a recombinant trimeric complex composed of a human GST-CIS construct (hCIS-SH2; residues 66-258) and Elongins B and C (hCIS-SH2-BC) against a panel of phosphotyrosine peptides corresponding to tyrosines within the IL-2 receptor complex (not shown). Isothermal calorimetry (ITC) was then used to validate binding to phosphopeptides identified in the screen. The hCIS-SH2-BC complex bound with high affinity (0.8-2.1 µM) to synthetic phosphorylated peptides corresponding to tyrosines within the IL-2Rβ cytoplasmic domain (Tyr355, Tyr361 and Tyr392), and within the JAK1 and JAK3 activation loops (Tyr1034 and Tyr980, respectively) (FIG. 3a; FIG. 9c).

Example 6—CIS Protein Downregulates JAK Levels in the Absence of the IL-2 Receptor Complex Via Targeted Proteasomal Degradation The inventors next investigated whether CIS could regulate JAK levels in the absence of the IL-2 receptor complex. Over-expression of JAK in 293T cells (which lack the IL-2R) results in constitutive JAK autophosphorylation. Co-expression of CIS or SOCS1 reduced JAK1 levels to a comparable extent, with a corresponding decrease in JAK1 phosphorylation. In contrast, SOCS3 was unable to inhibit JAK activity in this assay (SOCS3 requires receptor binding) (FIG. 3b). Surprisingly, although the inventors observed CIS binding to the JAK3 Tyr980 peptide (FIG. 3a), JAK3 phosphorylation was not inhibited in this assay (FIG. 3b).

The inventors next interrogated which CIS domains were required for JAK1 inhibition. Mutation of either the CIS-SH2 domain (R107K) or the Cullin-5 binding site in the SOCS box (P241A/L242A/P243A) was sufficient to diminish CIS inhibitory activity (FIG. 3c). Further, pre-incubation of the cells with a proteasomal inhibitor (MG132) reduced CIS-mediated regulation of JAK1 phosphorylation (FIG. 3c), supporting a model whereby CIS binds to JAK1 via its SH2 domain and then targets JAK1 for proteasomal degradation. Co-immunoprecipitation was used to demonstrate complex formation between JAK1 and CIS (FIG. 3d). To formally demonstrate CIS-mediated ubiquitination of JAK1, Flag-tagged full-length JAK1 protein (generated by expression in 293T cells) was incubated in a cell-free system with recombinant hCIS-SH2-SB complex, Cullin5, Rbx2, E1, E2 (UbcH5c) and free ubiquitin. CIS effectively mediated ubiquitination of phosphorylated JAK1 as indicated by the high molecular weight species detected by Western blotting (FIG. 3e). Together, these data demonstrate that CIS is capable of directly regulating JAK protein levels.

Example 7—CIS Protein Directly Inhibits JAK Enzymatic Activity Independently of its Downregulation of JAK Protein Levels Previously, only SOCS1 and SOCS3 have been shown to bind to and regulate JAK activity. SOCS1 and SOCS3 inhibit JAK via non-canonical SH2 binding to a "GQM" motif present in the JAK1, JAK2 and Tyk2 insertion loops and binding of the kinase inhibitory region (KIR) to the catalytic cleft (Kershaw et al.. 2013). CIS does not contain a "KIR" region and there was no prior suggestion that it was able to regulate JAK enzymatic activity. However, several lines of evidence suggested that an additional mechanism was involved. Firstly, the inventors occasionally observed inhibition of JAK1 phosphorylation in the absence of changes in total JAK1 levels (for example, FIG. 3c). Secondly, despite MG132 treatment of wild-type NK cells resulting in an increase in phosphorylation of endogenous JAK1, the inventors did not observe extended kinetics and indeed, JAK phosphorylation was rapidly curtailed. This correlated with increased expression of CIS, which was protected from proteasomal degradation (FIG. 9d). The inventors therefore asked whether CIS could inhibit JAK1 kinase activity. Using an in vitro kinase assay, the CIS-SH2-BC complex was able to inhibit JAK1 phosphorylation of a substrate peptide with an $IC_{50}$ of 0.12±0.02 µM. CIS inhibition of JAK1 was 20-fold or greater than its inhibition of JAK2, JAK3 or TYK2 (FIG. 3f, upper panel), suggesting a unique interface with JAK1 in addition to a canonical SH2 interaction with the conserved JAK activation-loop tyrosine. This concept was supported by the only partial reduction of inhibition seen when the JAK1 activation loop peptide was used as a competitor (FIG. 9e). Although CIS displayed specificity towards JAK1, it inhibited with ~100-fold lower efficiency that SOCS1 (FIG. 3f, lower panel). This suggests that the absolute level of CIS versus SOCS1 will contribute to both specificity and dominance. In this context, receptor recruitment of CIS may increase local concentration of CIS, enabling it to efficiently inhibit JAK1 activity (FIG. 3g). The post-translational regulation of CIS levels, be it proteasome or protease, adds another exquisite layer of control. These data suggest a new target (JAK1) and mechanism (kinase inhibition) for CIS action, and raise the possibility that CIS is fundamentally more similar to SOCS1 than previously thought.

Example 8—Adoptive Transfer of Cish$^{-/-}$ NK Cells in Mouse Tumour Models Results in Significantly Reduced Tumour Formation and Metastasis The markedly enhanced biological responses of Cish$^{-/-}$ NK cells exposed to high concentrations of IL-15 and the lack of an NK cell phenotype in healthy Cish$^{-/-}$ mice under homeostatic conditions, suggests that the steady-state IL-15 levels in vivo are below those required to induce Cish expression. Inflammation associated with tumour formation is likely to increase IL-15 trans-presentation by stroma or infiltrating myeloid lineages and augment resident NK cells activity (Mlecnik et al., 2014).

The inventors therefore investigated whether IL-15-induction of CIS acts as a checkpoint in NK cells in vivo, challenging Cish$^{+/+}$ and Cish$^{-/-}$ mice with a panel of syngeneic tumour cell lines, known to activate and be controlled by NK cells. Intravenous (i.v.) administration of B16F10 melanoma cells to Cish$^{+/+}$ mice resulted in extensive metastatic nodule formation in the lungs by 14 days. In contrast, B16F10 metastatic nodules were largely absent from Cish$^{-/-}$ mice (FIG. 4a). To confirm that the reduced B16F10 metastasis observed in Cish$^{-/-}$ mice was dependent on enhanced NK cell activity, Cish$^{+/+}$ and Cish$^{-/-}$ mice were treated with anti-asiolo GM1 (to deplete NK cells), anti-CD8 (to deplete CD8 T cells), anti-IFN-γ (to block IFN-γ activity) or control anti-immunoglobulin (cIg). Depletion of NK cells or neutralisation of IFN-γ, but not depletion of CD8 T cells, rendered Cish$^{-/-}$ mice susceptible to B16F10 metastasis (FIG. 4b), identifying a role for CIS in the negative regulation of NK cell activity and IFN-γ in this model. Furthermore, when adoptively transferred into mice lacking NK cells (McII$^{f/f}$ Ncr1-iCre; Ncr1$^{McIIΔ/Δ}$), mice that received Cish$^{-/-}$ NK cells had significantly fewer B16F10 lung metastases than mice receiving Cish$^{+/+}$ NK cells (FIG. 4c), evidence that Cish$^{-/-}$ NK cells are intrinsically more active. Injection of Cish$^{+/+}$ and Cish$^{-/-}$ mice with a melanoma cell line expressing a mutated form of the serine/threonine kinase braf(LWT1 BRAF$^{V600E}$) (Davies et al., 2002), also resulted in significantly reduced lung metastases in CIS-deficient mice (FIG. 10a). This finding was not limited to melanoma, as similar differences in lung metastasis were observed when using the RM-1 prostate cancer cell line (FIG. 10b).

Similarly, when breast cancer cells (E0771.LMB-mCherry) were administered i.v to Cish$^{+/+}$, Cish$^{-/-}$ and NK cell-null mice, the inventors observed a reduced tumour burden in the lungs of Cish$^{-/-}$ mice compared to Cish$^{+/+}$ and NK-null mice (FIG. 4d). Histological analysis of lungs from these mice revealed the occasional E0771 micro-metastasis in Cish$^{-/-}$ mice, yet they were devoid of the large metastases frequently observed around blood vessels and enriched in the visceral pleura of Cish$^{+/+}$ mice (FIG. 4d). The growth of orthotopic E0771.LMB mammary tumours was also significantly improved in Cish$^{-/-}$ mice compared to Cish$^{+/+}$ mice (FIG. 4g). When similarly sized primary orthotopic tumours were surgically resected, only Cish$^{+/-}$ mice developed spontaneous E0771.LMB metastases in the lung, whereas Cish$^{-/-}$ mice did not (FIG. 4f and FIG. 10c, d), further evidence that CIS is a potent negative regulator of metastatic anti-tumour immunity.

Example 9—Adoptive Transfer of Cish$^{-/-}$ NK Cells in a Mouse Melanoma Model is More Effective than Anti-PD-1/CTLA-4 Immunotherapy Alone, and has Greater Efficacy in Combination with Anti-PD-1/CTLA-4 Immunotherapy Combination immunotherapy using antibodies directed against the inhibitory receptors PD-1 and CTLA-4 is currently the most effective treatment against advanced melanoma in humans (Larkin et al., 2015; Postow et al., 2015; Yoshimura et al., 2015). To compare this benchmark immunotherapy with Cish deletion in NK cells, Cish$^{-/-}$ and Cish$^{+/+}$ mice were injected with a high dose of B16F10 melanoma (to elicit both an NK cell and CD8 T cell response) and treated with a combination of anti-PD-1/CTLA-4 antibodies or cIg. Anti-PD-1/CTLA-4 treatment significantly reduced melanoma metastases when compared to cIg in Cish$^{+/+}$ mice, however this was inferior to the protection afforded by Cish-deletion alone (Cish$^{-/-}$ mice+ cIg; FIG. 4g). Remarkably, Cish$^{-/-}$ mice treated with anti-PD-1/CTLA-4 developed even fewer metastases than Cish$^{-/-}$ mice treated with cIg (FIG. 4g), highlighting the potential therapeutic benefit that could be achieved if anti-CTLA-4/PD-1 therapy was combined with loss of CIS function.

Induction of Cish was first demonstrated in response to interleukin (IL)-3, IL-2 and erythropoietin (EPO) and forced expression of CIS has been shown to inhibit signalling through these receptors (Matsumoto et al., 1997; Aman et al., 1999). Despite these observations, evidence for a physiological role in these pathways has been limited. Aged (10-18 month) Cish$^{-/-}$ mice were reported to develop an inflammatory lung condition associated with perturbed IL-4/STAT6 and IL-2/STAT5 signalling in CD4$^+$ T cells (Yang et al., 2013), whilst a recent report suggested that antigen receptor signaling was enhanced in Cish$^{-/-}$ CD8$^-$ T cells (Palmer et al., 2015). However, adult Cish$^{-/-}$ mice showed no pathology or alteration in T cell frequencies (Yang et al., 2013) and in the inventors hands, Cish$^{-/-}$ CD8$^-$ T cell development and antigen-specific responses to mouse cytomegalovirus were normal (data not shown). Given that Cish$^{-/-}$ mice remain healthy, our observations suggest that antagonising CIS therapeutically would be unlikely to have any major side effects.

Severe off-target effects and drug resistance currently limit our use of conventional chemotherapies, usually the first line of treatment for most cancers. Thus, there is an unmet need to find new, targeted therapies and immunotherapies that can be used in combination and as an adjunct to chemotherapy.

Ipilimumab is an antibody-based therapy that targets CTLA-4 on effector and regulatory T cells and is approved for the treatment of advanced malignant melanoma, affording 10-12% tumour responses with some complicating immune-related adverse events. This is a first-in-class of the monoclonal antibodies targeting so-called immune checkpoint molecules. Antibodies (of the same class) recognise PD-1 (expressed on T cells and NK cells) or its ligand, PD-L1 (expressed on many tumours once T cell activation has occurred), and pembrolizumab and nivolumab (anti-human PD-1) are already producing 20-50% objective response rates in phase I/II trials in advanced melanoma, renal cancer, non small cell lung cancer (NSCLC), and other cancer indications. Nivolumab and ipilimumab in combination against advanced malignant melanoma have produced even more rapid and impressive anti-cancer effects, including against metastatic disease. Despite these advances, some cancers (eg. prostate, colorectal) show less impressive responses and even in melanoma there remains a large number of patients where anti-CTLA-4 and anti-PD-1/PD-L1 combinations will fail.

Here the inventors have shown that IL-15-induced CIS accumulation in NK cells acts as an intracellular immune checkpoint that limits NK cell function. Ablation of CIS function releases a brake on NK cell activity resulting in a dramatic decrease in experimental tumour metastasis, greater than that observed with CTLA-4/PD-1 blockade and with no sign of adverse reactions. Our results reveal CIS as a novel NK cell checkpoint and suggest that effective therapeutic blockade of CIS function in humans could improve the prognosis of certain cancers.

Example 10—Deletion of Either the CIS N-Terminal Region or PEST Motif Enhances the Ability of CIS to Inhibit JAK1 Kinase Activity To investigate the role of the CIS N-terminal region and PEST motif, the inventors generated *E. coli* expression constructs for human CIS which lacked either the PEST motif (residues 173-202; ΔPEST), the first 24 residues (ΔN34), the N-terminal region (residues 1-66) and the PEST motif (ΔNTΔPEST), or corresponded to full-length protein (CIS). All CIS proteins were expressed together with elongins B and C and the trimeric complex was purified as described. The ability to inhibit the JAK1 kinase domain (JH1) was then assessed using an in vitro kinase reaction. Consistent with previous data (FIG. 3F), CIS-ΔNTΔPEST inhibited JAK1 with an IC$_{50}$ of ~0.6 μM. In contrast, the full-length protein showed a greatly reduced ability to inhibit JAK1 (IC$_{50}$ ~32.3), as did CIS-ΔN34 (IC$_{50}$ ~96.77), suggesting that a region within the N-terminus (residues 35-66) is autoinhibitory. Deletion of the PEST alone was sufficient to increase the IC$_{50}$ to 3.32 mM (compared to full-length CIS) (FIG. 11A).

Example 11—CIS-SH2 Interaction with Phosphopeptide is Required for CIS Inhibition of JAK1 Kinase Activity The addition of phenyl phosphate (PP) into the in vitro kinase reaction abrogated the ability of all CIS constructs to inhibit JAK1 kinase activity (FIG. 11B). Similarly, the addition of free phosphopeptide corresponding to a singlyphosphorylated JAK1 or a double-phosphorylated JAK3, activation loop, dramatically reduced the ability of CIS to inhibit JAK1 kinase activity (FIG. 11C). These data further confirm that canonical binding of the SH2 domain to a phosphotyrosine motif is required for CIS to inhibit JAK1 activity.

Example 12—Deletion of the CIS N-Terminal Region or PEST Motif does not have a Major Impact on Binding to Phosphopeptide CIS constructs which lacked either the PEST motif (residues 173-202; ΔPEST), the first 24 residues (ΔN34), the N-terminal region (residues 1-66) and the PEST motif (ΔNTΔPEST), or which corresponded to full-length CIS, were expressed together with elongins B and C and tested using ITC for their ability to bind the JAK1 phosphopeptide. All constructs bound phosphopeptide with 2.2-10 µM affinity, with the greatest reduction in binding observed with deletion of the N-terminal 34 residues (FIG. 12A). Similarly, full-length CIS and CIS-ΔNTΔPEST bound JAK3 phosphopeptide with comparable affinity (FIG. 12B).

Together, these data suggest that the N-terminal region and/or PEST motif are autoinhibitory and that whilst these regions have minimal impact on the ability of the SH2 domain to bind phosphopeptide, they have a major impact on the ability of CIS to inhibit JAK1 kinase activity. Without wishing to be limited by theory, it is likely that post-translational modification or conformational changes (such as on binding to phosphotyrosine) release the autoinhibition and are required to activate CIS. This suggests that agents which stabilise the conformation/location of the N-terminal region and PEST motif, or block post-translational modification of CIS, could be effective CIS blockers. Similarly, agents which mimick the N-terminal region or PEST motif may also be effective CIS blockers.

Example 13—CIS-SH2 Domain Binds to an Extended Peptide Interface

ITC was used to investigate which of the residues flanking the phosphotyrosine (JAK1 Y1034) contributed to binding affinity (and specificity). Substitution of alanine at the +5, +3 or −3 positions had only a modest effect on binding (~4-fold reduction at +3) (FIG. 13). This suggests that the CIS-SH2 domain makes multiple contacts with its target peptide sequence.

Example 14—CIS Inhibition is Dose Dependent

A small molecule inhibitor of CIS is unlikely to recapitulate a total loss of CIS function. The inventors therefore investigated whether loss of one allele was sufficient to enhance the NK cell response to IL-15. NK cells were purified from $Cish^{+/+}$, $Cish^{+/-}$ and $Cish^{-/-}$ mice, labelled with CTV and expanded in vitro in the presence of increasing concentrations of IL-15, prior to analysis by flow cytometry. The enhanced proliferation of $Cish^{-/-}$ NK cells was recapitulated, whilst $Cish^{+/-}$ NK cells showed an intermediate phenotype, with enhanced proliferation compared to wild-type cells, yet still below that observed for $Cish^{-/-}$ cells (particularly at low IL-15 levels) (FIG. 14A). This result was reflected in the absolute numbers of cells following culture (FIG. 14B) and immunoblotting confirmed that loss of one CIS allele resulted in a corresponding loss of CIS protein (approximately 50%) (FIG. 14C). These data indicate the utility of inhibiting CIS function.

Example 15—Further Validation of the CIS-SH2 Domain as a Therapeutic Target

Using CRISPR technology, the inventors generated a "knock-in" mutant mouse which carries a germline mutation in the Cish gene. This mutation changes Arg107 to Lys in the SH2 domain and abrogates SH2 binding to phosphopeptide. The effect of the mutation was demonstrated using recombinant protein and ITC binding (not shown) and is consistent with data in FIG. 3C which shows that this mutation abrogates the ability of CIS to inhibit JAK1 phosphorylation. NK cells were purified from the SH2 mutant mouse ($Cish^{R107K}$), expanded in vitro for 10 days and absolute cell numbers compared to NK cells derived from $Cish^{+/+}$, $Cish^{+/-}$ and $Cish^{-/-}$ mice. $Cish^{R107K}$ NK cell numbers were closest to those derived from $Cish^{-/-}$ mice (FIG. 14B). The CIS-R107K protein was expressed at comparable levels to wild-type protein (FIG. 14C), evidence that the increased cell number resulted from loss of CIS-SH2 function. These preliminary data indicate that loss of phosphopeptide binding is sufficient to recapitulate Cish deletion, and further indicate that compounds which block SH2 function and in particular the ability to bind phosphopeptide, will be valid starting points for drug development.

Example 16—the Kinetics of CIS Induction are Consistent with Inhibition of JAK/STAT Signalling in Human NK Cells Human and mouse CIS are 90.7% identical at the amino acid level. Similarly, human and mouse JAK1 are 94.4% identical, whilst the activation loops are 100% conserved. Immunoblot analysis of primary human NK cells and various human NK cell lines, showed induction of CIS with 1-2 h IL-15 treatment, together with a concomitant decrease in JAK1 and STAT5 phosphorylation. These data are consistent with CIS inhibiting JAK/STAT signalling (FIG. 15). Furthermore, although 2 h treatment of primary human NK cells with IL-15 and a proteasomal inhibitor (MG-132) was sufficient to increase total JAK1 and CIS levels, JAK1 phosphorylation remained reduced (FIG. 15A). This supports the premise that, consistent with our results using mouse NK cells, CIS inhibits IL-15 signalling in human NK cells via both ubiquitination of JAK1 and inhibition of JAK autophosphorylation.

In addition, IL-15 treatment induced Cish mRNA in the human NK cell lines NK-92 and KHYG-1 (FIG. 16). Notably, the magnitude of Cish induction was much greater than that observed for Socs1 and Socs3 which were also induced, albeit at much lower levels (FIG. 16). This augers well for inhibition of CIS resulting in enhanced IL-15 signalling, without compensation by other SOCS family members.

Example 17—Identification of Phosphorylation and Ubiquitination Sites on CIS

The inventors had shown that CIS itself was regulated by proteasomal degradation (FIG. 9D and FIG. 15A) and further proposed that post-translational modification of CIS may regulate the N-terminal/PEST-mediated autoinhibition. To identify potential phosphorylation and ubiquitination sites, FLAG-tagged CIS was expressed in 293T cells and affinity purified, prior to analysis by mass spectrometry. Six phosphorylation sites were identified, with five of the sites conserved between mouse and human CIS (FIG. 17 and Table 3). Three of the phosphorylation events were detected within the PEST motif (pSDpSPDPAPpT), consistent with the idea that phosphorylation may alter the intra-molecular positioning and/or binding interactions of this motif and hence CIS function. Three ubiquitination sites were also identified (FIG. 17, Table 3) and agreed with a previous report (Jensik et al., 2015). These results identify a number of residues within CIS that can be modified by either ubiquitination or phosphorylation.

Example 18—CIS is a Therapeutic Target in Disease with Elevated and Functional TGF-β

Several clinical trials are ongoing using anti-TGF-β to prevent EMT (Epithelial to Mesenchymal Transformation), however TGF-β is also a potent immune suppressor (Chen et al., 2016). The inventors found that CIS-null NK cells are largely refractory to suppression of proliferation mediated by TGF-β in vitro (FIG. 18).

However, although CIS-null NK cells were resistant to TGF-β when compared to wild-type cells, there was still some inhibitory effects of TGF-β receptor signaling as CIS-null NK cells proliferated less than TGF-β receptor-null NK cells (TgfbRII$^{fl/fl}$). Thus the inventors next investigated whether blocking CIS and TGF-β in vivo would improve tumor outcomes over monotherapy. Wild-type and Cish$^{-/-}$ mice were injected with 1×10$^6$ BRAF mutant melanoma cell lines (SM1LWT1) and either control Ig, anti-TGF-β (1D11), BRAF inhibitor (PLX4720) or 1D11+PLX4720. Inhibition of both CIS and TGF-β (anti-TGF-β antibody, 1D11) resulted in a significantly reduced melanoma burden in the lungs at 14 days when compared to inhibition of either CIS or TGF-β in isolation (FIG. 19). Furthermore, inhibition of both CIS and BRAF resulted in a similar significantly reduced melanoma burden in the lungs at 14 days which was comparable to inhibition of CIS or BRAF. Triple therapy of CIS, BRAF and TGF-β inhibition all but prevents SM1LWT1 metastasis in the lung, suggesting BRAF mutant melanoma metastasis in humans might benefit from CIS-inhibition in combination with TGF-β or BRAF blockade.

Example 19—NK Cell-Dependent Anti-Metastatic Therapies are More Effective with Cish-Deficiency The inventors next sought to compare Cish-deficiency with contemporary immunotherapies, including immune checkpoint blockade (anti-PD-1, anti-CTLA-4, anti-CD96) and cytokines (IFNα/β, IL-2), which promote NK cell function, in the B16F10 experimental metastasis model. Notably, Cish-deficient mice were more resistant to B16F10 lung metastases than wild-type mice treated with a regimen of anti-PD-1, type I IFN (IFN-α43) or IL-2 (FIG. 20A). All of these immunotherapies have been used with some degree of success in the treatment of advanced human melanoma. Although the level of B16F10 metastasis was low in cIg-treated Cish$^{-/-}$ mice, both type I IFN and IL-2 treatment appeared to further reduce metastasis (FIG. 20A). A further experiment assessed a higher dose challenge with B16F10, and here it became apparent that both the anti-PD-1/anti-CTLA-4 combination and IL-2 were more effective than cIg in the Cish$^{-/-}$ mice (FIG. 20B). In particular, low dose IL-2 was ineffective in WT mice, but effective in Cish$^{-/-}$ mice. This improved effect of IL-2 in Cish$^{-/-}$ mice compared with WT mice was also observed in the RMA-S i.p. lymphoma model (FIG. 20C). This is of interest since NK cell-mediated control in WT and Cish$^{-/-}$ mice was equivalent in untreated or control treated mice treated with PBS (FIG. 20C). An additional experiment performed in a second experimental metastasis model, RM-1, indicated the superior anti-metastatic activity of Cish-deficiency combined with anti-PD-1/anti-CTLA-4 or anti-CD96 treatment (FIG. 20D). The superior activity of anti-CD96 in Cish$^{-/-}$ mice was also observed in the B16F10 experimental metastasis model (FIG. 20E).

Collectively, these experiments indicated that CIS regulation of NK cell anti-metastatic activity was independent of the anti-metastatic activities of immune checkpoint antibodies. Ultimately, the mice were challenged with the BRAF$^{v600E}$-mutant metastatic melanoma cell line LWT1, and again significantly less lung metastasis was observed in Cish$^{-/-}$ mice. This metastasis was further reduced by treating with the BRAF-inhibitor PLX4720 (FIG. 20F) or a MEK inhibitor (trametinib) alone or in combination with PLX4720 (FIG. 21). In summary, these data indicate that targeting CIS combines well with other immunotherapies and CIS holds great promise as a novel target in NK cell immunotherapy.

Example 20—Treatment of Sarcoma

Cish$^{-/-}$ mice were highly resistant to methylcholanthrene (MCA)-induced fibrosarcoma formation (FIG. 22A). Depletion of NK cells or neutralization of IFNγ again significantly reduced the survival of WT and Cish$^{-/-}$ mice, and completely abolished the protective effect of Cish– deficiency (FIG. 22B). The extent of protection from experimental metastasis and de novo carcinogenesis observed in Cish$^{-/-}$ mice is impressive and clearly indicated that targeting CIS holds promise as a novel target for NK cell-based immunotherapy. These results are consistent with IL-15 induction of CIS expression in NK cells and the observation that loss of Cish renders NK cells hypersensitive to IL-15 (Delconte et al., 2016).

Example 21—Treatment of Acute Myeloid Leukemia

A pioneering example of NK cell anti-tumor efficacy is in haplo-identical bone marrow transplantation where donor NK cells react strongly against host acute myloid leukemia (AML) (Ruggeri et al., 2016) suggesting that AML might be immunogenic to self NK cells, if such NK cells where sufficiently activated. The inventors found that when self bone marrow was infected with a lentivirus encoding the AML-inducing oncogene MLL-AF9 and injected into WT mice that these mice succumbed to AML at around 40 days post injection (FIG. 23). In contrast, if the Cish$^{-/-}$ host was injected with MLL-AF9 expressing bone marrow, AML onset was significantly delayed and only around 30% of the mice succumbed to AML compared to 100% of WT mice (FIG. 23). These data suggest MLL-AF9+ AML is detected and killed by NK cells and this is significantly enhanced in the absence of CIS.

Example 22—CIS Deficiency Promotes NK Cell Proliferation and Differentiation In Vivo Initial experiments indicated that in vivo, under homeostatic conditions, Cish$^{-/-}$ mice had similar NK cell numbers to Cish$^{+/+}$ mice. When the NK cells were examined in more depth, it was apparent that Cish$^{-/-}$ NK cells were more mature (M2, DNAM1+ KHLRGI+; FIG. 24A,B) and were cycling more rapidly (Ki67+; FIG. 24C) than wild-type cells. Given that total numbers remain consistent (FIG. 24A), this also indicates that Cish$^{-/-}$ NK cells are dying and/or being cleared more rapidly from the body.

Example 23—Enhanced Control of MCA1956 Sarcoma Requires Both NK Cells and CD8 T Cells When injected subcutaneously with the immunogenic MCA-induced fibrosarcoma, MCA1956, Cish$^{-/-}$ mice showed better tumor control than WT mice (FIG. 25). Whereas only 1/10 WT mice spontaneously rejected the tumor, 5/10 Cish$^{-/-}$ mice successfully cleared the primary tumor by day 30 after transplant (FIG. 25). Depletion of either NK cells or CD8β$^+$ T cells accelerated tumor growth and abrogated the differences seen in WT and Cish-deficient mice (FIG. 25). Whether NK cells control the growth of MCA1956 tumors directly or whether they play an indirect role by modulating T cell activity remains to be elucidated. Taken together, our data suggest Cish-deficiency primarily alters the natural growth of subcutaneous tumors where NK cells are critical.

Example 24—Cish$^{-/-}$ CD8 T Cells Exhibit Increased Proliferation and IFNγ Production Lack of an obvious CD8 T cell phenotype in vivo was somewhat surprising given the similarities between transcriptional regulation, effector programs and cytokine dependency of NK cells and CD8 T cells. To specifically test whether CD8 T cells were hyper-responsive to IL-15 or antigen receptor stimulation, peripheral lymph nodes (pooled, excluding mesenteric) from 6-8 wk old WT-Ly5.1 (n=3) and Cish$^{-/-}$-Ly5.2 (n=3) mice were processed to single cell suspensions. Samples were enriched for CD8$^+$ T cells by magnetic bead negative selection. Resulting cells were then labeled with 5 μM CTV. WT and Cish$^{-/-}$ cells were co-cultured in 96 well plates under conditions of IL-2+αCD3, IL-15+αCD3, IL-2+αCD28+αCD3 and IL-15+αCD28+αCD3 in IMDM+10% FCS. For all conditions, αCD3$^-$ wells were included as control (not shown). Wells were set-up in technical triplicate for statistical analysis. Congenic markers permitted examination of both genotypes within single wells. Cells were cultured at 37° C. with 5% $CO_2$.

IFNγ production was assessed by 4 hour stimulation with PMA/ionomycin followed by intracellular staining and FACS analysis. Under all conditions tested, Cish$^{-/-}$ CD8$^+$ T cells produced significantly more IFNγ in response to PMA/Ionomycin stimulation than wild-type (WT) cells (FIG. 26).

Cultures were examined at day 4 of culture by FACs analysis of proliferation via CTV dilution, and surface marker expression (FIG. 27). In the absence of αCD3 stimulation, up to 7 division events were observable in IL-15$^+$ cultures. Number of cells in each division cycle were determined, and plotted as a function of division number (FIG. 27A). Similar results were noted in IL-2 cultures (not shown).

Under all conditions examined, both WT and Cish$^{-/-}$ CD8$^+$ T cells were found to proliferate and produce IFNγ in response to stimulation. In the presence of αCD3, all cultures had proliferated maximally by day 4, making comparisons between the genotypes difficult (not shown). However, in the absence of αCD3 stimulation, analysis of cell number vs division number indicated that Cish$^{-/-}$ cells had proliferated more rapidly than WT controls by day 4 of culture (FIG. 27B). Taken together, these results indicate that under in vitro conditions, Cish$^{-/-}$ CD8$^+$ T cells proliferate more rapidly, and display enhanced effector function compared to their WT counterparts. These preliminary results are promising, however more detailed analysis of proliferation inducing conditions will provide greater insight into the enhanced phenotype noted in Cish$^{-/-}$ CD8$^+$ T cells.

Example 25—Elevated Levels of IL-15 in the Tumour Microenvironment Induce Increased Cish Levels in Tumour-Infiltrating NK Cells The inventors established that IL-15 rapidly induces Cish expression in cultured NK cells and that CIS protein expression is induced within 1 hour following IL-15 stimulation. To visualize Cish expression in vivo, a Cish-lacZ reporter (Cish$^{LacZ/+}$) mouse strain was utilized. IL-15$^{+/+}$ or IL-15$^{-/-}$ mice (stromal IL-15 status + or – respectively) were lethally irradiated and reconstituted with Cish$^{LacZ/+}$ bone marrow. 10 weeks later these chimeric mice were challenged with 1×10$^5$ E0771 breast cancer cells injected in the mammary fat pad or left unchallenged. One week later mice were sacrificed, mammary tumors harvested and dissociated and tumour resident NK cells were stained for β-galactosidase (Cish expression) and analyzed by flow cytometry. The presence of stromal IL-15 significantly augmented Cish expression in NK cells by around 2-fold was observed (FIG. 28). NK cells infiltrating mammary tumors where IL-15 was present in the stroma displayed increased Cish expression and this was most evident in NK cells that infiltrated mammary tumors in mice whose stroma was devoid of IL-15. In both situations, NK cell Cish levels were greatest in tumor resident NK cells compared to mammary fat pad NK cells suggesting higher IL-15 levels in the E0771 tumor microenvironment. Given this tumor is tightly controlled by NK cells and a model that is extremely responsive to CIS loss of function, our data suggest that elevated IL-15 levels in tumors and increased Cish expression in tumor-resident NK cells is a prognostic for a tumor type likely to respond to a small molecule CIS inhibitor.

Example 26—Assessment of Human Cish$^{-/-}$ NK Cells Against Melanoma Metastases In Vivo (Prophetic)

In order to assess how closely human Cish$^{-/-}$ NK cells recapitulate the effect of mouse Cish$^{-/-}$ NK cells against tumour growth and metastasis in vivo, we will perform an adoptive cell transfer experiment in lymphoid mice (NOD/SCID/gammaC; NSG). For adoptive transfer models, NSG mice are injected i.v. with 5×10$^6$ in vitro expanded human Cish$^{+/+}$ or isogenic Cish$^{-/-}$ human NK cells or PBS. Mice are then injected 8 h later with 1×106 BRAF mutant patient derived melanoma cells that are maintained as a cell line in our lab. Mice are subsequently treated on day 1 with 1.5×10$^6$ in vitro expanded Cish$^{+/+}$ or Cish$^{-/-}$ NK cells or PBS delivered i.v. Mice are sacrificed on day 18 following tumour injection, and lung perfusion performed. Lungs and livers are then harvested and metastases counted.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

The present application claims priority from AU 2015905220 filed 16 Dec. 2016, the entire contents of which are incorporated herein by reference.

All publications cited herein are hereby incorporated by reference in their entirety. Where reference is made to a URL or other such identifier or address, it is understood that such identifiers can change and particular information on the internet can come and go, but equivalent information can be found by searching the internet. Reference thereto evidences the availability and public dissemination of such information.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this application.

TABLE 3

Summary of phosphorylation and ubiquitination sites detected in CIS.

| a.a. start site | a.a. stop site | Domain | Modified Sequence (ph = phospho, gl = gly-gly) | SEQ ID NO: | Modification site | m/z | Best score | charge | PPM error |
|---|---|---|---|---|---|---|---|---|---|
| 173 | 188 | PEST | S(ph)DSPDPAPTPALPMSK | 30 | S173 | 853.87 | 91.64 | 2 | -0.367 |
| 173 | 188 | PEST | SDS(ph)PDPAPTPALPMSK | 30 | S175 | 853.87 | 135.43 | 2 | 0.001 |
| 20 | 59 | N-TERM | RPLWAQS(ph)LELPGPAMQPLPTGAFPEEVTEETPVQAENEPK | 31 | S26 | 1120.79 | 58.482 | 4 | 0.037 |
| 20 | 59 | N-TERM | RPLWAQSLELPGPAMQPLPT(ph)GAFPEEVTEETPVQAENEPK | 31 | T39 | 1120.79 | 46.549 | 4 | -0.088 |
| 172 | 215 | PEST | SDSPDPAPT(ph)PALPMSKQDAPSDSVLPIPVATAVHLKLVQPFVR | 32 | T181 | 917.87 | 52.334 | 5 | -1.188 |
| 188 | 220 | SH2/SB | QDAPSDSVLPIPVATAVHLKLVQPFVRRS(ph)S(ph)AR | 33 | S217 or S218 | 707.78 | 75.78 | 5 | -0.150 |
| 60 | 72 | N-TERM | _VLDPEGDLLCIAK(gl)TFSYLR_ | 34 | K72 | 775.403349 | 177.6 | 3 | -0.146 |
| 94 | 107 | SH2 | _QHLQK(gl)M(ox)PEGTFLVR_ | 35 | K98 | 454.239898 | 164.68 | 4 | 0.203 |
| 108 | 124 | SH2 | _DSTHPSYLFTLSVK(gl)TTRGPINVR | 36 | K121 | 539.082802 | 104.18 | 5 | 0.327 |
| 173 | 208 | PEST | _SDSPDPAPTPALPM(ox)SK(gl)QDAPSDSVLPIPVATAVHLK_ | 37 | K188 | 945.734465 | 131.84 | 4 | 0.822 |
| 189 | 215 | SH2/SB | _QDAPSDSVLPIPVATAVHLK(gOLVQPFVR_ | 38 | K208 | 753.672374 | 101.86 | 4 | 1.010 |

REFERENCES

Alexander et al. (1999) Cell 98:597-608.
Allard et al. (2013) Clin Cancer Res 19:5626-5635.
Aman et al. (1999) J Biol Chem 274:30266-30272.
Babon et al. (2012) Immunity 36:239-250.
Babon et al. (2013) Methods Mol Biol 967:39-55.
Bohm et al. (1999) M. Med. Chem. Res. 9:445.
Borowsky (2011) Cold Spring Harb Perspect Biol, 3:a009670.
Bullock et al. (2006) Proc Natl Acad Sci USA 103:7637-7642.
Casalena et al. (2012) Methods Mol Biol, 803:249-263.
Cerqueira et al. (2015) Arch Biochem Biophys 582:56-67.
Chan et al. (2014) Nat Immunol 15:431-438.
Chen et al. (2016) Nat Immunol 16:723-740.
Childs et al. (2013) Hematology Am Soc Hematol Educ Program 2013:234-246.
Constantini et al. (2008) Cancer Biotherm Radiopharm 23: 3-24.
Cox et al. (2014) Mol Cell Proteomics 13:2513-2526.
Croker et al. (2003) Nat Immunol 4:540-545.
Davies et al. (2002) Nature 417:949-954.
De Coupade et al. (2005), Biochem J, 390:407-418.
De Esch et al. (2001) J. Med. Chem. 44:1666-1674.
Delconte et al. (2016) Nat Immunol 17:816-824.
Deshayes et al. (2008) Adv Drug Deliv Rev 60:537-47.
Ewing et al. (2001) J. Comput Aid. Mol. Design, 15:411.
Ferrari de Andrade et al. (2014) Cancer Res 74:7298-7308.
Floris et al. (2011) Molecular Informatics 31:12-20.
Giamann et al. (2006) 4:555-563.
Gilfillan et al. (2008) The J Exp Med 205:2965-2973.
Good (2001) Current Opinion in Drug Disc. Devel. 5:301.
Grabowska et al. (2014) Cancer Metastasis Rev 33:377-397.
Hoek et al. (2015) PLOS One, 10:e0118528.
Howl et al. (2007), Biochem Soc Trans 35:767-769.
Jang et al. (2012) Ann Clin Lab Sci 42:42-49.
Jensik et al. (2015) Mol Cell Endocrinol 401:130-141.
Johnstone et al. (2015) Dis Model Mech 8:237-251.
Keilhauer et al. (2015) Mol Cell Proteomics 14:120-135.
Kershaw et al. (2013) Nat Struct Mol Biol 20:469-476.
Koppelhus et al. (2008) Bioconj Chem 19:1526-34.
Kolesnik and Nicholson (2013) Methods Mol Biol 967:235-248.
Kopsidas et al. (2007) BMC Biotechnology 7:18-29.
Kuenemann et al. (2015) Prog. Biophys. Mol. Biol 119:20-32.
Larkin et al. (2015) N Engl J Med 373:23-34.
Lee et al. (2008) Blood 111:885-893.
Li and Wu (2009) Methods Mol Biol 570:67-76.
Linossi et al. (2013) PLoS One 8, e70536, doi:10.1371/journal.pone.0070536.
Male et al. (2013), Future Medicine, October 2013, 118-133.
Martinet et al. (2015), Cell Rep., 11(1):85-97.
Matsumoto et al. (1997) Blood 89:3148-3154.

Mills et al. (2001) J Comp. Aided Mol Des 15:81-96.
Mlecnik et al. (2014) Sci Transl Med 6:228-237.
Narni-Mancinelli et al. (2011) Proc Natl Acad Sci USA 108:18324-18329.
Needleman and Wunsch (1970) J. Mol. Biol., 48:444-453.
Nicholson et al. (1995) Blood 86:3698-3704.
Ng et al. (2003) Nucleic Acids Research 31:3812-3814.
Palmer et al. (2015) The Journal of Experimental Medicine 212:2095-2113.
Perkin et al. (1995) J Comp. Aided. Mol. Des. 9:479-490.
Postow et al. (2015) N Engl J Med 372:2006-2017.
Rautela et al. (2005) Cancer Immunol Res 3:1207-1217.
Rossi et al. (2014) Cell Death and Disease, 5:e1203.
Ruggeri et al. (2016) Blood 128(23):2616-2623.
Sathe et al. (2014) Nat Commun 5:4539.
Schirle et al. (2012) in Kinase Inhibitors Vol. 795 Methods in Molecular Biology (ed Bernhard Kuster) Ch. 11, 161-177 (Humana Press).
Shihab et al. (2013) Human Mutation 34:57-65.
Sim et al. (2012) Nucleic Acids Research 40(Web Server Issue):W452-457.
Stagg et al. (2011a) Cancer Res 71:2892-2900.
Stagg et al. (2011b) Proc Natl Acad Sci USA 108:7142-7147.
Swann et al. (2007) J Immunol 178:7540-7549.
Von Ahsen et al. (2005) Chembiochem 6:481-490.
Walker et al. (2011) Pigment Cell Melanoma Res 24:1158-1176.
Walzer et al. (2007) Proc Natl Acad Sci USA 104:3384-3389.
Westermaier et al. (2015) Methods, 71:44057.
Whiteside (2002) Biotechniques 33:S4-S15.
Wisniewski et al. (2009) Nat Methods 6:359-362.
Wu (2013) J Mol Genet Med, 7:85.
Yao et al. (2005) Methods Mol Biol 298:91-103.
Yang et al. (2013) Nat Immunol 14:732-740.
Yoshimura et al. (2015) Embo J 14:2816-2826.
Zetsche et al. (2015) Cell 163:1-3
Zhang et al. (1999) Proc Natl Acad Sci USA 96:2071-2076.
Zhang et al. (2015) J. Chem. Inf. Model 54:324-337.
Zhu et al. (2009) J Biomolecular Screening 14:1157-1164.

The invention claimed is:

1. A method for adoptive cell therapy or prophylaxis comprising administering CIS-inhibited NK cells to a subject suffering from or determined to be at risk of suffering from a cancer or an infection, wherein the CIS-inhibited NK cells are NK cells genetically modified to have reduced expression of CIS, or are modified to express a dominant negative CIS sequence variant or dominant negative fragment thereof, wherein the method further comprises administering IL-15 to the subject.

2. The method of claim 1, wherein the CIS-inhibited NK cells and the IL-15 are administered in combination.

3. The method of claim 1, wherein the CIS-inhibited NK cells are genetically modified to express IL-15.

4. The method of claim 1, wherein the method further comprises administering a TGF-beta receptor antagonist.

5. The method of claim 4, wherein the TGF-beta receptor antagonist is specific for TGF-beta receptor 2.

6. The method of claim 1, wherein the CIS-inhibited NK cells are genetically modified to have reduced expression of a TGF-beta receptor.

7. The method of claim 6, wherein the CIS-inhibited NK cells are genetically modified to have reduced expression of TGF-beta receptor 2.

8. The method of claim 1, wherein the CIS-inhibited NK cells are genetically modified to have reduced expression of CIS.

9. The method of claim 8, wherein the CIS-inhibited NK cells are $Cish^{-/-}$.

10. The method of claim 1, wherein the subject is suffering from a cancer, or is determined to be at risk of suffering from a cancer.

11. The method of claim 10, wherein the cancer is selected from the group consisting of: metastatic melanoma, metastatic prostate cancer, metastatic breast cancer, triple negative breast cancer, bladder cancer, brain cancer, esophageal cancer, liver cancer, head and neck cancer, squamous cell lung cancer, non-small lung cell cancer, Merkel cell carcinoma, sarcoma, hepatocellular cancer, multiple myeloma, pancreatic cancer, colorectal carcinoma, cervical cancer, gastric carcinoma, kidney cancer, metastatic renal cell carcinoma, leukemia, ovarian cancer, and malignant glioma.

12. The method of claim 1, wherein the genetic modification is a deletion or a substitution in the Cish gene.

* * * * *

SEQUENCE LISTING

```
<160> NUMBER OF SEQ ID NOS: 38

<210> SEQ ID NO 1
<211> LENGTH: 16
<212> TYPE: PRT
<213> ORGANISM: Homo sapiens
<220> FEATURE:
<221> NAME/KEY: MISC_FEATURE
<222> LOCATION: (8)..(8)
<223> OTHER INFORMATION: phosphorylated tyrosine

<400> SEQUENCE: 1

Ala Ile Glu Thr Asp Lys Glu Tyr Tyr Thr Val Lys Asp Asp Arg Asp
1               5                   10                  15

<210> SEQ ID NO 2
<211> LENGTH: 5
<212> TYPE: PRT
<213> ORGANISM: Homo sapiens
<220> FEATURE:
<221> NAME/KEY: X
<222> LOCATION: (3)..(3)
<223> OTHER INFORMATION: [F2PMP]2 - a phosphotyrosyl mimetic
      4-(phosphonodifluoromethyl)phenylalanine moiety

<400> SEQUENCE: 2

Lys Glu Xaa Thr Val
1               5

<210> SEQ ID NO 3
<211> LENGTH: 12
<212> TYPE: PRT
<213> ORGANISM: Homo sapiens
<220> FEATURE:
<221> NAME/KEY: MISC_FEATURE
<222> LOCATION: (4)..(4)
<223> OTHER INFORMATION: phosphorylated residue

<400> SEQUENCE: 3

Cys Gln Val Tyr Phe Thr Tyr Asp Pro Tyr Ser Glu
1               5                   10

<210> SEQ ID NO 4
<211> LENGTH: 12
<212> TYPE: PRT
```

```
<213> ORGANISM: Homo sapiens
<220> FEATURE:
<221> NAME/KEY: MISC_FEATURE
<222> LOCATION: (4)..(4)
<223> OTHER INFORMATION: phosphorylated tyrosine

<400> SEQUENCE: 4

Tyr Asp Pro Tyr Ser Glu Glu Asp Pro Asp Glu Gly
1               5                   10

<210> SEQ ID NO 5
<211> LENGTH: 12
<212> TYPE: PRT
<213> ORGANISM: Homo sapiens
<220> FEATURE:
<221> NAME/KEY: MISC_FEATURE
<222> LOCATION: (4)..(4)
<223> OTHER INFORMATION: phosphorylated tyrosine

<400> SEQUENCE: 5

Asp Asp Ala Tyr Cys Thr Phe Pro Ser Arg Asp Asp
1               5                   10

<210> SEQ ID NO 6
<211> LENGTH: 258
<212> TYPE: PRT
<213> ORGANISM: Homo sapiens

<400> SEQUENCE: 6

Met Val Leu Cys Val Gln Gly Pro Arg Pro Leu Leu Ala Val Glu Arg
1               5                   10                  15

Thr Gly Gln Arg Pro Leu Trp Ala Pro Ser Leu Glu Leu Pro Lys Pro
            20                  25                  30

Val Met Gln Pro Leu Pro Ala Gly Ala Phe Leu Glu Glu Val Ala Glu
        35                  40                  45

Gly Thr Pro Ala Gln Thr Glu Ser Glu Pro Lys Val Leu Asp Pro Glu
    50                  55                  60

Glu Asp Leu Leu Cys Ile Ala Lys Thr Phe Ser Tyr Leu Arg Glu Ser
65                  70                  75                  80

Gly Trp Tyr Trp Gly Ser Ile Thr Ala Ser Glu Ala Arg Gln His Leu
                85                  90                  95

Gln Lys Met Pro Glu Gly Thr Phe Leu Val Arg Asp Ser Thr His Pro
            100                 105                 110

Ser Tyr Leu Phe Thr Leu Ser Val Lys Thr Thr Arg Gly Pro Thr Asn
        115                 120                 125

Val Arg Ile Glu Tyr Ala Asp Ser Ser Phe Arg Leu Asp Ser Asn Cys
    130                 135                 140

Leu Ser Arg Pro Arg Ile Leu Ala Phe Pro Asp Val Val Ser Leu Val
145                 150                 155                 160

Gln His Tyr Val Ala Ser Cys Thr Ala Asp Thr Arg Ser Asp Ser Pro
                165                 170                 175

Asp Pro Ala Pro Thr Pro Ala Leu Pro Met Pro Lys Glu Asp Ala Pro
            180                 185                 190

Ser Asp Pro Ala Leu Pro Ala Pro Pro Ala Thr Ala Val His Leu
        195                 200                 205

Lys Leu Val Gln Pro Phe Val Arg Arg Ser Ser Ala Arg Ser Leu Gln
    210                 215                 220

His Leu Cys Arg Leu Val Ile Asn Arg Leu Val Ala Asp Val Asp Cys
225                 230                 235                 240
```

```
Leu Pro Leu Pro Arg Arg Met Ala Asp Tyr Leu Arg Gln Tyr Pro Phe
            245                 250                 255

Gln Leu

<210> SEQ ID NO 7
<211> LENGTH: 164
<212> TYPE: PRT
<213> ORGANISM: Homo sapiens

<400> SEQUENCE: 7

Asp Leu Leu Cys Ile Ala Lys Thr Phe Ser Tyr Leu Arg Glu Ser Gly
1               5                   10                  15

Trp Tyr Trp Gly Ser Ile Thr Ala Ser Glu Ala Arg Gln His Leu Gln
            20                  25                  30

Lys Met Pro Glu Gly Thr Phe Leu Val Arg Asp Ser Thr His Pro Ser
        35                  40                  45

Tyr Leu Phe Thr Leu Ser Val Lys Thr Thr Arg Gly Pro Thr Asn Val
    50                  55                  60

Arg Ile Glu Tyr Ala Asp Ser Ser Phe Arg Leu Asp Ser Asn Cys Leu
65                  70                  75                  80

Ser Arg Pro Arg Ile Leu Ala Phe Pro Asp Val Val Ser Leu Val Gln
                85                  90                  95

His Tyr Val Ala Ser Cys Thr Ala Asp Thr Arg Ser Ala Thr Ala Val
            100                 105                 110

His Leu Lys Leu Val Gln Pro Phe Val Arg Arg Ser Ser Ala Arg Ser
        115                 120                 125

Leu Gln His Leu Cys Arg Leu Val Ile Asn Arg Leu Val Ala Asp Val
    130                 135                 140

Asp Cys Leu Pro Leu Pro Arg Arg Met Ala Asp Tyr Leu Arg Gln Tyr
145                 150                 155                 160

Pro Phe Gln Leu

<210> SEQ ID NO 8
<211> LENGTH: 41
<212> TYPE: PRT
<213> ORGANISM: Homo sapiens

<400> SEQUENCE: 8

Ser Ser Ala Arg Ser Leu Gln His Leu Cys Arg Leu Val Ile Asn Arg
1               5                   10                  15

Leu Val Ala Asp Val Asp Cys Leu Pro Leu Pro Arg Arg Met Ala Asp
            20                  25                  30

Tyr Leu Arg Gln Tyr Pro Phe Gln Leu
        35                  40

<210> SEQ ID NO 9
<211> LENGTH: 257
<212> TYPE: PRT
<213> ORGANISM: Mus musculus

<400> SEQUENCE: 9

Met Val Leu Cys Val Gln Gly Ser Cys Pro Leu Leu Ala Val Glu Gln
1               5                   10                  15

Ile Gly Arg Arg Pro Leu Trp Ala Gln Ser Leu Glu Leu Pro Gly Pro
            20                  25                  30

Ala Met Gln Pro Leu Pro Thr Gly Ala Phe Pro Glu Glu Val Thr Glu
        35                  40                  45
```

-continued

```
Glu Thr Pro Val Gln Ala Glu Asn Glu Pro Lys Val Leu Asp Pro Glu
    50                  55                  60

Gly Asp Leu Leu Cys Ile Ala Lys Thr Phe Ser Tyr Leu Arg Glu Ser
65                  70                  75                  80

Gly Trp Tyr Trp Gly Ser Ile Thr Ala Ser Glu Ala Arg Gln His Leu
                85                  90                  95

Gln Lys Met Pro Glu Gly Thr Phe Leu Val Arg Asp Ser Thr His Pro
            100                 105                 110

Ser Tyr Leu Phe Thr Leu Ser Val Lys Thr Thr Arg Gly Pro Thr Asn
        115                 120                 125

Val Arg Ile Glu Tyr Ala Asp Ser Ser Phe Arg Leu Asp Ser Asn Cys
    130                 135                 140

Leu Ser Arg Pro Arg Ile Leu Ala Phe Pro Asp Val Val Ser Leu Val
145                 150                 155                 160

Gln His Tyr Val Ala Ser Cys Ala Ala Asp Thr Arg Ser Asp Ser Pro
                165                 170                 175

Asp Pro Ala Pro Thr Pro Ala Leu Pro Met Ser Lys Gln Asp Ala Pro
            180                 185                 190

Ser Asp Ser Val Leu Pro Ile Pro Val Ala Thr Ala Val His Leu Lys
        195                 200                 205

Leu Val Gln Pro Phe Val Arg Arg Ser Ser Ala Arg Ser Leu Gln His
    210                 215                 220

Leu Cys Arg Leu Val Ile Asn Arg Leu Val Ala Asp Val Asp Cys Leu
225                 230                 235                 240

Pro Leu Pro Arg Arg Met Ala Asp Tyr Leu Arg Gln Tyr Pro Phe Gln
                245                 250                 255

Leu
```

<210> SEQ ID NO 10
<211> LENGTH: 257
<212> TYPE: PRT
<213> ORGANISM: Rattus norvegicus

<400> SEQUENCE: 10

```
Met Val Leu Cys Val Gln Gly Ser Cys Pro Leu Leu Val Val Glu Gln
1               5                   10                  15

Ile Gly Gln Arg Pro Leu Trp Ala Gln Ser Leu Glu Leu Pro Gly Pro
            20                  25                  30

Ala Met Gln Pro Leu Pro Thr Gly Ala Phe Pro Glu Glu Val Thr Glu
        35                  40                  45

Glu Thr Pro Val Gln Ser Glu Asn Glu Pro Lys Val Leu Asp Pro Glu
    50                  55                  60

Gly Asp Leu Leu Cys Ile Ala Lys Thr Phe Ser Tyr Leu Arg Glu Ser
65                  70                  75                  80

Gly Trp Tyr Trp Gly Ser Ile Thr Ala Ser Glu Ala Arg Gln His Leu
                85                  90                  95

Gln Lys Met Pro Glu Gly Thr Phe Leu Val Arg Asp Ser Thr His Pro
            100                 105                 110

Ser Tyr Leu Phe Thr Leu Ser Val Lys Thr Thr Arg Gly Pro Thr Asn
        115                 120                 125

Val Arg Ile Glu Tyr Ala Asp Ser Ser Phe Arg Leu Asp Ser Asn Cys
    130                 135                 140

Leu Ser Arg Pro Arg Ile Leu Ala Phe Pro Asp Val Val Ser Leu Val
145                 150                 155                 160
```

-continued

Gln His Tyr Val Ala Ser Cys Thr Ala Asp Thr Arg Ser Asp Ser Pro
                165                 170                 175

Asp Pro Ala Pro Thr Pro Ala Leu Pro Val Pro Lys Pro Asp Ala Pro
            180                 185                 190

Gly Asp Pro Val Leu Pro Ile Pro Val Ala Thr Ala Val His Leu Lys
        195                 200                 205

Leu Val Gln Pro Phe Val Arg Arg Ser Ser Ala Arg Ser Leu Gln His
    210                 215                 220

Leu Cys Arg Leu Val Ile Asn Arg Leu Val Thr Asp Val Asp Cys Leu
225                 230                 235                 240

Pro Leu Pro Arg Arg Met Ala Asp Tyr Leu Arg Gln Tyr Pro Phe Gln
            245                 250                 255

Leu

<210> SEQ ID NO 11
<211> LENGTH: 1154
<212> TYPE: PRT
<213> ORGANISM: Homo sapiens

<400> SEQUENCE: 11

Met Gln Tyr Leu Asn Ile Lys Glu Asp Cys Asn Ala Met Ala Phe Cys
1               5                   10                  15

Ala Lys Met Arg Ser Ser Lys Lys Thr Glu Val Asn Leu Glu Ala Pro
            20                  25                  30

Glu Pro Gly Val Glu Val Ile Phe Tyr Leu Ser Asp Arg Glu Pro Leu
        35                  40                  45

Arg Leu Gly Ser Gly Glu Tyr Thr Ala Glu Glu Leu Cys Ile Arg Ala
    50                  55                  60

Ala Gln Ala Cys Arg Ile Ser Pro Leu Cys His Asn Leu Phe Ala Leu
65                  70                  75                  80

Tyr Asp Glu Asn Thr Lys Leu Trp Tyr Ala Pro Asn Arg Thr Ile Thr
                85                  90                  95

Val Asp Asp Lys Met Ser Leu Arg Leu His Tyr Arg Met Arg Phe Tyr
            100                 105                 110

Phe Thr Asn Trp His Gly Thr Asn Asp Asn Glu Gln Ser Val Trp Arg
        115                 120                 125

His Ser Pro Lys Lys Gln Lys Asn Gly Tyr Glu Lys Lys Lys Ile Pro
    130                 135                 140

Asp Ala Thr Pro Leu Leu Asp Ala Ser Ser Leu Glu Tyr Leu Phe Ala
145                 150                 155                 160

Gln Gly Gln Tyr Asp Leu Val Lys Cys Leu Ala Pro Ile Arg Asp Pro
                165                 170                 175

Lys Thr Glu Gln Asp Gly His Asp Ile Glu Asn Glu Cys Leu Gly Met
            180                 185                 190

Ala Val Leu Ala Ile Ser His Tyr Ala Met Met Lys Lys Met Gln Leu
        195                 200                 205

Pro Glu Leu Pro Lys Asp Ile Ser Tyr Lys Arg Tyr Ile Pro Glu Thr
    210                 215                 220

Leu Asn Lys Ser Ile Arg Gln Arg Asn Leu Leu Thr Arg Met Arg Ile
225                 230                 235                 240

Asn Asn Val Phe Lys Asp Phe Leu Lys Glu Phe Asn Asn Lys Thr Ile
                245                 250                 255

Cys Asp Ser Ser Val Ser Thr His Asp Leu Lys Val Lys Tyr Leu Ala
            260                 265                 270

```
Thr Leu Glu Thr Leu Thr Lys His Tyr Gly Ala Glu Ile Phe Glu Thr
            275                 280                 285

Ser Met Leu Leu Ile Ser Ser Glu Asn Glu Met Asn Trp Phe His Ser
        290                 295                 300

Asn Asp Gly Gly Asn Val Leu Tyr Tyr Glu Val Met Val Thr Gly Asn
305                 310                 315                 320

Leu Gly Ile Gln Trp Arg His Lys Pro Asn Val Val Ser Val Glu Lys
                325                 330                 335

Glu Lys Asn Lys Leu Lys Arg Lys Leu Glu Asn Lys His Lys Lys
            340                 345                 350

Asp Glu Glu Lys Asn Lys Ile Arg Glu Glu Trp Asn Asn Phe Ser Tyr
            355                 360                 365

Phe Pro Glu Ile Thr His Ile Val Ile Lys Glu Ser Val Val Ser Ile
        370                 375                 380

Asn Lys Gln Asp Asn Lys Lys Met Glu Leu Lys Leu Ser Ser His Glu
385                 390                 395                 400

Glu Ala Leu Ser Phe Val Ser Leu Val Asp Gly Tyr Phe Arg Leu Thr
                405                 410                 415

Ala Asp Ala His His Tyr Leu Cys Thr Asp Val Ala Pro Pro Leu Ile
            420                 425                 430

Val His Asn Ile Gln Asn Gly Cys His Gly Pro Ile Cys Thr Glu Tyr
        435                 440                 445

Ala Ile Asn Lys Leu Arg Gln Glu Gly Ser Glu Gly Met Tyr Val
            450                 455                 460

Leu Arg Trp Ser Cys Thr Asp Phe Asp Asn Ile Leu Met Thr Val Thr
465                 470                 475                 480

Cys Phe Glu Lys Ser Glu Gln Val Gln Gly Ala Gln Lys Gln Phe Lys
                485                 490                 495

Asn Phe Gln Ile Glu Val Gln Lys Gly Arg Tyr Ser Leu His Gly Ser
            500                 505                 510

Asp Arg Ser Phe Pro Ser Leu Gly Asp Leu Met Ser His Leu Lys Lys
            515                 520                 525

Gln Ile Leu Arg Thr Asp Asn Ile Ser Phe Met Leu Lys Arg Cys Cys
530                 535                 540

Gln Pro Lys Pro Arg Glu Ile Ser Asn Leu Leu Val Ala Thr Lys Lys
545                 550                 555                 560

Ala Gln Glu Trp Gln Pro Val Tyr Pro Met Ser Gln Leu Ser Phe Asp
                565                 570                 575

Arg Ile Leu Lys Lys Asp Leu Val Gln Gly Glu His Leu Gly Arg Gly
            580                 585                 590

Thr Arg Thr His Ile Tyr Ser Gly Thr Leu Met Asp Tyr Lys Asp Asp
            595                 600                 605

Glu Gly Thr Ser Glu Glu Lys Lys Ile Lys Val Ile Leu Lys Val Leu
610                 615                 620

Asp Pro Ser His Arg Asp Ile Ser Leu Ala Phe Phe Glu Ala Ala Ser
625                 630                 635                 640

Met Met Arg Gln Val Ser His Lys His Ile Val Tyr Leu Tyr Gly Val
                645                 650                 655

Cys Val Arg Asp Val Glu Asn Ile Met Val Glu Phe Val Glu Gly
            660                 665                 670

Gly Pro Leu Asp Leu Phe Met His Arg Lys Ser Asp Val Leu Thr Thr
            675                 680                 685

Pro Trp Lys Phe Lys Val Ala Lys Gln Leu Ala Ser Ala Leu Ser Tyr
```

```
              690             695             700
Leu Glu Asp Lys Asp Leu Val His Gly Asn Val Cys Thr Lys Asn Leu
705                 710                 715                 720

Leu Leu Ala Arg Glu Gly Ile Asp Ser Glu Cys Gly Pro Phe Ile Lys
                725                 730                 735

Leu Ser Asp Pro Gly Ile Pro Ile Thr Val Leu Ser Arg Gln Glu Cys
                740                 745                 750

Ile Glu Arg Ile Pro Trp Ile Ala Pro Glu Cys Val Glu Asp Ser Lys
                755                 760                 765

Asn Leu Ser Val Ala Ala Asp Lys Trp Ser Phe Gly Thr Thr Leu Trp
                770                 775                 780

Glu Ile Cys Tyr Asn Gly Glu Ile Pro Leu Lys Asp Lys Thr Leu Ile
785                 790                 795                 800

Glu Lys Glu Arg Phe Tyr Glu Ser Arg Cys Arg Pro Val Thr Pro Ser
                805                 810                 815

Cys Lys Glu Leu Ala Asp Leu Met Thr Arg Cys Met Asn Tyr Asp Pro
                820                 825                 830

Asn Gln Arg Pro Phe Phe Arg Ala Ile Met Arg Asp Ile Asn Lys Leu
                835                 840                 845

Glu Glu Gln Asn Pro Asp Ile Val Ser Glu Lys Lys Pro Ala Thr Glu
                850                 855                 860

Val Asp Pro Thr His Phe Glu Lys Arg Phe Leu Lys Arg Ile Arg Asp
865                 870                 875                 880

Leu Gly Glu Gly His Phe Gly Lys Val Glu Leu Cys Arg Tyr Asp Pro
                885                 890                 895

Glu Gly Asp Asn Thr Gly Glu Gln Val Ala Val Lys Ser Leu Lys Pro
                900                 905                 910

Glu Ser Gly Gly Asn His Ile Ala Asp Leu Lys Lys Glu Ile Glu Ile
                915                 920                 925

Leu Arg Asn Leu Tyr His Glu Asn Ile Val Lys Tyr Lys Gly Ile Cys
                930                 935                 940

Thr Glu Asp Gly Gly Asn Gly Ile Lys Leu Ile Met Glu Phe Leu Pro
945                 950                 955                 960

Ser Gly Ser Leu Lys Glu Tyr Leu Pro Lys Asn Lys Asn Lys Ile Asn
                965                 970                 975

Leu Lys Gln Gln Leu Lys Tyr Ala Val Gln Ile Cys Lys Gly Met Asp
                980                 985                 990

Tyr Leu Gly Ser Arg Gln Tyr Val His Arg Asp Leu Ala Ala Arg Asn
                995                 1000                1005

Val Leu Val Glu Ser Glu His Gln Val Lys Ile Gly Asp Phe Gly
1010                1015                1020

Leu Thr Lys Ala Ile Glu Thr Asp Lys Glu Tyr Tyr Thr Val Lys
1025                1030                1035

Asp Asp Arg Asp Ser Pro Val Phe Trp Tyr Ala Pro Glu Cys Leu
1040                1045                1050

Met Gln Ser Lys Phe Tyr Ile Ala Ser Asp Val Trp Ser Phe Gly
1055                1060                1065

Val Thr Leu His Glu Leu Leu Thr Tyr Cys Asp Ser Asp Ser Ser
1070                1075                1080

Pro Met Ala Leu Phe Leu Lys Met Ile Gly Pro Thr His Gly Gln
1085                1090                1095

Met Thr Val Thr Arg Leu Val Asn Thr Leu Lys Glu Gly Lys Arg
1100                1105                1110
```

Leu Pro Cys Pro Pro Asn Cys Pro Asp Glu Val Tyr Gln Leu Met
1115                1120                    1125

Arg Lys Cys Trp Glu Phe Gln Pro Ser Asn Arg Thr Ser Phe Gln
1130                1135                    1140

Asn Leu Ile Glu Gly Phe Glu Ala Leu Leu Lys
1145                1150

<210> SEQ ID NO 12
<211> LENGTH: 1124
<212> TYPE: PRT
<213> ORGANISM: Homo sapiens

<400> SEQUENCE: 12

Met Ala Pro Pro Ser Glu Glu Thr Pro Leu Ile Pro Gln Arg Ser Cys
1               5                   10                  15

Ser Leu Leu Ser Thr Glu Ala Gly Ala Leu His Val Leu Leu Pro Ala
                20                  25                  30

Arg Gly Pro Gly Pro Pro Gln Arg Leu Ser Phe Ser Phe Gly Asp His
            35                  40                  45

Leu Ala Glu Asp Leu Cys Val Gln Ala Ala Lys Ala Ser Gly Ile Leu
        50                  55                  60

Pro Val Tyr His Ser Leu Phe Ala Leu Ala Thr Glu Asp Leu Ser Cys
65                  70                  75                  80

Trp Phe Pro Pro Ser His Ile Phe Ser Val Glu Asp Ala Ser Thr Gln
                85                  90                  95

Val Leu Leu Tyr Arg Ile Arg Pro Tyr Phe Pro Asn Trp Phe Gly Leu
            100                 105                 110

Glu Lys Cys His Arg Phe Gly Leu Arg Lys Asp Leu Ala Ser Ala Ile
        115                 120                 125

Leu Asp Leu Pro Val Leu Glu His Leu Phe Ala Gln His Arg Ser Asp
    130                 135                 140

Leu Val Ser Gly Arg Leu Pro Val Gly Leu Ser Leu Lys Glu Gln Gly
145                 150                 155                 160

Glu Cys Leu Ser Leu Ala Val Leu Asp Leu Ala Arg Met Ala Arg Glu
                165                 170                 175

Gln Ala Gln Arg Pro Gly Glu Leu Leu Lys Thr Val Ser Tyr Lys Ala
            180                 185                 190

Cys Leu Pro Pro Ser Leu Arg Asp Leu Ile Gln Gly Leu Ser Phe Val
        195                 200                 205

Thr Arg Arg Arg Ile Arg Arg Thr Val Arg Arg Ala Leu Arg Arg Val
    210                 215                 220

Ala Ala Cys Gln Ala Asp Arg His Ser Leu Met Ala Lys Tyr Ile Met
225                 230                 235                 240

Asp Leu Glu Arg Leu Asp Pro Ala Gly Ala Ala Glu Thr Phe His Val
                245                 250                 255

Gly Leu Pro Gly Ala Leu Gly Gly His Asp Gly Leu Gly Leu Leu Arg
            260                 265                 270

Val Ala Gly Asp Gly Gly Ile Ala Trp Thr Gln Gly Glu Gln Glu Val
        275                 280                 285

Leu Gln Pro Phe Cys Asp Phe Pro Glu Ile Val Asp Ile Ser Ile Lys
    290                 295                 300

Gln Ala Pro Arg Val Gly Pro Ala Gly Glu His Arg Leu Val Thr Val
305                 310                 315                 320

Thr Arg Thr Asp Asn Gln Ile Leu Glu Ala Glu Phe Pro Gly Leu Pro

```
                    325                 330                 335
Glu Ala Leu Ser Phe Val Ala Leu Val Asp Gly Tyr Phe Arg Leu Thr
                340                 345                 350

Thr Asp Ser Gln His Phe Phe Cys Lys Glu Val Ala Pro Pro Arg Leu
            355                 360                 365

Leu Glu Glu Val Ala Glu Gln Cys His Gly Pro Ile Thr Leu Asp Phe
        370                 375                 380

Ala Ile Asn Lys Leu Lys Thr Gly Gly Ser Arg Pro Gly Ser Tyr Val
385                 390                 395                 400

Leu Arg Arg Ser Pro Gln Asp Phe Asp Ser Phe Leu Leu Thr Val Cys
                405                 410                 415

Val Gln Asn Pro Leu Gly Pro Asp Tyr Lys Gly Cys Leu Ile Arg Arg
            420                 425                 430

Ser Pro Thr Gly Thr Phe Leu Leu Val Gly Leu Ser Arg Pro His Ser
        435                 440                 445

Ser Leu Arg Glu Leu Leu Ala Thr Cys Trp Asp Gly Gly Leu His Val
    450                 455                 460

Asp Gly Val Ala Val Thr Leu Thr Ser Cys Cys Ile Pro Arg Pro Lys
465                 470                 475                 480

Glu Lys Ser Asn Leu Ile Val Val Gln Arg Gly His Ser Pro Pro Thr
                485                 490                 495

Ser Ser Leu Val Gln Pro Gln Ser Gln Tyr Gln Leu Ser Gln Met Thr
            500                 505                 510

Phe His Lys Ile Pro Ala Asp Ser Leu Glu Trp His Glu Asn Leu Gly
        515                 520                 525

His Gly Ser Phe Thr Lys Ile Tyr Arg Gly Cys Arg His Glu Val Val
    530                 535                 540

Asp Gly Glu Ala Arg Lys Thr Glu Val Leu Leu Lys Val Met Asp Ala
545                 550                 555                 560

Lys His Lys Asn Cys Met Glu Ser Phe Leu Glu Ala Ala Ser Leu Met
                565                 570                 575

Ser Gln Val Ser Tyr Arg His Leu Val Leu Leu His Gly Val Cys Met
            580                 585                 590

Ala Gly Asp Ser Thr Met Val Gln Glu Phe Val His Leu Gly Ala Ile
        595                 600                 605

Asp Met Tyr Leu Arg Lys Arg Gly His Leu Val Pro Ala Ser Trp Lys
    610                 615                 620

Leu Gln Val Val Lys Gln Leu Ala Tyr Ala Leu Asn Tyr Leu Glu Asp
625                 630                 635                 640

Lys Gly Leu Pro His Gly Asn Val Ser Ala Arg Lys Val Leu Leu Ala
                645                 650                 655

Arg Glu Gly Ala Asp Gly Ser Pro Pro Phe Ile Lys Leu Ser Asp Pro
            660                 665                 670

Gly Val Ser Pro Ala Val Leu Ser Leu Glu Met Leu Thr Asp Arg Ile
        675                 680                 685

Pro Trp Val Ala Pro Glu Cys Leu Arg Glu Ala Gln Thr Leu Ser Leu
    690                 695                 700

Glu Ala Asp Lys Trp Gly Phe Gly Ala Thr Val Trp Glu Val Phe Ser
705                 710                 715                 720

Gly Val Thr Met Pro Ile Ser Ala Leu Asp Pro Ala Lys Lys Leu Gln
                725                 730                 735

Phe Tyr Glu Asp Arg Gln Gln Leu Pro Ala Pro Lys Trp Thr Glu Leu
            740                 745                 750
```

```
Ala Leu Leu Ile Gln Gln Cys Met Ala Tyr Glu Pro Val Gln Arg Pro
            755                 760                 765

Ser Phe Arg Ala Val Ile Arg Asp Leu Asn Ser Leu Ile Ser Ser Asp
    770                 775                 780

Tyr Glu Leu Leu Ser Asp Pro Thr Pro Gly Ala Leu Ala Pro Arg Asp
785                 790                 795                 800

Gly Leu Trp Asn Gly Ala Gln Leu Tyr Ala Cys Gln Asp Pro Thr Ile
                805                 810                 815

Phe Glu Glu Arg His Leu Lys Tyr Ile Ser Gln Leu Gly Lys Gly Asn
            820                 825                 830

Phe Gly Ser Val Glu Leu Cys Arg Tyr Asp Pro Leu Gly Asp Asn Thr
                835                 840                 845

Gly Ala Leu Val Ala Val Lys Gln Leu Gln His Ser Gly Pro Asp Gln
850                 855                 860

Gln Arg Asp Phe Gln Arg Glu Ile Gln Ile Leu Lys Ala Leu His Ser
865                 870                 875                 880

Asp Phe Ile Val Lys Tyr Arg Gly Val Ser Tyr Gly Pro Gly Arg Gln
                885                 890                 895

Ser Leu Arg Leu Val Met Glu Tyr Leu Pro Ser Gly Cys Leu Arg Asp
    900                 905                 910

Phe Leu Gln Arg His Arg Ala Arg Leu Asp Ala Ser Arg Leu Leu Leu
            915                 920                 925

Tyr Ser Ser Gln Ile Cys Lys Gly Met Glu Tyr Leu Gly Ser Arg Arg
    930                 935                 940

Cys Val His Arg Asp Leu Ala Ala Arg Asn Ile Leu Val Glu Ser Glu
945                 950                 955                 960

Ala His Val Lys Ile Ala Asp Phe Gly Leu Ala Lys Leu Leu Pro Leu
                965                 970                 975

Asp Lys Asp Tyr Tyr Val Val Arg Glu Pro Gly Gln Ser Pro Ile Phe
            980                 985                 990

Trp Tyr Ala Pro Glu Ser Leu Ser Asp Asn Ile Phe Ser Arg Gln Ser
    995                 1000                1005

Asp Val Trp Ser Phe Gly Val Val Leu Tyr Glu Leu Phe Thr Tyr
    1010                1015                1020

Cys Asp Lys Ser Cys Ser Pro Ser Ala Glu Phe Leu Arg Met Met
    1025                1030                1035

Gly Cys Glu Arg Asp Val Pro Ala Leu Cys Arg Leu Leu Glu Leu
    1040                1045                1050

Leu Glu Glu Gly Gln Arg Leu Pro Ala Pro Ala Cys Pro Ala
    1055                1060                1065

Glu Val His Glu Leu Met Lys Leu Cys Trp Ala Pro Ser Pro Gln
    1070                1075                1080

Asp Arg Pro Ser Phe Ser Ala Leu Gly Pro Gln Leu Asp Met Leu
    1085                1090                1095

Trp Ser Gly Ser Arg Gly Cys Glu Thr His Ala Phe Thr Ala His
    1100                1105                1110

Pro Glu Gly Lys His His Ser Leu Ser Phe Ser
    1115                1120

<210> SEQ ID NO 13
<211> LENGTH: 551
<212> TYPE: PRT
<213> ORGANISM: Homo sapiens
```

```
<400> SEQUENCE: 13

Met Ala Ala Pro Ala Leu Ser Trp Arg Leu Pro Leu Leu Ile Leu Leu
1               5                   10                  15

Leu Pro Leu Ala Thr Ser Trp Ala Ser Ala Val Asn Gly Thr Ser
            20                  25                  30

Gln Phe Thr Cys Phe Tyr Asn Ser Arg Ala Asn Ile Ser Cys Val Trp
            35                  40                  45

Ser Gln Asp Gly Ala Leu Gln Asp Thr Ser Cys Gln Val His Ala Trp
50                  55                  60

Pro Asp Arg Arg Arg Trp Asn Gln Thr Cys Glu Leu Leu Pro Val Ser
65                  70                  75                  80

Gln Ala Ser Trp Ala Cys Asn Leu Ile Leu Gly Ala Pro Asp Ser Gln
                85                  90                  95

Lys Leu Thr Thr Val Asp Ile Val Thr Leu Arg Val Leu Cys Arg Glu
            100                 105                 110

Gly Val Arg Trp Arg Val Met Ala Ile Gln Asp Phe Lys Pro Phe Glu
            115                 120                 125

Asn Leu Arg Leu Met Ala Pro Ile Ser Leu Gln Val Val His Val Glu
            130                 135                 140

Thr His Arg Cys Asn Ile Ser Trp Glu Ile Ser Gln Ala Ser His Tyr
145                 150                 155                 160

Phe Glu Arg His Leu Glu Phe Glu Ala Arg Thr Leu Ser Pro Gly His
                165                 170                 175

Thr Trp Glu Glu Ala Pro Leu Leu Thr Leu Lys Gln Lys Gln Glu Trp
            180                 185                 190

Ile Cys Leu Glu Thr Leu Thr Pro Asp Thr Gln Tyr Glu Phe Gln Val
            195                 200                 205

Arg Val Lys Pro Leu Gln Gly Glu Phe Thr Thr Trp Ser Pro Trp Ser
210                 215                 220

Gln Pro Leu Ala Phe Arg Thr Lys Pro Ala Ala Leu Gly Lys Asp Thr
225                 230                 235                 240

Ile Pro Trp Leu Gly His Leu Leu Val Gly Leu Ser Gly Ala Phe Gly
                245                 250                 255

Phe Ile Ile Leu Val Tyr Leu Leu Ile Asn Cys Arg Asn Thr Gly Pro
            260                 265                 270

Trp Leu Lys Lys Val Leu Lys Cys Asn Thr Pro Asp Pro Ser Lys Phe
            275                 280                 285

Phe Ser Gln Leu Ser Ser Glu His Gly Gly Asp Val Gln Lys Trp Leu
290                 295                 300

Ser Ser Pro Phe Pro Ser Ser Ser Phe Ser Pro Gly Gly Leu Ala Pro
305                 310                 315                 320

Glu Ile Ser Pro Leu Glu Val Leu Glu Arg Asp Lys Val Thr Gln Leu
                325                 330                 335

Leu Leu Gln Gln Asp Lys Val Pro Glu Pro Ala Ser Leu Ser Ser Asn
            340                 345                 350

His Ser Leu Thr Ser Cys Phe Thr Asn Gln Gly Tyr Phe Phe Phe His
            355                 360                 365

Leu Pro Asp Ala Leu Glu Ile Glu Ala Cys Gln Val Tyr Phe Thr Tyr
370                 375                 380

Asp Pro Tyr Ser Glu Glu Asp Pro Asp Glu Gly Val Ala Gly Ala Pro
385                 390                 395                 400

Thr Gly Ser Ser Pro Gln Pro Leu Gln Pro Leu Ser Gly Glu Asp Asp
                405                 410                 415
```

```
Ala Tyr Cys Thr Phe Pro Ser Arg Asp Asp Leu Leu Leu Phe Ser Pro
                420                 425                 430

Ser Leu Leu Gly Gly Pro Ser Pro Ser Thr Ala Pro Gly Gly Ser
            435                 440                 445

Gly Ala Gly Glu Glu Arg Met Pro Pro Ser Leu Gln Glu Arg Val Pro
        450                 455                 460

Arg Asp Trp Asp Pro Gln Pro Leu Gly Pro Pro Thr Pro Gly Val Pro
465                 470                 475                 480

Asp Leu Val Asp Phe Gln Pro Pro Glu Leu Val Leu Arg Glu Ala
                485                 490                 495

Gly Glu Glu Val Pro Asp Ala Gly Pro Arg Gly Val Ser Phe Pro
                500                 505                 510

Trp Ser Arg Pro Pro Gly Gln Gly Glu Phe Arg Ala Leu Asn Ala Arg
            515                 520                 525

Leu Pro Leu Asn Thr Asp Ala Tyr Leu Ser Leu Gln Glu Leu Gln Gly
            530                 535                 540

Gln Asp Pro Thr His Leu Val
545                 550

<210> SEQ ID NO 14
<211> LENGTH: 118
<212> TYPE: PRT
<213> ORGANISM: Homo sapiens

<400> SEQUENCE: 14

Met Asp Val Phe Leu Met Ile Arg Arg His Lys Thr Thr Ile Phe Thr
1               5                   10                  15

Asp Ala Lys Glu Ser Ser Thr Val Phe Glu Leu Lys Arg Ile Val Glu
            20                  25                  30

Gly Ile Leu Lys Arg Pro Pro Asp Glu Gln Arg Leu Tyr Lys Asp Asp
        35                  40                  45

Gln Leu Leu Asp Asp Gly Lys Thr Leu Gly Glu Cys Gly Phe Thr Ser
    50                  55                  60

Gln Thr Ala Arg Pro Gln Ala Pro Ala Thr Val Gly Leu Ala Phe Arg
65                  70                  75                  80

Ala Asp Asp Thr Phe Glu Ala Leu Cys Ile Glu Pro Phe Ser Ser Pro
                85                  90                  95

Pro Glu Leu Pro Asp Val Met Lys Pro Gln Asp Ser Gly Ser Ser Ala
            100                 105                 110

Asn Glu Gln Ala Val Gln
        115

<210> SEQ ID NO 15
<211> LENGTH: 112
<212> TYPE: PRT
<213> ORGANISM: Homo sapiens

<400> SEQUENCE: 15

Met Asp Gly Glu Glu Lys Thr Tyr Gly Gly Cys Glu Gly Pro Asp Ala
1               5                   10                  15

Met Tyr Val Lys Leu Ile Ser Ser Asp Gly His Glu Phe Ile Val Lys
            20                  25                  30

Arg Glu His Ala Leu Thr Ser Gly Thr Ile Lys Ala Met Leu Ser Gly
        35                  40                  45

Pro Gly Gln Phe Ala Glu Asn Glu Thr Asn Glu Val Asn Phe Arg Glu
    50                  55                  60
```

-continued

```
Ile Pro Ser His Val Leu Ser Lys Val Cys Met Tyr Phe Thr Tyr Lys
 65                  70                  75                  80

Val Arg Tyr Thr Asn Ser Ser Thr Glu Ile Pro Glu Phe Pro Ile Ala
                 85                  90                  95

Pro Glu Ile Ala Leu Glu Leu Leu Met Ala Ala Asn Phe Leu Asp Cys
            100                 105                 110

<210> SEQ ID NO 16
<211> LENGTH: 780
<212> TYPE: PRT
<213> ORGANISM: Homo sapiens

<400> SEQUENCE: 16

Met Ala Thr Ser Asn Leu Leu Lys Asn Lys Gly Ser Leu Gln Phe Glu
  1               5                  10                  15

Asp Lys Trp Asp Phe Met Arg Pro Ile Val Leu Lys Leu Leu Arg Gln
             20                  25                  30

Glu Ser Val Thr Lys Gln Gln Trp Phe Asp Leu Phe Ser Asp Val His
         35                  40                  45

Ala Val Cys Leu Trp Asp Asp Lys Gly Pro Ala Lys Ile His Gln Ala
 50                  55                  60

Leu Lys Glu Asp Ile Leu Glu Phe Ile Lys Gln Ala Gln Ala Arg Val
 65                  70                  75                  80

Leu Ser His Gln Asp Asp Thr Ala Leu Leu Lys Ala Tyr Ile Val Glu
                 85                  90                  95

Trp Arg Lys Phe Phe Thr Gln Cys Asp Ile Leu Pro Lys Pro Phe Cys
            100                 105                 110

Gln Leu Glu Ile Thr Leu Met Gly Lys Gln Gly Ser Asn Lys Lys Ser
        115                 120                 125

Asn Val Glu Asp Ser Ile Val Arg Lys Leu Met Leu Asp Thr Trp Asn
130                 135                 140

Glu Ser Ile Phe Ser Asn Ile Lys Asn Arg Leu Gln Asp Ser Ala Met
145                 150                 155                 160

Lys Leu Val His Ala Glu Arg Leu Gly Glu Ala Phe Asp Ser Gln Leu
                165                 170                 175

Val Ile Gly Val Arg Glu Ser Tyr Val Asn Leu Cys Ser Asn Pro Glu
            180                 185                 190

Asp Lys Leu Gln Ile Tyr Arg Asp Asn Phe Glu Lys Ala Tyr Leu Asp
        195                 200                 205

Ser Thr Glu Arg Phe Tyr Arg Thr Gln Ala Pro Ser Tyr Leu Gln Gln
    210                 215                 220

Asn Gly Val Gln Asn Tyr Met Lys Tyr Ala Asp Ala Lys Leu Lys Glu
225                 230                 235                 240

Glu Glu Lys Arg Ala Leu Arg Tyr Leu Glu Thr Arg Arg Glu Cys Asn
                245                 250                 255

Ser Val Glu Ala Leu Met Glu Cys Cys Val Asn Ala Leu Val Thr Ser
            260                 265                 270

Phe Lys Glu Thr Ile Leu Ala Glu Cys Gln Gly Met Ile Lys Arg Asn
        275                 280                 285

Glu Thr Glu Lys Leu His Leu Met Phe Ser Leu Met Asp Lys Val Pro
    290                 295                 300

Asn Gly Ile Glu Pro Met Leu Lys Asp Leu Glu Glu His Ile Ile Ser
305                 310                 315                 320

Ala Gly Leu Ala Asp Met Val Ala Ala Glu Thr Ile Thr Thr Asp
```

-continued

```
                325                 330                 335
Ser Glu Lys Tyr Val Glu Gln Leu Leu Thr Leu Phe Asn Arg Phe Ser
                340                 345                 350
Lys Leu Val Lys Glu Ala Phe Gln Asp Asp Pro Arg Phe Leu Thr Ala
                355                 360                 365
Arg Asp Lys Ala Tyr Lys Ala Val Val Asn Asp Ala Thr Ile Phe Lys
                370                 375                 380
Leu Glu Leu Pro Leu Lys Gln Lys Gly Val Gly Leu Lys Thr Gln Pro
385                 390                 395                 400
Glu Ser Lys Cys Pro Glu Leu Leu Ala Asn Tyr Cys Asp Met Leu Leu
                405                 410                 415
Arg Lys Thr Pro Leu Ser Lys Lys Leu Thr Ser Glu Ile Glu Ala
                420                 425                 430
Lys Leu Lys Glu Val Leu Leu Val Leu Lys Tyr Val Gln Asn Lys Asp
                435                 440                 445
Val Phe Met Arg Tyr His Lys Ala His Leu Thr Arg Arg Leu Ile Leu
                450                 455                 460
Asp Ile Ser Ala Asp Ser Glu Ile Glu Glu Asn Met Val Glu Trp Leu
465                 470                 475                 480
Arg Glu Val Gly Met Pro Ala Asp Tyr Val Asn Lys Leu Ala Arg Met
                485                 490                 495
Phe Gln Asp Ile Lys Val Ser Glu Asp Leu Asn Gln Ala Phe Lys Glu
                500                 505                 510
Met His Lys Asn Asn Lys Leu Ala Leu Pro Ala Asp Ser Val Asn Ile
                515                 520                 525
Lys Ile Leu Asn Ala Gly Ala Trp Ser Arg Ser Glu Lys Val Phe
                530                 535                 540
Val Ser Leu Pro Thr Glu Leu Glu Asp Leu Ile Pro Glu Val Glu Glu
545                 550                 555                 560
Phe Tyr Lys Lys Asn His Ser Gly Arg Lys Leu His Trp His His Leu
                565                 570                 575
Met Ser Asn Gly Ile Ile Thr Phe Lys Asn Glu Val Gly Gln Tyr Asp
                580                 585                 590
Leu Glu Val Thr Thr Phe Gln Leu Ala Val Leu Phe Ala Trp Asn Gln
                595                 600                 605
Arg Pro Arg Glu Lys Ile Ser Phe Glu Asn Leu Lys Leu Ala Thr Glu
                610                 615                 620
Leu Pro Asp Ala Glu Leu Arg Arg Thr Leu Trp Ser Leu Val Ala Phe
625                 630                 635                 640
Pro Lys Leu Lys Arg Gln Val Leu Leu Tyr Glu Pro Gln Val Asn Ser
                645                 650                 655
Pro Lys Asp Phe Thr Glu Gly Thr Leu Phe Ser Val Asn Gln Glu Phe
                660                 665                 670
Ser Leu Ile Lys Asn Ala Lys Val Gln Lys Arg Gly Lys Ile Asn Leu
                675                 680                 685
Ile Gly Arg Leu Gln Leu Thr Thr Glu Arg Met Arg Glu Glu Glu Asn
                690                 695                 700
Glu Gly Ile Val Gln Leu Arg Ile Leu Arg Thr Gln Glu Ala Ile Ile
705                 710                 715                 720
Gln Ile Met Lys Met Arg Lys Lys Ile Ser Asn Ala Gln Leu Gln Thr
                725                 730                 735
Glu Leu Val Glu Ile Leu Lys Asn Met Phe Leu Pro Gln Lys Lys Met
                740                 745                 750
```

```
Ile Lys Glu Gln Ile Glu Trp Leu Ile Glu His Lys Tyr Ile Arg Arg
    755                 760                 765

Asp Glu Ser Asp Ile Asn Thr Phe Ile Tyr Met Ala
    770                 775                 780
```

<210> SEQ ID NO 17
<211> LENGTH: 301
<212> TYPE: PRT
<213> ORGANISM: Homo sapiens

<400> SEQUENCE: 17

```
Asp Ile Val Ser Glu Lys Lys Pro Ala Thr Glu Val Asp Pro Thr His
1               5                   10                  15

Phe Glu Lys Arg Phe Leu Lys Arg Ile Arg Asp Leu Gly Glu Gly His
                20                  25                  30

Phe Gly Lys Val Glu Leu Cys Arg Tyr Asp Pro Glu Gly Asp Asn Thr
            35                  40                  45

Gly Glu Gln Val Ala Val Lys Ser Leu Lys Pro Glu Ser Gly Gly Asn
        50                  55                  60

His Ile Ala Asp Leu Lys Lys Glu Ile Glu Ile Leu Arg Asn Leu Tyr
65                  70                  75                  80

His Glu Asn Ile Val Lys Tyr Lys Gly Ile Cys Thr Glu Asp Gly Gly
                85                  90                  95

Asn Gly Ile Lys Leu Ile Met Glu Phe Leu Pro Ser Gly Ser Leu Lys
            100                 105                 110

Glu Tyr Leu Pro Lys Asn Lys Asn Lys Ile Asn Leu Lys Gln Gln Leu
        115                 120                 125

Lys Tyr Ala Val Gln Ile Cys Lys Gly Met Asp Tyr Leu Gly Ser Arg
    130                 135                 140

Gln Tyr Val His Arg Asp Leu Ala Ala Arg Asn Val Leu Val Glu Ser
145                 150                 155                 160

Glu His Gln Val Lys Ile Gly Asp Phe Gly Leu Thr Lys Ala Ile Glu
                165                 170                 175

Thr Asp Lys Glu Tyr Tyr Thr Val Lys Asp Asp Arg Asp Ser Pro Val
            180                 185                 190

Phe Trp Tyr Ala Pro Glu Cys Leu Met Gln Ser Lys Phe Tyr Ile Ala
        195                 200                 205

Ser Asp Val Trp Ser Phe Gly Val Thr Leu His Glu Leu Leu Thr Tyr
    210                 215                 220

Cys Asp Ser Asp Ser Ser Pro Met Ala Leu Phe Leu Lys Met Ile Gly
225                 230                 235                 240

Pro Thr His Gly Gln Met Thr Val Thr Arg Leu Val Asn Thr Leu Lys
                245                 250                 255

Glu Gly Lys Arg Leu Pro Cys Pro Asn Cys Pro Asp Glu Val Tyr
            260                 265                 270

Gln Leu Met Arg Lys Cys Trp Glu Phe Gln Pro Ser Asn Arg Thr Ser
        275                 280                 285

Phe Gln Asn Leu Ile Glu Gly Phe Glu Ala Leu Leu Lys
    290                 295                 300
```

<210> SEQ ID NO 18
<211> LENGTH: 18
<212> TYPE: PRT
<213> ORGANISM: Homo sapiens

<400> SEQUENCE: 18

```
Arg Arg Ala Lys Ala Ala Asp Gly Tyr Val Lys Pro Gln Ile Lys Gln
1               5                   10                  15

Val Val

<210> SEQ ID NO 19
<211> LENGTH: 16
<212> TYPE: PRT
<213> ORGANISM: Homo sapiens

<400> SEQUENCE: 19

Ala Ile Glu Thr Asp Lys Glu Tyr Tyr Thr Val Lys Asp Asp Arg Asp
1               5                   10                  15

<210> SEQ ID NO 20
<211> LENGTH: 16
<212> TYPE: PRT
<213> ORGANISM: Homo sapiens
<220> FEATURE:
<221> NAME/KEY: MISC_FEATURE
<222> LOCATION: (8)..(8)
<223> OTHER INFORMATION: phosphorylated tyrosine

<400> SEQUENCE: 20

Leu Leu Pro Leu Asp Lys Asp Tyr Tyr Val Val Arg Glu Pro Gly Gln
1               5                   10                  15

<210> SEQ ID NO 21
<211> LENGTH: 12
<212> TYPE: PRT
<213> ORGANISM: Homo sapiens
<220> FEATURE:
<221> NAME/KEY: MISC_FEATURE
<222> LOCATION: (4)..(4)
<223> OTHER INFORMATION: phosphorylated tyrosine

<400> SEQUENCE: 21

Asn Gln Gly Tyr Phe Phe Phe His Leu Pro Asp Ala
1               5                   10

<210> SEQ ID NO 22
<211> LENGTH: 12
<212> TYPE: PRT
<213> ORGANISM: Homo sapiens
<220> FEATURE:
<221> NAME/KEY: MISC_FEATURE
<222> LOCATION: (4)..(4)
<223> OTHER INFORMATION: phosphorylated tyrosine

<400> SEQUENCE: 22

Tyr Phe Thr Tyr Asp Pro Tyr Ser Glu Glu Asp Pro
1               5                   10

<210> SEQ ID NO 23
<211> LENGTH: 12
<212> TYPE: PRT
<213> ORGANISM: Homo sapiens
<220> FEATURE:
<221> NAME/KEY: MISC_FEATURE
<222> LOCATION: (4)..(4)
<223> OTHER INFORMATION: phosphorylated tyrosine

<400> SEQUENCE: 23

Gln Asp Asp Tyr Cys Ala Phe Pro Pro Arg Asp Asp
1               5                   10

<210> SEQ ID NO 24
```

```
<211> LENGTH: 12
<212> TYPE: PRT
<213> ORGANISM: Homo sapiens
<220> FEATURE:
<221> NAME/KEY: MISC_FEATURE
<222> LOCATION: (4)..(4)
<223> OTHER INFORMATION: phosphorylated tyrosine

<400> SEQUENCE: 24

Thr Asp Ala Tyr Leu Ser Leu Gln Glu Leu Gln Gly
1               5                   10

<210> SEQ ID NO 25
<211> LENGTH: 11
<212> TYPE: PRT
<213> ORGANISM: Homo sapiens
<220> FEATURE:
<221> NAME/KEY: MISC_FEATURE
<222> LOCATION: (5)..(5)
<223> OTHER INFORMATION: phosphorylated tyrosine

<400> SEQUENCE: 25

Leu Val Thr Glu Tyr Gln Gly Asn Phe Ser Ala
1               5                   10

<210> SEQ ID NO 26
<211> LENGTH: 11
<212> TYPE: PRT
<213> ORGANISM: Homo sapiens
<220> FEATURE:
<221> NAME/KEY: MISC_FEATURE
<222> LOCATION: (5)..(5)
<223> OTHER INFORMATION: phosphorylated tyrosine

<400> SEQUENCE: 26

Leu Gln Pro Asp Tyr Ser Glu Arg Phe Cys His
1               5                   10

<210> SEQ ID NO 27
<211> LENGTH: 11
<212> TYPE: PRT
<213> ORGANISM: Homo sapiens
<220> FEATURE:
<221> NAME/KEY: MISC_FEATURE
<222> LOCATION: (5)..(5)
<223> OTHER INFORMATION: phosphorylated tyrosine

<400> SEQUENCE: 27

Ile His Ser Pro Tyr Trp Pro Pro Pro Cys Tyr
1               5                   10

<210> SEQ ID NO 28
<211> LENGTH: 11
<212> TYPE: PRT
<213> ORGANISM: Homo sapiens
<220> FEATURE:
<221> NAME/KEY: MISC_FEATURE
<222> LOCATION: (5)..(5)
<223> OTHER INFORMATION: phosphorylated tyrosine

<400> SEQUENCE: 28

Pro Pro Pro Cys Tyr Ser Leu Lys Pro Glu Ala
1               5                   10

<210> SEQ ID NO 29
<211> LENGTH: 38
<212> TYPE: PRT
<213> ORGANISM: Homo sapiens
<220> FEATURE:
```

```
<221> NAME/KEY: MISC_FEATURE
<222> LOCATION: (6)..(6)
<223> OTHER INFORMATION: phosphorylated serine
<220> FEATURE:
<221> NAME/KEY: MISC_FEATURE
<222> LOCATION: (8)..(8)
<223> OTHER INFORMATION: phosphorylated serine
<220> FEATURE:
<221> NAME/KEY: MISC_FEATURE
<222> LOCATION: (14)..(14)
<223> OTHER INFORMATION: phosphorylated threonine
<220> FEATURE:
<221> NAME/KEY: MISC_FEATURE
<222> LOCATION: (21)..(21)
<223> OTHER INFORMATION: ubiquitinated lysine

<400> SEQUENCE: 29

Ala Ala Asp Thr Arg Ser Asp Ser Pro Asp Pro Ala Pro Thr Pro Ala
1               5                   10                  15

Leu Pro Met Ser Lys Gln Asp Ala Pro Ser Asp Ser Val Leu Pro Ile
            20                  25                  30

Pro Val Ala Thr Ala Val
            35

<210> SEQ ID NO 30
<211> LENGTH: 16
<212> TYPE: PRT
<213> ORGANISM: Homo sapiens

<400> SEQUENCE: 30

Ser Asp Ser Pro Asp Pro Ala Pro Thr Pro Ala Leu Pro Met Ser Lys
1               5                   10                  15

<210> SEQ ID NO 31
<211> LENGTH: 40
<212> TYPE: PRT
<213> ORGANISM: Homo sapiens

<400> SEQUENCE: 31

Arg Pro Leu Trp Ala Gln Ser Leu Glu Leu Pro Gly Pro Ala Met Gln
1               5                   10                  15

Pro Leu Pro Thr Gly Ala Phe Pro Glu Glu Val Thr Glu Glu Thr Pro
            20                  25                  30

Val Gln Ala Glu Asn Glu Pro Lys
            35                  40

<210> SEQ ID NO 32
<211> LENGTH: 43
<212> TYPE: PRT
<213> ORGANISM: Homo sapiens

<400> SEQUENCE: 32

Ser Asp Ser Pro Asp Pro Ala Pro Thr Pro Ala Leu Pro Met Ser Lys
1               5                   10                  15

Gln Asp Ala Pro Ser Asp Ser Val Leu Pro Ile Pro Val Ala Thr Ala
            20                  25                  30

Val His Leu Lys Leu Val Gln Pro Phe Val Arg
            35                  40

<210> SEQ ID NO 33
<211> LENGTH: 32
<212> TYPE: PRT
<213> ORGANISM: Homo sapiens

<400> SEQUENCE: 33
```

Gln Asp Ala Pro Ser Asp Ser Val Leu Pro Ile Pro Val Ala Thr Ala
1               5                   10                  15

Val His Leu Lys Leu Val Gln Pro Phe Val Arg Arg Ser Ala Arg
            20                  25                  30

<210> SEQ ID NO 34
<211> LENGTH: 19
<212> TYPE: PRT
<213> ORGANISM: Homo sapiens

<400> SEQUENCE: 34

Val Leu Asp Pro Glu Gly Asp Leu Leu Cys Ile Ala Lys Thr Phe Ser
1               5                   10                  15

Tyr Leu Arg

<210> SEQ ID NO 35
<211> LENGTH: 14
<212> TYPE: PRT
<213> ORGANISM: Homo sapiens

<400> SEQUENCE: 35

Gln His Leu Gln Lys Met Pro Glu Gly Thr Phe Leu Val Arg
1               5                   10

<210> SEQ ID NO 36
<211> LENGTH: 23
<212> TYPE: PRT
<213> ORGANISM: Homo sapiens

<400> SEQUENCE: 36

Asp Ser Thr His Pro Ser Tyr Leu Phe Thr Leu Ser Val Lys Thr Thr
1               5                   10                  15

Arg Gly Pro Thr Asn Val Arg
            20

<210> SEQ ID NO 37
<211> LENGTH: 36
<212> TYPE: PRT
<213> ORGANISM: Homo sapiens

<400> SEQUENCE: 37

Ser Asp Ser Pro Asp Pro Ala Pro Thr Pro Ala Leu Pro Met Ser Lys
1               5                   10                  15

Gln Asp Ala Pro Ser Asp Ser Val Leu Pro Ile Pro Val Ala Thr Ala
            20                  25                  30

Val His Leu Lys
            35

<210> SEQ ID NO 38
<211> LENGTH: 27
<212> TYPE: PRT
<213> ORGANISM: Homo sapiens

<400> SEQUENCE: 38

Gln Asp Ala Pro Ser Asp Ser Val Leu Pro Ile Pro Val Ala Thr Ala
1               5                   10                  15

Val His Leu Lys Leu Val Gln Pro Phe Val Arg
            20                  25